(12) United States Patent
Jang et al.

(10) Patent No.: US 11,841,361 B2
(45) Date of Patent: Dec. 12, 2023

(54) MICROFLUIDIC PROXIMAL TUBULE KIDNEY-ON-CHIP

(71) Applicant: EMULATE, INC., Boston, MA (US)

(72) Inventors: Kyung-Jin Jang, Boston, MA (US); Janey Ronxhi, Quincy, MA (US); Josiah Sliz, Boston, MA (US); Sauveur Jeanty, Canton, MA (US); Sushma Jadalannagari, Chelmsford, MA (US); Ananth Nookala, Boston, MA (US); Hyoungshin Park, Newton, MA (US)

(73) Assignee: EMULATE, INC., Boston, MA (US)

( * ) Notice: Subject to any disclaimer, the term of this patent is extended or adjusted under 35 U.S.C. 154(b) by 105 days.

(21) Appl. No.: 17/406,732

(22) Filed: Aug. 19, 2021

(65) Prior Publication Data

US 2022/0042976 A1    Feb. 10, 2022

Related U.S. Application Data

(63) Continuation of application No. PCT/US2020/019512, filed on Feb. 24, 2020, which
(Continued)

(51) Int. Cl.
*G01N 33/50* (2006.01)
*C12N 5/071* (2010.01)

(52) U.S. Cl.
CPC ....... *G01N 33/5088* (2013.01); *C12N 5/0684* (2013.01); *C12N 5/0691* (2013.01);
(Continued)

(58) Field of Classification Search
CPC .. C12N 5/0697; C12N 5/0684; C12N 5/0691; B01L 3/502715; B01L 2200/0652;
(Continued)

(56) References Cited

U.S. PATENT DOCUMENTS

| 10,125,342 B2 | 11/2018 | Levner et al. |
| 2007/0048727 A1 | 3/2007 | Shuler et al. ............... 435/325 |

(Continued)

FOREIGN PATENT DOCUMENTS

WO PCT/US2009/050830    7/2009
WO PCT/US2012/026934    9/2012
(Continued)

OTHER PUBLICATIONS

Paoli et al., "Mimicking the Kidney: A Key Role in Organ-on-Chip Development", 2016, Micromachines, pp. 1-16 (Year: 2016).*
(Continued)

*Primary Examiner* — Jennifer Wecker
*Assistant Examiner* — Kathryn Elizabeth Limbaugh
(74) *Attorney, Agent, or Firm* — Medlen & Carroll, LLP

(57) ABSTRACT

The present invention relates to microfluidic fluidic devices, methods and systems as microfluidic kidney on-chips, e.g. human Proximal Tubule-Kidney-Chip, Glomerulus (Kidney)-Chip, Collecting Duct (Kidney)-Chip. Devices, methods and systems are described for drug testing including drug transport and renal clearance. Further, such devices, methods and systems are used for determining drug-drug interactions and their effect upon renal transporter functions. Importantly, they may be used for pre-clinical and clinical drug development for treating kidney diseases and for personalized medicine.

7 Claims, 95 Drawing Sheets
(52 of 95 Drawing Sheet(s) Filed in Color)

Related U.S. Application Data is a continuation-in-part of application No. 16/454,753, filed on Jun. 27, 2019, which is a continuation-in-part of application No. 16/352,234, filed on Mar. 13, 2019, now Pat. No. 11,534,753, which is a continuation-in-part of application No. PCT/US2019/019250, filed on Feb. 22, 2019.

(52) U.S. Cl.
CPC ....... *C12N 5/0697* (2013.01); *G01N 33/5014* (2013.01); *G01N 33/5044* (2013.01); *G01N 33/5064* (2013.01)

(58) Field of Classification Search
CPC ... B01L 2200/10; C12M 23/16; C12M 25/02; C12Q 1/32; G01N 33/5005; G01N 33/5014; G01N 33/5082; G01N 33/5088; G01N 33/5044; G01N 33/5064
See application file for complete search history.

(56) References Cited

U.S. PATENT DOCUMENTS

| | | | |
|---|---|---|---|
| 2009/0263849 A1 | 10/2009 | Sun et al. | 435/29 |
| 2010/0098742 A1 | 4/2010 | Vacanti et al. | 424/424 |
| 2012/0179381 A1 | 7/2012 | McKim | 702/19 |
| 2013/0130223 A1 | 5/2013 | Levtchenko et al. | 435/1.1 |
| 2016/0243738 A1 | 8/2016 | Katrycz et al. | |

FOREIGN PATENT DOCUMENTS

| | | |
|---|---|---|
| WO | PCT/US2012/068725 | 6/2013 |
| WO | PCT/US2012/068766 | 6/2013 |
| WO | WO 2014/008358 | 1/2014 |
| WO | PCT/US2014/044417 | 12/2014 |
| WO | PCT/US2014/047694 | 1/2015 |
| WO | PCT/US2014/071570 | 9/2015 |
| WO | PCT/US2014/071611 | 9/2015 |
| WO | WO 2016/179242 | 11/2016 |

OTHER PUBLICATIONS

U.S. Appl. No. 61/810,944, filed Apr. 11, 2013.
U.S. Appl. No. 61/839,702, filed Jun. 26, 2013.
Barry III, et al., "Direct-Write Assembly of 3D Hydrogel Scaffolds for Guided Cell Growth." *Advanced Materials*, 21:2407-2410 (2009).
Benjamini and Hochberg, "Controlling the False Discovery Rate: A Practical and Powerful Approach to Multiple Testing." *Journal of the Royal Statistical Society: Series B (Methodological)*, 57(1):289-300 (1995).
Bhatia and Ingber, "Microfluidic Organs-on-Chips." *Nature Biotechnology*, 32(8):760-772 (2014).
Bischel, et al., "A Practical Method for Patterning Lumens through ECM Hydrogels Via Viscous Finger Patterning." *Journal of Laboratory Automation*, 17(2):96-103 (2012).
Hanson Shepherd, et al., "3D Microperiodic Hydrogel Scaffolds for Robust Neuronal Cultures." *Advanced Functional Materials*, 21(1):47-54 (2011).
Jang and Suh, "A Multi-Layer Microfluidic Device for Efficient Culture and Analysis of Renal Tubular Cells." *Lab on a Chip*, 10(1):36-42 (2010).
Jang, et al., "Fluid-Shear-Stress-Induced Translocation of Aquaporin-2 and Reorganization of Actin Cytoskeleton in Renal Tubular Epithelial Cells." *Integrative Biology: Quantitative Biosciences From Nano to Macro*, 3(2):134-141 (2011).
Jang, et al., "Human Kidney Proximal Tubule-on-a-Chip for Drug Transport and Nephrotoxicity Assessment." *Integrative Biology: Quantitative Biosciences From Nano to Macro*, 5(9): 1119-1129 (2013).
Kamiguchi, et al., "A 96-Well Plate Assay for CYP4503A Induction Using Cryopreserved Human Hepatocytes." *Drug Metabolism and Disposition*, 38(11):1912-1916 (2010).
Maggiorani, et al., "Shear Stress-Induced Alteration of Epithelial Organization in Human Renal Tubular Cells." *PloS One*, 10(7):e0131416 (2015).
Mather and Pollock, "Glucose Handling by the Kidney." *Kidney international. Supplement* (120):S1-6 (2011).
Miner "Renal Basement Membrane Components." *Kidney international*, 56(6):2016-2024 (1999).
Sun, et al., "Direct-Write Assembly of 3D Silk/Hydroxyapatite Scaffolds for Bone Co-Cultures." *Advanced Healthcare Materials*, 1(6):729-735 (2012).
Thangawng, et al., "An Ultra-Thin PDMS Membrane as a Bio/Micro-Nano Interface: Fabrication and Characterization." *Biomedical Microdevices*, 9(4):587-595 (2007).
Whitesides, et al., "Soft Lithography in Biology and Biochemistry." *Annual Review of Biomedical Engineering*, 3:335-373 (2001).
Wu, et al., "Direct-Write Assembly of Biomimetic Microvascular Networks for Efficient Fluid Transport." *Soft Matter*, 6(4):739-742 (2010).
Wu, et al., "Omnidirectional Printing of 3D Microvascular Networks." *Advanced Materials* (Deerfield Beach, Fla.), 23(24):H178-183 (2011).
Zhang and Radisic, "Organ-on-a-Chip Devices Advance to Market." *Lab on a Chip*, 17(14):2395-2420 (2017).
Bariety, et al., "Transdifferentiation of Epithelial Glomerular Cells", *Journal of the American Society of Nephrology*, vol. 14, Suppl 1, p. S42-S47, 2003.
Vedula, et al., "A microfluidic renal proximal tubule with active reabsorption function", *PLoS ONE*, pp. 1-15 (2017).
Weber, et al., "Development of a microphysiological model of human kidney proximal tubule function", Elsevier Inc., *Kidney International*, 90, pp. 627-637 (2016).
Wilmer, et al., "Kidney-on-a-Chip Technology for Drug-Induced Nephrotoxicity Screening", Feb. 2016, *Trends in Biotechnology*, vol. 34, No. 2, pp. 156-170 (2016).
Maschmeyer, et al., "A four-organ-chip for interconnected long-term co-culture of humane intestine, liver, skin and kidney equivalents", *Lab on a Chip*, 15, pp. 2688-2699 (2015).

\* cited by examiner

Low flow rate (30ul/h)

high shear chip, ECM1 (KidneySpec)　　　S1 chip, ECM1 (KidneySpec)

High shear chip, ECM2 (Col IV)　　　S1 chip, ECM2 (Col IV)

High flow high shear chip, ECM1 (KidneySpec)

S1 chip, ECM1 (KidneySpec)

high shear chip, ECM2 (Col IV)

S1 chip, ECM2 (Col IV)

Low flow rate (30ul/h)

high shear chip, ECM1 (KidneySpec)

S1 chip, ECM1 (KidneySpec)

High shear chip, ECM2 (Col IV)

S1 chip, ECM2 (Col IV)

High flow rate (150ul/h)

high shear chip, ECM1 (KidneySpec)

S1 chip, ECM1 (KidneySpec)

high shear chip, ECM2 (Col IV)

S1 chip, ECM2 (Col IV)

Fig. 59A-D
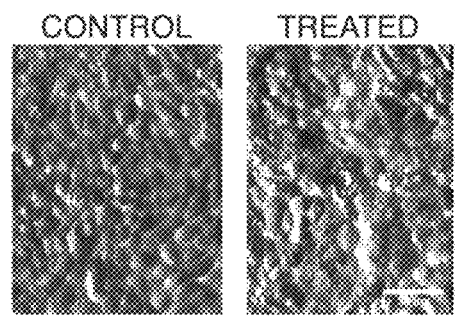
FIG. 59A
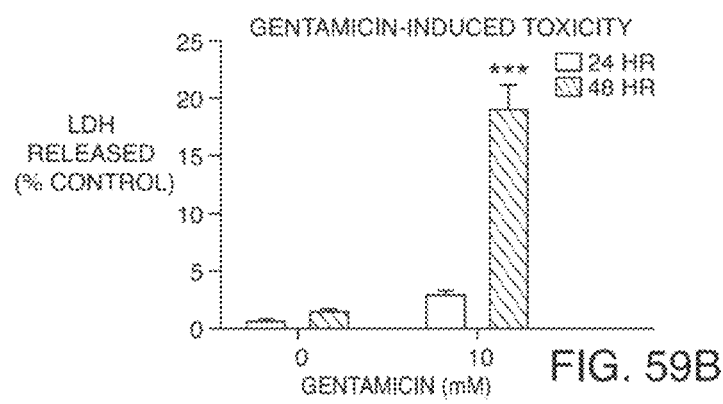
FIG. 59B
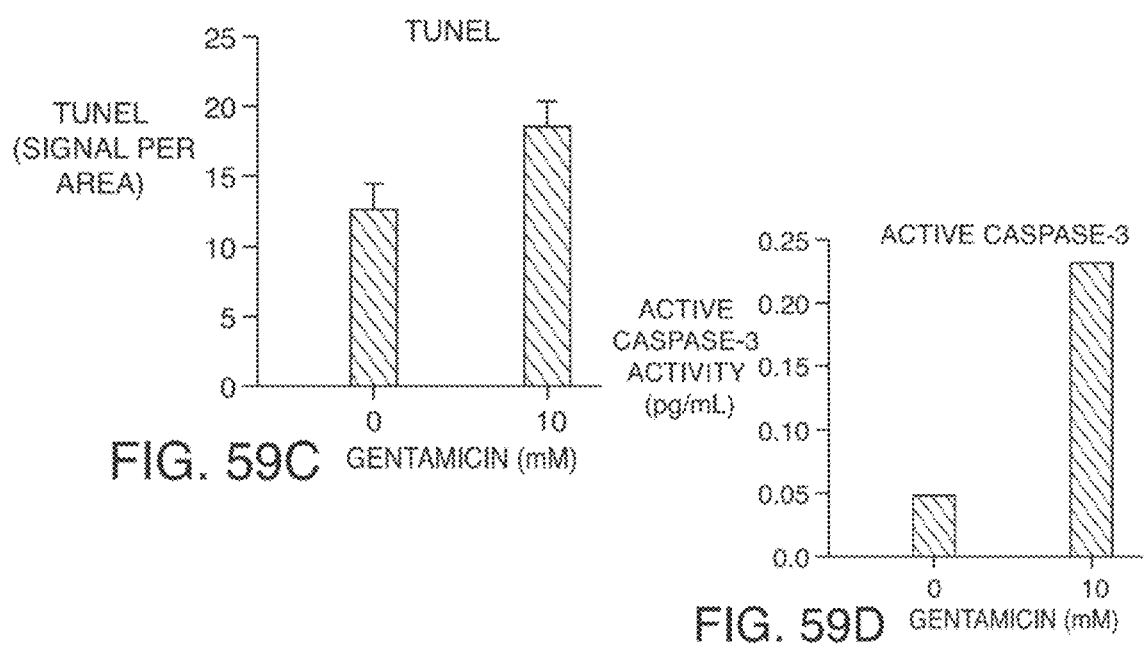
FIG. 59C
FIG. 59D

Fig. 61A-D

KIDNEY DAMAGE
LDH LEAKAGE

MICROFLUIDIC PROXIMAL TUBULE KIDNEY-ON-CHIP

CROSS-REFERENCE TO RELATED APPLICATIONS

This application is a Continuation of, and claims priority to, PCT Patent Application Serial No. PCT/US20/19512, filed Feb. 24, 2020; Continuation-in-Part application Ser. No. 16/454,753, filed Jun. 27, 2019; Continuation-in-Part application Ser. No. 16/352,234, filed Mar. 13, 2019 which claims priority to PCT Application Serial No. PCT/US19/19250 filed on Feb. 22, 2019 now expired, the contents of which are incorporated herein in their entirety.

FIELD OF THE INVENTION

The present invention relates to microfluidic fluidic devices, methods and systems as microfluidic kidney on-chips, e.g. human Proximal Tubule-Kidney-Chip, Glomerulus (Kidney)-Chip, Collecting Duct (Kidney)-Chip. Such devices, methods and systems may be used for drug testing by (for example) measuring changes in transporter biomarkers, e.g. gene and protein expression of transporter molecules and injury molecules, e.g. changes in acetylated tubulin, along with changes in functions such as for albumin uptake, glucose transport, creatinine transport, PAH Transport, drug transport, and renal clearance. Further, such devices, methods and systems may be used for determining drug-drug interactions and their effect upon renal transporter functions. Importantly, they may be used for pre-clinical and clinical drug development for treating kidney diseases and for personalized medicine.

BACKGROUND

The kidney plays a role in elimination of xenobiotics and endogenous compounds through its complicated and efficient uptake and efflux transporting systems. Thus, drug interactions with renal tubular transporters should be investigated systematically to increase our understanding of drug disposition and toxicity, and for predicting potential drug-drug interactions in human.

However, currently available cell-based models often fail to predict renal transporter activity and are not scalable to a predictive clinical outcome due to in vitro-in vivo discrepancy.

Therefore, new ways to assess renal transporter-based drug-drug interactions and tests for drug-associated kidney toxicities are needed.

SUMMARY OF THE INVENTION

The present invention relates to microfluidic fluidic devices, methods and systems as microfluidic kidney on-chips, e.g. human Proximal Tubule-Kidney-Chip, Glomerulus (Kidney)-Chip, Collecting Duct (Kidney)-Chip. Such devices, methods and systems may be used for drug testing by (for example) measuring changes in transporter biomarkers, e.g. gene and protein expression of transporter molecules and injury molecules, e.g. changes in acetylated tubulin, along with changes in functions such as for albumin uptake, glucose transport, creatinine transport, PAH Transport, drug transport, and renal clearance. Further, such devices, methods and systems may be used for determining drug-drug interactions and their effect upon renal transporter functions. Importantly, they may be used for pre-clinical and clinical drug development for treating kidney diseases and for personalized medicine.

In one embodiment, the present invention provides a microfluidic device, comprising a membrane (or other porous or semi-porous barrier), said membrane comprising a first surface and a second surface, said first surface comprising proximal tubule cells and said second surface comprising endothelial cells, and more preferably glomerular microvascular endothelial cells. In one embodiment, said proximal tubule cells are human primary proximal tubular epithelial cells. In one embodiment, said membrane contains pores (which allows for fluidic communication). In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. The microchannels can connect other components (such as reservoirs), i.e., keep components in communication and more particularly, in fluidic communication. The microchannels can be in fluidic communication with each other. In one embodiment, said human primary proximal tubular epithelial cells express tight junction protein ZO-1. In one embodiment, said human primary proximal tubular epithelial cells express beta-catenin. In one embodiment, said human primary proximal tubular epithelial cells express occludin. In one embodiment, said human primary proximal tubular epithelial cells express aquaporin 1 (AQP1). In one embodiment, said human primary proximal tubular epithelial cells express Na/K-ATPase. In one embodiment, said human primary proximal tubular epithelial cells comprise cilia. In one embodiment, said human primary proximal tubular epithelial cells comprise express one or more uptake and efflux transporters. In one embodiment, said endothelial cells express VE-Cadherin.

In one embodiment, the present invention provides a method of culturing, comprising: a) providing a microfluidic device comprising a membrane (or other porous or semi-porous barrier), said membrane comprising a first surface and a second surface, said first surface comprising proximal tubule cells and said second surface comprising endothelial cells, and more preferably glomerular microvascular endothelial cells; and b) culturing said cells under continuous flow of media, e.g. culture media. In one embodiment, said proximal tubule cells are human primary proximal tubular epithelial cells. In one embodiment, said membrane contains pores. In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. In one embodiment, said human primary proximal tubular epithelial cells express tight junction protein ZO-1. In one embodiment, said human primary proximal tubular epithelial cells express beta-catenin. In one embodiment, said human primary proximal tubular epithelial cells express occludin. In one embodiment, said human primary proximal tubular epithelial cells express aquaporin 1 (AQP1). In one embodiment, said human primary proximal tubular epithelial cells express Na/K-ATPase. In one embodiment, said human primary proximal tubular epithelial cells comprise cilia. In one embodiment, said human primary proximal tubular epithelial cells comprise express one or more uptake and efflux transporters. In one embodiment, said endothelial cells express VE-Cadherin.

The kidney is a vital organ for the elimination of therapeutic drugs and their metabolites. Renal drug transporters, which are primarily located in the renal proximal tubules, play a role in tubular secretion and reabsorption of drug molecules in the kidney. Tubular secretion is characterized by high clearance capacities, broad substrate specificities, and distinct charge selectivity for organic cations and anions. In one embodiment, the present invention contemplates using the microfluidic devices described herein to explore the roles of transporters in drug disposition, efficacy, toxicity and drug-drug interactions (DDIs). In the kidney, several transporters are involved in renal handling of organic cation (OC) and organic anion (OA) drugs. These transporters are increasingly recognized as the target for clinically significant DDIs.

In one embodiment, the present invention provides a method of measuring transport, comprising: a) providing a microfluidic device comprising a membrane (or other porous or semi-porous barrier), said membrane comprising a first surface and a second surface, said first surface comprising proximal tubule cells and said second surface comprising endothelial cells, and more preferably glomerular microvascular endothelial cells; b) culturing said cells under continuous flow of media; c) introducing an agent; and d) detecting transport of said agent. In one embodiment, said transport detected in step d) comprises transcellular transport. In one embodiment, said proximal tubule cells are human primary proximal tubular epithelial cells. In one embodiment, said membrane contains pores. In one embodiment, said human primary proximal tubular epithelial cells are attached to the top of said membrane and said glomerular microvascular endothelial cells are attached to the opposite side of the same membrane. In one embodiment, said first surface of said membrane is part of a first microfluidic channel and said second surface of said membrane is part of a second microfluidic channel. In one embodiment, said transport detected in step d) comprises transporter-mediated secretion from the second channel to the first channel. In one embodiment, said agent is a drug or drug candidate.

In one embodiment, the present invention provides a method of measuring toxicity, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; b) culturing said cells under continuous flow of media; c) introducing an agent; and d) detecting toxicity of said agent. In one embodiment, said detecting comprises measuring release of a compound from said cells. In one embodiment, said compound comprises Lactate dehydrogenase (LDH). In one embodiment, said agent is a drug or drug candidate.

In one embodiment, the present invention provides a method of measuring clearance, comprising: a) providing a microfluidic device comprising a membrane (or other porous or semi-porous barrier), said membrane comprising a first surface and a second surface, said first surface comprising proximal tubule cells and said second surface comprising glomerular microvascular endothelial cells; b) culturing said cells under continuous flow of media; c) introducing an agent; and d) detecting clearance of said agent. In one embodiment, said agent is a drug or candidate drug.

In one embodiment, the present invention provides a method of measuring active transport, comprising: a) providing a microfluidic device comprising a membrane, said membrane comprising a first surface and a second surface, said first surface comprising proximal tubule cells and said second surface comprising glomerular microvascular endothelial cells, wherein said first surface of said membrane is part of a first microfluidic channel and said second surface of said membrane is part of a second microfluidic channel; b) culturing said cells under a flow (preferably a continuous flow) of media; c) introducing an agent; and d) detecting active transport of said agent in said microfluidic device wherein (in a comparison) transwells failed to predict active transport of said agent. In one embodiment, proximal tubule cells are human primary proximal tubular epithelial cells. In one embodiment, said membrane contains pores. In one embodiment, said active transport detected in step d) comprises transporter-mediated secretion from said first channel to said second channel. In one embodiment, active transport in said microfluidic device is detected by an efflux ratio greater than 2. In one embodiment, the agent is a drug. In one embodiment, the drug is metformin.

In yet another embodiment, the present invention provides a method of measuring active transport, comprising: a) providing a microfluidic device comprising a membrane, said membrane comprising a first surface and a second surface, said first surface comprising proximal tubule cells and said second surface comprising glomerular microvascular endothelial cells, wherein said first surface of said membrane is part of a first microfluidic channel and said second surface of said membrane is part of a second microfluidic channel; b) culturing said cells under a fow (preferably a continuous flow) of media; c) introducing an agent; and d) detecting active transport of said agent in said microfluidic device wherein (in a comparison) there is no detectable active transport of said agent in transwells. In one embodiment, proximal tubule cells are human primary proximal tubular epithelial cells. In one embodiment, said membrane contains pores. In one embodiment, said active transport detected in step d) comprises transporter-mediated secretion from said first channel to said second channel. In one embodiment, active transport in said microfluidic device is detected by an efflux ratio greater than 2. In one embodiment, the agent is a drug. In one embodiment, the drug is metformin.

In still another embodiment, the present invention provides a method of measuring clearance, comprising: a) providing a microfluidic device comprising a membrane, said membrane comprising a first surface and a second surface, said first surface comprising proximal tubule cells and said second surface comprising glomerular microvascular endothelial cells; b) culturing said cells under flow (preferably under a continuous flow) of media; c) introducing an agent; and d) detecting clearance of said agent in said microfluidic device that predicts a clearance value that is at least 60% of the actual (in vivo) clinical clearance value for said agent. In one embodiment, proximal tubule cells are human primary proximal tubular epithelial cells. In one embodiment, said membrane contains pores. In one embodiment, the agent is a drug. In one embodiment, the drug is metformin. In one embodiment, said microfluidic device predicts a clearance value that is at least 70% of the actual clinical clearance value for said agent. In one embodiment, said microfluidic device predicts a clearance value that is at least 80% of the actual clinical clearance value for said agent.

BRIEF DESCRIPTION OF THE DRAWINGS

Exemplary embodiments are illustrated in referenced figures. It is intended that the embodiments and figures disclosed herein are to be considered illustrative rather than restrictive.

The file of this patent contains at least one drawing executed in color. Copies of this patent with color drawings will be provided by the Patent and Trademark Office upon request and payment of the necessary fee.

FIG. 3A lower middle image shows one exemplary schematic of a human Proximal Tubule-Chip 200 engineered using an S-1 Chip from Emulate, Inc., which is made of polydimethylsiloxane (PDMS) and contains an upper channel (1 mm high×1 mm wide) and a lower channel (0.2 mm high×1 mm wide), separated by a porous PDMS membrane that is coated with optimized extracellular matrix (ECM). The upper channel serves as a tubular lumen and is lined in one embodiment by primary human epithelial cells seeded on the ECM coated membrane. The lower channel, lined with endothelial cells, represents the peritubular vasculature.

FIG. 3A further illustrates, upper left, a human kidney, including a cortex area comprising a proximal convoluted tubule, Bownan's capsule, glomuerulus, distal convoluted tubule and medulla comprising a Loop of Henie, and collecting tubules. Jang and Suh, Lab Chip 10, 36 (2010). Front cover; Jang, et al., Integrative Biology. 3, 134 (2011); Jang, et al., Integrative Biology, 5, 1119 (2013) Front cover. The illustration in the upper right shows exemplary extracellular components found in each of the regions. Right schematic showing types of ECM in regions of the Kidney, Kidney International (1999) 56, 2016-2024. K.-J. Jang and K. Y. Suh, Lab Chip 10, 36 (2010). The illustrations shown in the lower row show one embodiment of a Kidney (left) as a Human Proximal Tubule-Chip (middle) model (right) comprising primary proximal tubular epithelial cells (upper channel-green), a membrane (white) separating renal microvascular endothelial cells (lower channel-red). Blue arrow (upper) and red arrow (lower) shows directional fluid flow.

FIG. 3B shows an exemplary schematic of a fluidic chip (device) as in FIG. 3A, left, aligned with a schematic of cellular compartments (right). An exemplary layer of Proximal Tubular Epithelial Cells (above—green or gold) and Endothelial Cells (below—red or blue) separated by a membrane (grey). Examples of in vivo kidney cell functions contemplated for use in readouts of kidney activity in vitro, comprising measuring expression of or levels of albumin transport, glucose transport, Na+ transport, Megalin, Cubuin, SGLT1/2 on the apical side, while OCT2 and creatinine transport on the endothelial cell layer side, for non-limiting examples.

FIG. 3C shows an exemplary schematic of a fluidic chip. Polydimethylsiloxane (PDMS) (top of chip) 400. Arrow shows directional fluid flow over the top of the parenchymal cells (green), e.g. kidney cells, attached to a membrane (dotted lines) with endothelial cells depicted in red. Dye may be perfused through the fluid flowing through the bottom channel lined with endothelial cells over the bottom of the chip (PDMS).

FIG. 3D shows exemplary embodiments of a kidney-on-a-chip in which human kidney proximal tubular epithelial cells are cultured on the top of a porous membrane separating two channels, enabling analysis of transcellular transport, uptake and secretion (top-schematic). The upper fluorescence image of the epithelium shows enhanced formation of primary cilia (green) on the apical cell surfaces (cell nuclei stained and colored blue); the lower fluorescence cross-sectional view shows repolarization of Na+K+ATPase (magenta) to the basal side of the cells while green cilia are shown on the apical side of the kidney epithelial cells. FIG. 3D was published previously in Jang and Suh, Lab Chip 10, 36 (2010).

FIG. 4A shows exemplary microscopic images demonstrating a defined and orderly expression of the epithelial tight junction protein ZO-1 (upper right, green) and the endothelial adherent protein VE-Cadherin (lower right, green). Nuclei staining is colored blue.

FIG. 4B shows exemplary microscopic images of proximal tubule cells demonstrating polarized proximal tubular epithelial cells expressing specific biomarkers known to be abundant along the in vivo human proximal tubule, including in the upper channel: beta-catenin (red), aquaporin 1 (AQP1) (green), and representative cilia (green), (the cilia staining was published in Jang, 2013), and Na/K-ATPase (pink), with scanning electron microscope (SEM) images showing cilia and a brush border, see lower right panel, labeled arrows. In the lower channel, occludin (green). Cell source: Lonza; Chip type: S1 Tall Channel; Flow: 30 μL/hr culture module. Blue stained nuclei.

FIG. 9A shows exemplary phase contract microscopic analysis of the proximal tubular epithelium (control-left panel: treated-right panel). Lower panels show lower power images of corresponding Gentamicin treatments (control-left panel: treated with Gentamicin-right panel). (Lonza cells; S1; Flow: 60 µL/hr provided by a culture module).

FIG. 9B shows exemplary Gentamicin-Induced Toxicity by LDH release in medium effluent (% control) that revealed significant cell damage after 10 mM of Gentamicin treatment for 48 hours. (*** p<0.001). Cell source: Lonza. Flow: 30 µL/hr with a culture module.

From top panel to the bottom panel: Tall channel device with a flow rate of 30 µl/hr; Tall channel device with a flow rate of 150 µl/hr; High Shear channel device with a flow rate of 30 µl/hr; and a High Shear channel device with a flow rate of 150 µl/hr.

Figure 19:
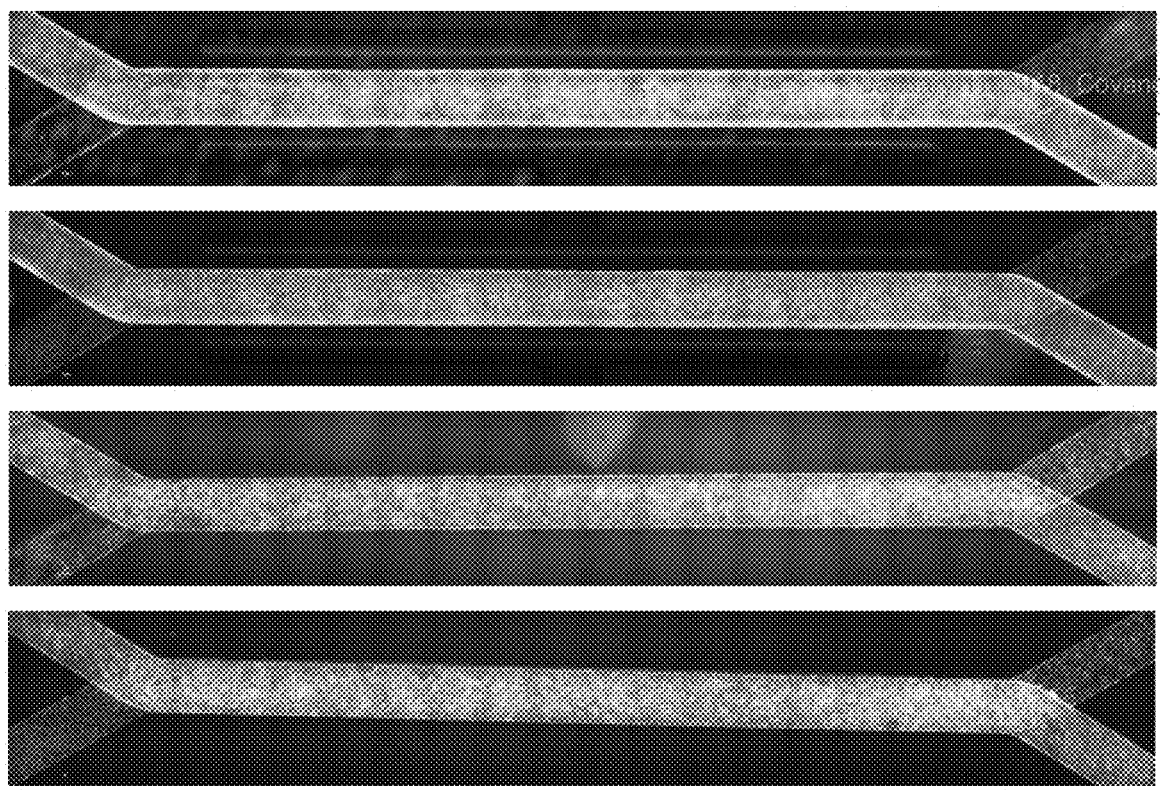

FIG. 19 shows exemplary results showing differences in transporter molecule expression between two exemplary microfluidic devices and two different flow rates. Upper panels show immunostaining results of the top channel stained for MRP2 (red); OAT1 (green) nuclear material stained with DAPI, colored blue; Phalloidin visualized using Cy5, colored light blue. Bottom channel stained for VE-Cadherin (green); nuclear material stained with DAPI, colored blue.; and Phalloidin visualized using Cy5, colored light blue.

Figure 20:
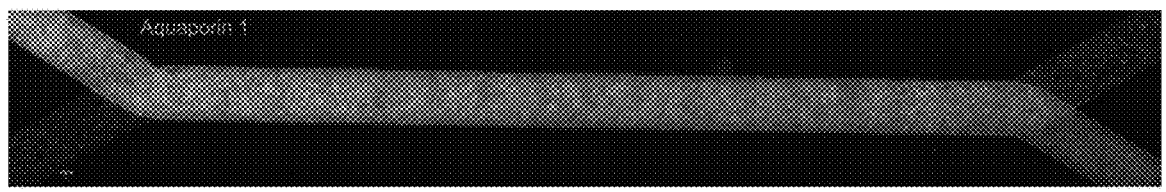
Figure 20:
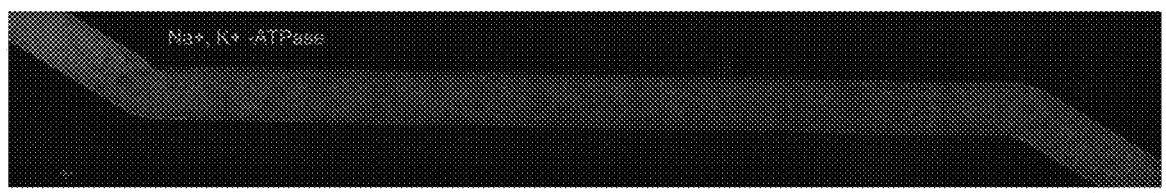

FIG. 20 shows exemplary results IHC (immunohistochemistry)-Data: High shear chip device with high flow, stain 1. Aquaporin 1 (green); Na+, K+-ATPase (red).

Figure 21:
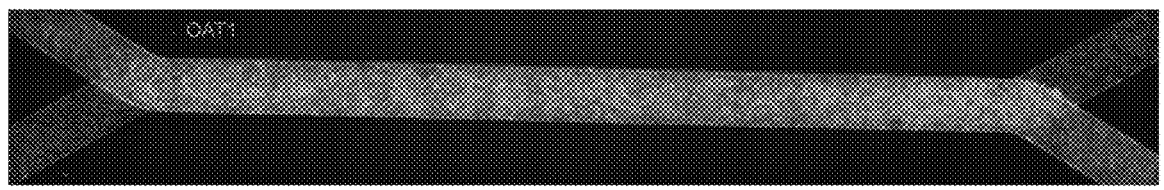
Figure 21:
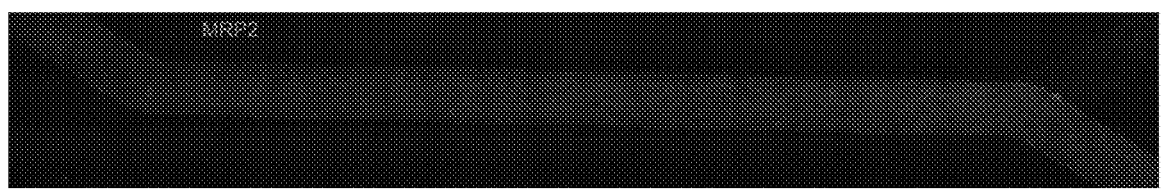

FIG. 21 shows exemplary results IHC-Data: High shear chip device with high flow, stain 2. OAT1 (green); MRP2 (red).

Figure 22:
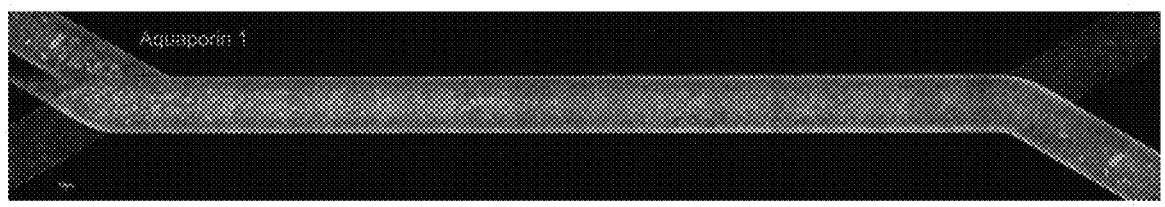
Figure 22:
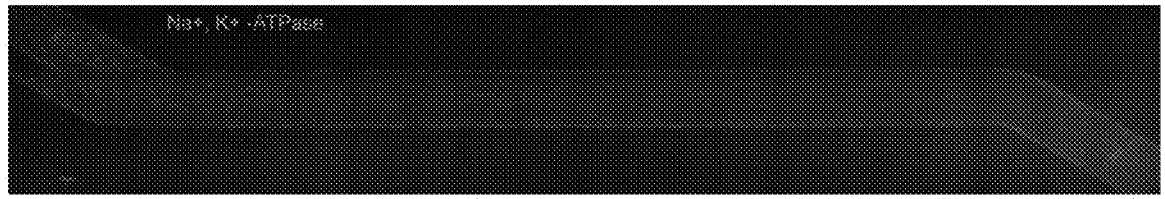

FIG. 22 shows exemplary results IHC-Data: High shear chip device with low flow, stain 1. Aquaporin 1 (green); Na+, K+-ATPase (red).

Figure 23:
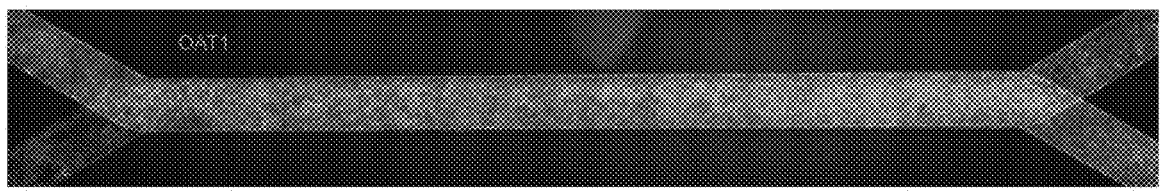
Figure 23:
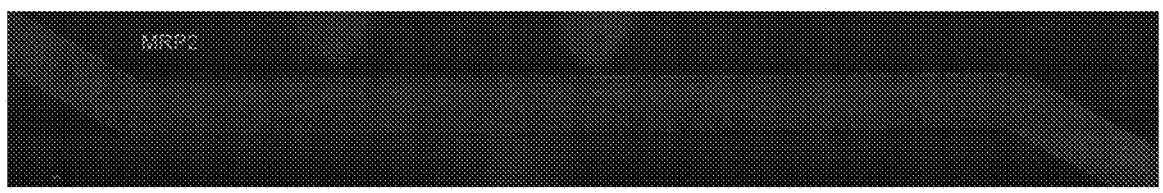

FIG. 23 shows exemplary results IHC-Data: High shear chip device with low flow, stain 2. OAT1 (green); MRP2 (red).

Figure 24:
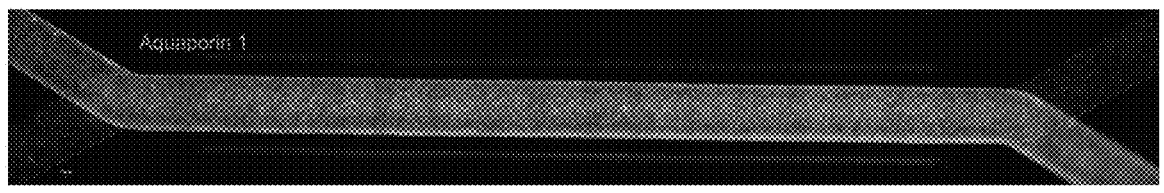
Figure 24:
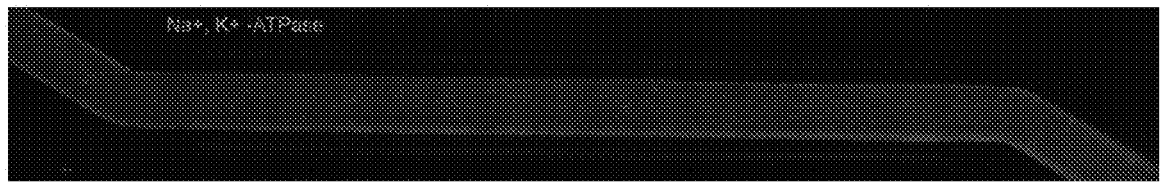

FIG. 24 shows exemplary results IHC-Data: Tall channel chip device with high flow, stain 1. Aquaporin 1 (green); Na+, K+-ATPase (red).

Figure 25:
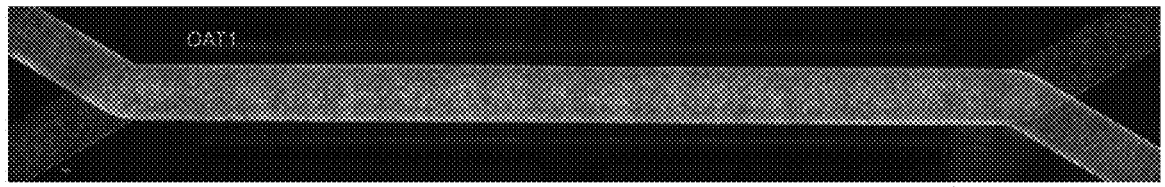
Figure 25:
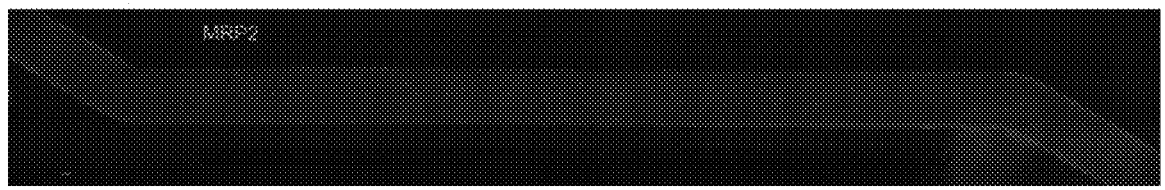

FIG. 25 shows exemplary results IHC-Data: Tall channel chip device with high flow, stain 2. OAT1 (green); MRP2 (red).

Figure 26:
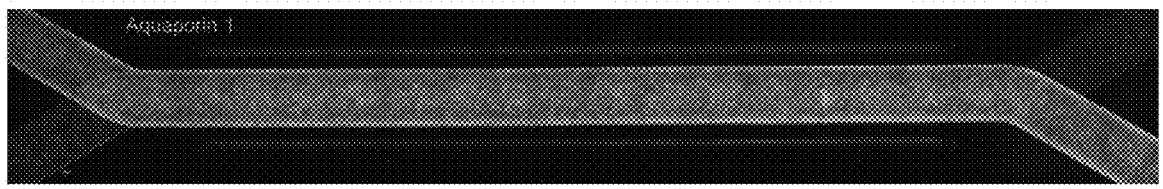
Figure 26:

FIG. 26 shows exemplary results IHC-Data: Tall channel chip device with low flow, stain 1. Aquaporin 1 (green); Na+, K+-ATPase (red).

Figure 27:
Figure 27:
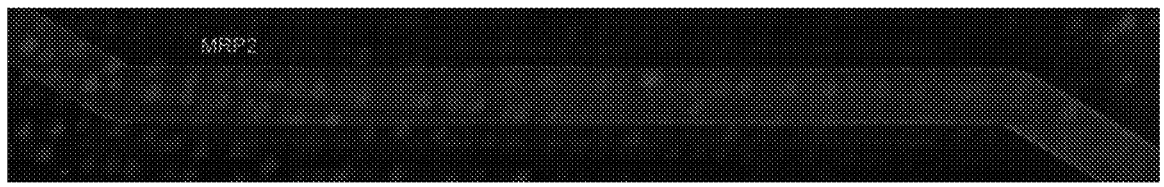

FIG. 27 shows exemplary results IHC-Data: Tall channel chip device with low flow, stain 2. OAT1 (green); MRP2 (red).

Figure 28:
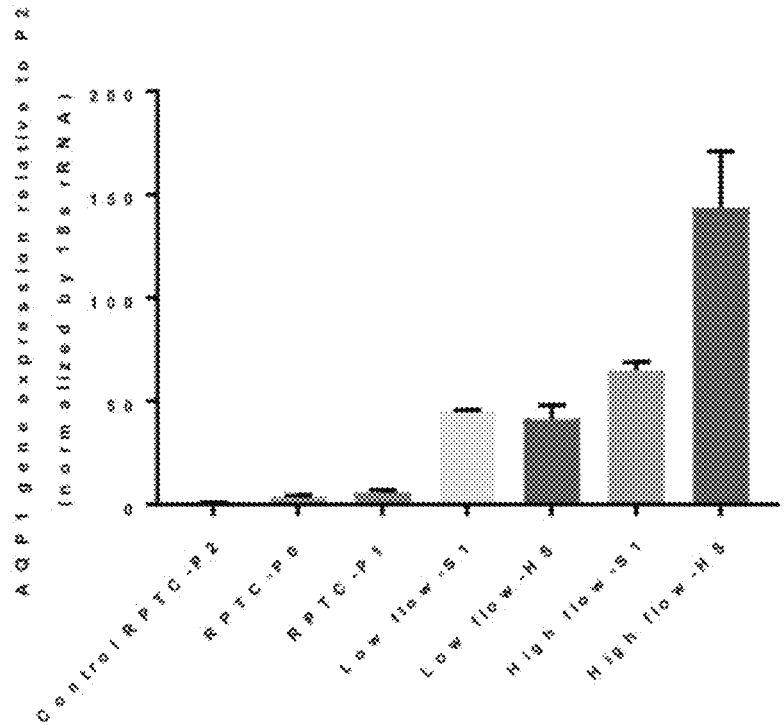
Figure 28:
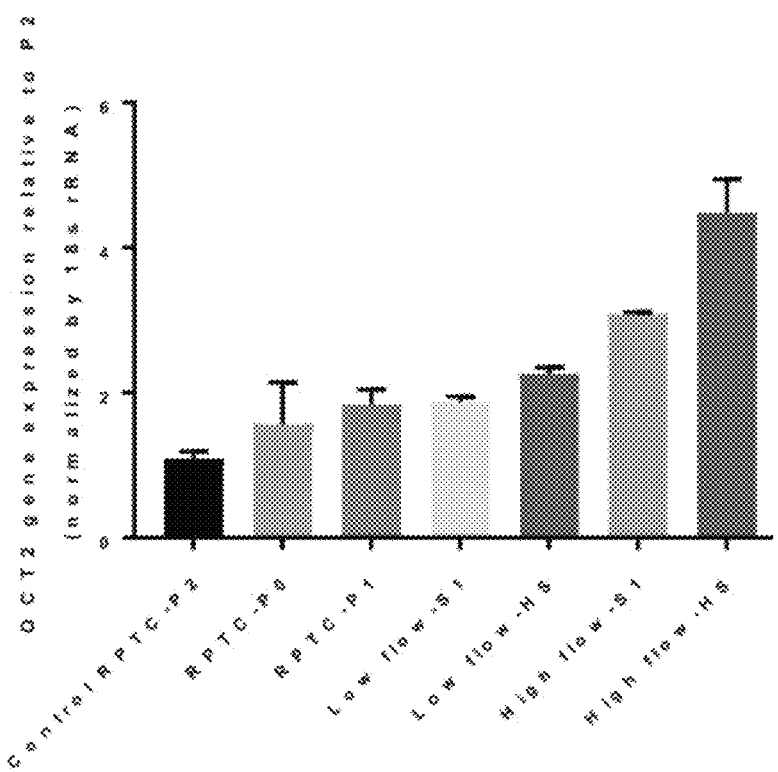

FIG. 28 shows an exemplary quantification AQP1 (upper) and OCT2 (lower) Gene Expression relative to Primary Renal Proximal Tubule Epithelial Cells; Normal, Human (RPTC) P2 cells (used as a control) (normalize by 18S rRNA). RPTC cells in different chip configurations, under low or high flow.

Figure 29A:
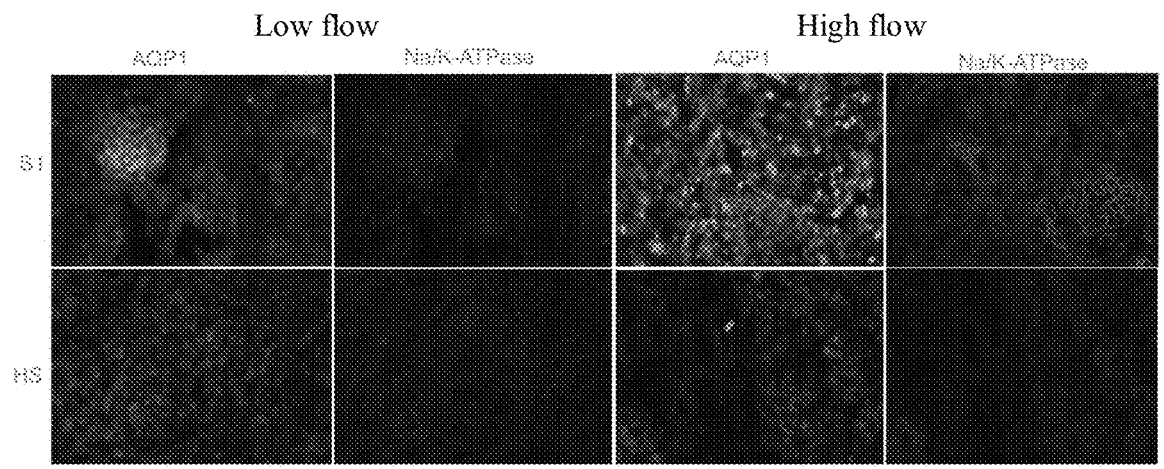

FIG. 29A shows exemplary polarization and cuboidal morphology of Renal Proximal Epithelial Cells co-cultured in one embodiment of a PT-Kidney Cell Chip. Immunostaining of. Aquaporin 1 (green)/Na/K-ATPase (red). Left panels: Low flow; right panels: High flow. S1 upper row. HS lower row. AQP1 and Na/K-ATPase expression in S1 chip under high flow condition showed increased expression than the cells from HS chip.

Figure 29B:
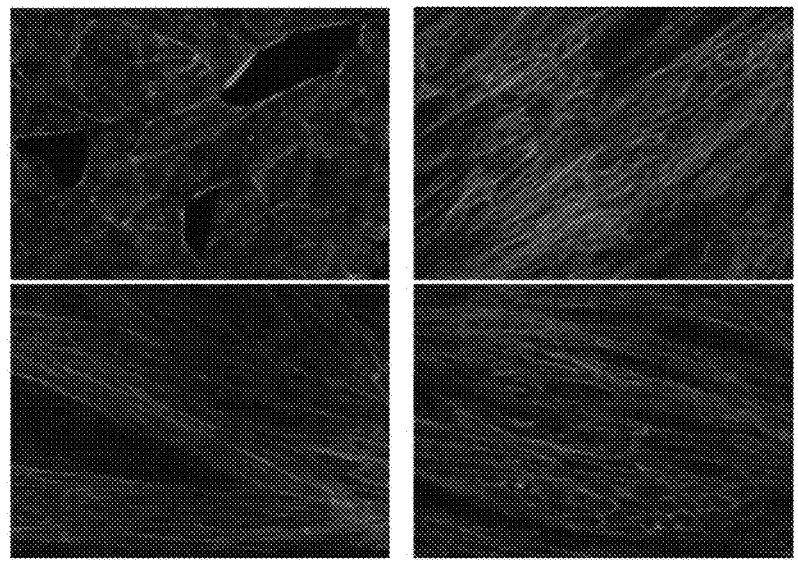

FIG. 29B shows exemplary Immunostaining of Kidney Microvascular Endothelial Cells. Glomerular Endothelial Cells (F-actin (pink)/Nuclei (blue)). Cells under high shear stress showed elongated morphology compared to the cells from low shear stress.

Figure 30A:
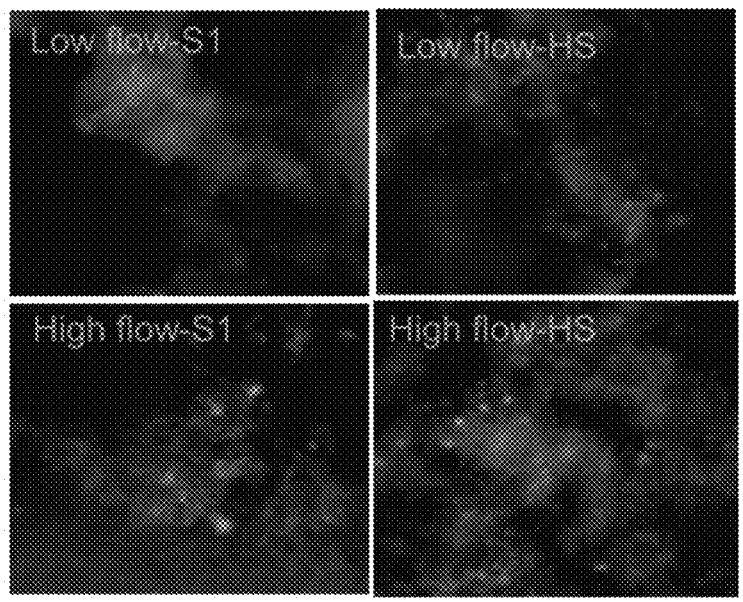
Figure 30B:
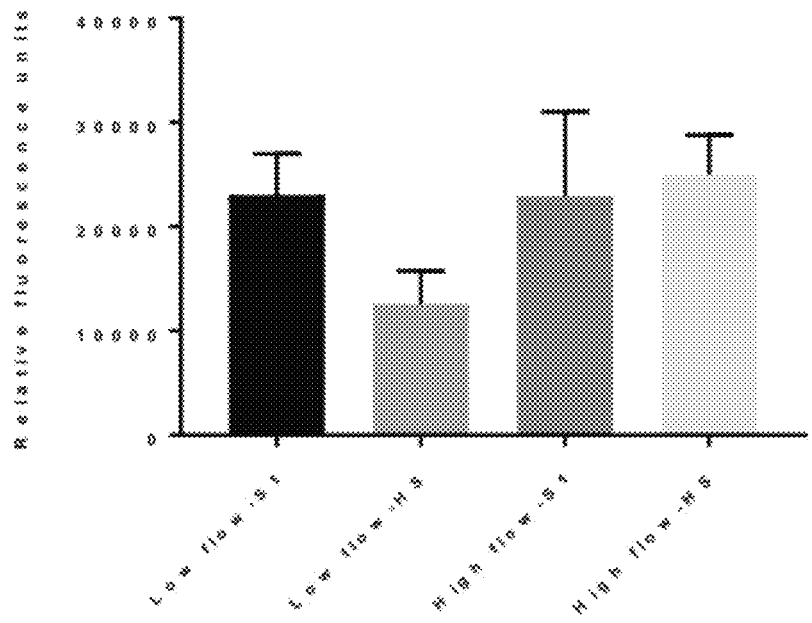

FIG. 30A shows an exemplary quantitative analysis for albumin uptake showing a trend towards higher albumin uptake under higher flow chip conditions with an ECM2 coating. FIG. 30A shows immunofluorescent micrographs. FIG. 30B is a chart showing relative fluorescence units of albumin uptake between different embodiments of PT Kidney chips (normalized by control).

Figure 31:
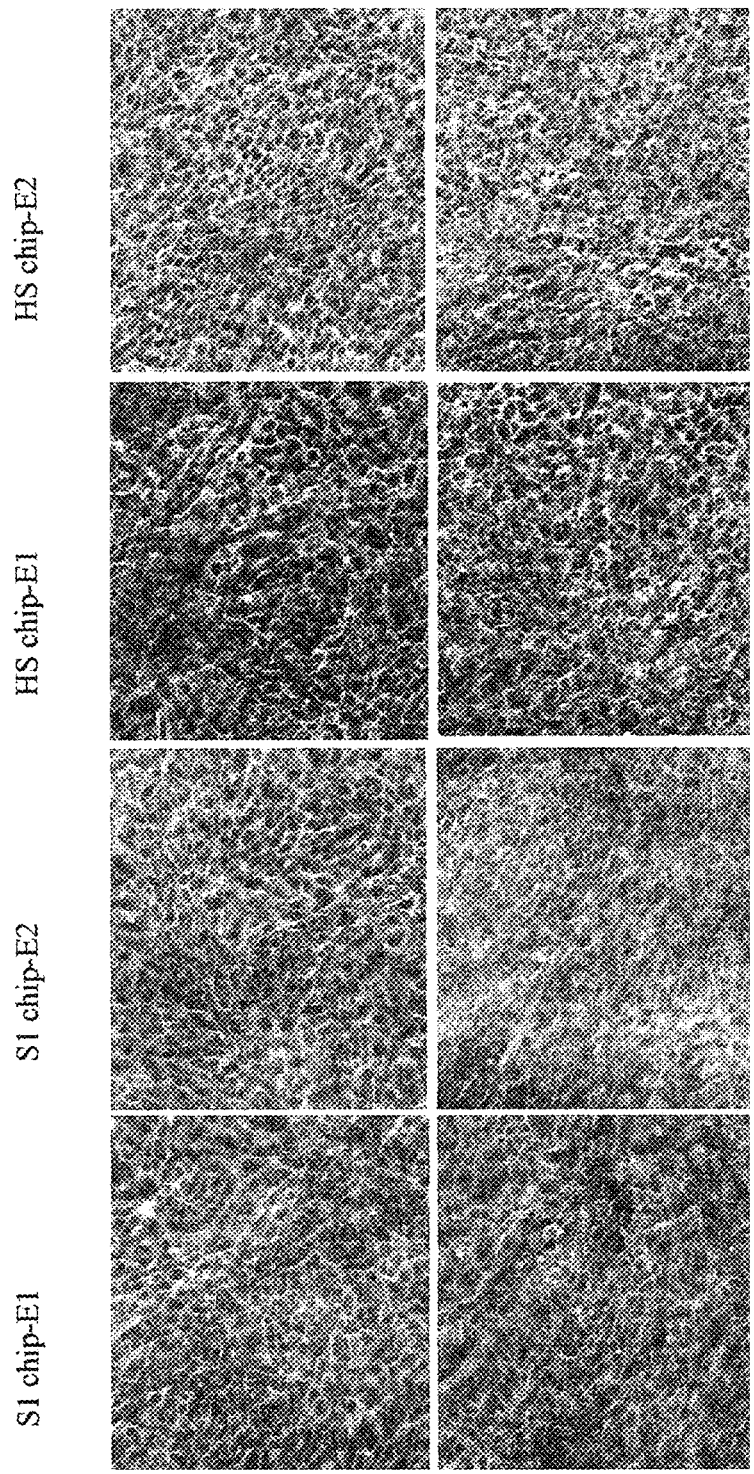

FIG. 31 shows micrographs demonstrating an exemplary uniform monolayer and cuboidal morphology at Day 8 of PT Kidney cells co-cultured in microfluidic chips. From left to right, S1 chip-ECM1; S1 chip-ECM2; HS chip-ECM1; HS chip-ECM2. Upper row shows results using low shear (30 μL/h). Lower row shows results using high shear (150 μL/h). Lonza cells.

Figure 32:
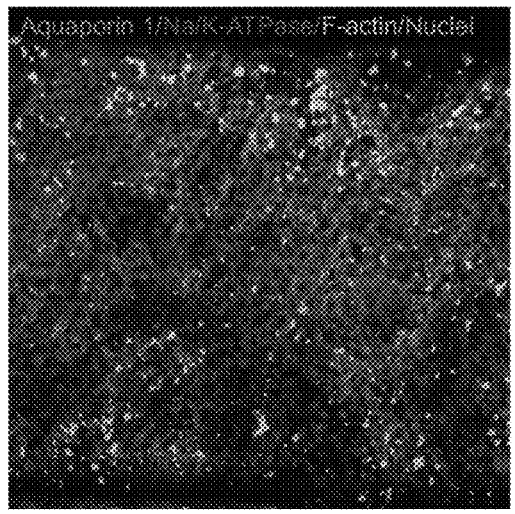
Figure 32:
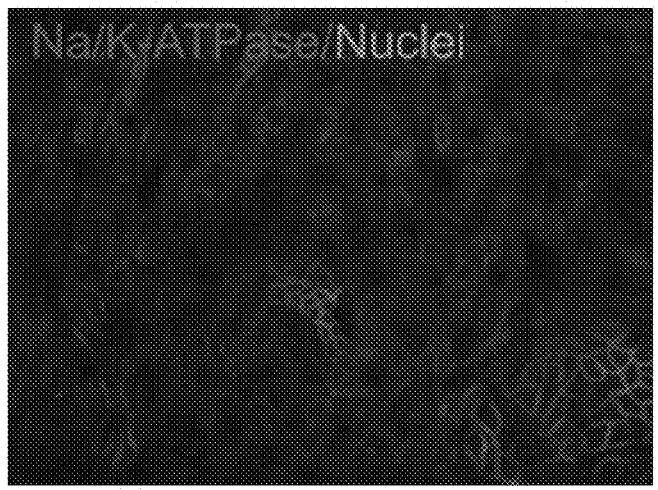
Figure 32:
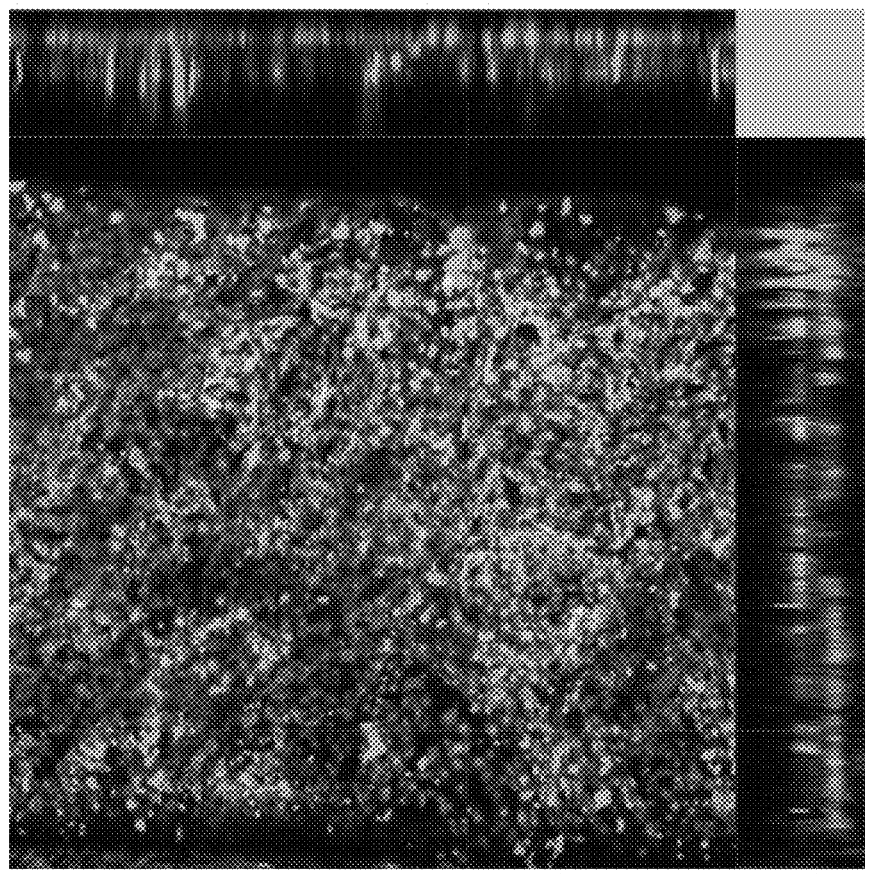

FIG. 32 shows immunofluorescent micrographs demonstrating exemplary polarization of PT cells. HF-SL-ECM2. Upper left image shows Aquaporin 1 (green), Na/K-ATPase (red), F-actin (pink) and Nuclei in blue. Upper left image shows Na/K-ATPase (red) and Nuclei in blue. Lower image shows Z-section images along the top and right side, where the apical region is at the top or far right showing the majority of Aquaporin 1 (green) while the majority of Na/K-ATPase (red) is in the basolateral region below the apical region. Lonza cells.

Figure 33:
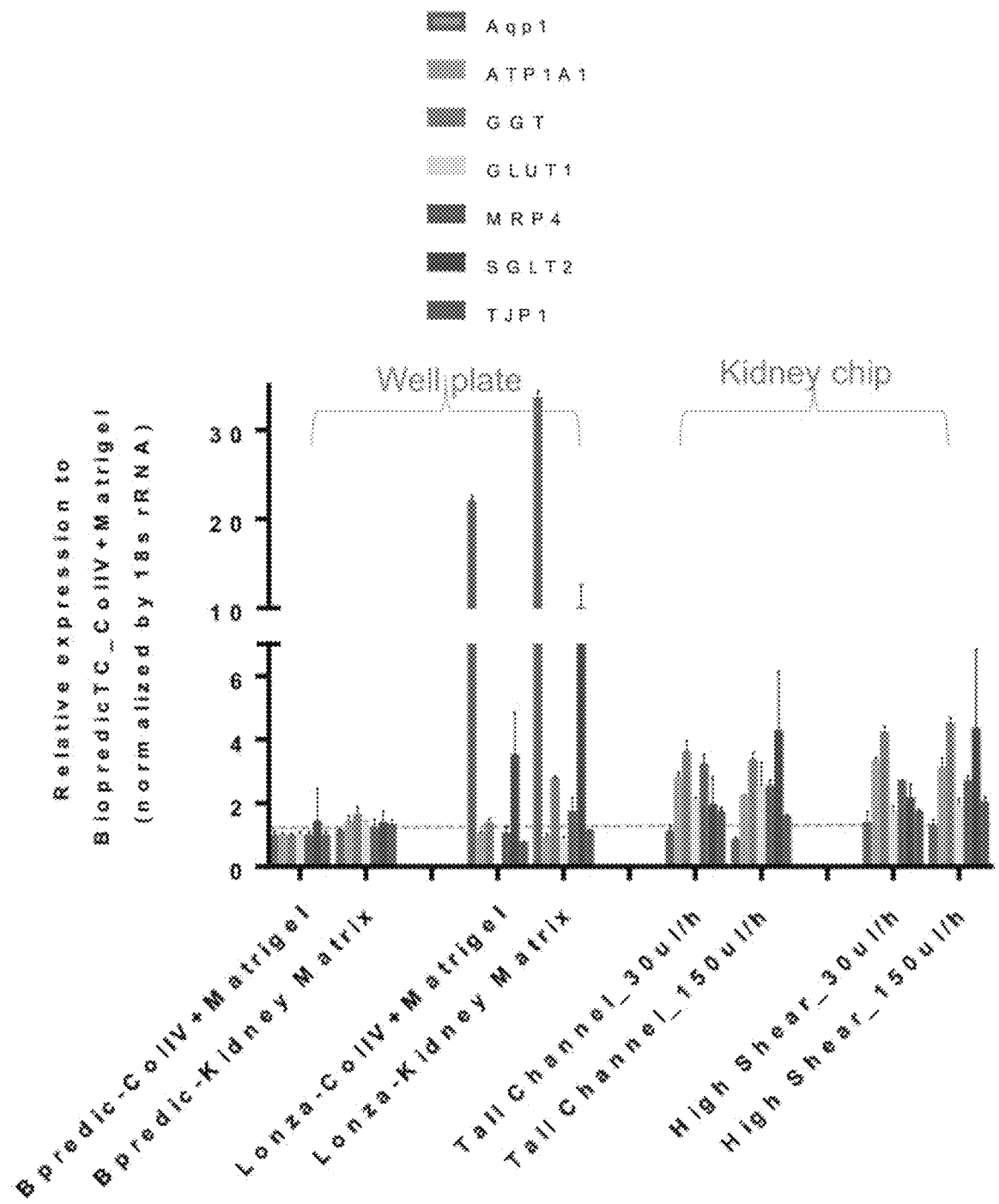

FIG. 33 shows exemplary Gene Expression: Well Plate versus Kidney Chip. These exemplary results further show a comparison of Lonza PT cells vs. Biopredic PT cells cultured in well plates vs. two different embodiments of microfluidic devices as described herein. PT cells were cultured in embodiments of tall channel (S1) microfluidic devices vs. high shear (HS) microfluidic devices, each under low vs. high flow rates. Additionally, ECM comparison results are shown between Matrigel and a commercial Kidney Matrix, as described herein. Expression was evaluated as a relative expression to Biopredic TC_ColIV+ Matrigel (normalized by 18 s rRNA).

Figure 34:
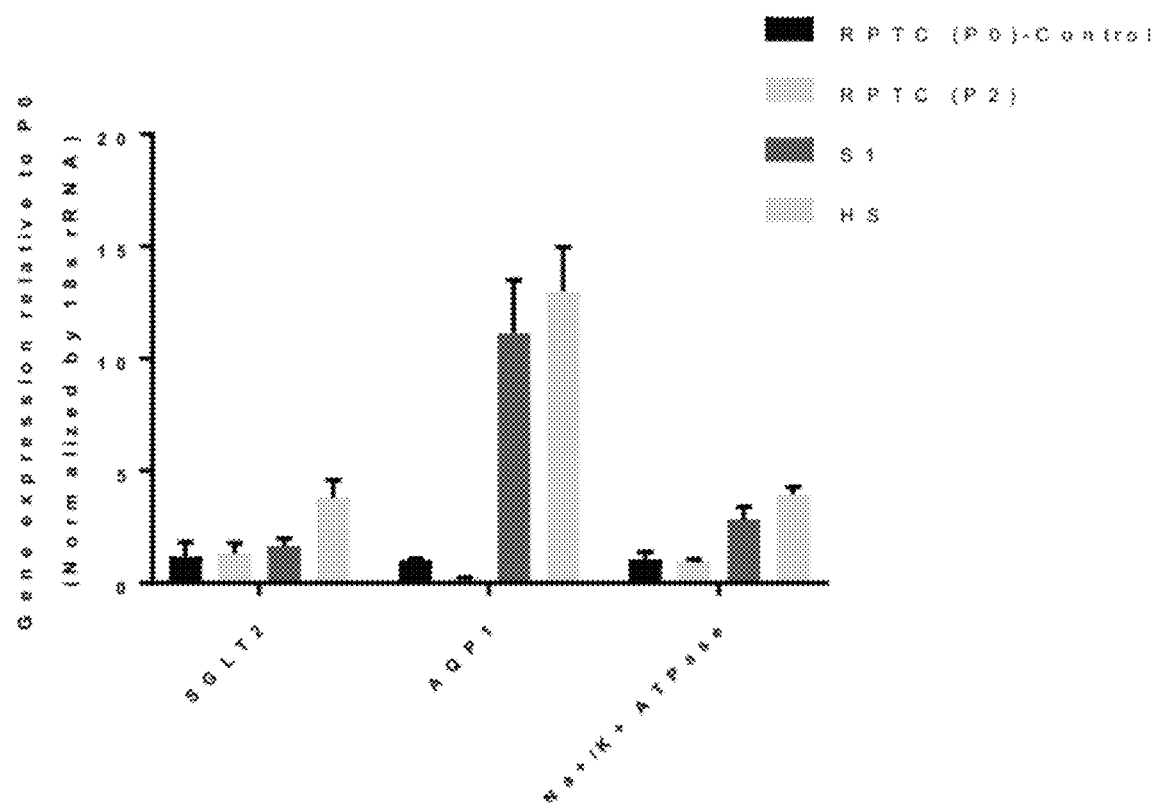

FIG. 34 shows exemplary Gene Expression: Well Plate versus Kidney Chip using ECM2 coated membranes and Human Renal PT cells (RPTC) from Lonza. P2 proximal tubule cells were typically used in Kidney-Chips. RPTC (P0)-Control; RPTC (P2); RPTC (P2) seeded into an S1 PT-Kidney Chip; RPTC (P2) seeded into an HS PT-Kidney Chip. Stable SGLT2 expression in RPTC P0, P2 and kidney chip. AQP1 and Sodium/potassium ATPase expression were increased in kidney chip.

Figure 35A:
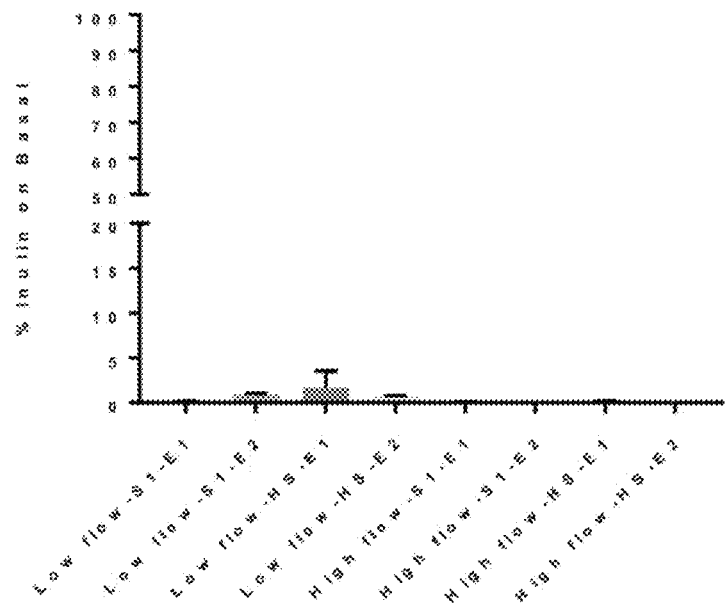
Figure 35B:
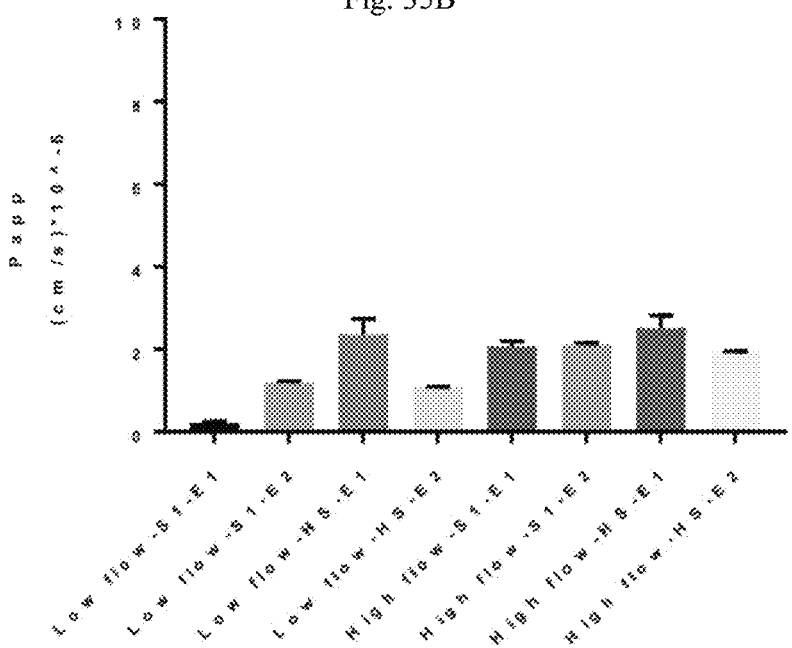

FIG. 35A demonstrates that no significant inulin leakage was measured and apparent permeability was similar, FIG. 35B, compared between the embodiments/conditions tested using a PT Kidney-Chip indicating the presence of a tight barrier function. % Inulin leakage into the basal channel on the Y-axis, test conditions shown on the X-axis. S1 chip-LF-ECM1; S1 chip-LF-ECM2; S1 chip-HF-ECM1; S1 chip-HF-ECM2; HS chip-LF-ECM1; HS chip-LF-ECM2; HS chip-HF-ECM1; HS chip-HF-ECM2. Lonza cells.

Figure 36:
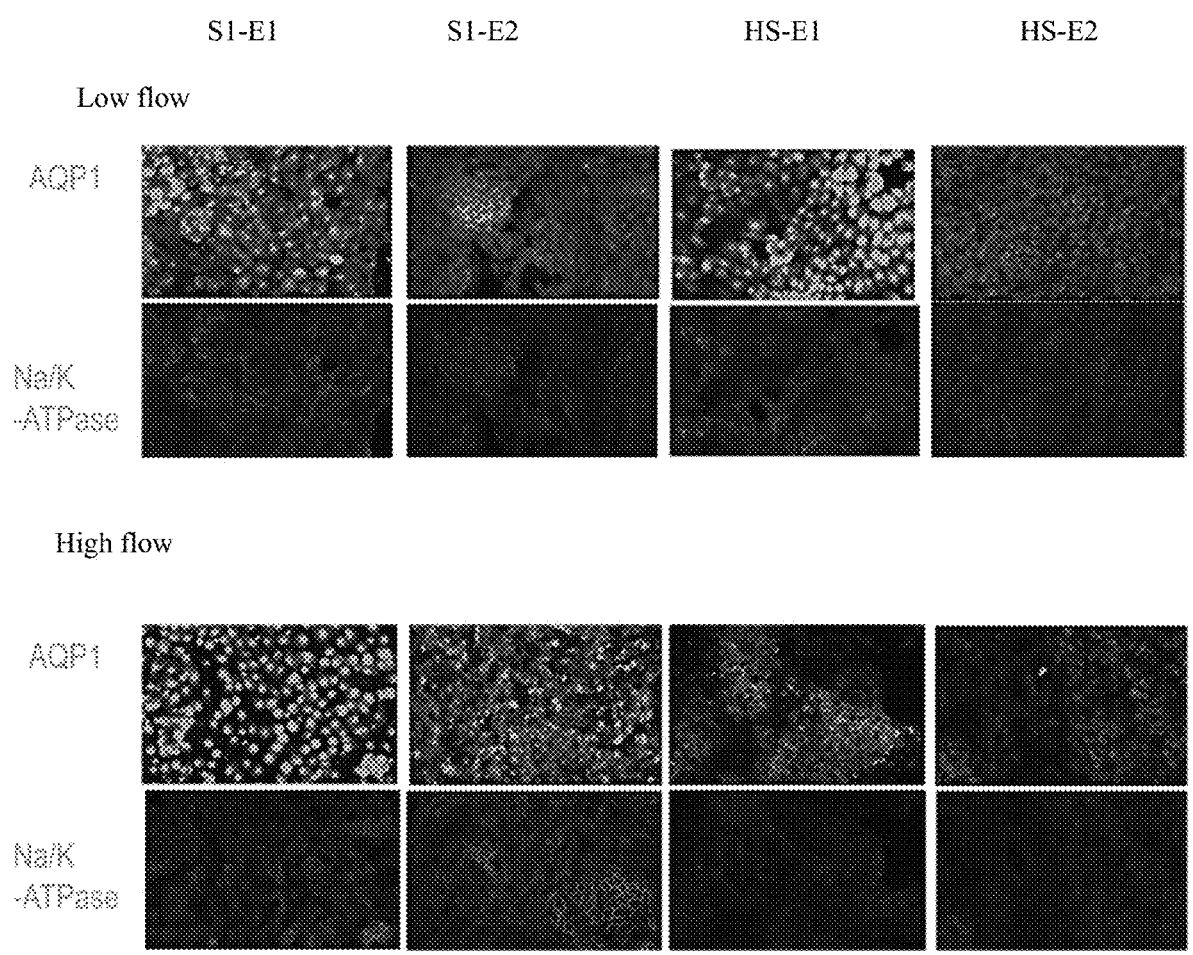

FIG. 36 shows exemplary polarization of human Renal Proximal Epithelial Cells co-cultured in different embodiments of a PT Kidney chip. From left to right: S1-E1; S1-E2; HS-E1; HS-E2. Low flow upper panels. High-flow lower panels. Aquaporin 1—green. Na/K-ATPase —red.

Figure 37:
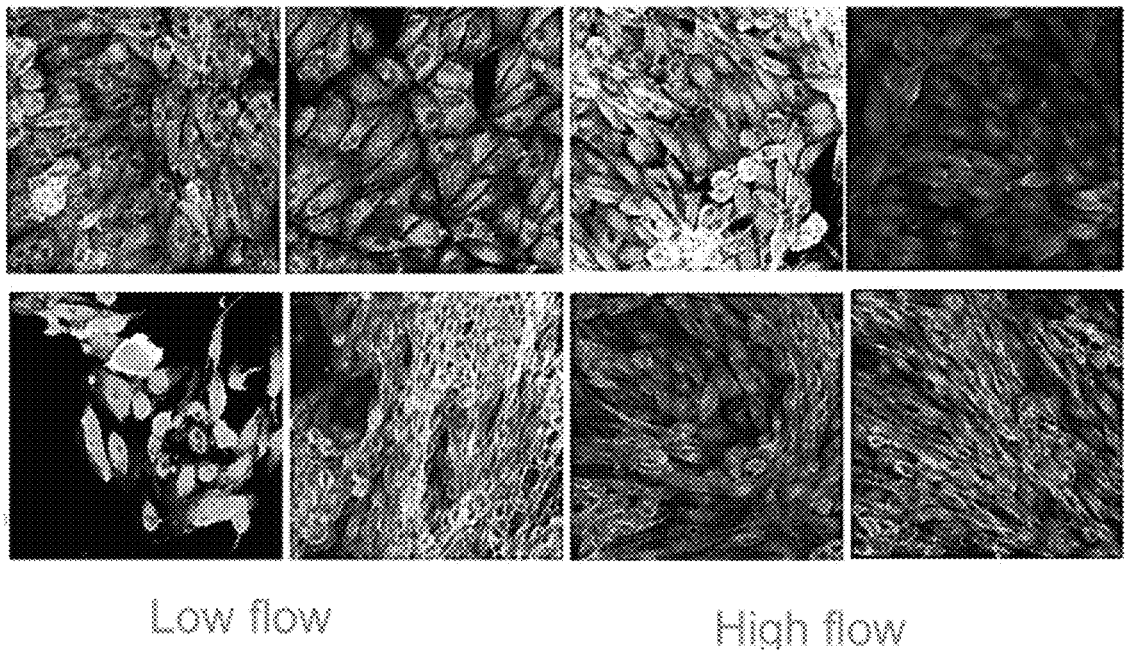

FIG. 37 shows exemplary Immunostaining of Kidney Microvascular Endothelial Cells. Glomerular Endothelial Cells (VE-Cadherin (green)/F-actin (pink)/Nuclei (blue)). From left to right: S1-E1; S1-E2; HS-E1; HS-E2. Low flow left, high flow right.

Figure 38:
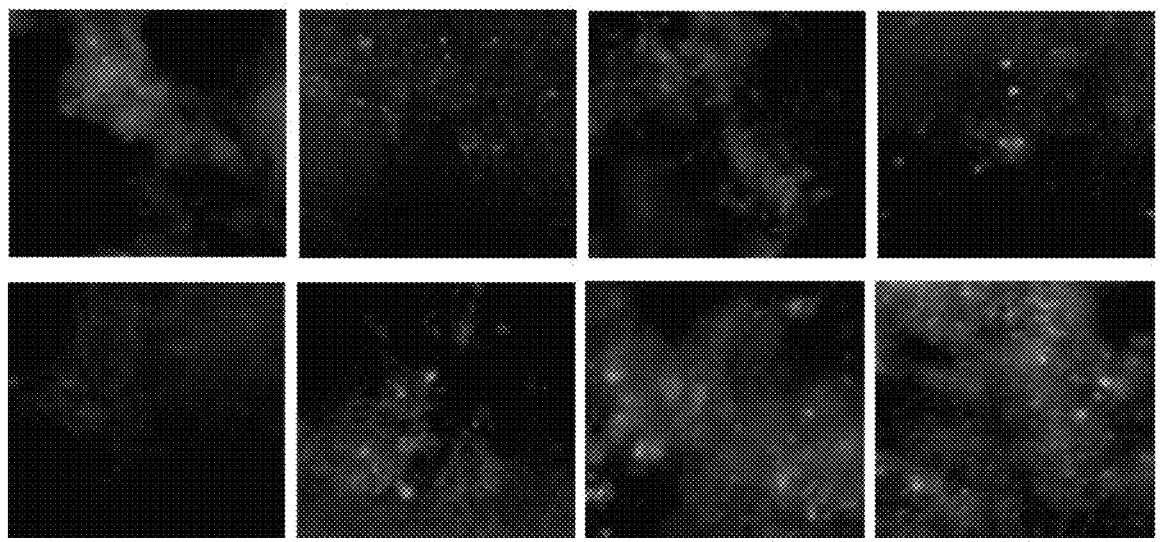
Figure 38:
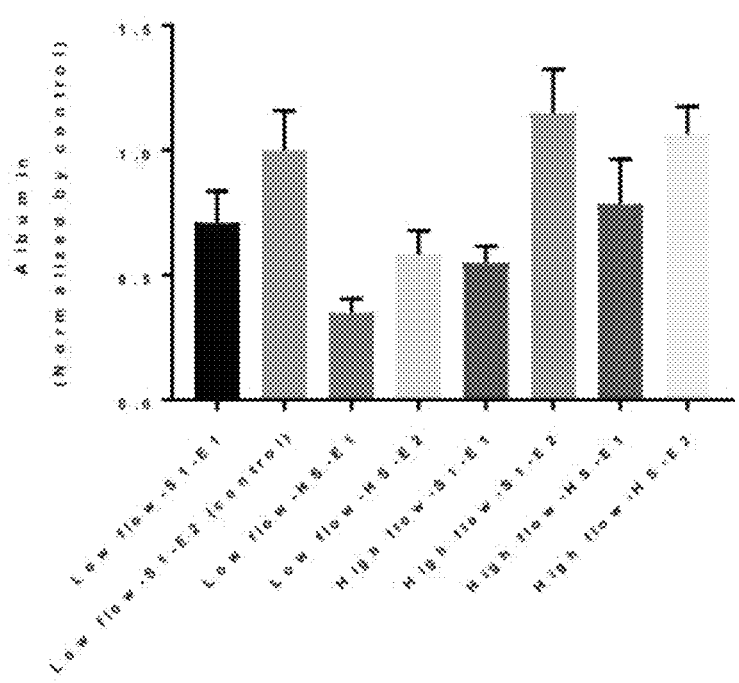

FIG. 38 demonstrates exemplary higher albumin uptake in HS chips with high shear (high flow) by florescence microscopy. From left to right, S1 chip-ECM1; S1 chip-ECM2; HS chip-ECM1; HS chip-ECM. Upper row shows results using low flow (30 μL/h). Lower row shows results using high flow (150 μL/h). Lonza cells.

Figure 39:
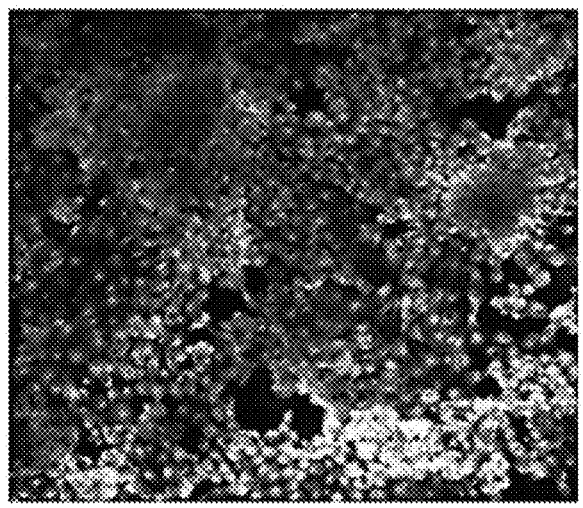
Figure 39:
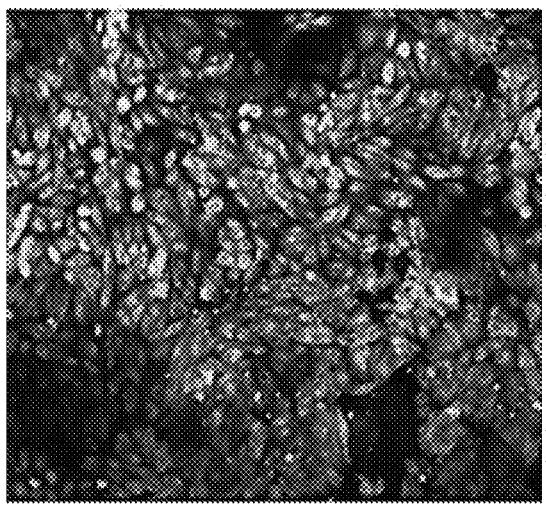
Figure 39:
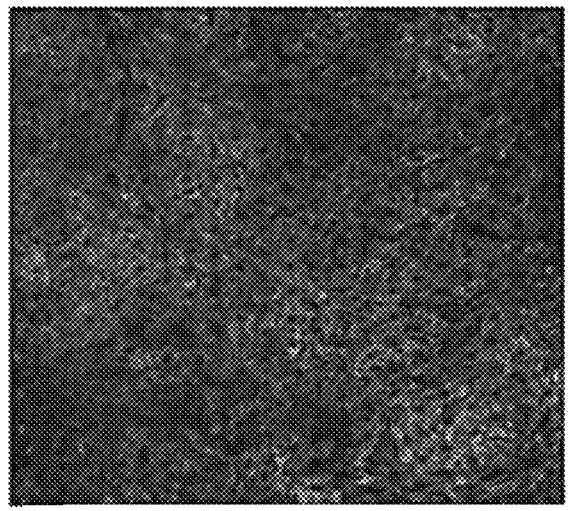
Figure 39:
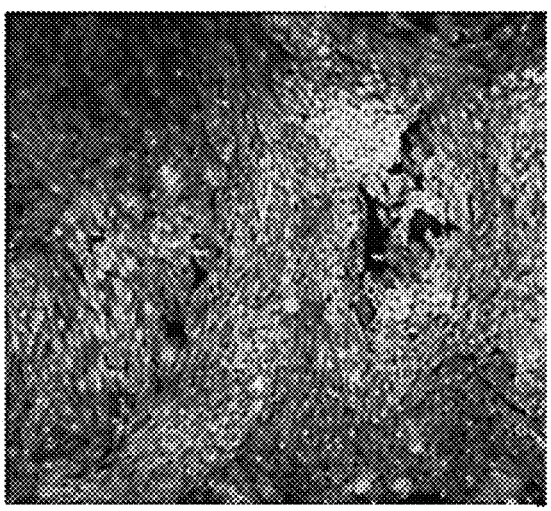

FIG. 39 shows exemplary immunostaining for cells in a top channel: Renal Proximal Epithelial Cells (Aquaporin 1—green/Na/K-ATPase—red/Nuclei—blue). Low flow rate (30 μl/hour). High Shear Chip left panels; S1 chip right panels; upper row ECM1 (KidneySpec); lower row ECM2 (Col IV).

Figure 40:
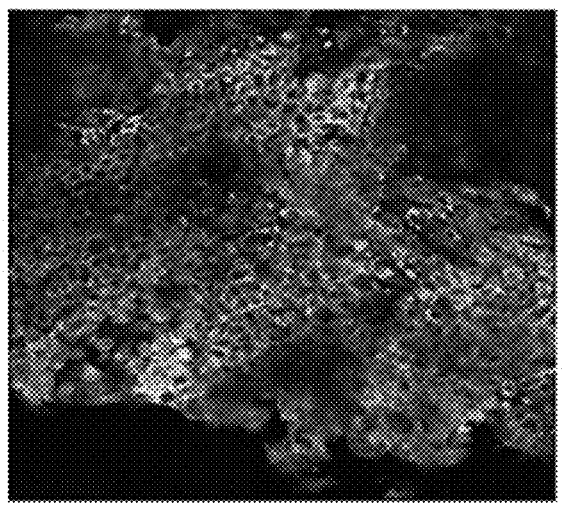
Figure 40:
Figure 40:
Figure 40:

FIG. 40 shows exemplary immunostaining for cells in a top channel: Renal Proximal Epithelial Cells (Aquaporin 1—green/Na/K-ATPase—red/Nuclei—blue). High flow rate (150 μl/hour). High Shear Chip left panels; S1 chip right panels; upper row ECM1 (KidneySpec); lower row ECM2 (Col IV).

Figure 41:
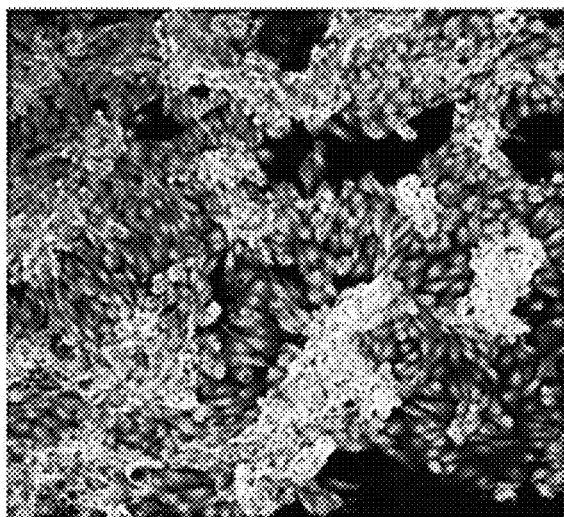
Figure 41:
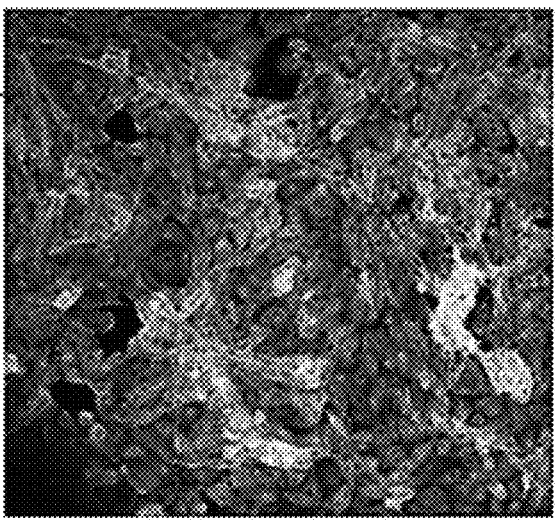
Figure 41:
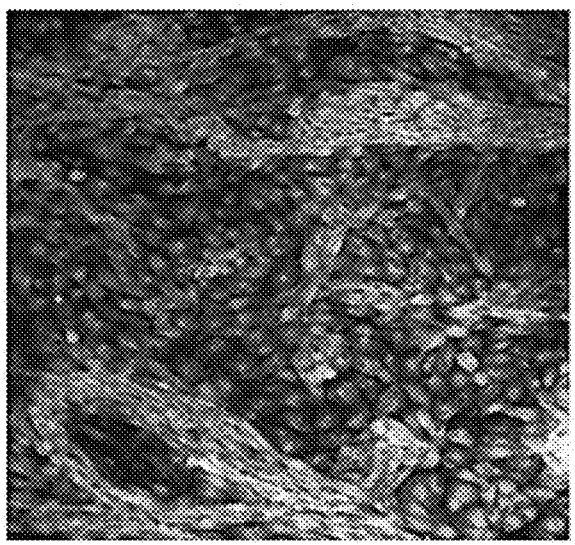
Figure 41:
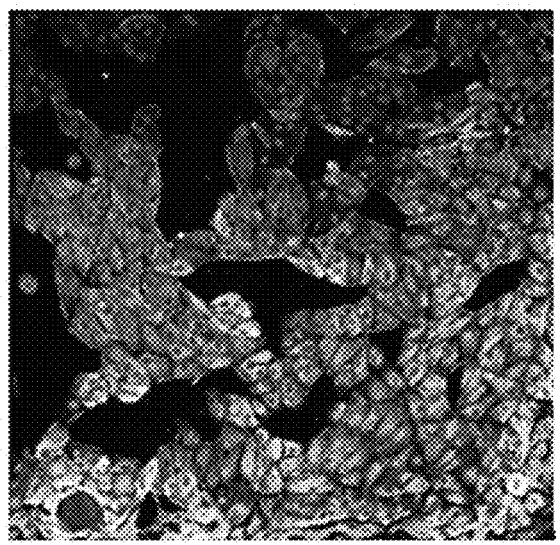

FIG. 41 shows exemplary immunostaining of Bottom channel cells: Golmerular endothelial cells (VE-Cadherin—green/F-actin—pink/Nuclei—blue). Low flow rate (30 μl/hour). High Shear Chip left panels; S1 chip right panels; upper row ECM1 (KidneySpec); lower row ECM2 (Col IV).

Figure 42:
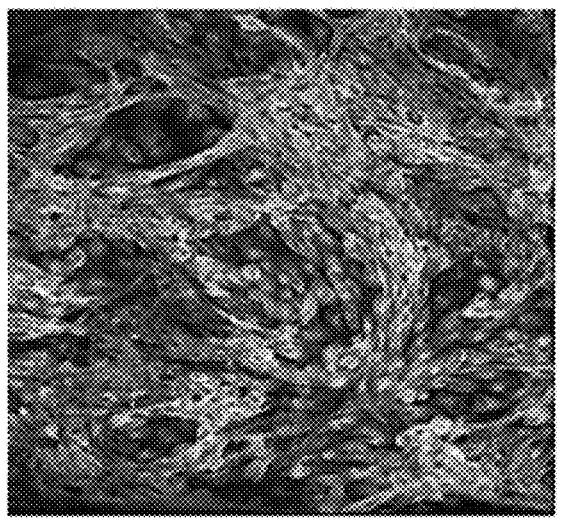
Figure 42:
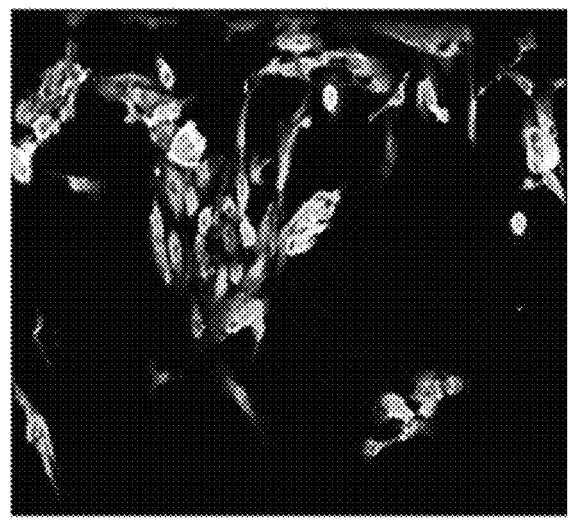
Figure 42:
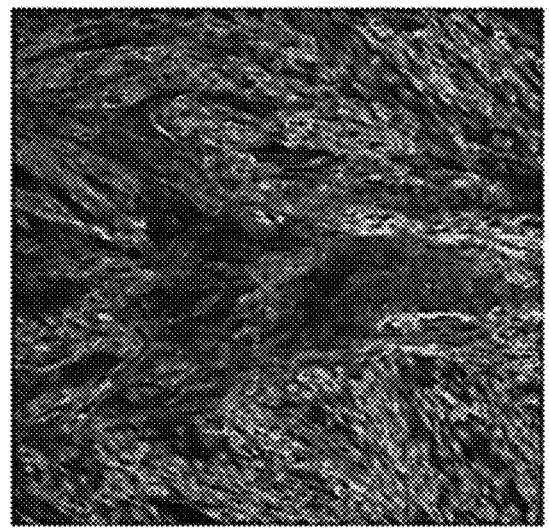
Figure 42:
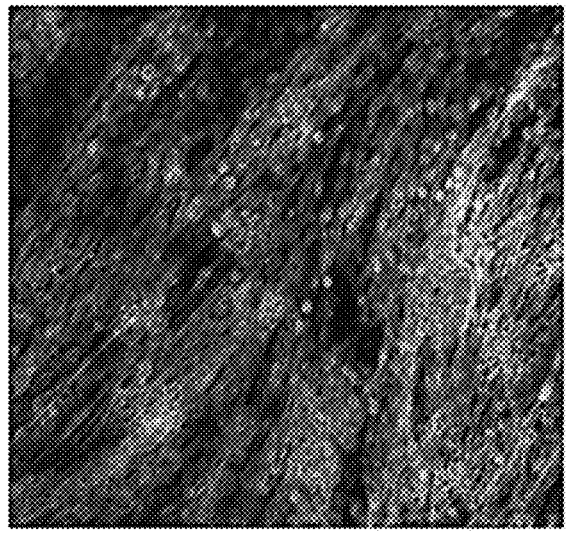

FIG. 42 shows exemplary immunostaining of Bottom channel cells: Golmerular endothelial cells (VE-Cadherin/F-actin/Nuclei—blue). High flow rate (150 μl/hour). High Shear Chip left panels; S1 chip right panels; upper row ECM1 (KidneySpec); lower row ECM2 (Col IV).

Figure 43:
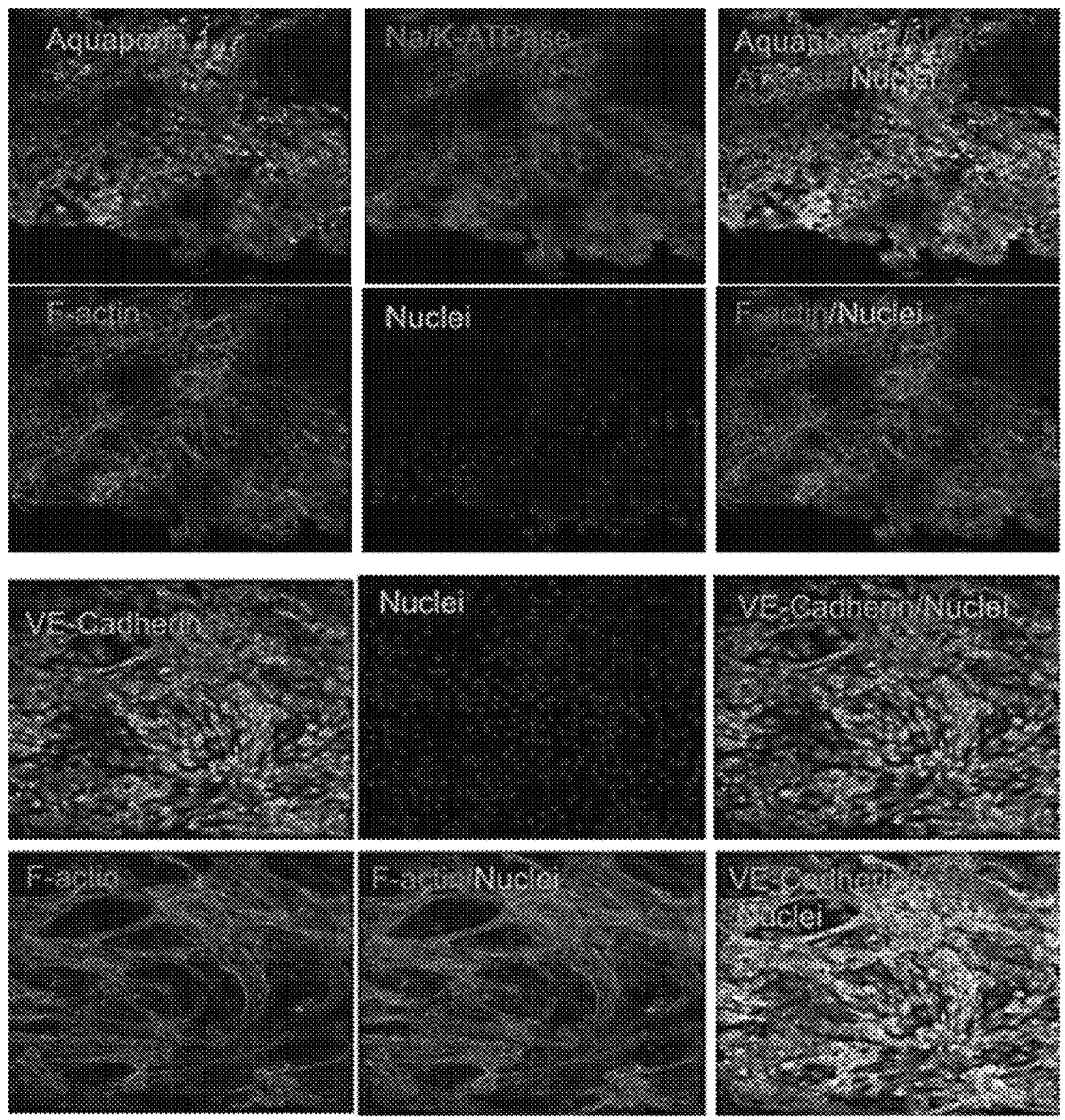

FIG. 43 shows exemplary immunostaining under High flow in high shear chip with ECM1 (KidneySpec). Top channel (upper two rows of panels): Renal Proximal Epithelial Cells (Aquaporin 1—green/Na/K-ATPase—red/F-actin—pink/Nuclei—blue) and Bottom channel: Golmerular endothelial cells (VE-Cadherin—green/F-actin—pink/Nuclei—blue).

Figure 44:
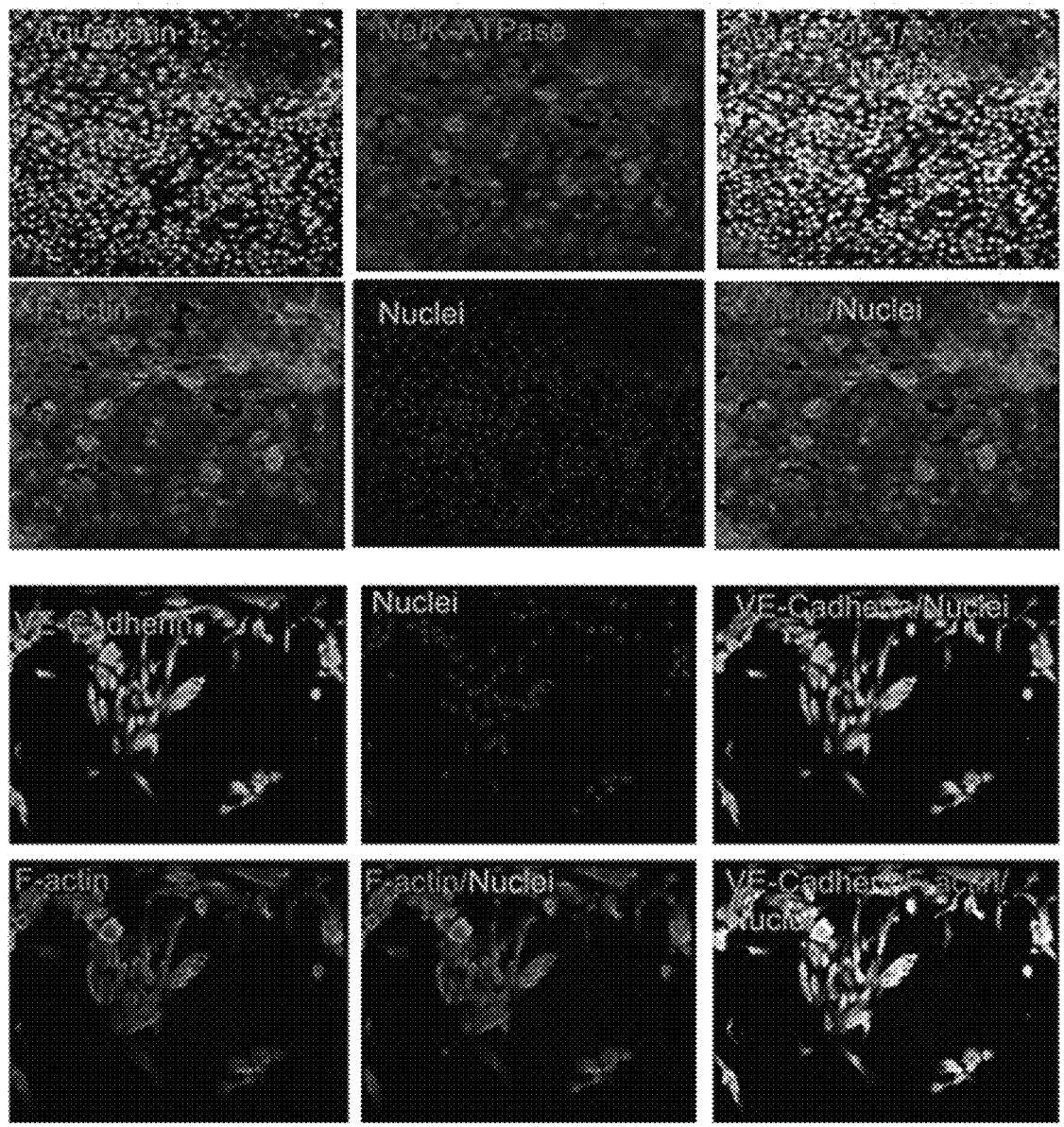

FIG. 44 shows exemplary immunostaining under High flow in Tall channel chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 45:
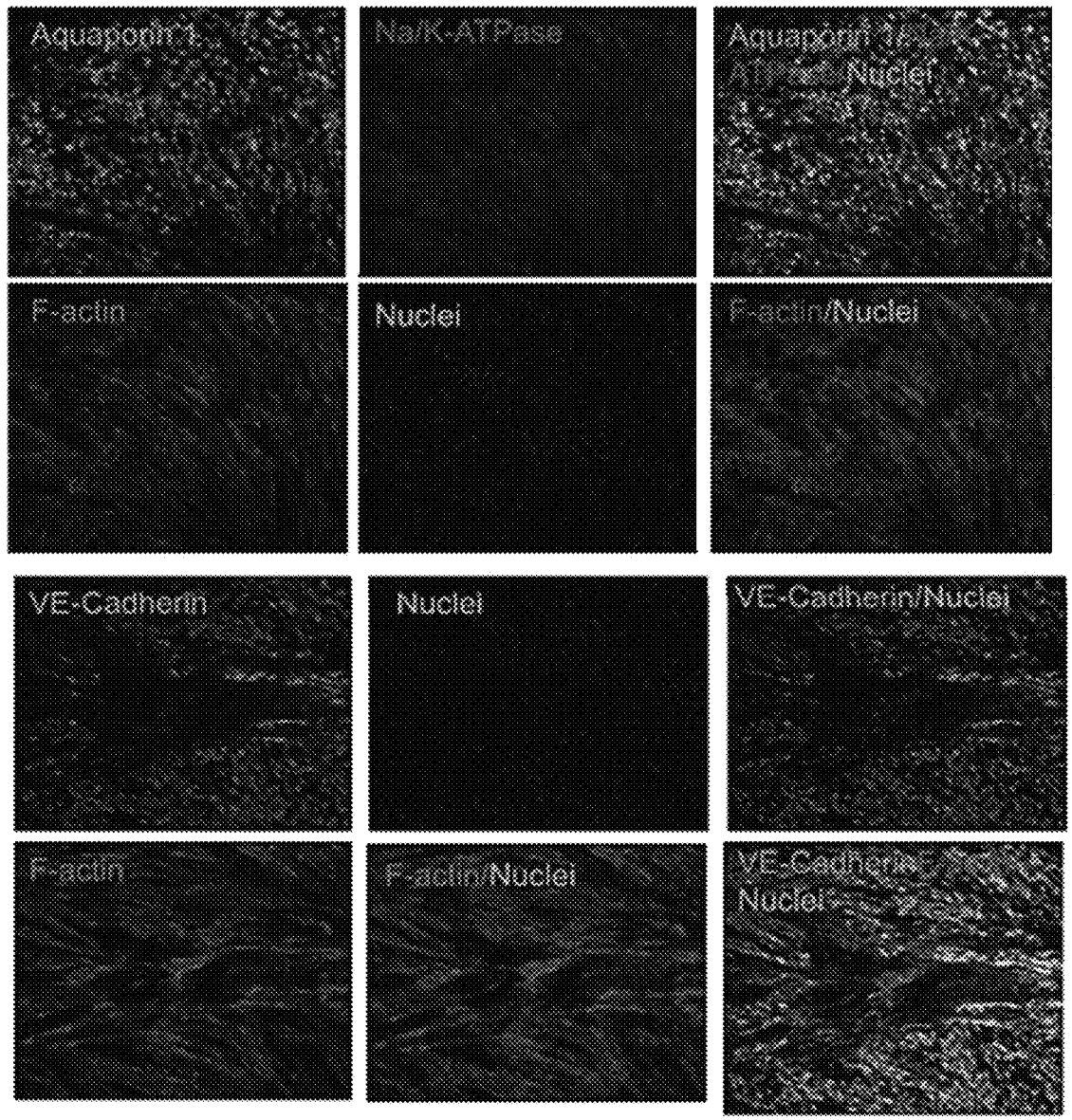

FIG. 45 shows exemplary immunostaining under High flow in high shear chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 46:
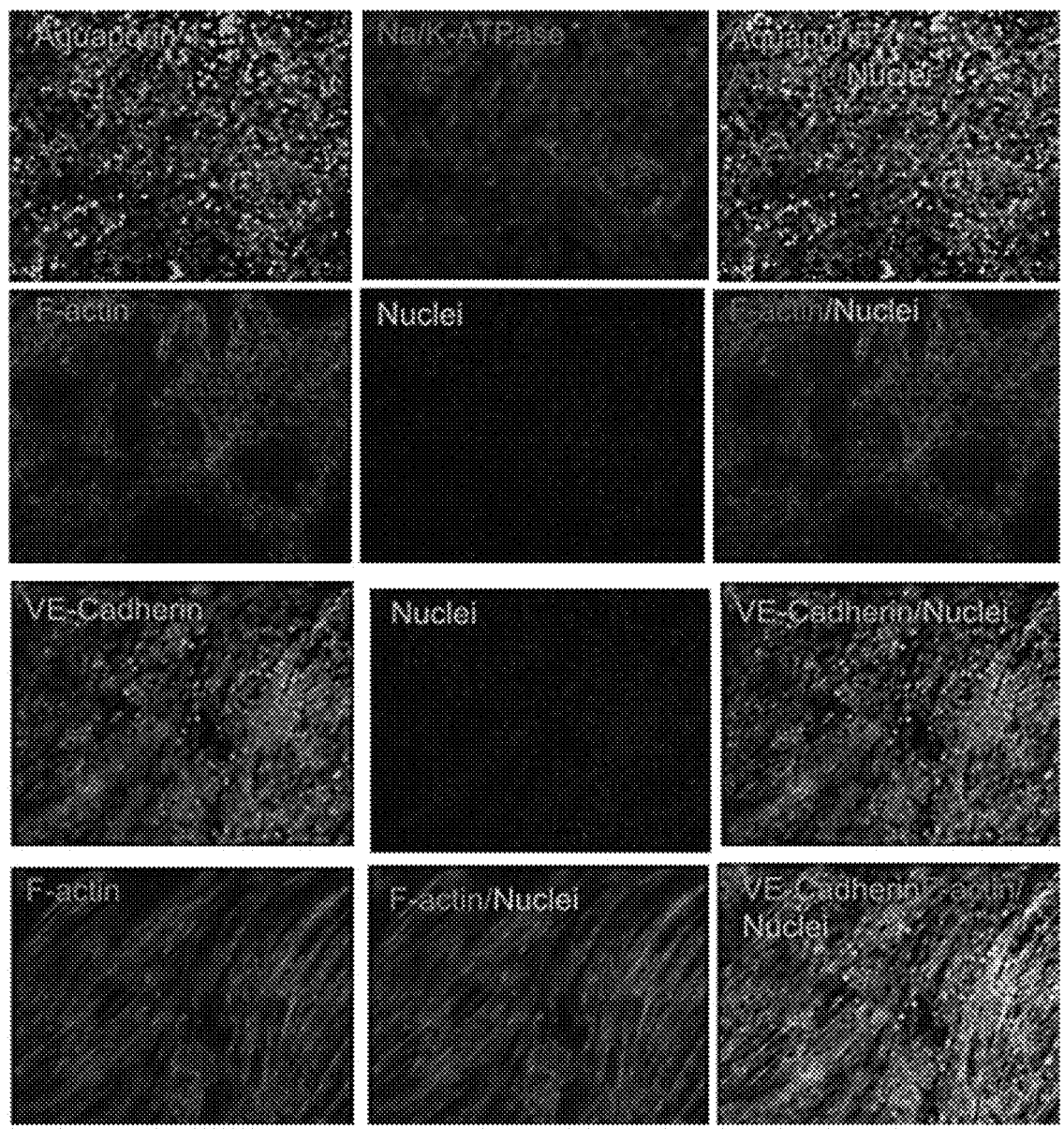

FIG. 46 shows exemplary immunostaining under High flow in Tall Channel chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 47:
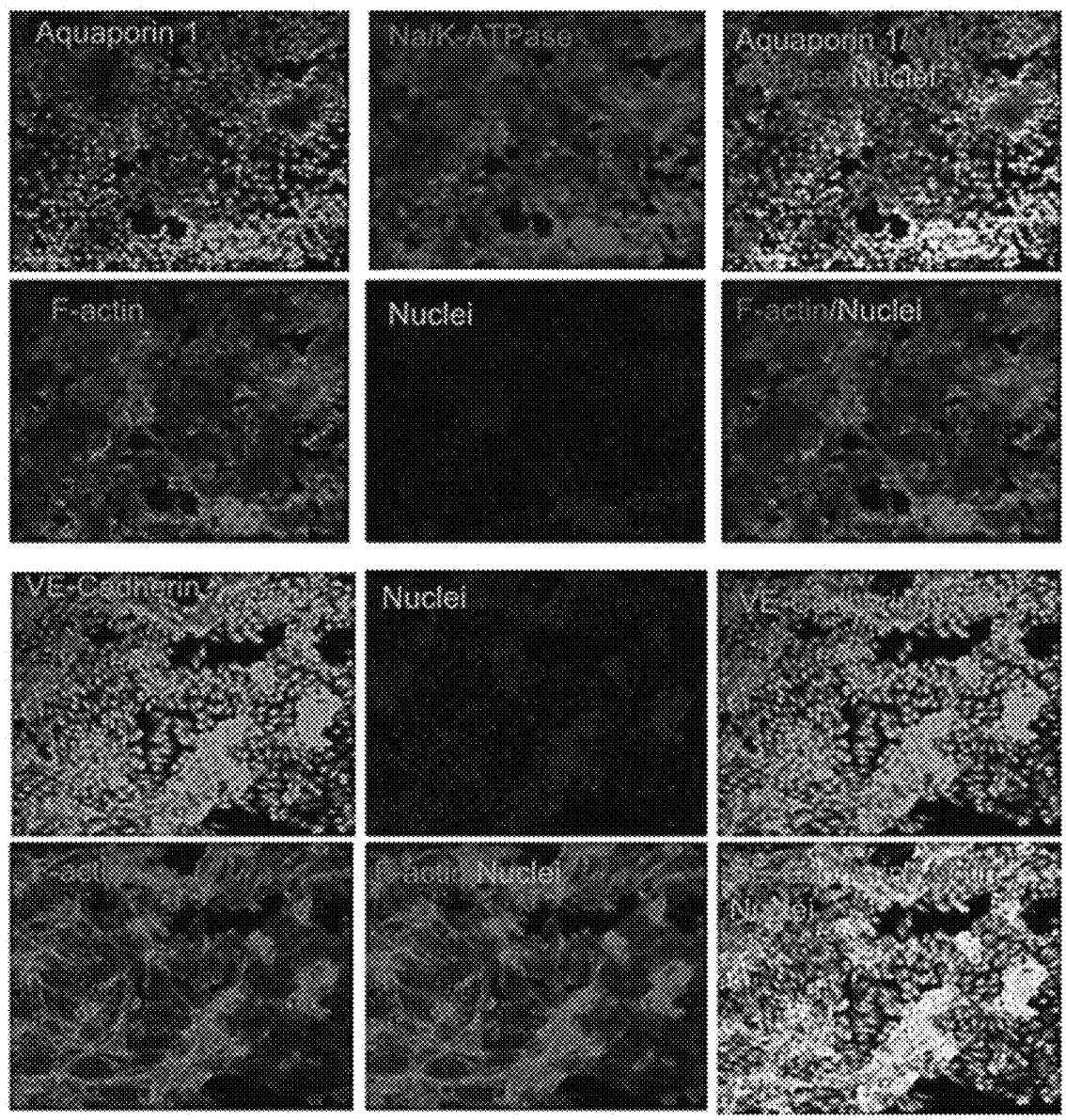

FIG. 47 shows exemplary immunostaining under Low flow in high shear chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 48:
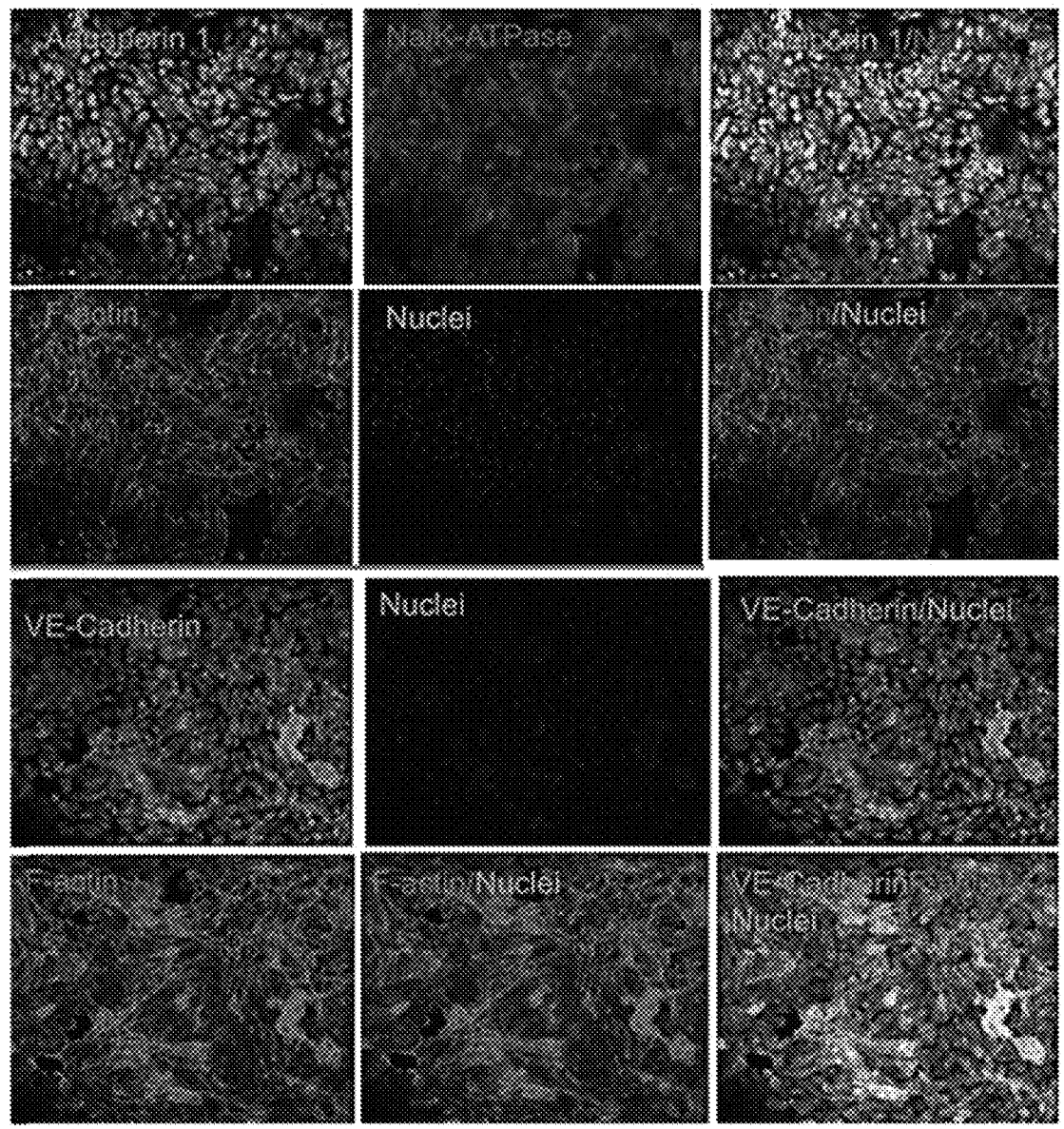

FIG. 48 shows exemplary immunostaining under Low flow in tall channel chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 49:
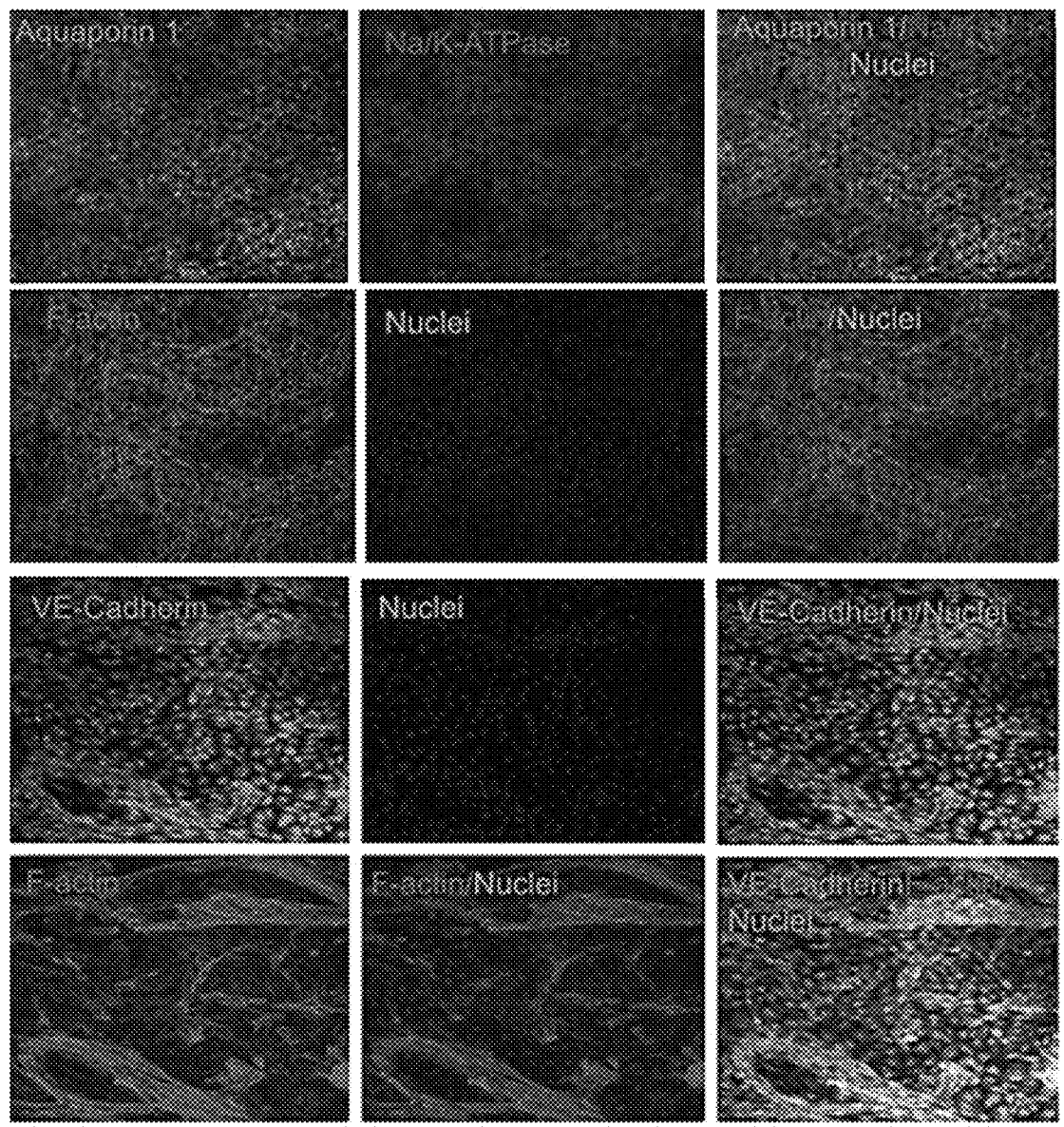

FIG. 49 shows exemplary immunostaining under Low flow inhigh shear chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 50:
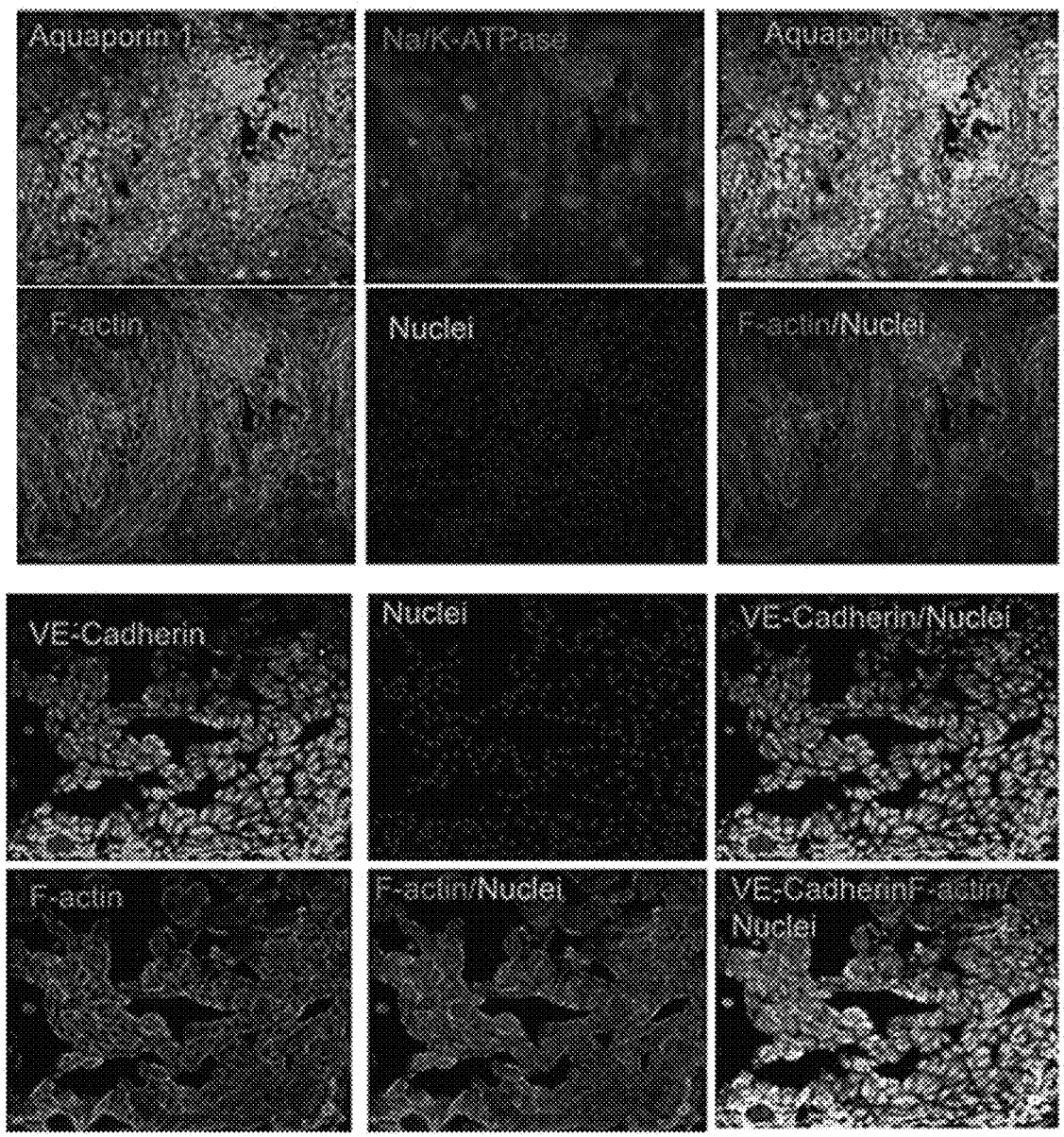

FIG. 50 shows exemplary immunostaining under Low flow in tall channel chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

Figure 51A:
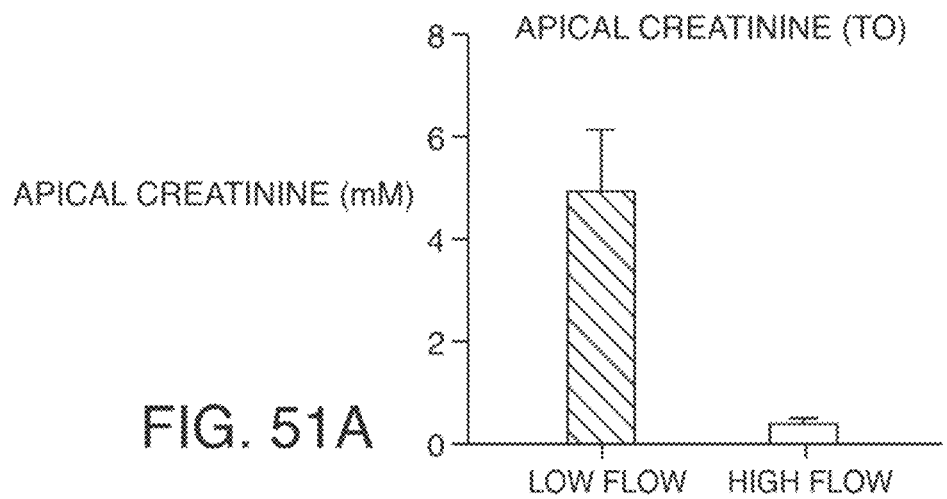
Figure 51B:
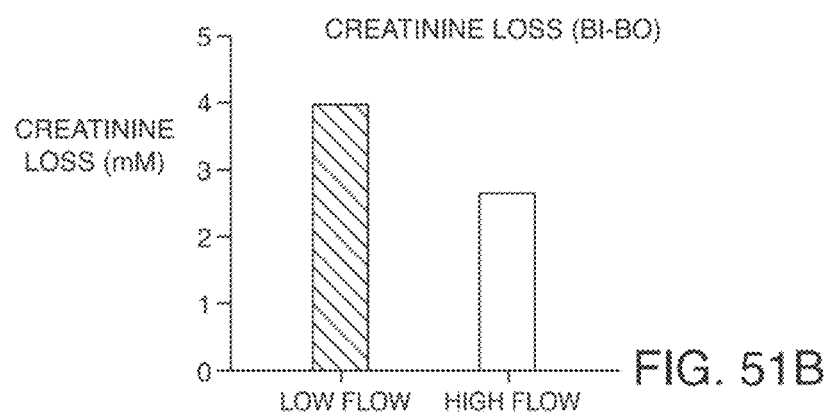
Figure 51C:
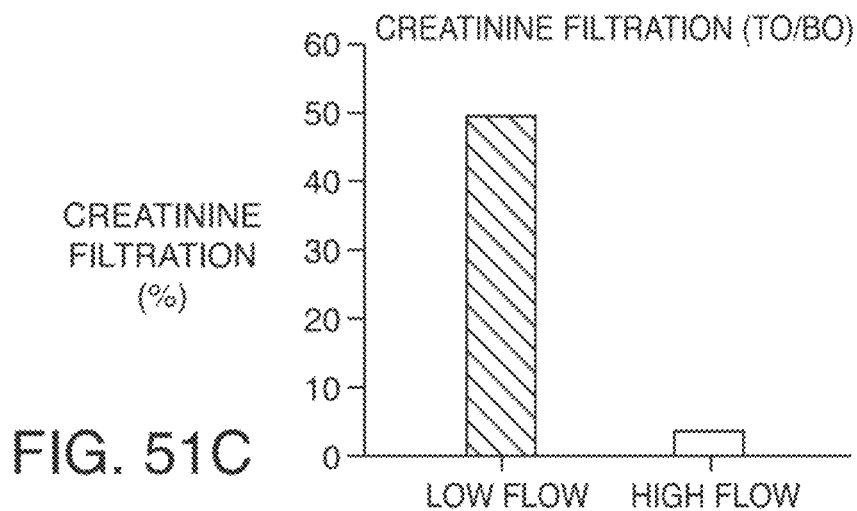

FIG. 51A-C shows exemplary Creatinine Secretion under low and high flow rates. BI: bottom inlet; BO: bottom outlet; TO: top outlet and Lonza cells. FIG. 51B Creatinine loss (mM); FIG. 51C Creatinine Filtration (%) and FIG. 51A Apical Creatinine (mM).

Figure 52A:
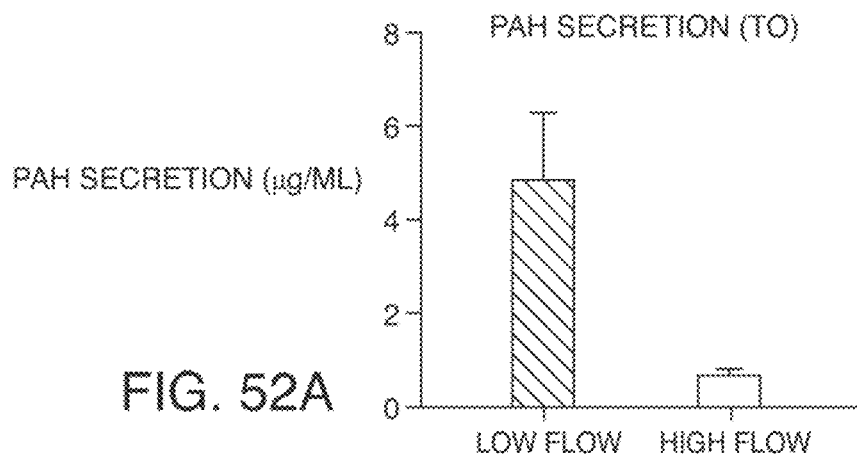
Figure 52B:
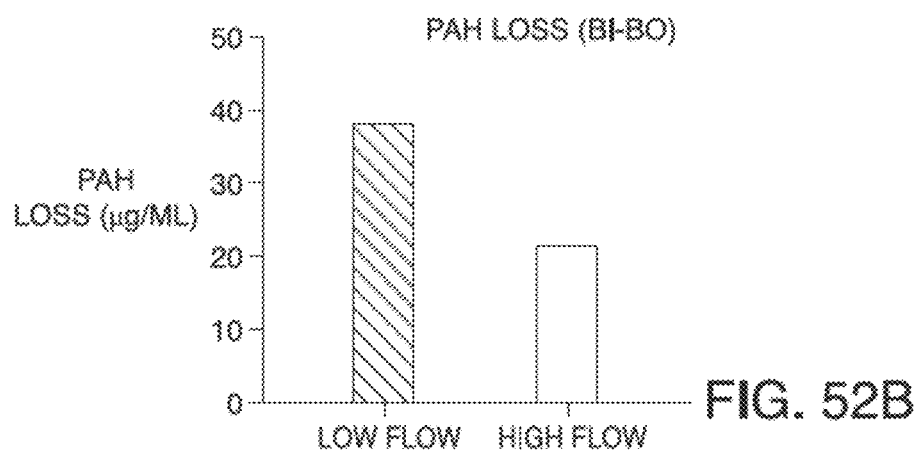
Figure 52C:
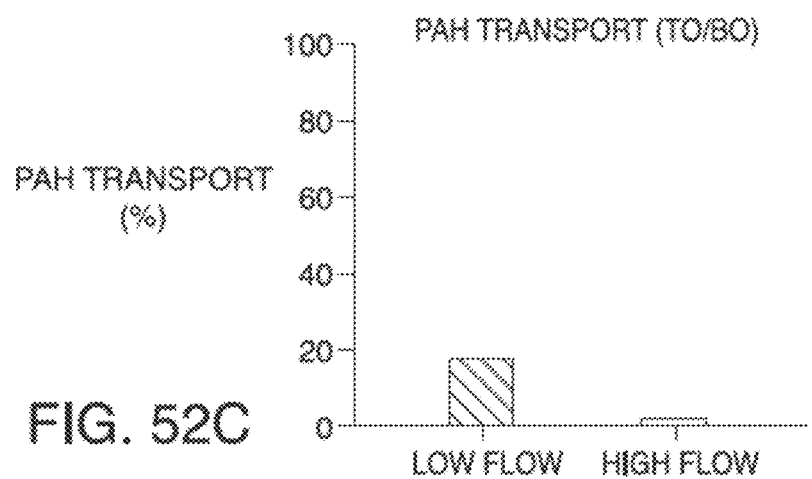

FIG. 52A-C shows exemplary PAH Secretion under low and high flow rates. BI: bottom inlet; BO: bottom outlet; TO: top outlet and Lonza cells. FIG. 52B PAH loss (micrograms/ML); FIG. 52C PAH Transport (%) and FIG. 52A PAH Secretion (micrograms/M).

Figure 53A:
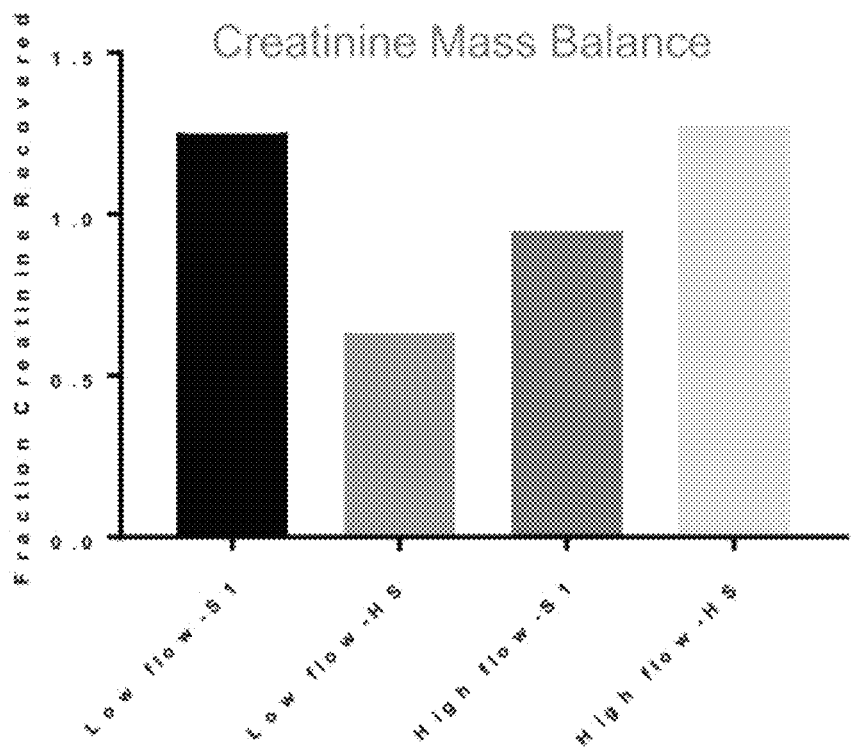
Figure 53B:
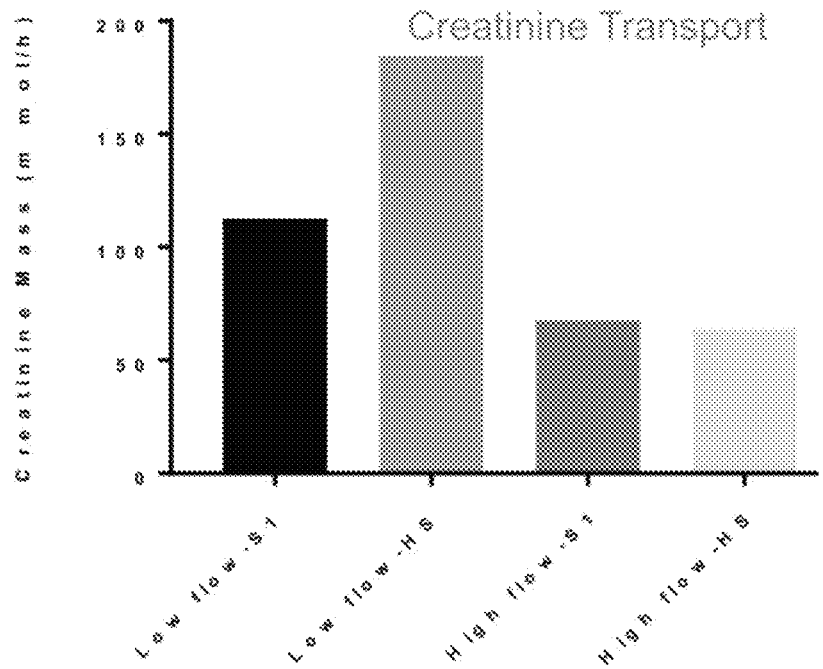

FIG. 53A-B shows an exemplary Creatinine Mass Balance and Creatinine Transport on PT-Kidney-chips under low and high flow on both S1 tall channel chips and HS chips.

Figure 54:
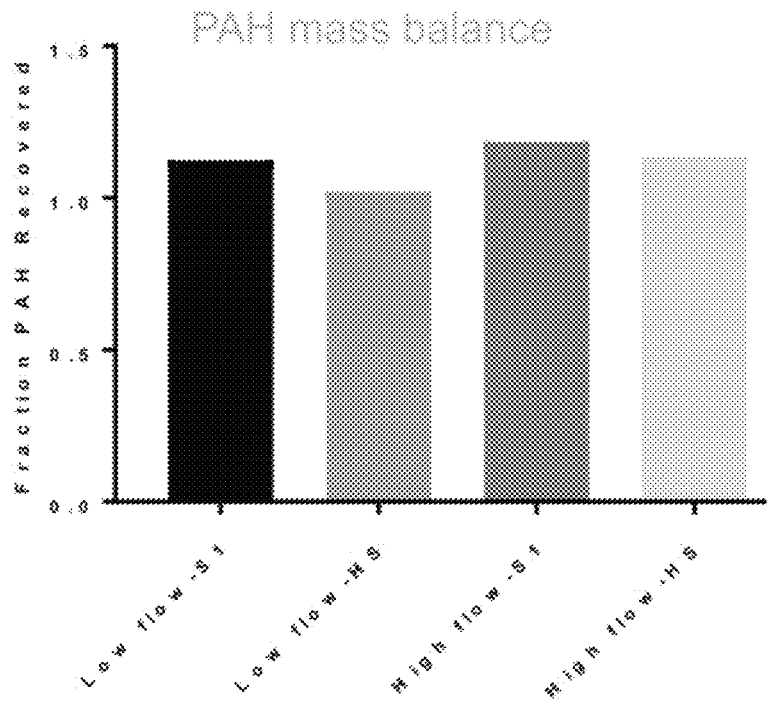
Figure 54:
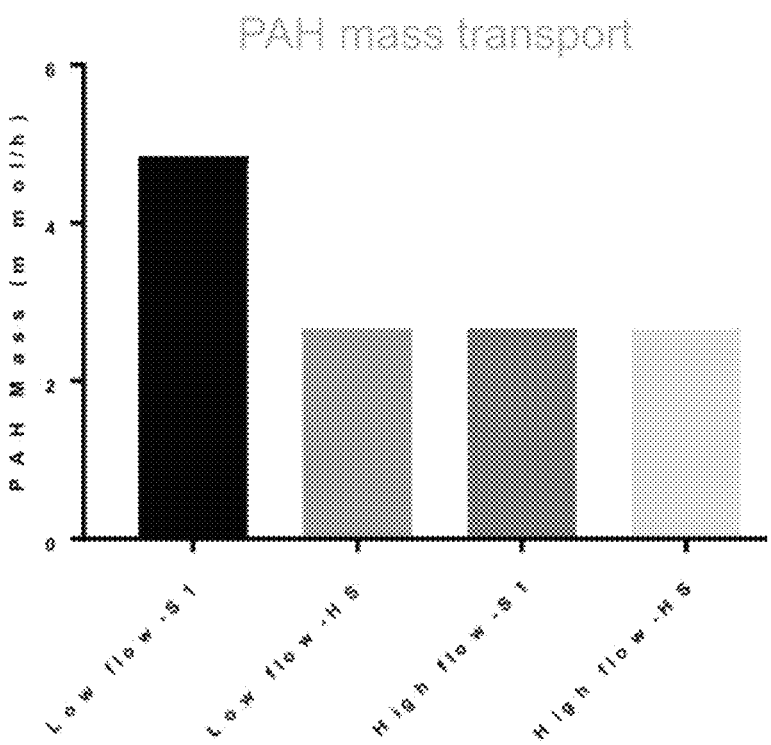

FIG. 54 shows exemplary PAH Mass Balance and shows exemplary PAH mass Transport on PT-Kidney-chips under low and high flow on both S1 tall channel chips and HS chips.

Figure 55:
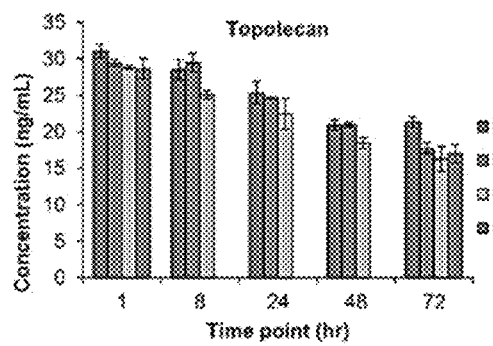
Figure 55:
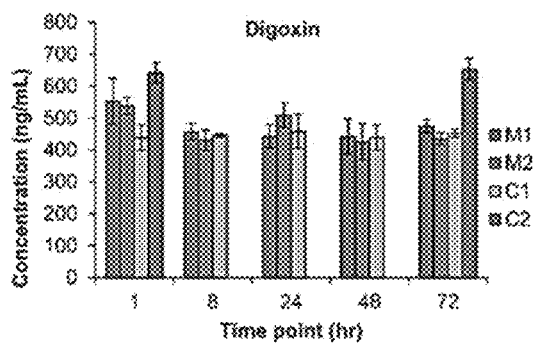
Figure 55:
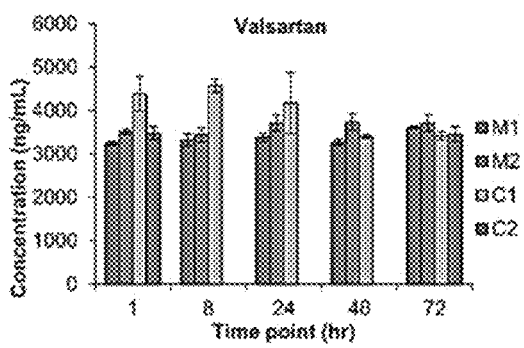
Figure 55:
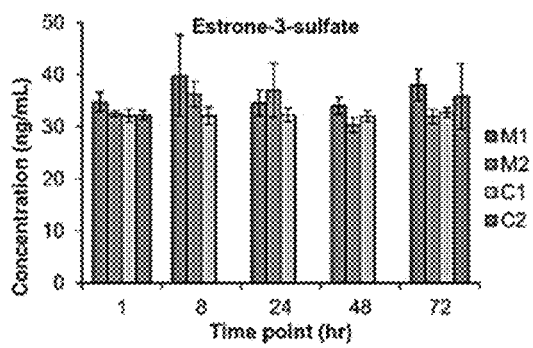
Figure 55:
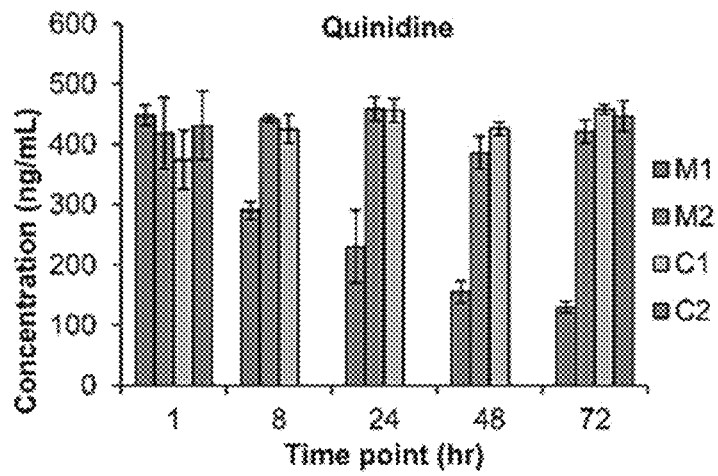

FIG. 55 shows Minimal absorption into chip material in all four compounds except Quinidine.

Figure 56:
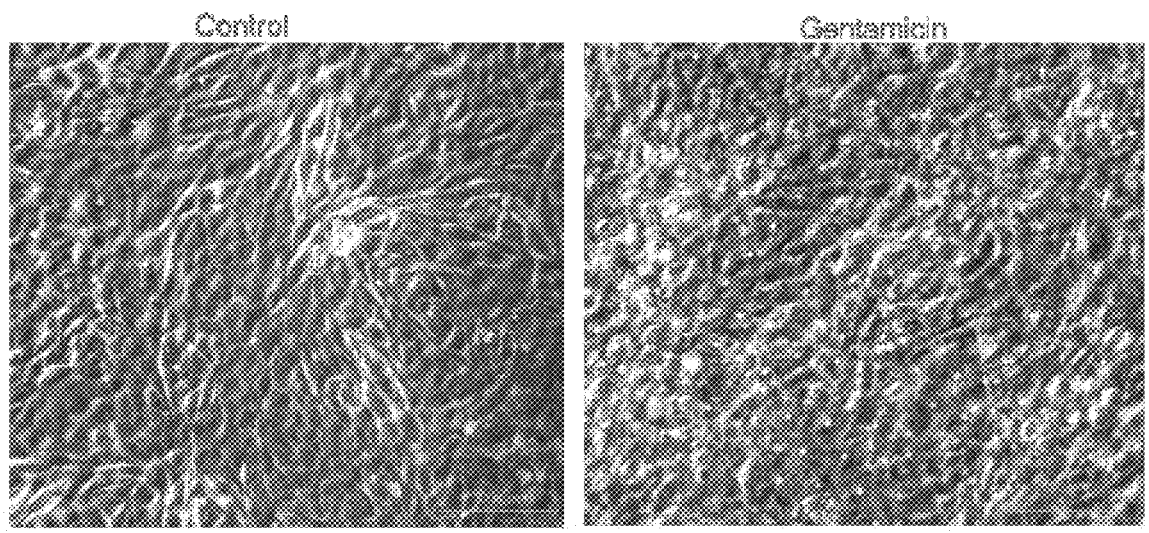

FIG. 56 shows exemplary Gentamicin Toxicity Testing: Morphology Observations. Gentamicin treatment, right image; exemplary control cells, left image (Lonza cells; S1; Flow: 30 µL/hr provided by a culture module).

Figure 57:
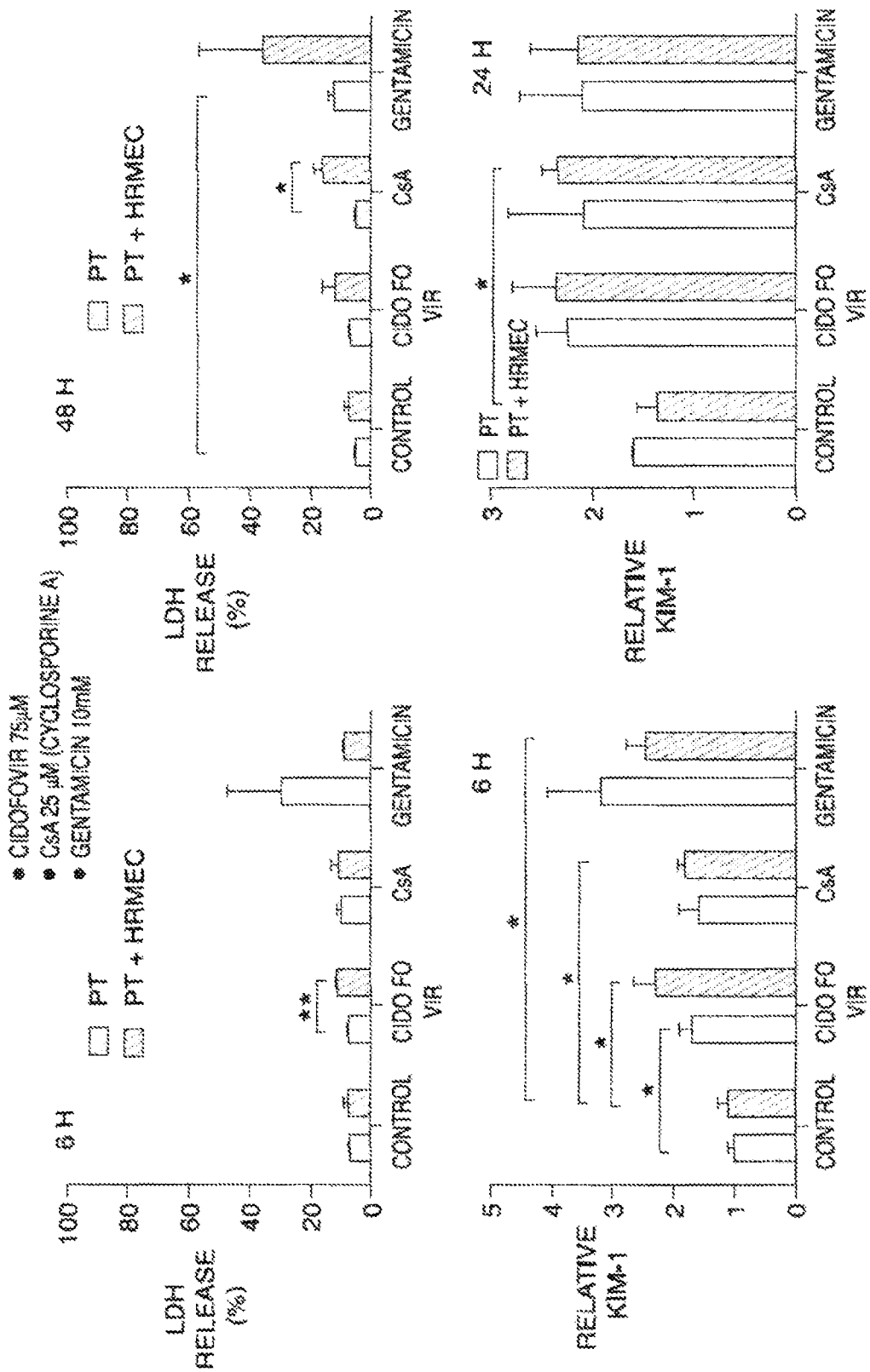

FIG. 57 shows exemplary Gentamicin Toxicity Testing: Acute Tubular Injury and biomarker identification: LDH and relative KIM-1 release, respectively, in response to 75 µM Cidofovir, 25 µM Cyclosporine (CsA), and 10 mM Gentamicin. (Biopredict PT Kidney cells; HRMEC; High Shear Chip; fluid flow: 60 µL/hr provided by a Syringe pump).

Figure 58:
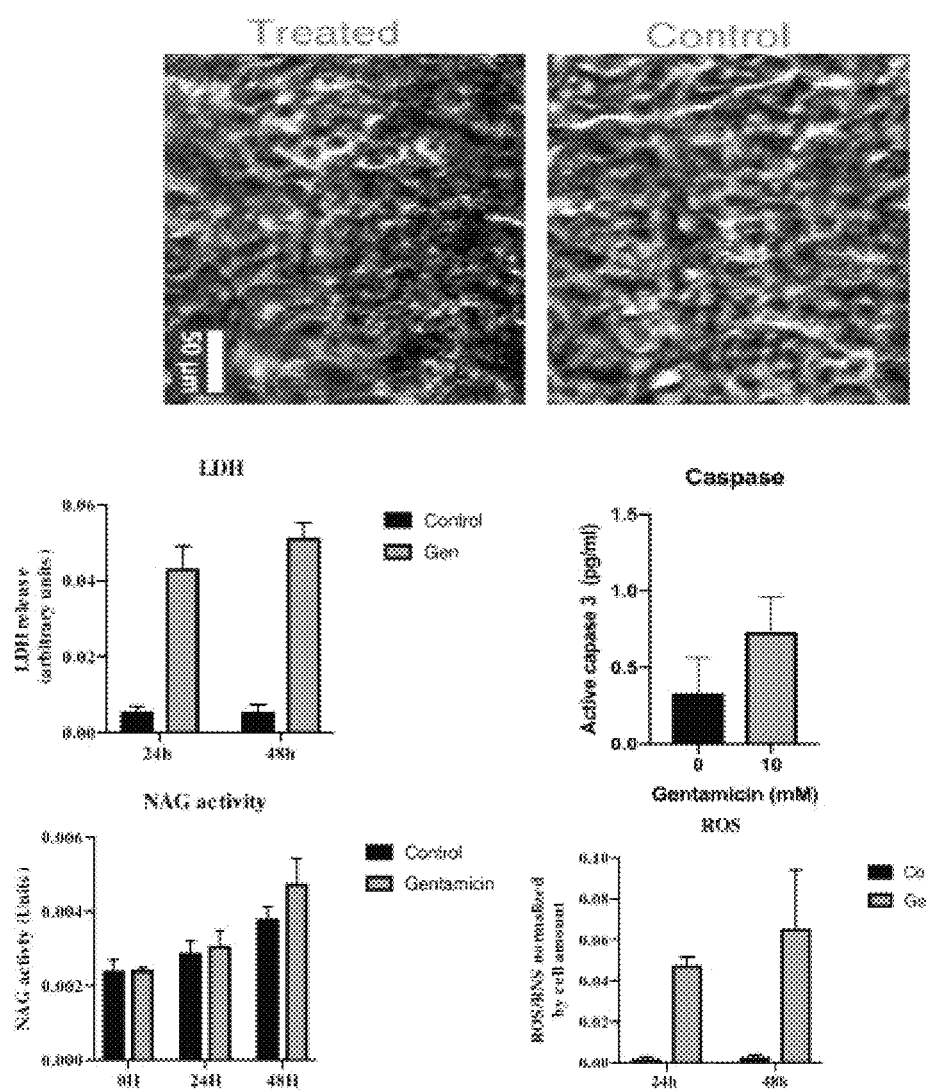

FIG. 58 shows exemplary Gentamicin Toxicity Testing: LDH, NAG, reactive oxygen species (ROS), reactive nitrogen species (RNS); Active Caspase, & morphology. (PT Kidney cells-Lonza; HRMEC; S1; Flow: 60 µL/hr provided by a culture module).

FIG. 59A-D shows exemplary Gentamicin Toxicity Testing: FIG. 59B LDH and FIG. 59A Morphology, FIG. 59C TUNEL, FIG. 59D Active Caspse-3. (Lonza PT Kidney cells; HRMEC; S1; Flow: 60 µL/hr provided by a culture module).

Figure 60:
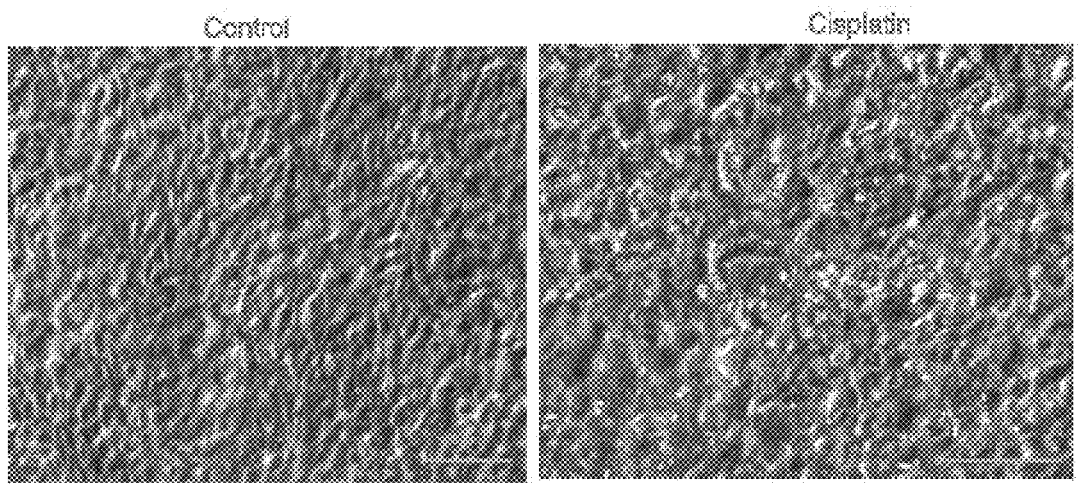

FIG. 60 shows exemplary Cisplatin Toxicity Testing: Acute Tubular Injury during as structural damage of epithelial layer caused by exposure to 10 µM Cisplatin. Control left, treated right. (PT Kidney cells-Lonza; HRMEC; S1; Flow: 30 µL/hr provided by a culture module).

Figure 61A:
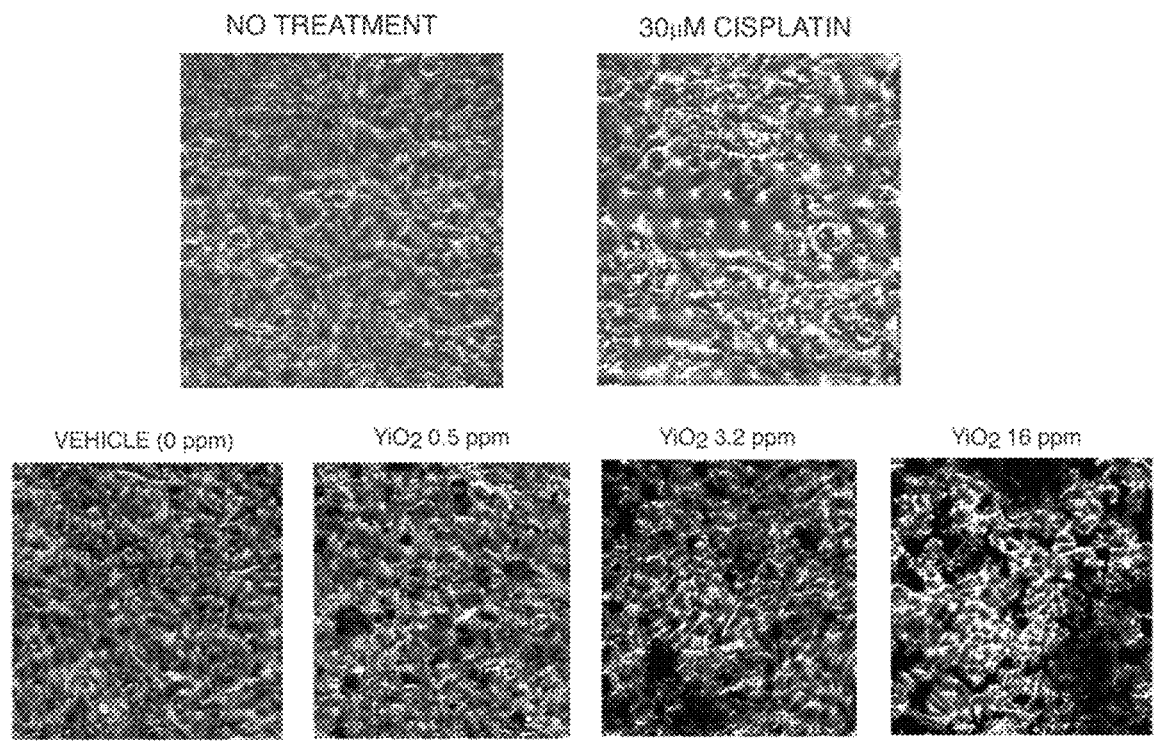
Figure 61B:
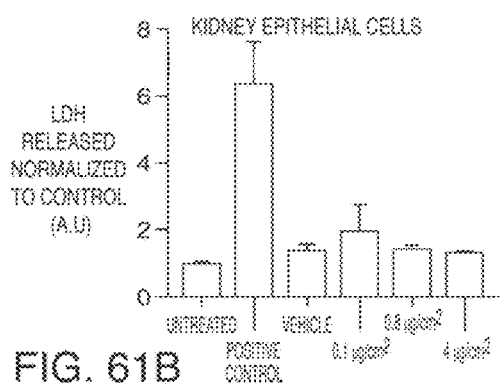
Figure 61C:
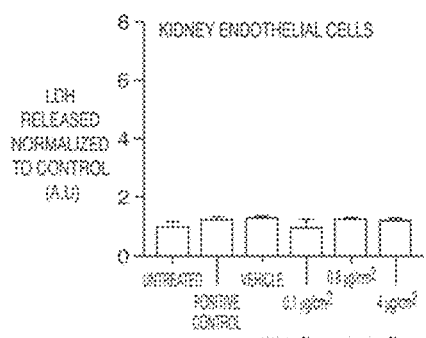
Figure 61D:
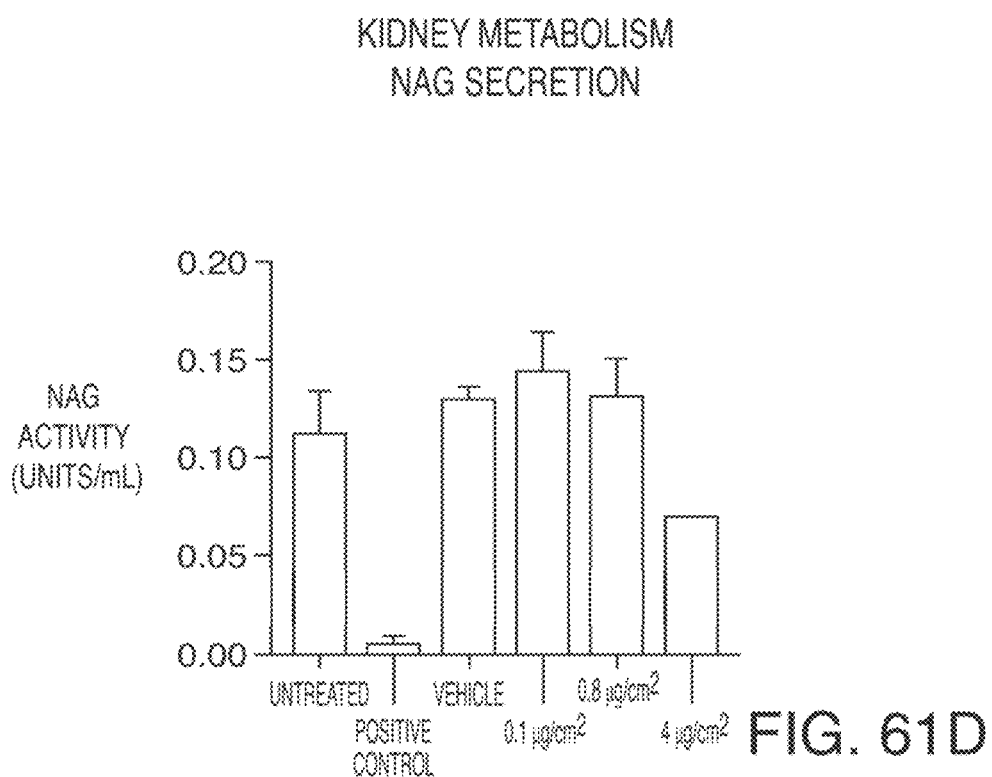

FIG. 61A-C shows exemplary Cisplatin Toxicity Testing: FIG. 61B-C LDH, FIG. 61D NAG & FIG. 61A morphology. Tattoo ink (TiO2) toxicity is compared to Cisplatin Toxicity. (PT Kidney cells-Lonza; HRMEC; S1; Flow: 60 µL/hr provided by a culture module).

Figure 62A:
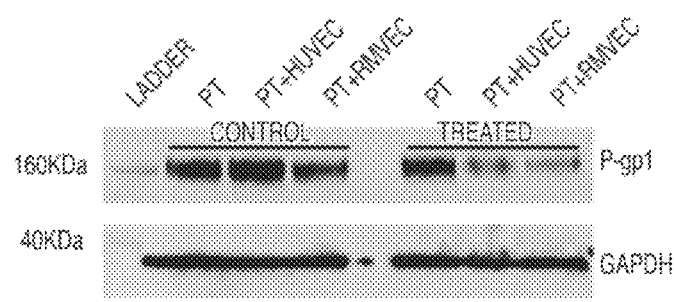
Figure 62B:
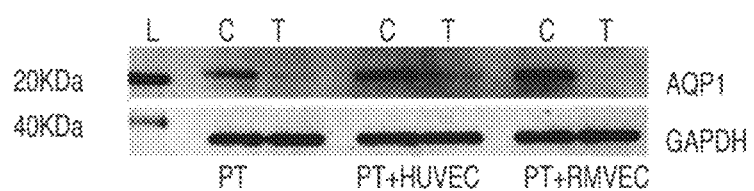
Figure 62C:
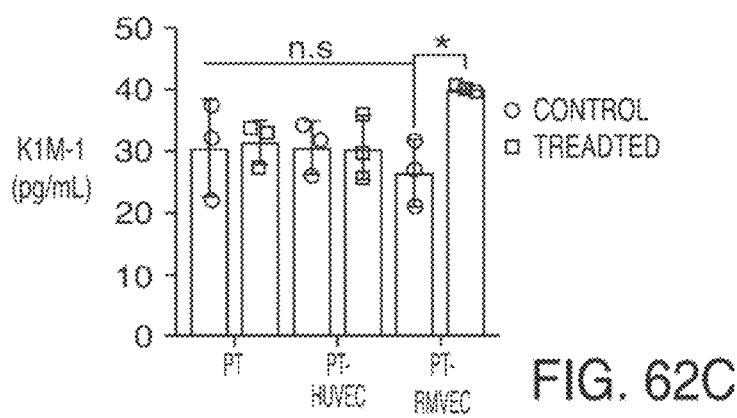
Figure 62D:
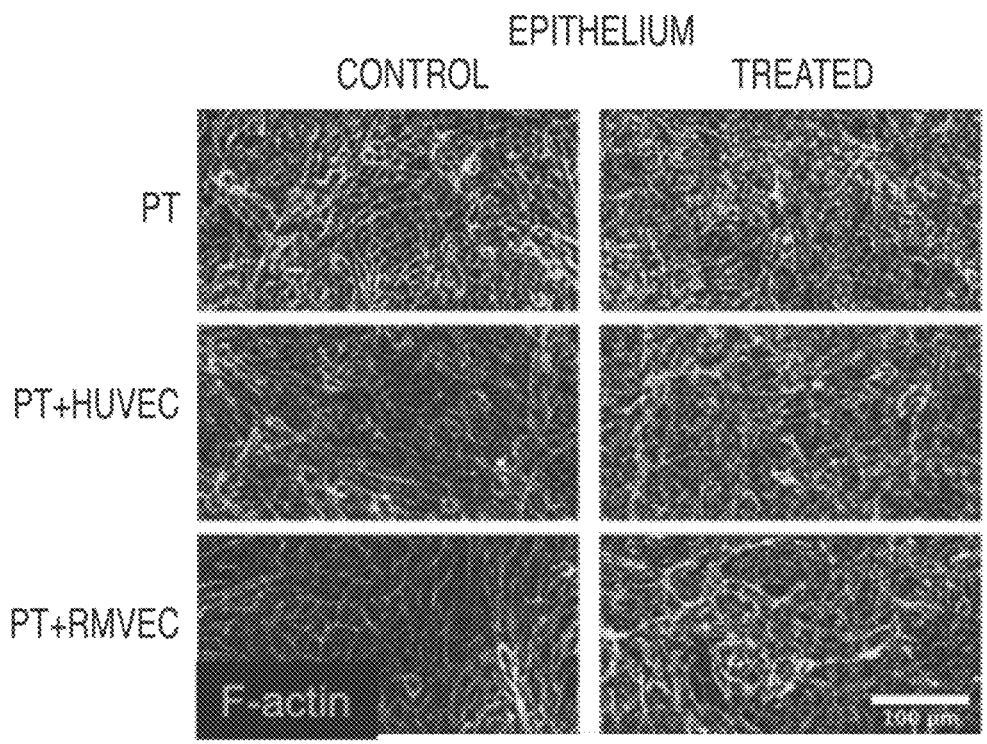
Figure 62E:
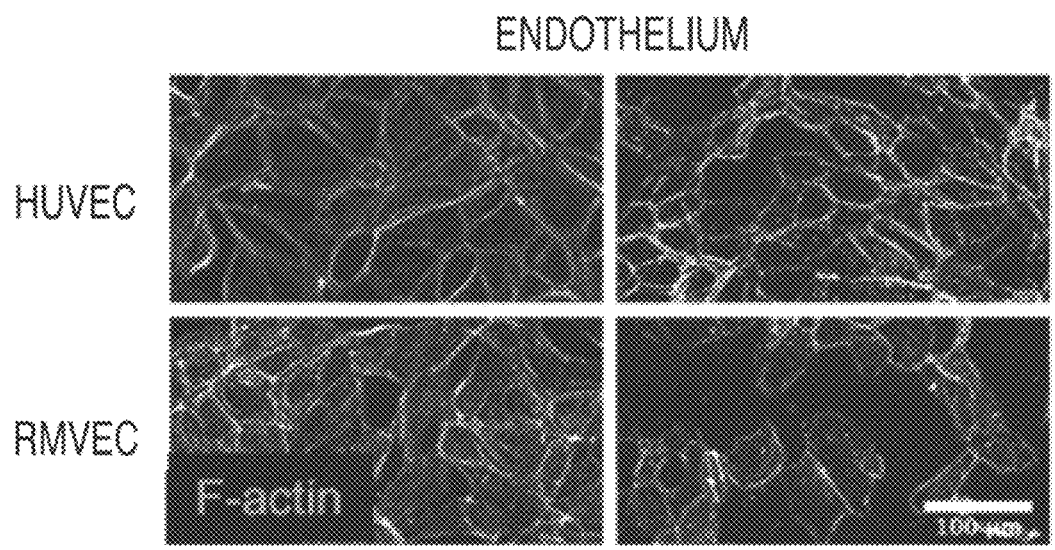

FIG. 62A-E shows exemplary Cisplatin Toxicity Testing: Acute Tubular Injury; Biomarker Identification (KIM-1); Mechanism of Action, e.g. Cytoskeletal rearrangement, in response to two different types of endothelium co-cultured with human PT cells, e.g. Human renal microvascular endothelial cells (HRMEC) and Human Umbilical Vein Endothelial Cells (HUVEC). FIG. 62A-C P-gp1, AQP1 and Kim-1 were evaluated, (PT Kidney cells-ScienCell; Tall Channel; Flow: 60 µL/hr provided by a peristaltic pump). Morphological observations were following immunohistochemistry, FIG. 62D F-actin white/green, upper panel and FIG. 62E white/yellow, lower panel. (PT Kidney cells-Lonza; S1; Flow: 60 µL/hr provided by a culture module).

Figure 63A:
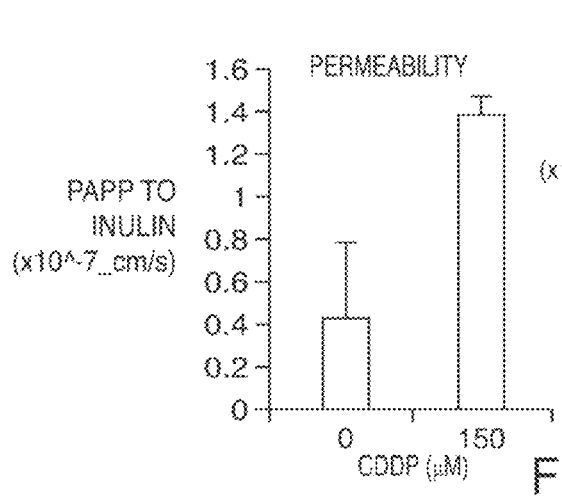
Figure 63B:
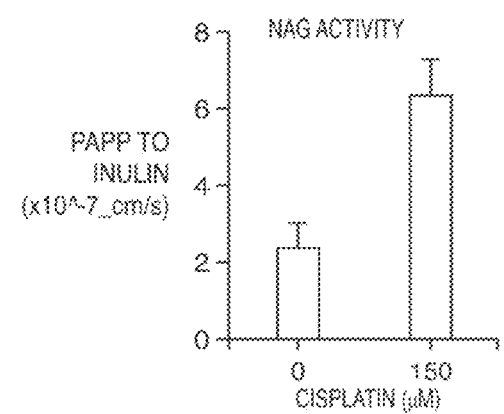
Figure 63C:
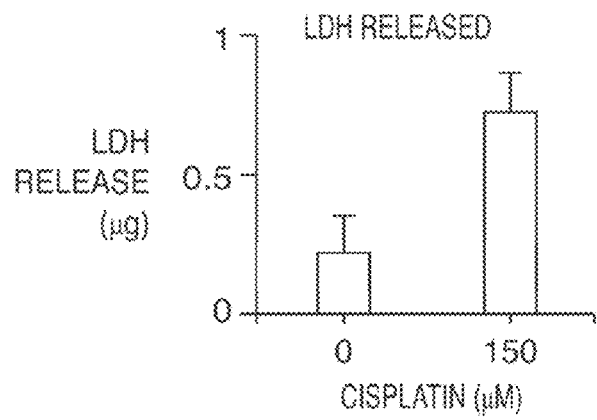
Figure 63D:
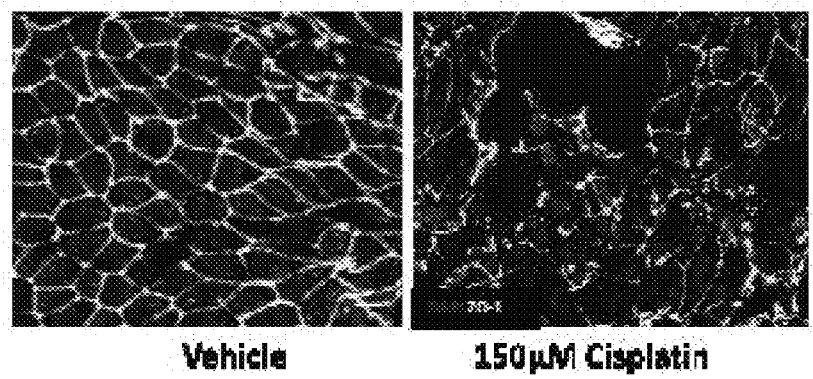

FIG. 63A-D shows exemplary Cisplatin (CDDP) Toxicity Testing: Acute Tubular Injury; Biomarker Identification; and Mechanism of Action: FIG. 63B NAG, FIG. 63C LDH, FIG. 63A Permeability, FIG. 63D Immunostaining, e.g. ZO-1 (yellow), nuclei (blue). (PT Kidney cells-ScienCell; HRMEC; Tall Channel; Flow: 60 µL/hr provided by a peristaltic pump).

Figure 64A:
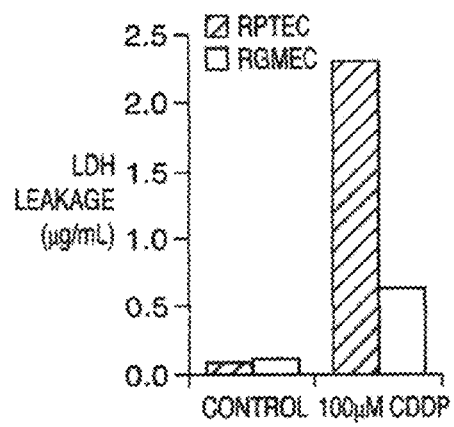
Figure 64B:
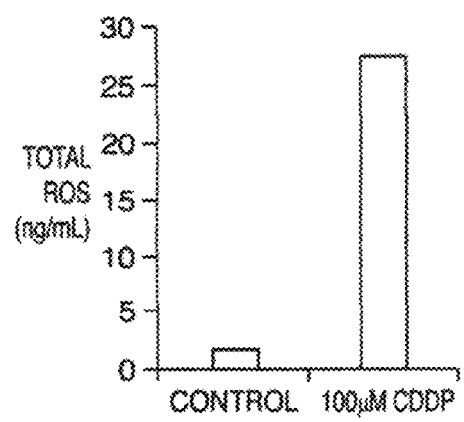
Figure 64C:
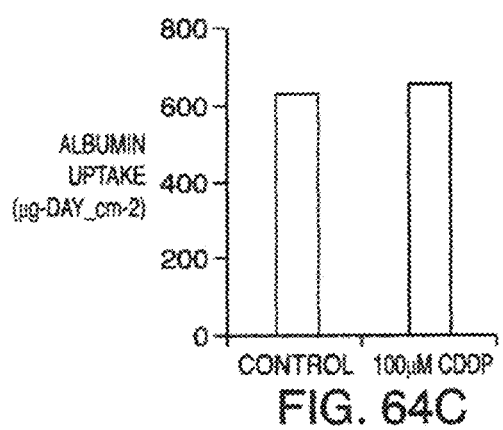
Figure 64D:
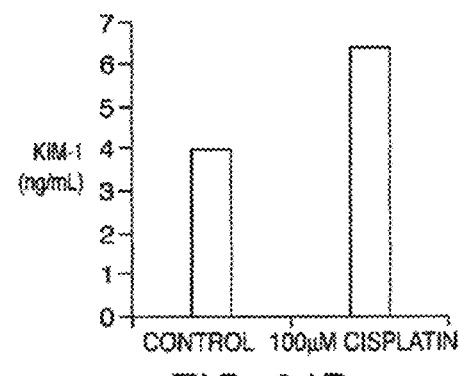
Figure 64E:
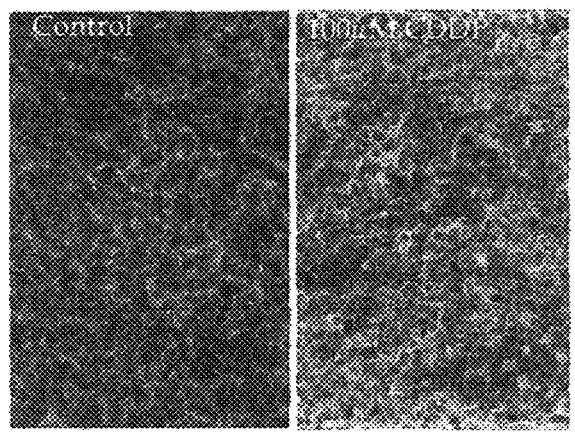

FIG. 64A-E shows exemplary Cisplatin Toxicity Testing: Acute Tubular Injury; Biomarker Identification; and Mechanism of Action: FIG. 64A LDH, FIG. 64B Total ROS, FIG. 64C Albumin uptake, and FIG. 64D Kim-1. RPTEC (Primary Human Renal Proximal Tubule Epithelial *Cells*) and RGMEC (Primary Human *Glomerular Microvascular Endothelial Cells*). (PT Kidney-Biopredict cells; HRMEC; High Shear Chip; Flow: 60 µL/hr provided by interrogator). FIG. 64E Morphology showing (PT Kidney cells-BioPredict; HRMEC; High Shear Chip; Flow: 60 µL/hr provided by interrogator).

Figure 65A:
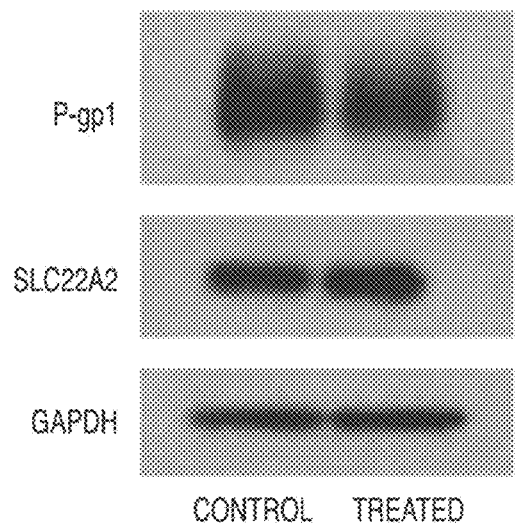
Figure 65B:
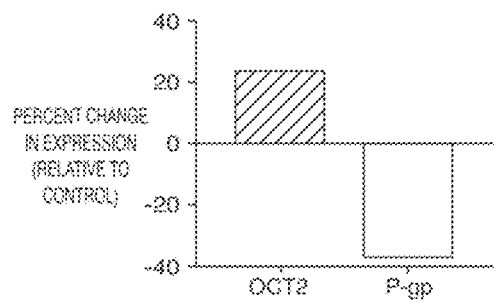
Figure 65C:
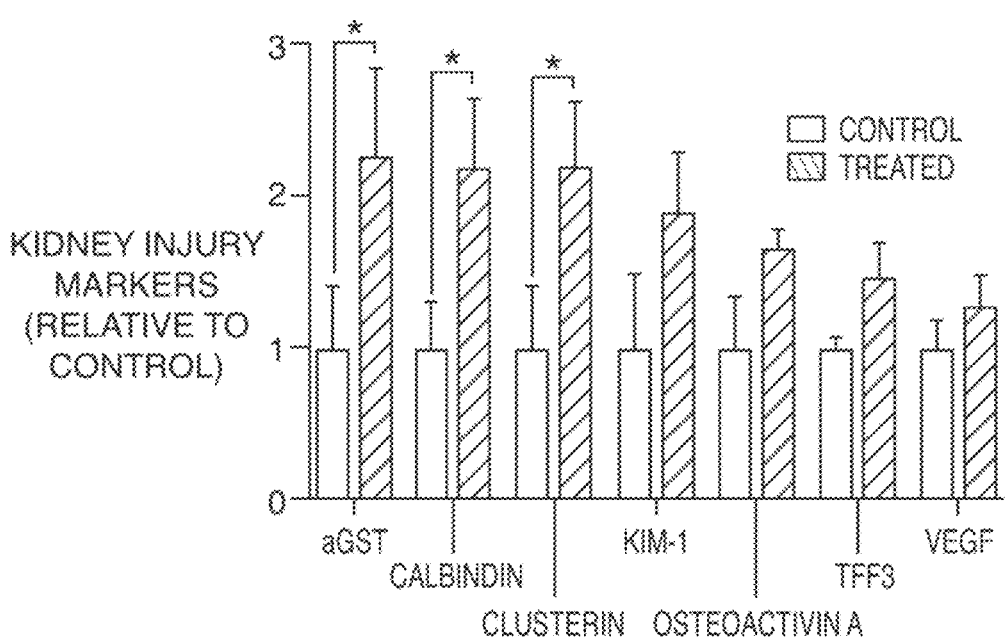

FIG. 65A-C shows exemplary Cisplatin Toxicity Testing: Acute Tubular Injury; Mechanism of Action: FIG. 65C Kidney Injury Marker Panel (MSD) and FIG. 65A western blot; FIG. 65B. (PT Kidney cells-ScienCell; HRMEC; Tall Channel; Flow: 60 µL/hr provided by a peristaltic pump).

Figure 66:
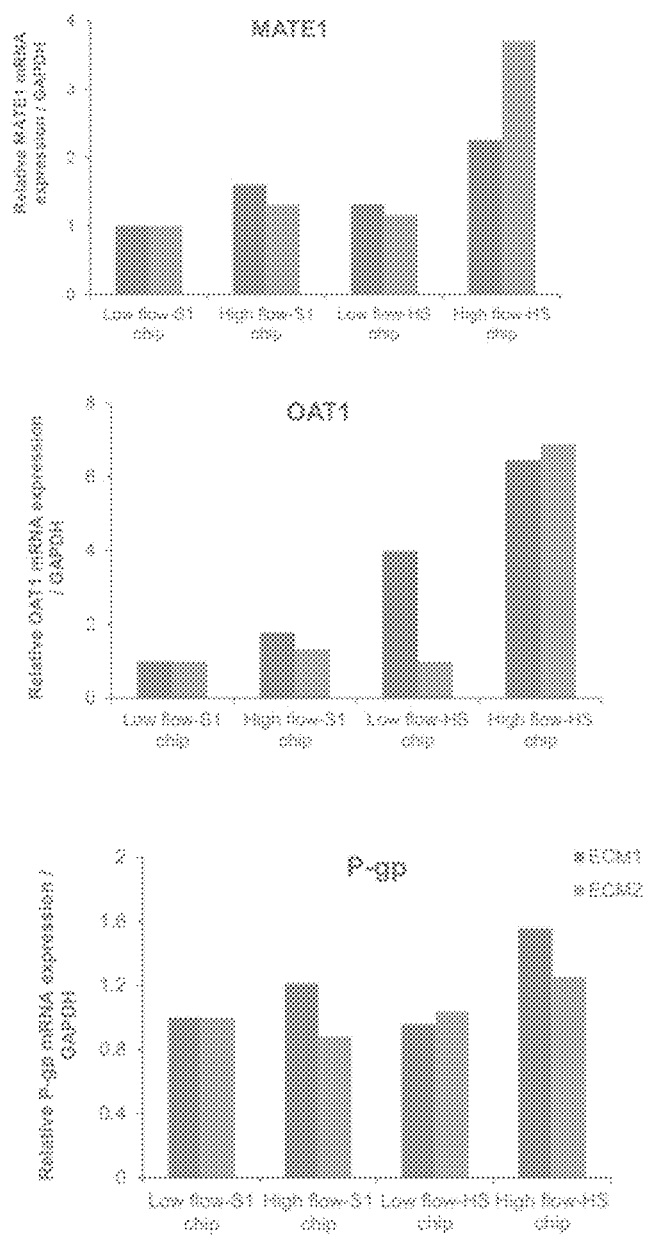
Figure 66:
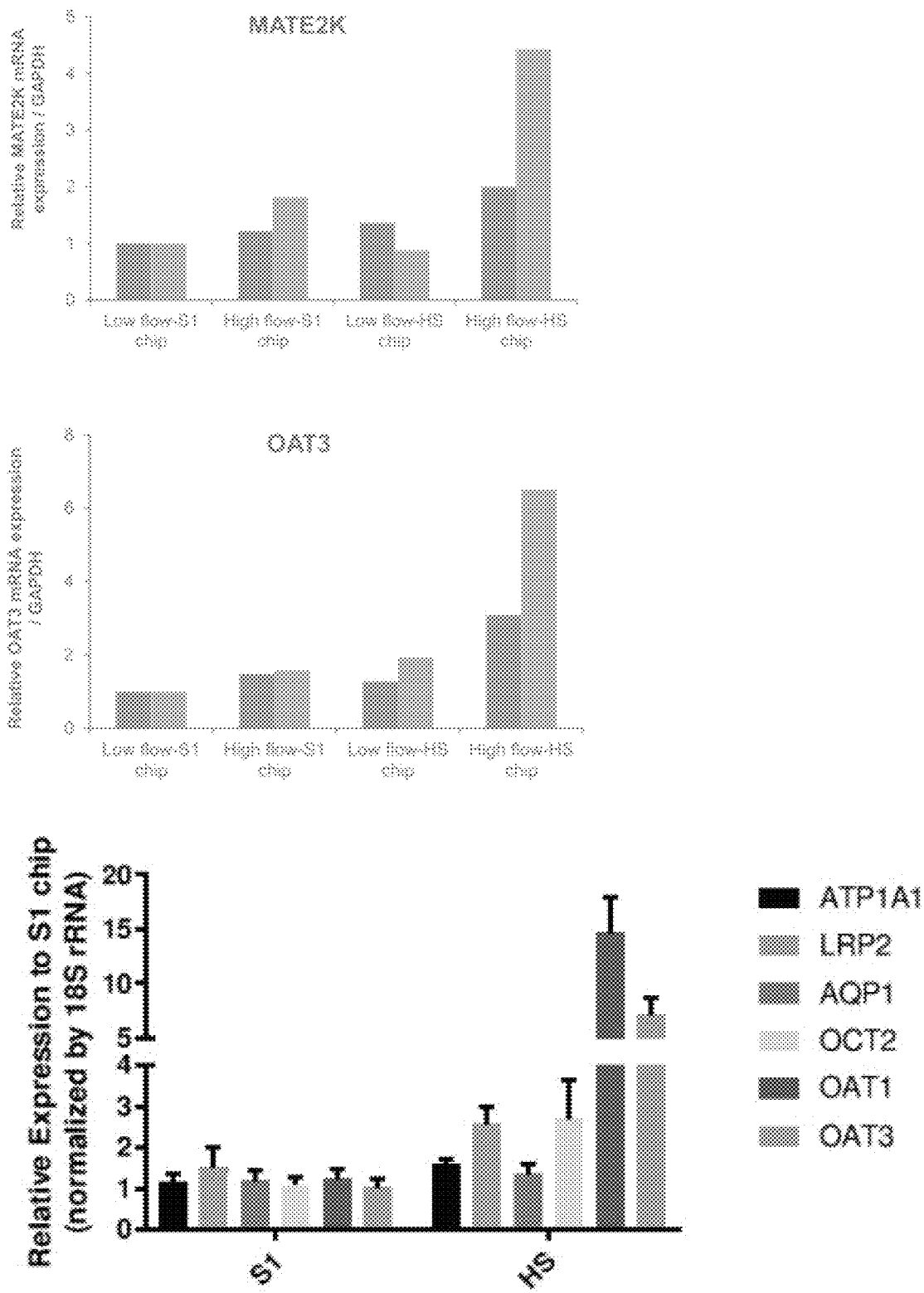

FIG. 66 shows exemplary Transporter function: Active Transporter Expression Assessment comparing chip configurations under low and high fluid flow. Exemplary transporter molecules include MATE1, MATE2K, OAT1, OAT3 and P-gp gene expression under Low flow-S1 chip; High flow-S1 chip; Low flow-HS chip; High flow-HS chip in addition to ECM1 (blue) vs. ECM2 (grey). Relative Expression of Markers comparing Chip Configurations: AQP1A1; LRP2; AQP1; OCT2, OAT1; and OAT3. (PT Kidney cells-Lonza; HS & S1; Flow: 30 µL/hr & 150 µL/hr provided by a culture module).

Figure 67:
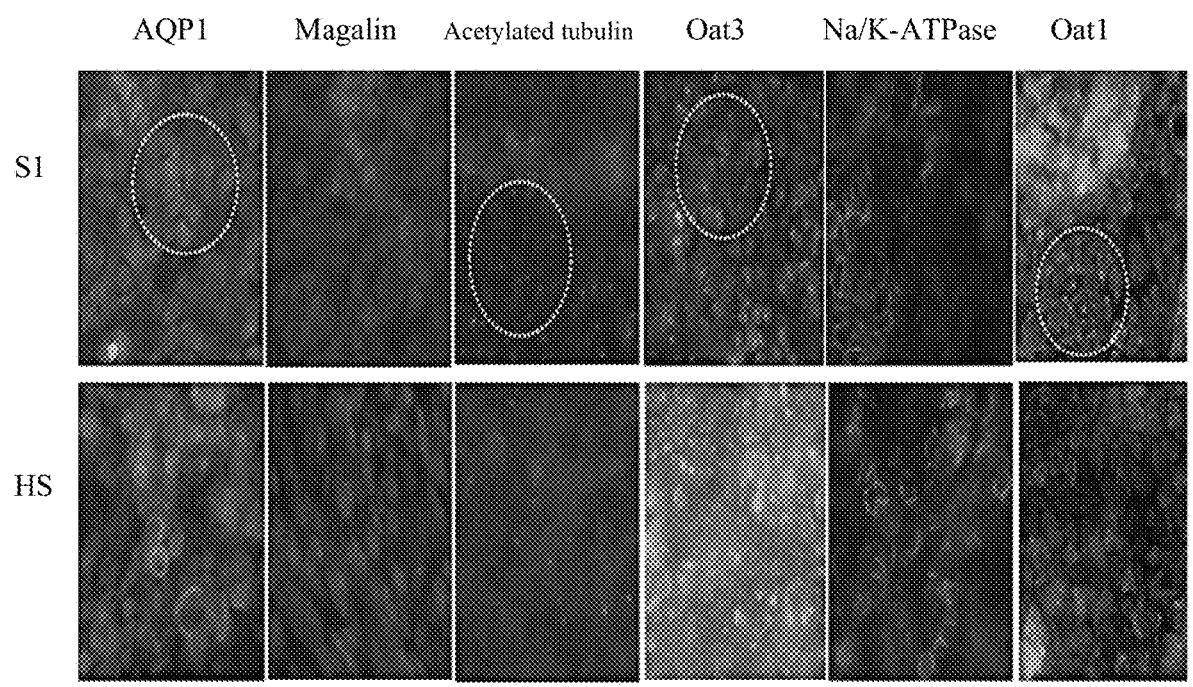

FIG. 67 shows exemplary Active Transporter Expression Assessment: Confocal imaging Kidney Proximal Tubular Cells on chip. Left to right: AQP1 (green); Megalin (red); Acetylated tubulin (red); Oat3 (green); Na/K-ATPase (red); Oat1 (green) and nuclei (blue). S1 upper row, high shear lower row. (PT Kidney cells-Lonza; HS & S1; Flow: 60 µL/hr provided by a culture module).

Figure 68:
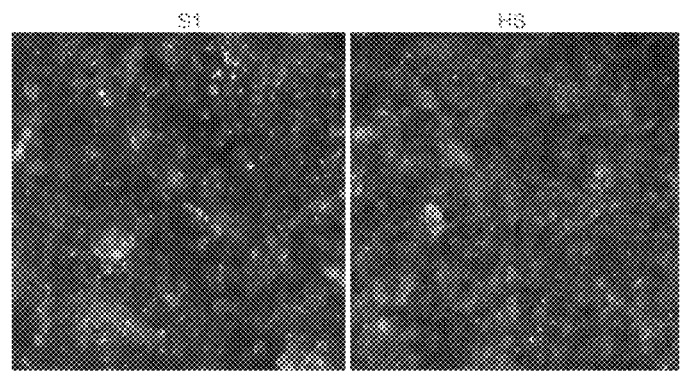
Figure 68:
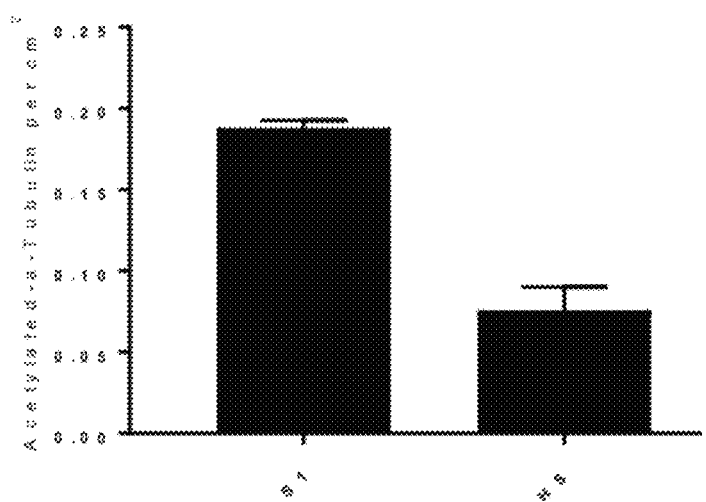

FIG. 68 shows exemplary Acetylated Tubulin: S1 Kidney Chip versus HS Kidney Chip, both membranes coated with ECM2. Immunoflorescence images showing acetylated tubulin (light color), left S1, right HS. acetylated tubulin per cm2 shows quantitavely there is more in S1 than in HS. (PT Kidney cells-Lonza; HS & S1; Flow: 60 µL/hr provided by a culture module).

Figure 69A:
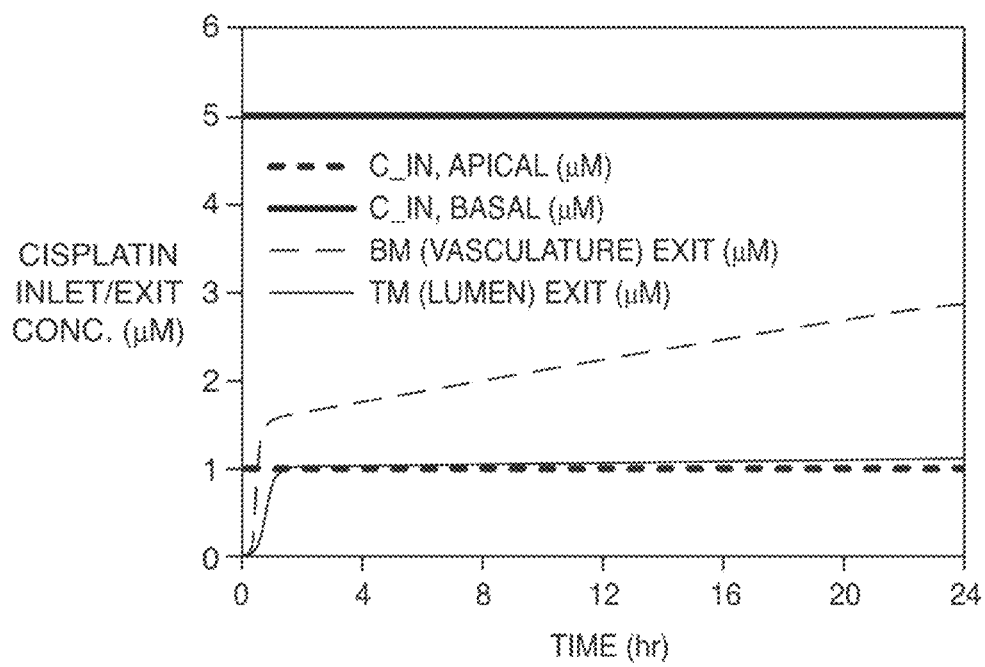
Figure 69B:
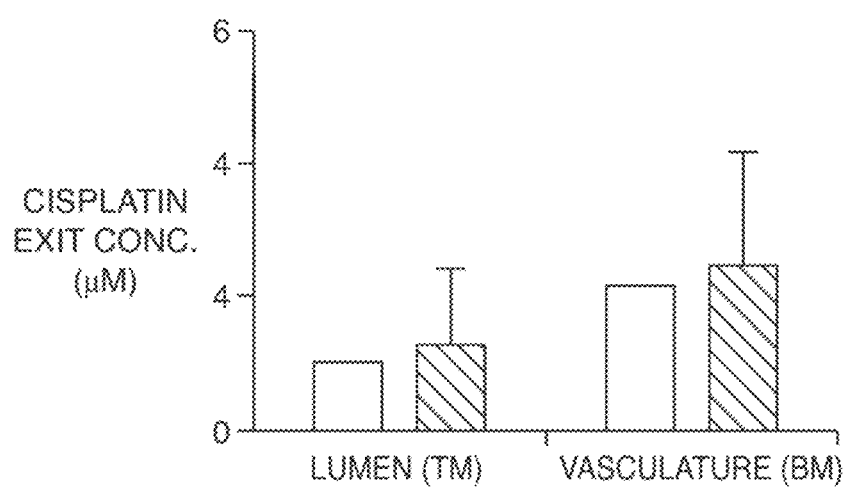

FIG. 69A-B shows exemplary Renal Cisplatin Clearance assays. FIG. 69A Cisplatin Inlet/Exit Concentration (µM). FIG. 69B Cisplatin Exit Concentration µM). (PT Kidney cells—ScienCell; Tall Channel; Flow: 60 µL/hr provided by a peristaltic pump).

Figure 70:
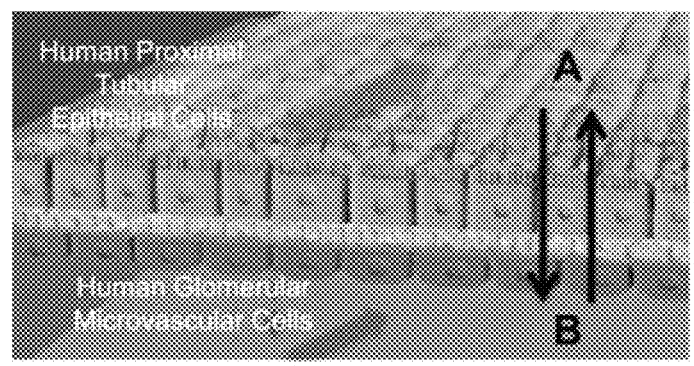
Figure 70:
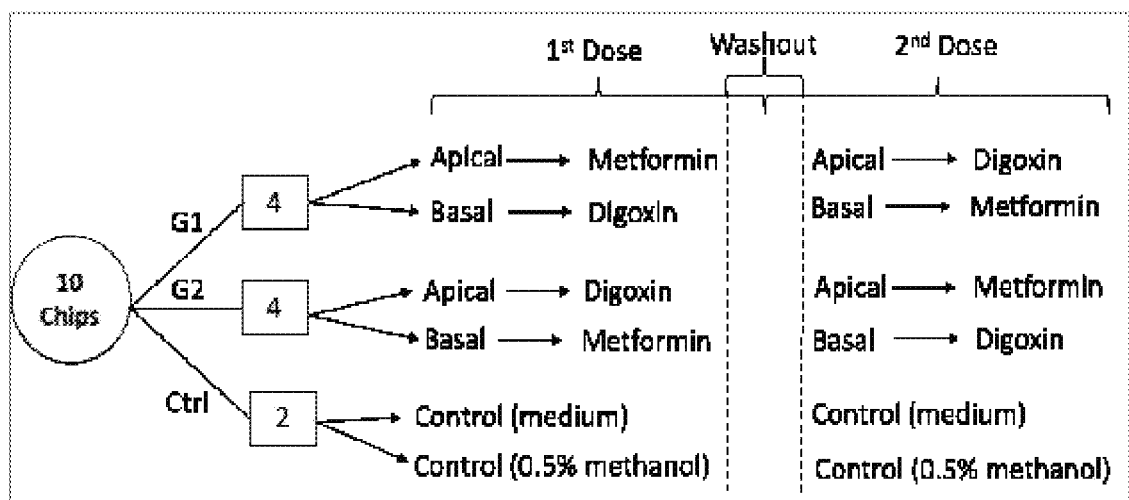

FIG. 70 illustrates active transport between the PT kidney epithelial cells and microvasculature endothelial cells in a PT-Kidney-Chip (upper) A to B and B to A. An illustration of an exemplary experimental plan (lower) is provided for assessing functionality of active transporters of proximal tubule epithelial cells using the proximal tubule Kidney Chip (lower). Functionality includes transporter function; drug interaction; and renal clearance for exemplary drugs Metformin and Digoxin. Metformin or Digoxin administered in the apical channel then after a washout the other drug is administered in the basal channel. (PT Kidney cells-Lonza; HS & S1; Flow: 30 µL/hr provided by a culture module).

Figure 71:
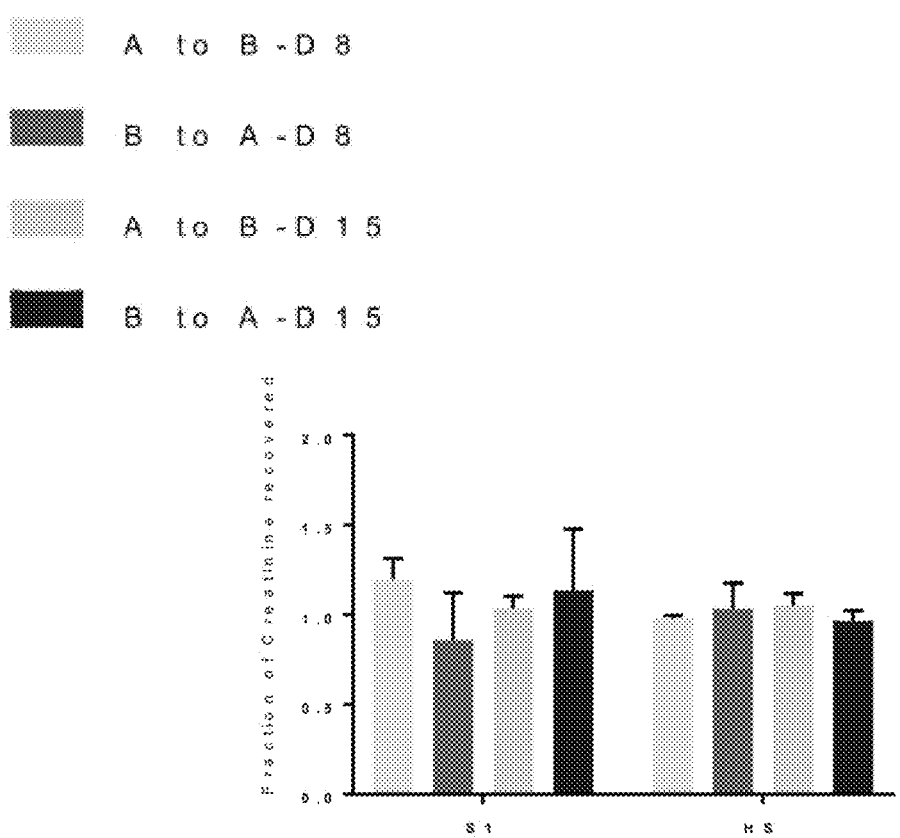

FIG. 71 shows exemplary Compound Efflux Testing Transporter function: Renal Clearance and Drug interaction: as a fraction of Creatine recovered on Day 8 and Day 15. (PT Kidney cells-Lonza; Chip type: HS & S1; Flow: 30 µL/hr provided by a culture module).

Figure 72:
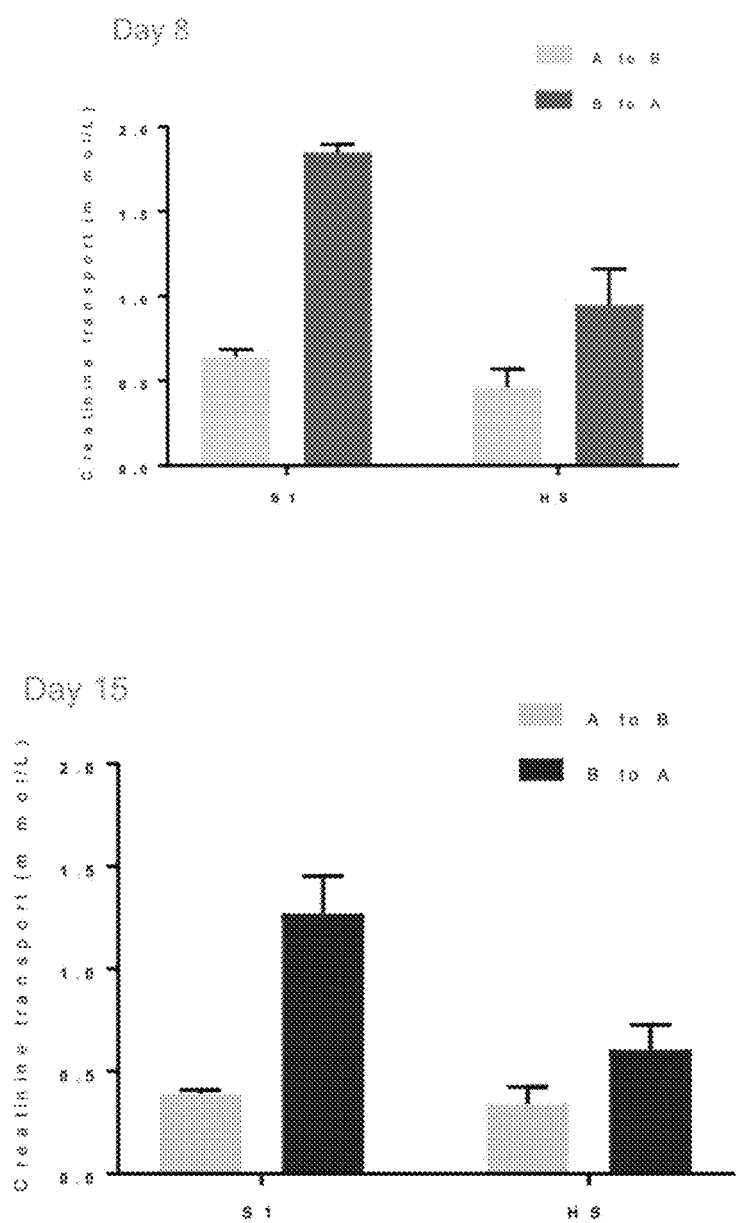

FIG. 72 shows exemplary Compound Efflux Testing Transporter function: Renal Clearance; Drug interaction and Transporter function. Creatine transport (m mol/L) Day 8 and Day 15. (PT Kidney cells-Lonza; Chip type: HS & S1; Flow: 30 µL/hr provided by a culture module).

Figure 73:
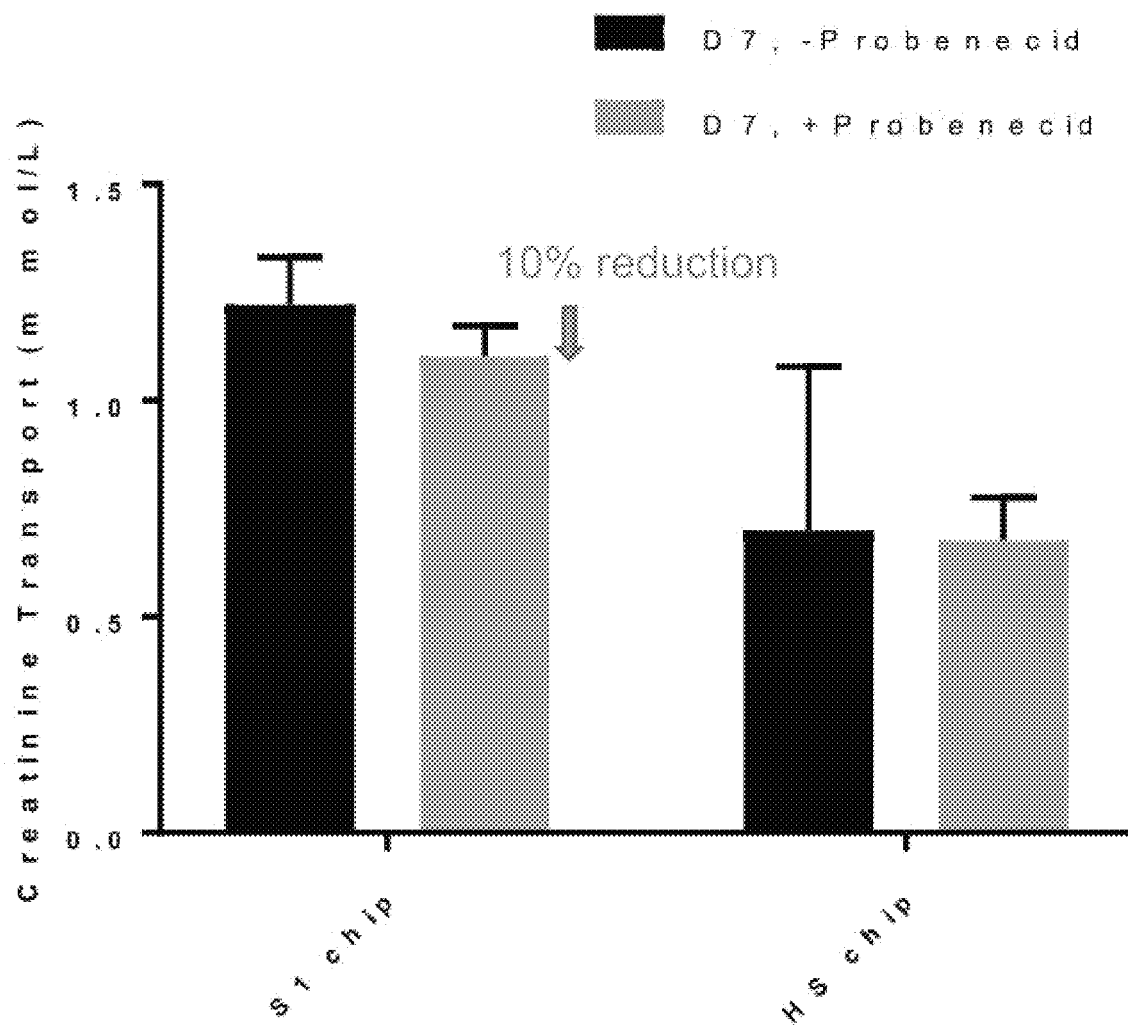

FIG. 73 shows exemplary Creatinine Transport (m mol/L), Basal to Apical (B to A), in the presence of an inhibitor Probenecid Day 7 on S1 and HS chips. (PT Kidney cells-Lonza; Chip type: HS & S1; Flow: 30 µL/hr provided by a culture module).

Figure 74:
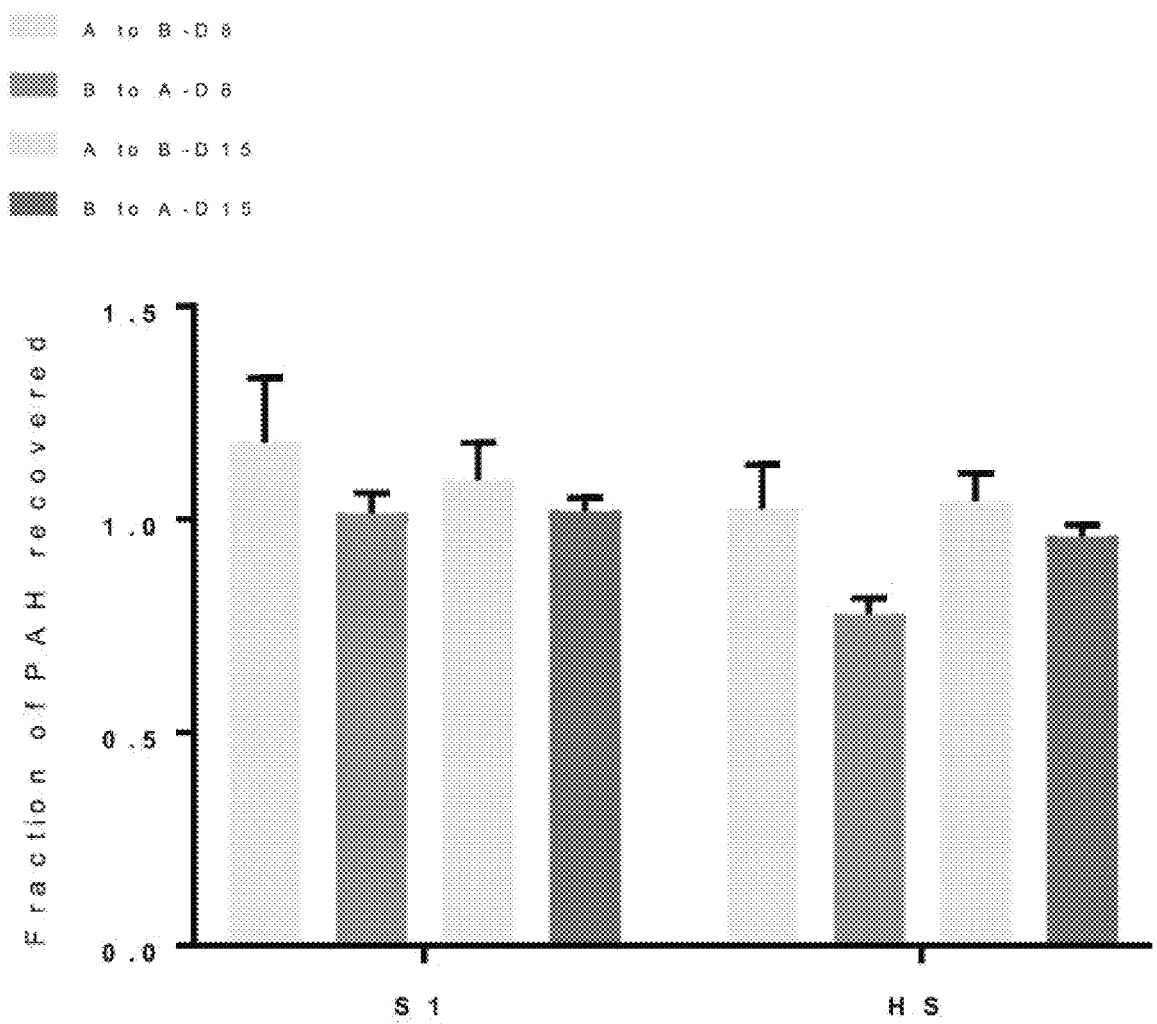

FIG. 74 shows exemplary Compound Efflux Testing as fraction of fraction of PAH recovered Day 8 and Day 15. (PT Kidney cells-Lonza; Chip type: HS & S1; Flow: 30 µL/hr provided by a culture module).

Figure 75:
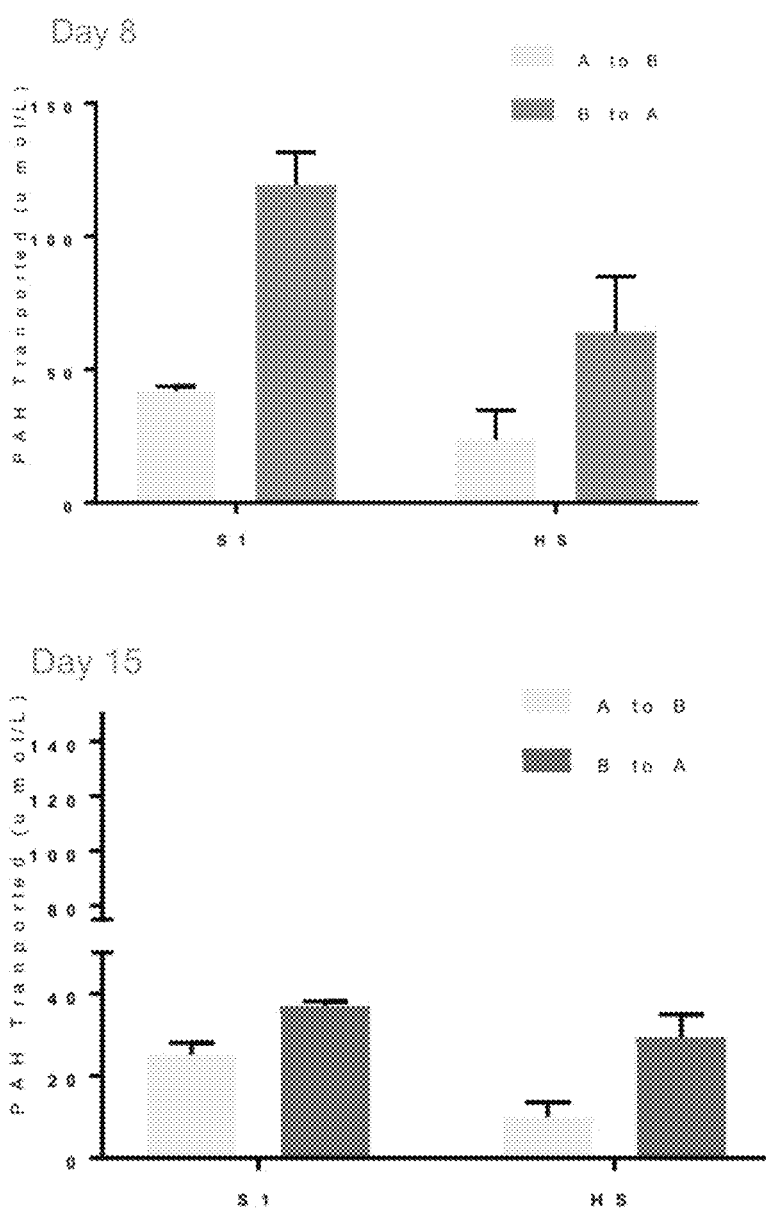

FIG. 75 shows exemplary Compound Efflux Testing Transporter function as PAH transport (m mol/L) Day 8 and Day 15. (PT Kidney cells-Lonza; Chip type: HS & S1; Flow: 30 µL/hr provided by a culture module).

Figure 76:
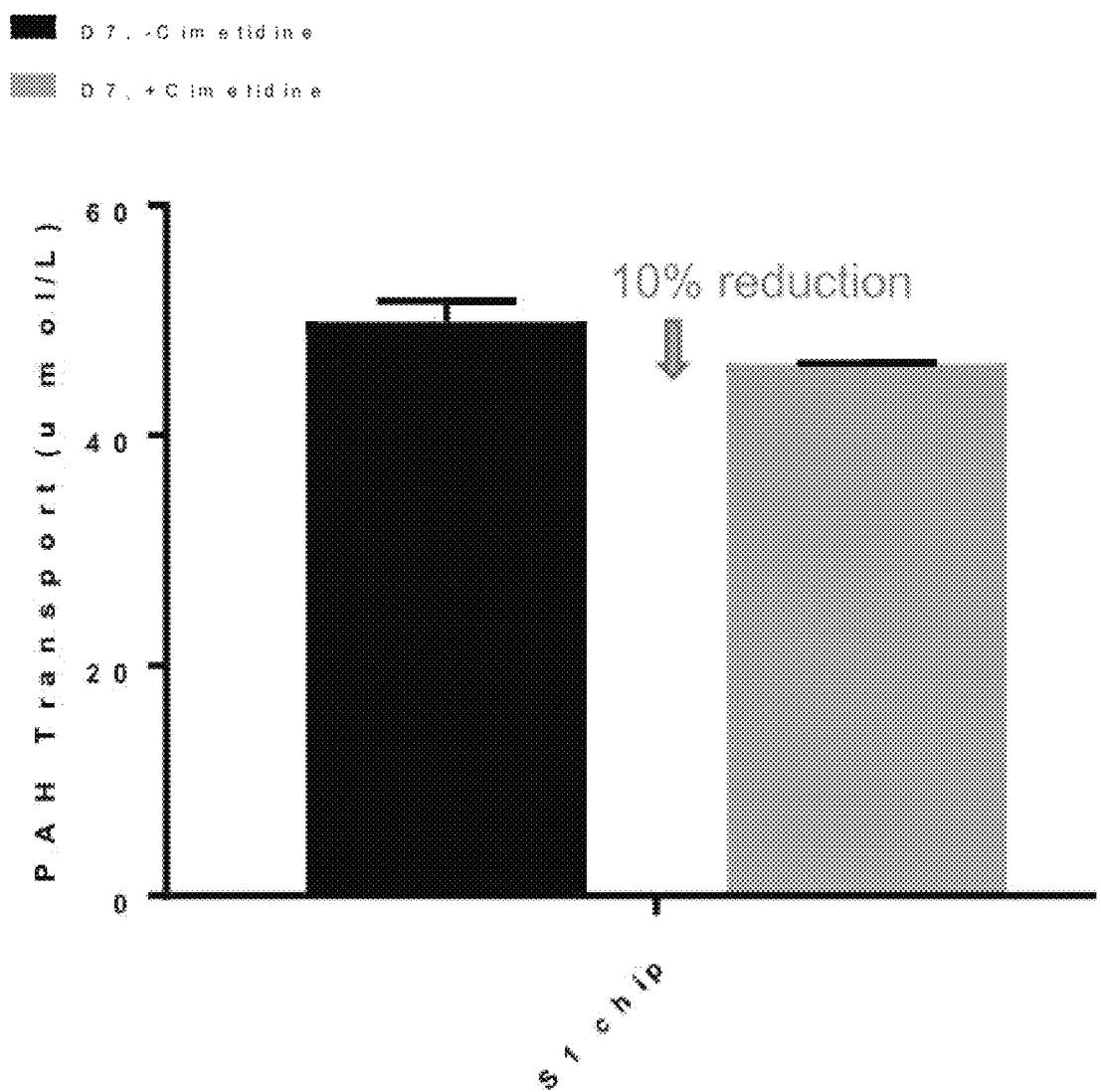

FIG. 76 shows exemplary PAH Transport in the presence of an inhibitor Cimetidine Day 7 on S1 chips. Day 8 and Day 15. (PT Kidney cells-Lonza; Chip type: HS & S1; Flow: 30 µL/hr provided by a culture module).

Figure 77:
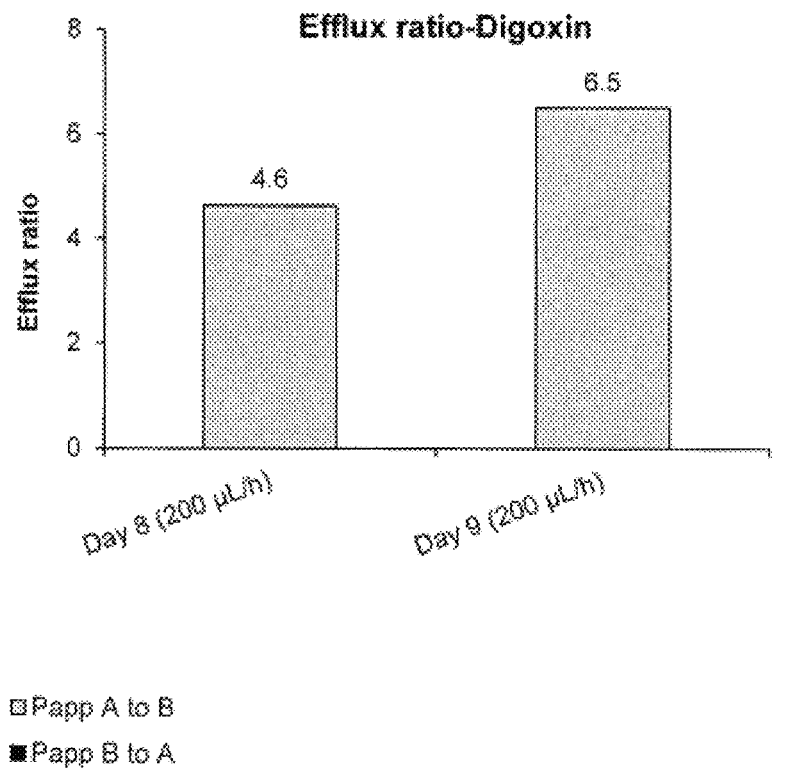
Figure 77:
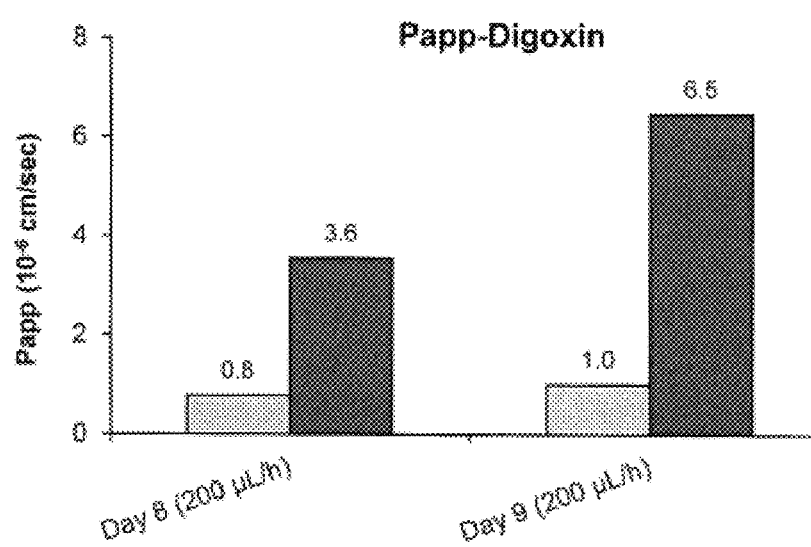

FIG. 77 shows exemplary efflux ratios and permeability of Digoxin treated embodiments of a PT Kidney chip on Days 8 and 9.

Figure 78:
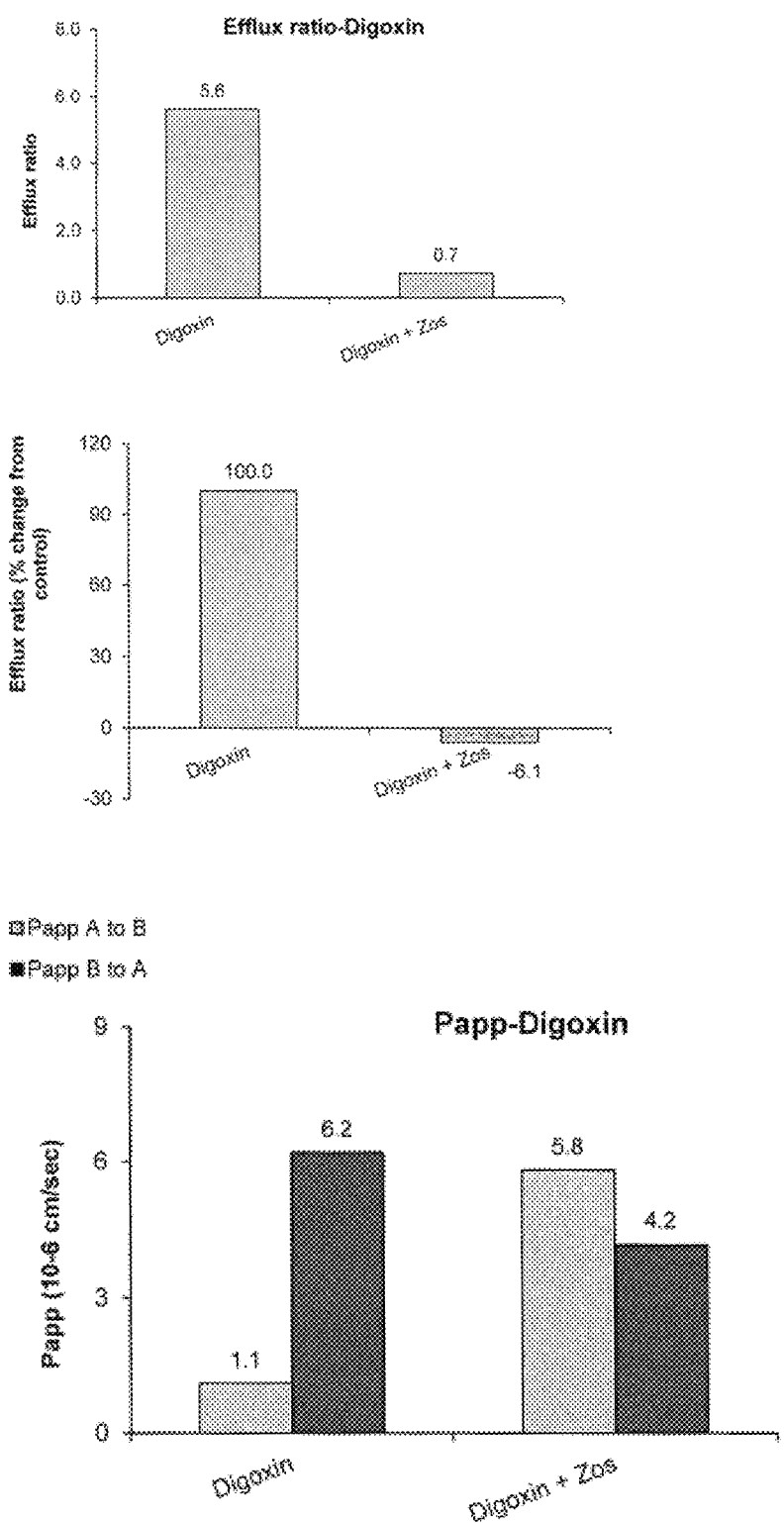

FIG. 78 shows exemplary efflux ratios and permeability of Day 14 Digoxin treated compared to Digoxin coadministered with an inhibitor, e.g. Zosuquidar (Zos), to embodiments of a PT Kidney chip.

Figure 79:
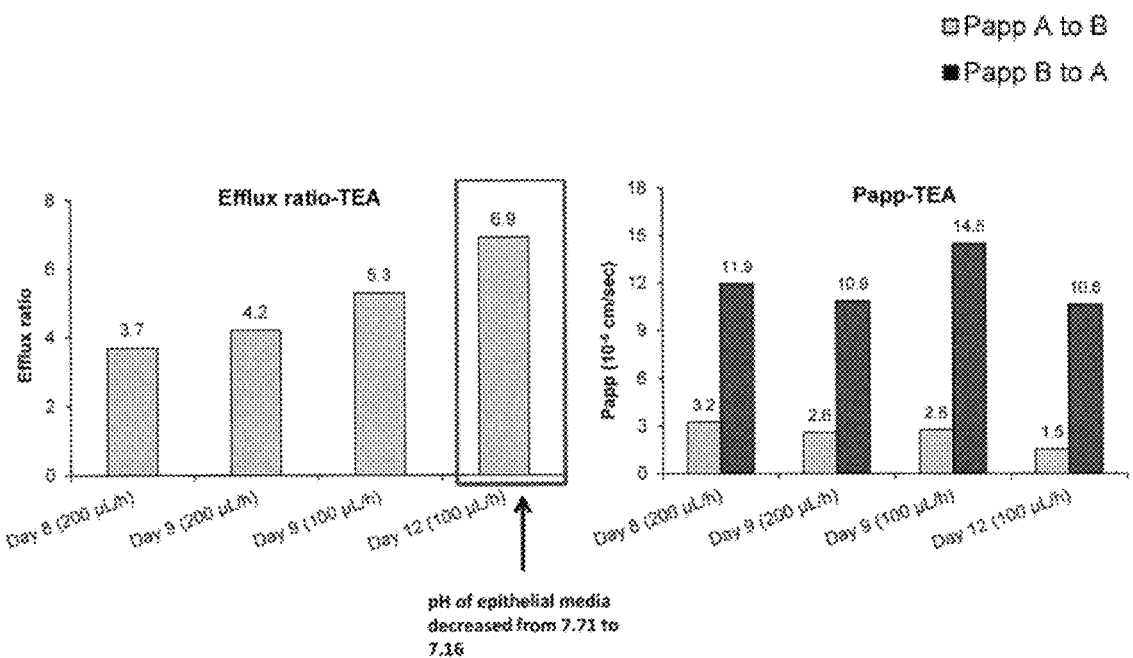

FIG. 79 shows exemplary efflux ratios and permeability of etraethylammonium (TEA) treated embodiments of a PT Kidney chip on Days 8, 9 and 12. Day 9 data is show comparing 100 uL/hr flow rtes with 200 uL/hr flow rates. Also shown is a pH decrease in the epithelial media on Day 12.

Figure 80:
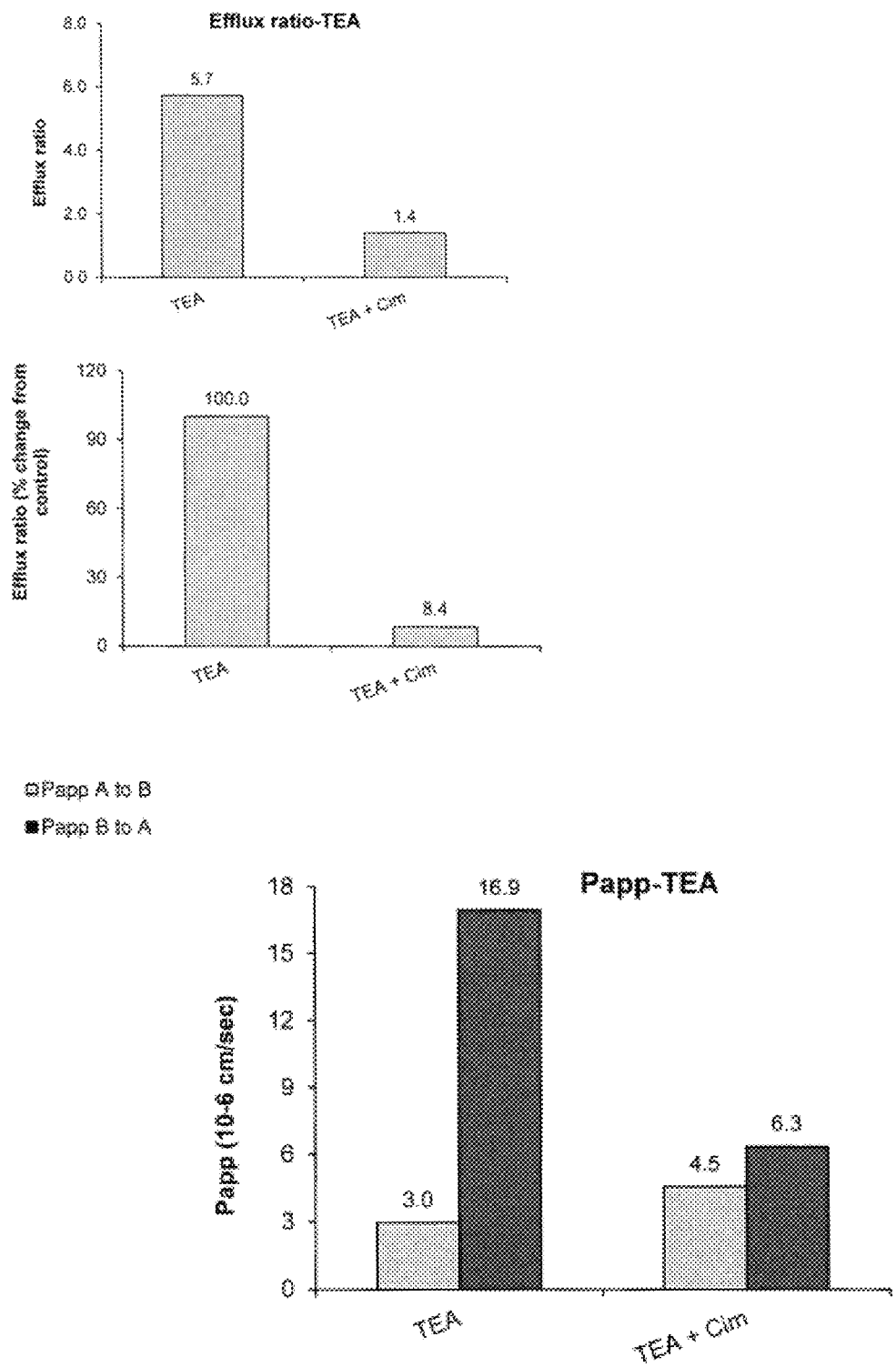

FIG. 80 shows exemplary efflux ratios and permeability of Day 14 TEA treated compared to TEA coadministered with an inhibitor, e.g. cimetidine, to embodiments of a PT Kidney chip.

Figure 81:
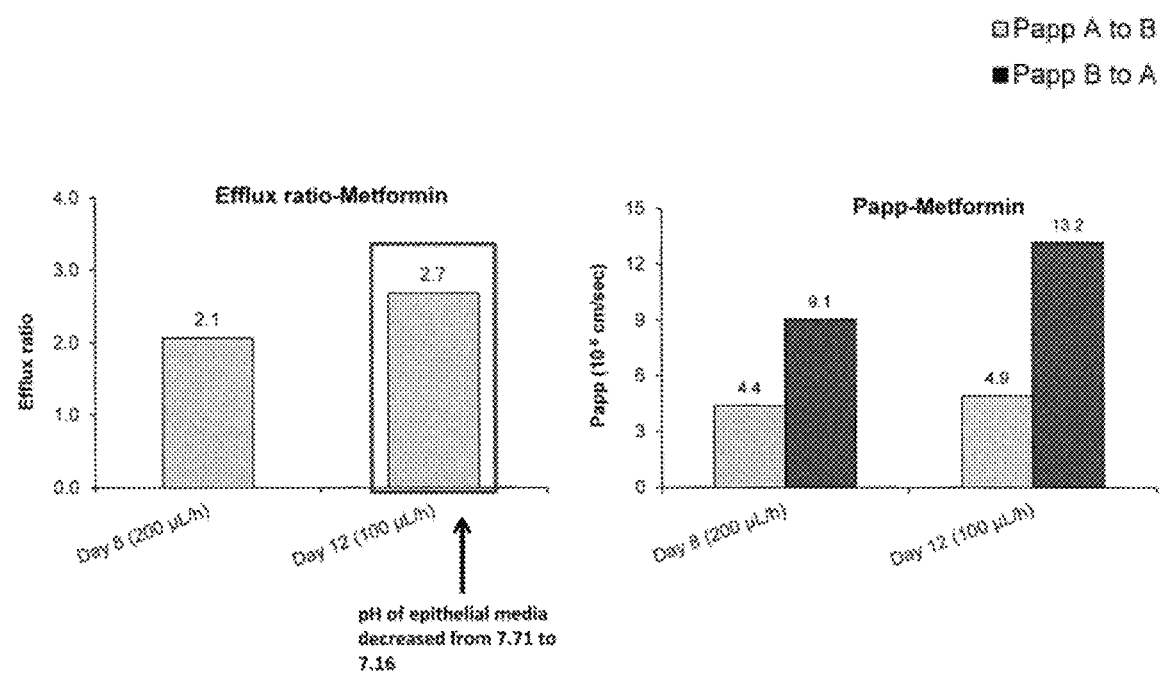

FIG. 81 shows exemplary efflux ratios and permeability of Metformin treated embodiments of a PT Kidney chip on Days 8 and 12 at different flow rates.

Figure 82:
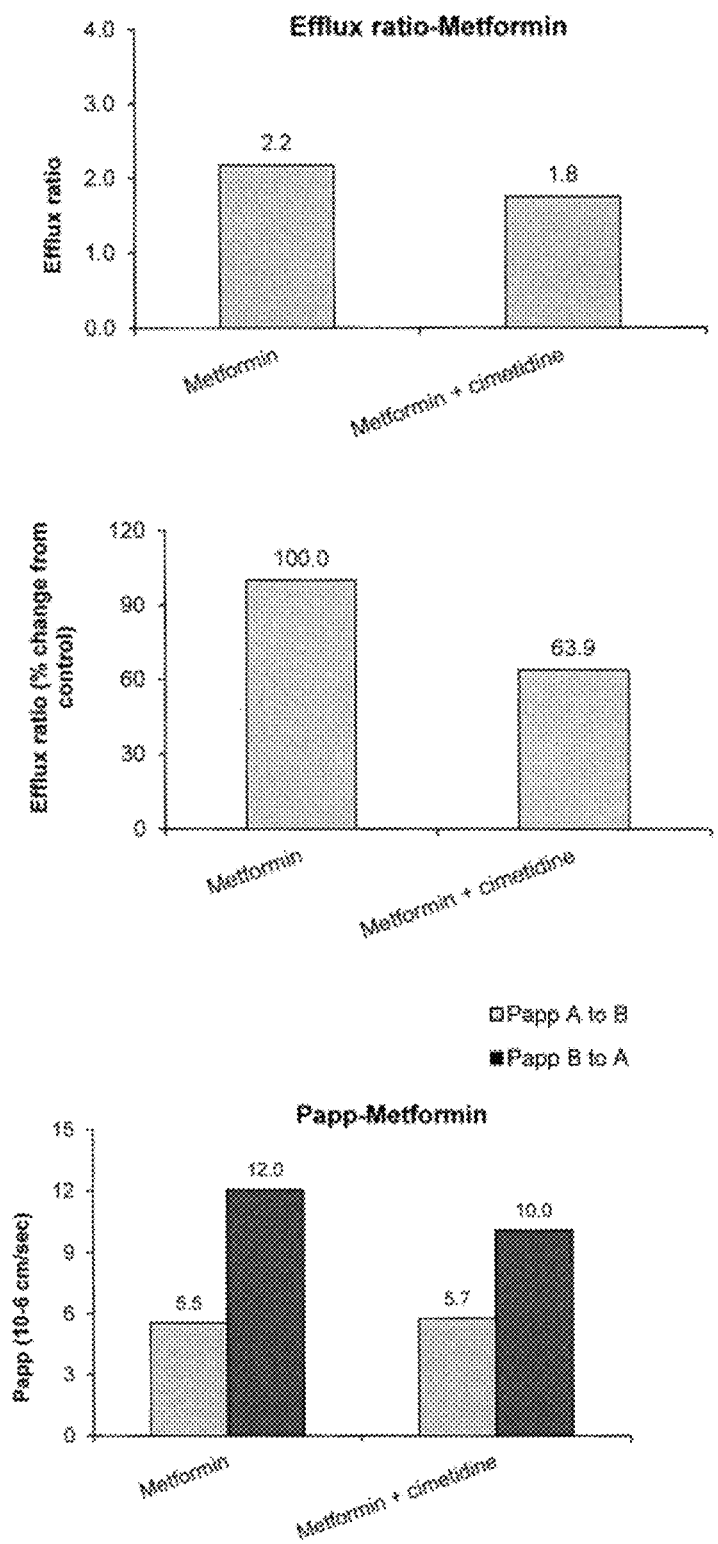

FIG. 82 shows exemplary efflux ratios and permeability of Day 8 Metformin treated compared to Metformin coadministered with an inhibitor, e.g. cimetidine, to embodiments of a PT Kidney chip.

Figure 83:
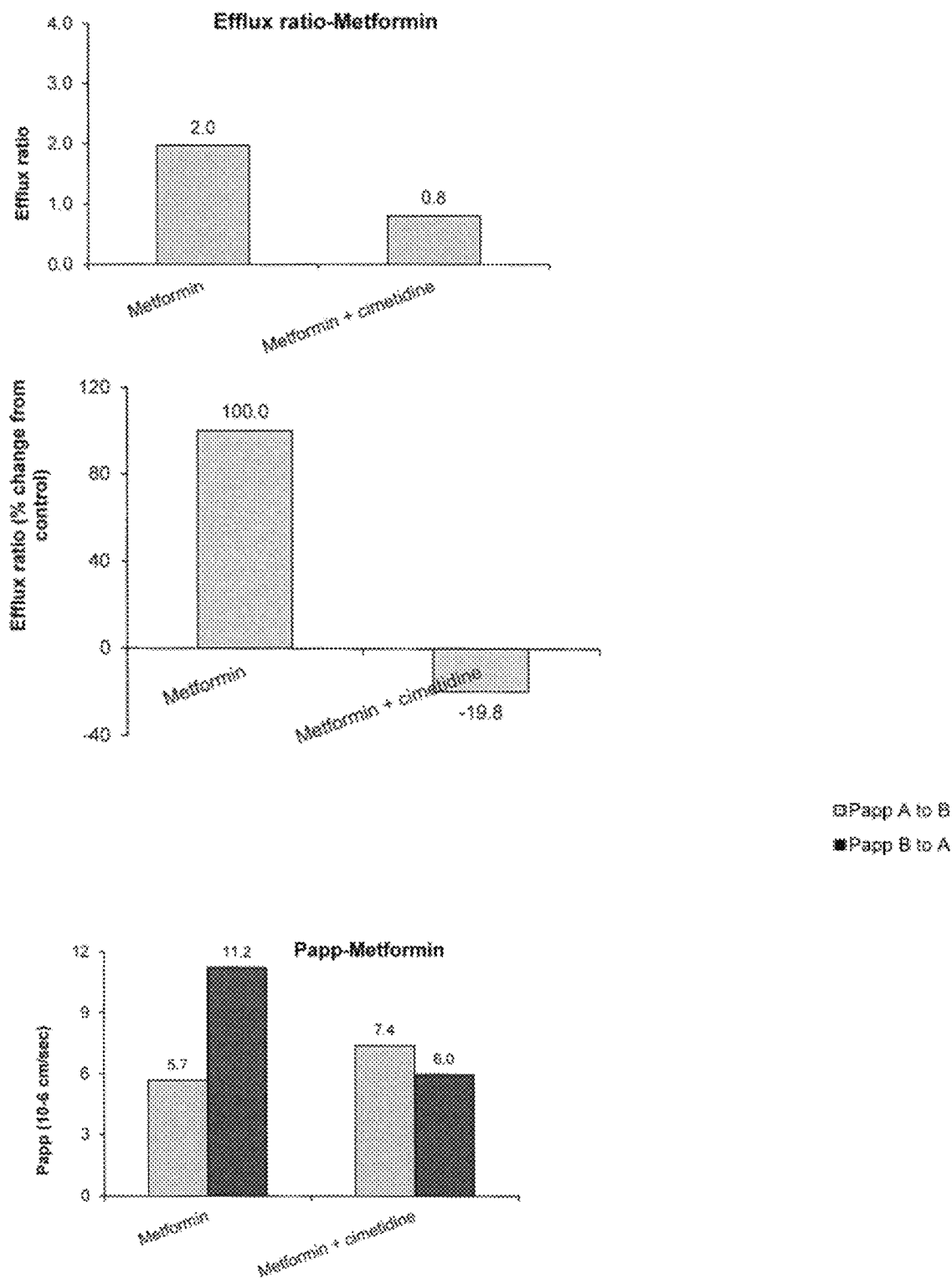

FIG. 83 shows exemplary efflux ratios and permeability of Day 10 Metformin treated compared to Metformin coadministered with an inhibitor, e.g. cimetidine, to embodiments of a PT Kidney chip.

Figure 84:
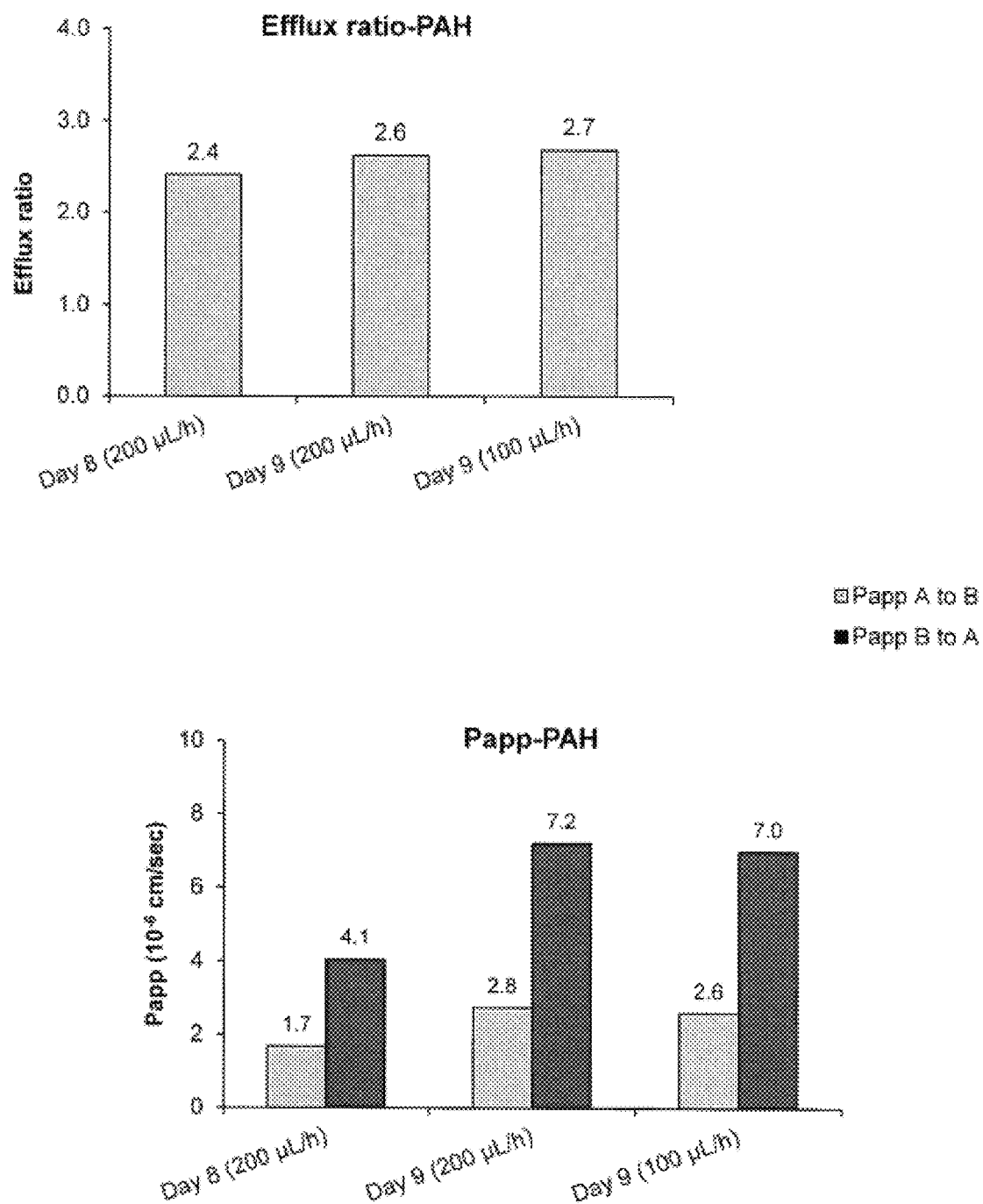

FIG. 84 shows exemplary efflux ratios, and efflux ratios as a percent change from control, and permeability of p-aminohippuric acid (PAH) treated embodiments of a PT Kidney chip on Days 8 and 12 at different flow rates.

Figure 85:
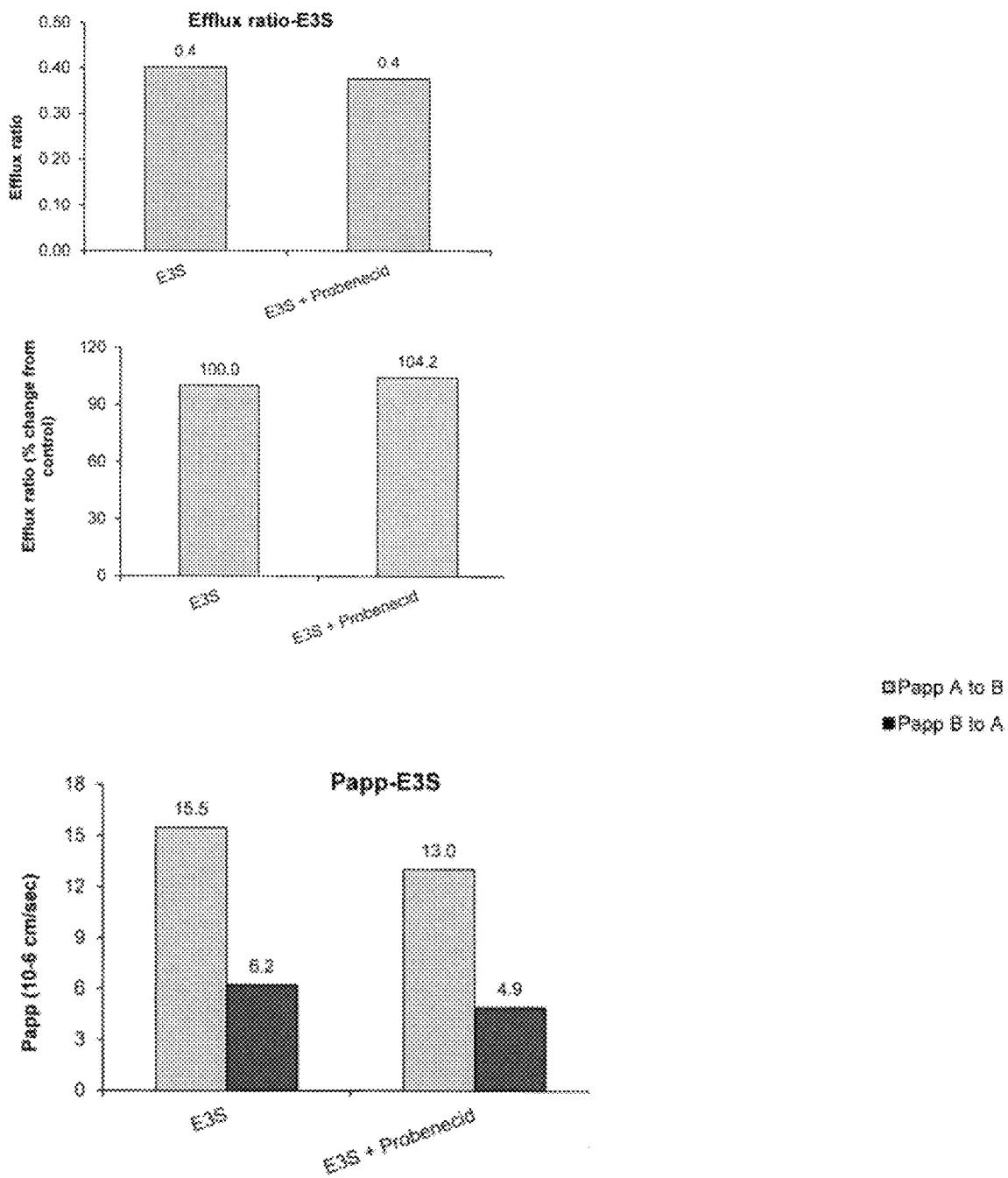

FIG. 85 shows exemplary efflux ratios and permeability of Day 10 Estrone-3-sulfate (E3S) treated compared to E3S coadministered with an inhibitor, e.g. probenicid, to embodiments of a PT Kidney chip.

Figure 86:
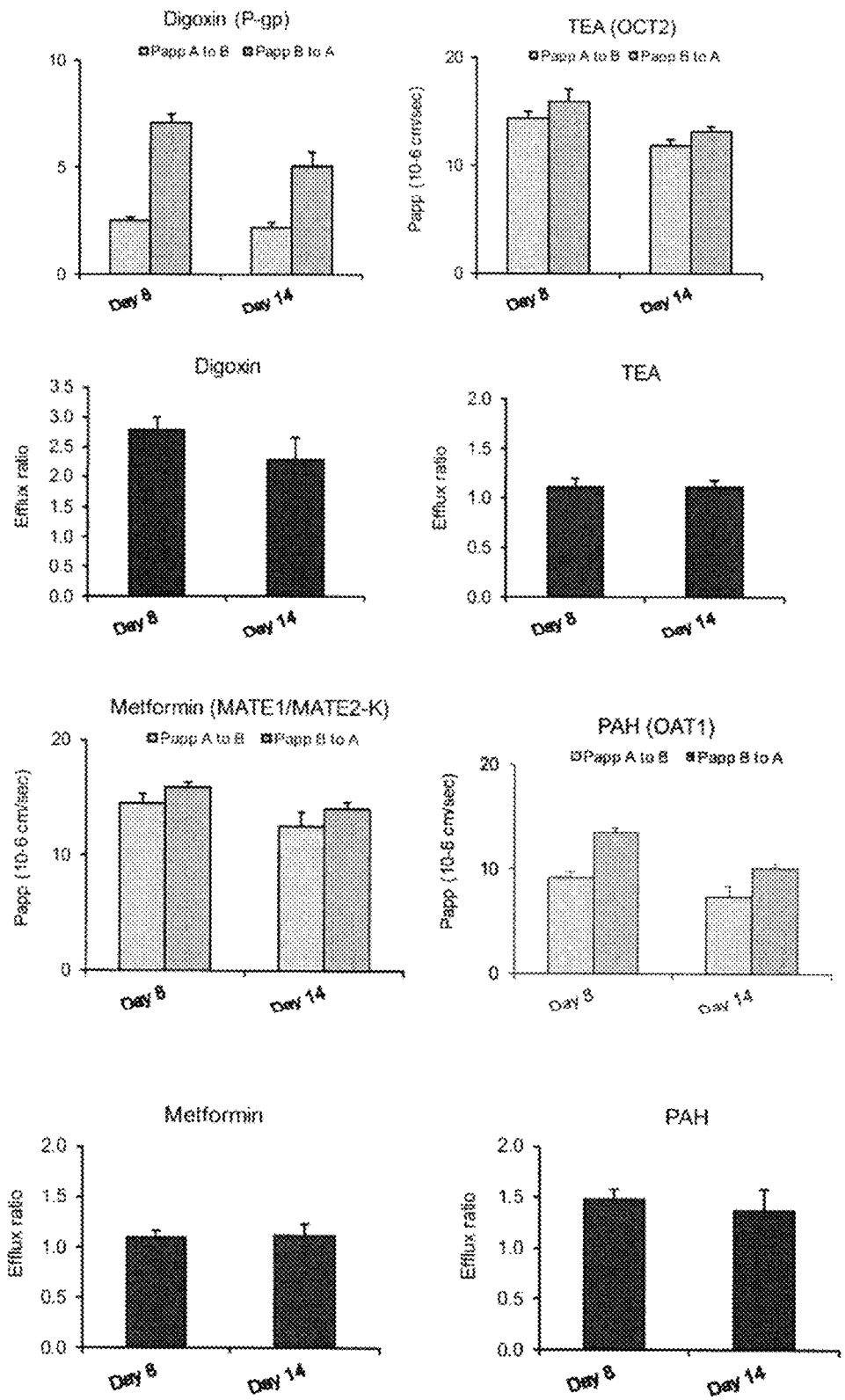

FIG. 86 shows exemplary transport activity data showing a loss of transporter activity of a substrate over time in Transwell kidney cell cultures (e.g. Digoxin for testing P-pg transporter molecule, TEA for testing Oct2 transporter molecules, Meformin for testing MATE1/MATE2-K transporter molecules, and PHA for testing OAT1 transporter molecules). Bar graphs show transport and efflux ratio comparisons between Day 8 and Day 14 of Papp A to B then Papp B to A of exemplary substrates for each transporter molecules.

Figure 87:
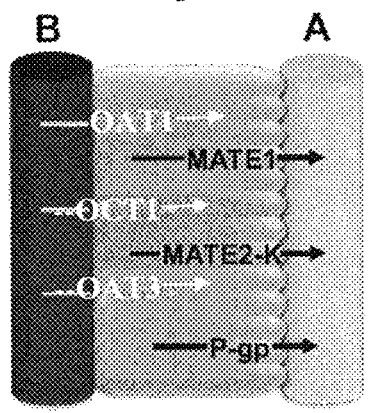
Figure 87:
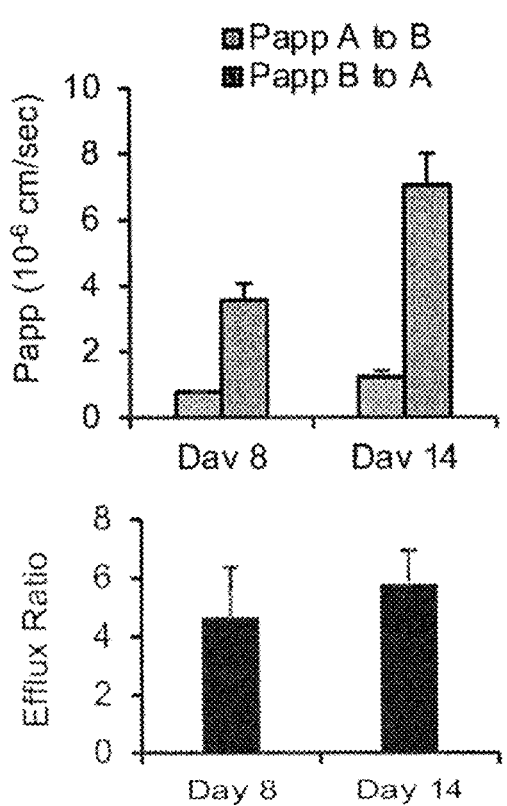
Figure 87:
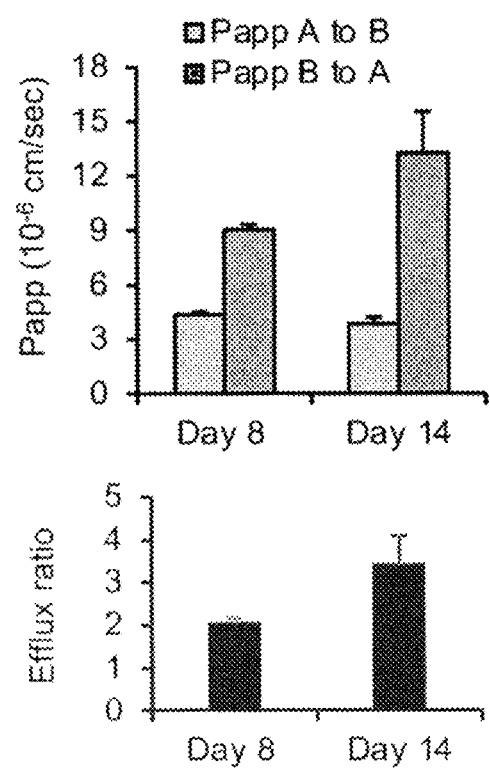

FIG. 87 shows exemplary chip based activity of apical membrane transporters showing maintenance of transport activity of a substrate over time in embodiments of Kidney-chips, as opposed to kidney cells in transwells, e.g. as in FIG. 86 (e.g. Digoxin for P-pg transporter molecules and Meformin for MATE1/MATE2-K transporter molecules). Bar graphs show transport and efflux ratio comparisons between Day 8 and Day 14 of Papp A to B then Papp B to A of exemplary substrates. Efflux ratio >2 is considered active transport. An efflux ratio less than 2 is not considered to show active transport.

Figure 88:
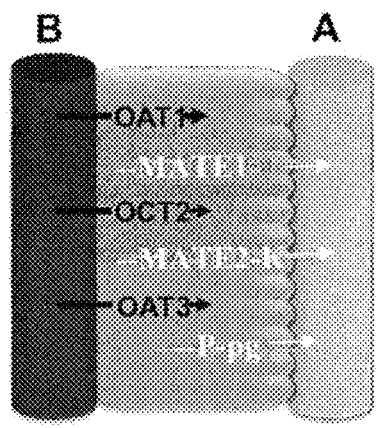
Figure 88:
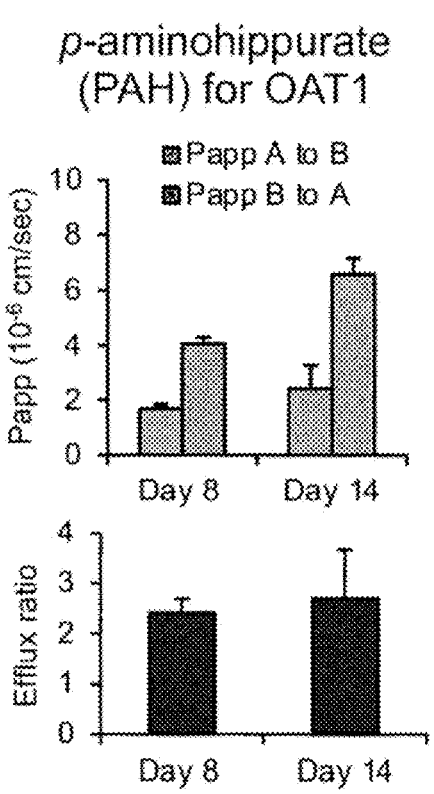
Figure 88:
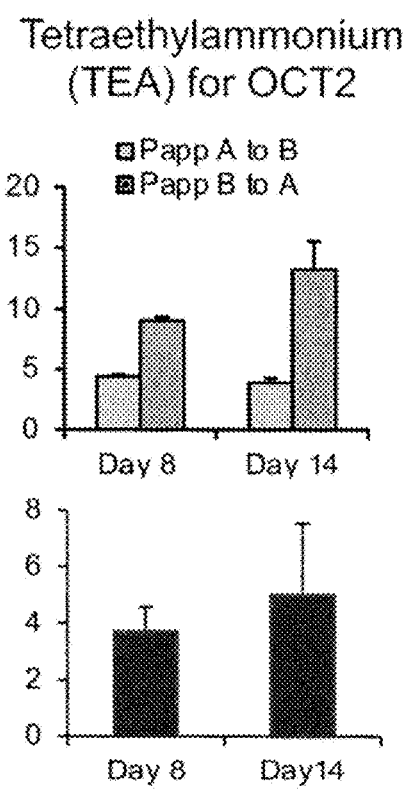

FIG. 88 shows exemplary chip-based activity of basolateral membrane transporters showing maintenance of transport activity a substrate over time in embodiments of Kidney-chips (e.g. PHA for OAT1 transporter molecules and TEA for OCT 2 transporter molecules). Bar graphs show transport and efflux ratio comparisons between Day 8 and Day 14 of Papp A to B then Papp B to A of exemplary substrates. Efflux ratio >2 is considered active tran An efflux ratio less than 2 is not considered to show active transport.sport.

Figure 89:
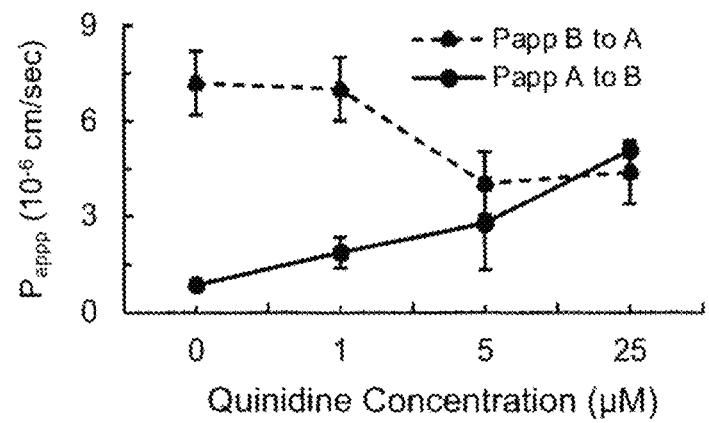
Figure 89:
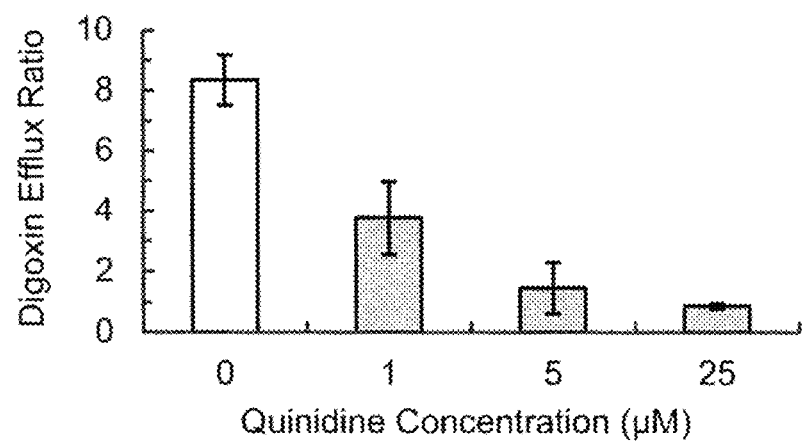
Figure 89:
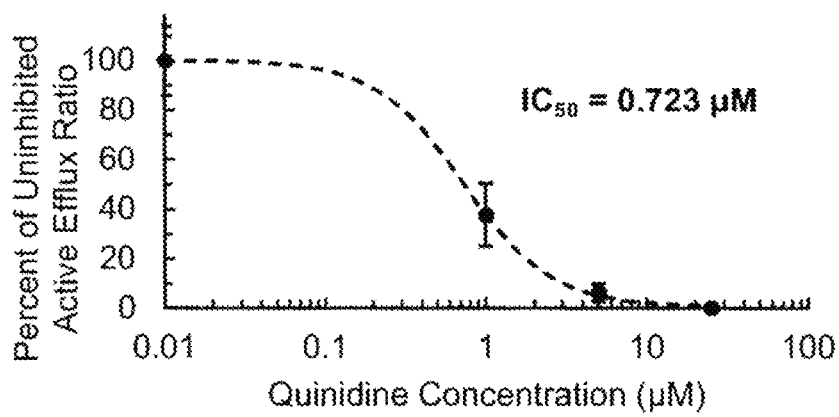

FIG. 89 shows exemplary concentration-dependent inhibition of high starting efflux ratio for Digoxin-Quinidine mediated DDI (P-gp). Victim is Digoxin. Perpetrator is Quinidine. Substrates for transporters are termed "victim". Inhibitors are termed "perpetrator". See, Table 23.

Figure 90:
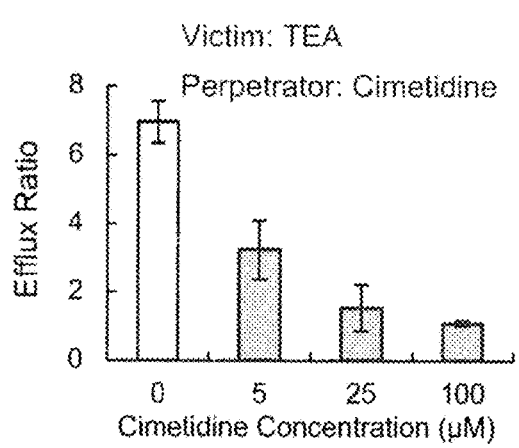
Figure 90:
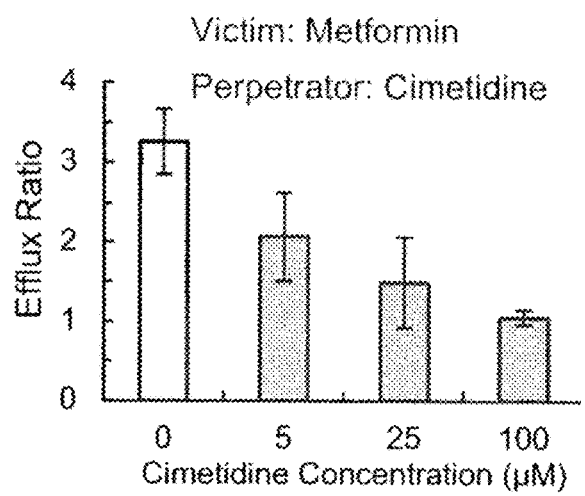
Figure 90:
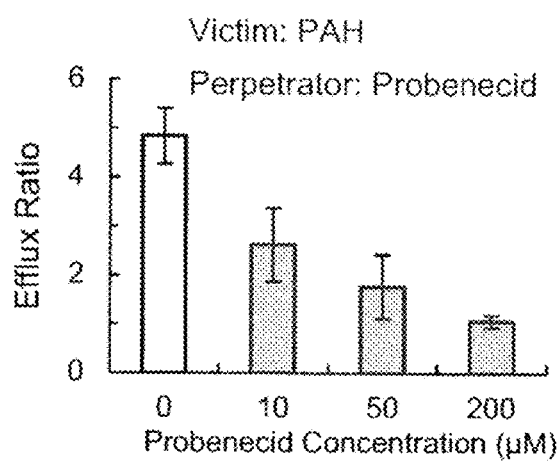
Figure 90:
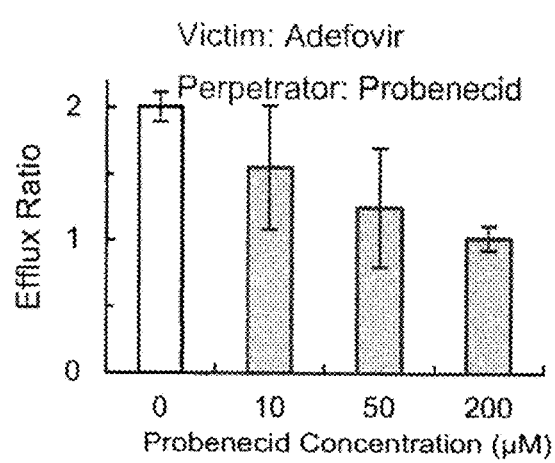

FIG. 90 shows exemplary assessment of drug-transporter interactions. Substrates for transporters are termed "victim". Inhibitors are termed "perpetrator". Transporter molecules are part of the transport system in Table 24.

Figure 91:
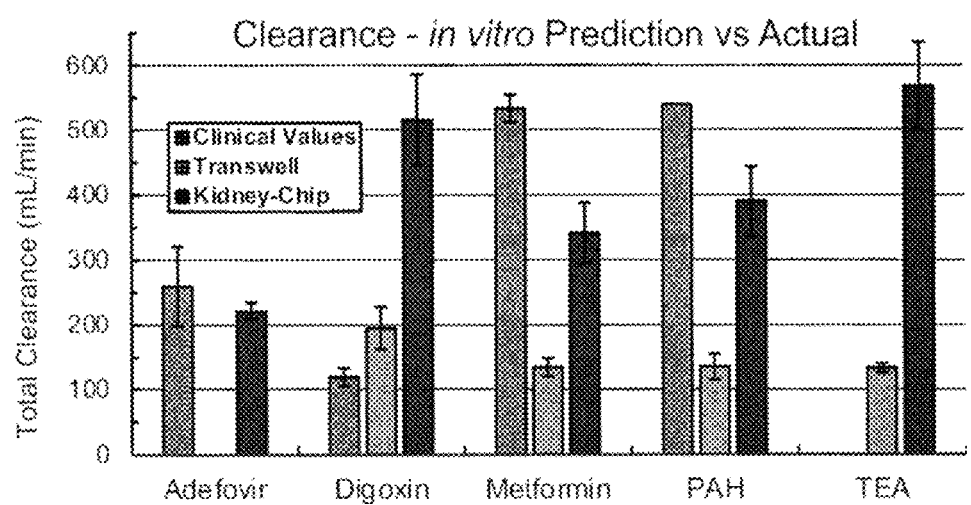

FIG. 91 shows exemplary prediction of clearance comparing in vitro prediction clearance (clinical values) vs. Transwell and Kidney-Chip data when no inhibitor is used. Bar graphs show exemplary comparisons between clinical values, Transwell cultures and Kidney-chips as total clearance (mL/min). For each substrate group: the left bar=clinical values, the middle bar=Transwell data, the right bar=Kidney-Chip data. See, also Table 25.

DEFINITIONS

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit).

As used herein, the term "biopsy" refers to a sample of tissue that is removed from a body.

As used herein, the term "parenchymal cells" refer to functional cells of an organ in the body, such as ciliated epithelial cells and nonciliated epithelial cells, e.g. kidney cells, keratinocytes, hepatocytes, etc. This is in contrast to the stroma or non-parenchymal cells, which refers to the structural tissue of organs, e.g., connective tissues including but not limited to several cell types and extracellular products such as ECM, blood vessels, nerves, ducts, etc. Examples include but are not limited to: parenchyma of the kidney referring to epithelial tissue (including renal tubules and corpuscles) whereas blood vessels, nerves, and supporting connective tissue of the kidney comprise kidney stroma. The parenchyma of the brain is nervous tissue (nerve cells and glia cells). The blood vessels within the brain and the connective tissue associated with these blood vessels are referred to as stroma. The parenchyma of a malignant neoplasm comprises cancer cells. Other tissues, including blood vessels, which grow to support the tumor, are referred to as stroma. Non-parenchymal cells or "NPC" may include human Renal Microvascular Endothelial Cells (hRMVECs).

As used herein, "Proximal Tubule-Chip" is interchangeable with "Proximal Tubule Kidney-Chip" and "PT-Kidney-Chip" and "PT Kidney Chip."

DESCRIPTION OF INVENTION

The present invention relates to microfluidic fluidic devices, methods and systems as microfluidic kidney on-chips, e.g. human Proximal Tubule-Chip, Glomerulus (Kidney)-Chip, and Collecting Duct (Kidney)-Chip. Such devices, methods and systems may be used for drug testing by (for example) measuring changes in transporter biomarkers, e.g. gene and protein expression of transporter molecules and injury molecules, e.g. changes in acetylated tubulin, along with changes in functions such as for albumin uptake, glucose transport, creatinine transport, PAH Transport, drug transport, and renal clearance. Further, such devices, methods and systems may be used for determining drug-drug interactions and their effect upon renal transporter functions. Importantly, they may be used for pre-clinical and clinical drug development for treating kidney diseases and for personalized medicine.

In one embodiment, a human Proximal Tubule-Chip was developed, as described herein. In one embodiment, a human Proximal Tubule-Chip is contemplated for use in assessment of renal transporter-based drug-drug interactions. In one embodiment, a Proximal Tubule-Chip is an engineered microphysiological system where human proximal tubule cells and glomerular microvascular endothelial cells are co-cultured under (preferably continuous) medium flow and (optionally) mechanical forces (e.g. stretch).

A preferred embodiment of a Proximal Tubule-(Kidney) Chip is a closed stretchable S1 (S-1) tall channel configuration creating a microenvironment including epithelial cells in the top channel and endothelial cells in the bottom channel. Top and bottom channels are separated by a porous stretchable membrane that allows for cell-cell interaction simulating kidney interactions observed in vivo. These two channels are fluidically independent for purposes of fluid flow, however molecules may diffuse between channels under certain conditions. One or more extracellular matrix proteins can be used in one or both channels. For example, in one embodiment, cells in each channel are seeded with organ-specific and/or cell-specific extracellular matrix proteins (ECM), and can be maintained in static culture for up to four days, depending on cell types used and/or desired use, before being connected to a cell culture module which may provide a continuous flow of cell culture media. Preferred perfusion manifolds and cell culture modules are described in U.S. Pat. No. 10,125,342, hereby incorporated by reference. When connected to a perfusion manifold and a cell culture module, conditions created in PT Kidney Chips simulate a human kidney's dynamic in vivo cellular microenvironment, including tissue-to-tissue interfaces, blood flow, and mechanical forces. Exemplary protocols describe methodology for embodiments of a Proximal Tubule Kidney-Chip. One embodiment of an environment created within each Proximal Tubule Kidney Chip-S1 simulates the function of a healthy human kidney. In other embodiments, a Proximal Tubule Kidney Chip simulates a malfunctioning or diseased human kidney. In other embodiments, a Proximal Tubule Kidney Chip can be used for drug testing, e.g. for increasing the function of a malfunctioning kidney, compensating for a diseased kidney, etc. In some embodiments, a Proximal Tubule Kidney Chip comprises primary kidney tubule cells isolated from a human biopsy for use in personalized medicine, e.g. functional tests, genetically based functional tests, drug testing, e.g. as described herein, etc.

Human primary proximal tubular epithelial cells were cultured in the proximal tubule channel on top of the porous membrane whereas (renal) glomerular microvascular endothelial cells were cultured on the opposite side of the same membrane in the vascular channel under continuous physiological flow to form a functional Proximal Tubule-Chip. This human Proximal Tubule-Chip recreates the natural tissue-tissue interface of the human kidney proximal tubule and the peritubular capillary. Thus a human Proximal Tubule-Chip may offer new ways to assess renal transporter-based drug-drug interactions and test for drug-associated kidney disorders.

In some embodiments, a Proximal Tubule-Kidney chip does not have endothelium. In some embodiments, a Proximal Tubule-Kidney chip has endothelium.

It is not meant to limit a Kidney Chip to a PT Kidney Chip. Indeed, several other types of Kidney chips are contemplated for production and use. Thus, embodiments of Kidney-Chip microfluidic devices further include but are not limited to an exemplary Glomerulus (Kidney)-Chip model comprising primary podocytes (upper channel), a membrane (white) separating renal microvascular endothelial cells (lower channel); an exemplary Collecting Duct (Kidney)-Chip model comprising primary collecting duct epithelial cells (upper channel), a membrane (white) separating renal microvascular endothelial cells (lower channel). In some embodiments, such types of Kidney chip do not have endothelium. In some embodiments, such types of Kidney chip have endothelium. See Table 1 and exemplary areas of a human kidney illustrated in FIG. 3A, upper left and upper right.

Figure 3A:
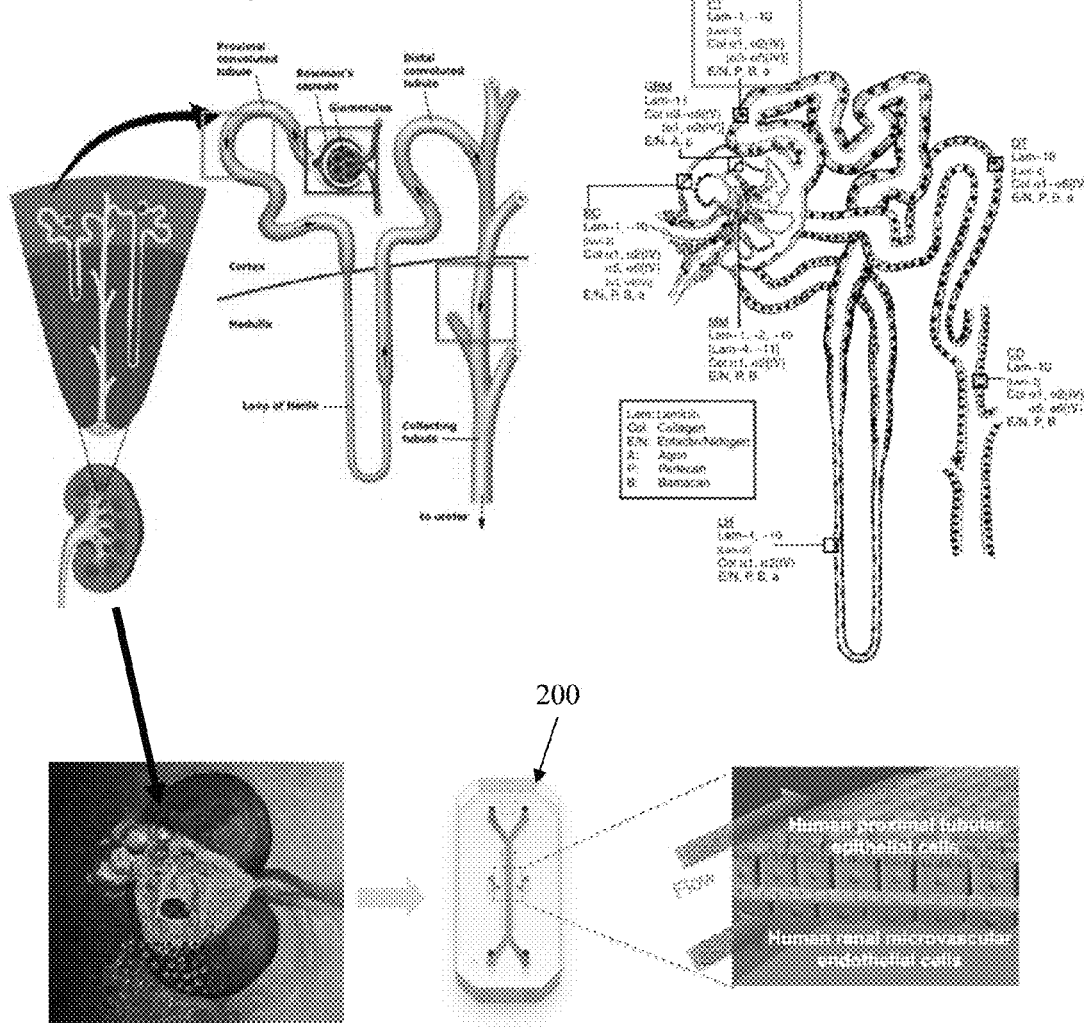
FIG. 3A-D shows exemplary schematic embodiments of types of Kidney-chips based upon physiologically different parts of a kidney, as shown schematically here (FIGS. 3A-3D).
Figure 3B:
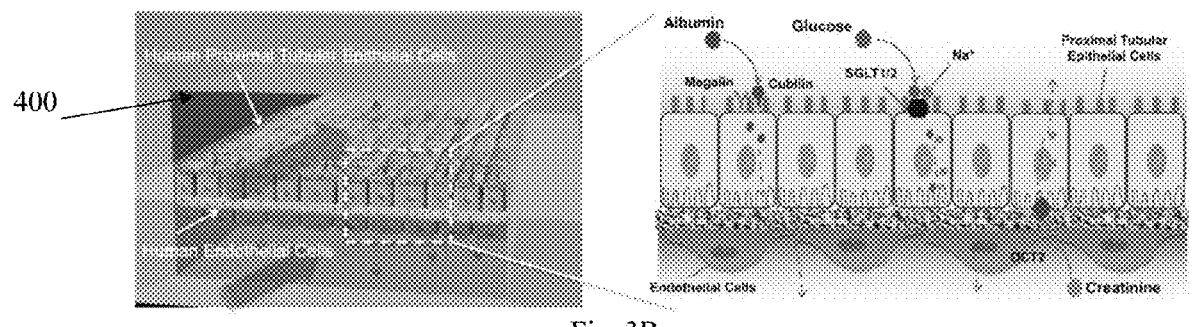
Figure 3C:
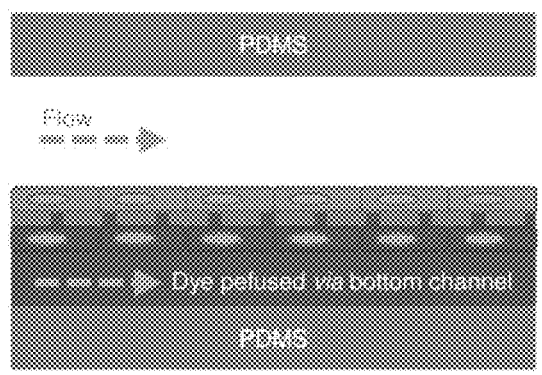

FIG. 3A-C shows exemplary schematic embodiments of types of Kidney-chips based upon physiologically different parts of a kidney, as shown schematically here (FIGS. 3A-3C).

Figure 3D:
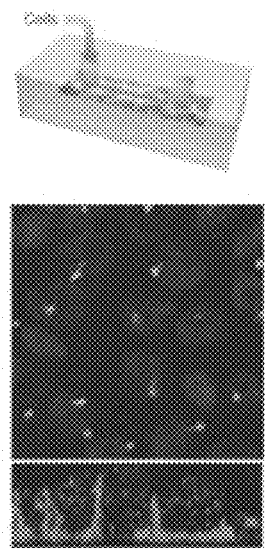

FIG. 3D shows, exemplary images of immunofluorescent staining showing cellular compartments from one embodiment of a PT Kidney Chip without endothelial cells (FIG. 3D), Jan et al., 2013.

FIG. 3A lower middle image shows one exemplary schematic of a human Proximal Tubule-Chip 200 engineered using an S-1 Chip from Emulate, Inc., which is made of polydimethylsiloxane (PDMS) and contains an upper channel (1 mm high×1 mm wide) and a lower channel (0.2 mm high×1 mm wide), separated by a porous PDMS membrane that is coated with optimized extracellular matrix (ECM). The upper channel serves as a tubular lumen and is lined in one embodiment by primary human epithelial cells seeded on the ECM coated membrane. The lower channel, lined with endothelial cells, represents the peritubular vasculature.

FIG. 3A further illustrates, upper left, a human kidney, including a cortex area comprising a proximal convoluted tubule, Bownan's capsule, glomuerulus, distal convoluted tubule and medulla comprising a Loop of Henie, and collecting tubules. Jang and Suh, Lab Chip 10, 36 (2010). Front cover; Jang, et al., Integrative Biology. 3, 134 (2011); Jang, et al., Integrative Biology, 5, 1119 (2013) Front cover. The illustration in the upper right shows exemplary extracellular components found in each of the regions. Right schematic showing types of ECM in regions of the Kidney, Kidney International (1999) 56, 2016-2024. K.-J. Jang and K. Y. Suh, Lab Chip 10, 36 (2010). The illustrations shown in the lower row show one embodiment of a Kidney (left) as a Human Proximal Tubule-Chip (middle) model (right) comprising primary proximal tubular epithelial cells (upper channel-green), a membrane (white) separating renal microvascular endothelial cells (lower channel-red). Blue arrow (upper) and red arrow (lower) shows directional fluid flow.

FIG. 3B shows an exemplary schematic of a fluidic chip (device) as in FIG. 3A, left, aligned with a schematic of cellular compartments (right). An exemplary layer of Proximal Tubular Epithelial Cells (above—green or gold) and Endothelial Cells (below—red or blue) separated by a membrane (grey). Examples of in vivo kidney cell functions contemplated for use in readouts of kidney activity in vitro, comprising measuring expression of or levels of albumin transport, glucose transport, Na+ transport, Megalin, Cubuin, SGLT1/2 on the apical side, while OCT2 and creatinine transport on the endothelial cell layer side, for non-limiting examples. Polydimethylsiloxane (PDMS) (top of chip) 400. Arrow shows directional fluid flow over the top of the parenchymal cells (green), e.g. kidney cells, attached to a membrane (dotted lines) with endothelial cells depicted in red. Dye may be perfused through the fluid flowing through the bottom channel lined with endothelial cells over the bottom of the chip (PDMS).

FIG. 3C shows one exemplary embodiment of a kidney-on-a-chip in which human kidney proximal tubular epithelial cells are cultured on the top of a porous membrane separating two channels, enabling analysis of transcellular transport, uptake and secretion (top-schematic). The upper fluorescence image of the epithelium shows enhanced formation of primary cilia (green) on the apical cell surfaces; the lower fluorescence cross-sectional view shows repolarization of Na+K+ ATPase (magenta) to the basal side.

FIG. 3D shows one exemplary embodiment of a kidney-on-a-chip without endothelial cells in which human kidney proximal tubular epithelial cells are cultured on the top of a porous membrane separating two channels, enabling analysis of transcellular transport, uptake and secretion (top-schematic). The upper fluorescence image of the epithelium shows a horizontal overview of enhanced formation of primary cilia (green) on the apical cell surfaces (cell nuclei stained and colored blue); the lower fluorescence cross-sectional view shows repolarization of Na+K+ ATPase (magenta) to the basal side while green cilia are shown on the apical side of the kidney epithelial cells.

TABLE 1

Kidney-Chip Models; Exemplary Parameters and Endpoint Analysis Assays.

| Kidney-Chip Model | Flow | Stretching | Endpoint Analysis Assays (e.g. read-out) |
|---|---|---|---|
| Proximal tubule (PT)-kidney-chip | 30-150 μl/hr (up to 720 to 3600 μl total fluid volume as flow-through per day) | In some embodiments, stretching is applied. In some preferred embodiments stretching in not applied. | Immunostaining (AQP1, Na pump, cilia, etc), SEM, Albumin uptake, ALP activity, glucose and phosphate reabsorption, creatinine and PAH secretion, Inulin filtration, transporter expression |
| Glomerulus-kidney-chip | 60 μl/hr (up to 720 μl total fluid volume as flow-through per day) | In some embodiments, stretching is applied using a cyclic strain (around 10%), with a frequency of 1 Hz. | See, above for examples. |
| Collecting Duct-kidney-chip | 100 μl/hr (up to 2400 μl total volume per day) | In some embodiments, stretching is applied. In some preferred embodiments stretching in not applied. | See, above for examples. |

In some embodiments, a microfluidic Glomerulus-kidney chip (nephron-on-chip) comprising opposed layers of glomerular endothelial cells and podocytes that experience fluid flow of physiological conditions to mimic one embodiment of an in vivo glomerular microenvironment.

In some embodiments, a microfluidic Collecting Duct-kidney-chip comprises primary cultured inner medullary collecting duct cells of kidneys, including but not limited to distal tubule, cortex and/or medullary collecting duct cells (collectively kidney collecting duct cells) isolated from or derived from human and mammalian kidney tissues. In some embodiments, kidney collecting duct cells are a mixture of cells isolated from or derived from more than one individual. In some embodiments, kidney collecting duct cells are the majority of cells in a mixed population of kidney cells. In some embodiments, a microfluidic Collecting Duct-kidney chip comprises endothelial (vascular) cells in a channel on the opposite side of a membrane in contact with Collecting Duct-kidney cells. In some embodiments, endothelial cells are HUVEC Human Umbilical Vein Endothelial Cells (HUVEC) cells. In some embodiments, endothelial cells are Primary Human Glomerular Microvascular Endothelial Cells (HGMECs) or renal glomerular endothelial cells (GEC).

In some embodiments, a Kidney-Chip is contemplated to assess functions, including but not limited to: Overall active transport of pharmaceutical compounds; Clinical relevance of renal transporter-based drug interactions using a nonclinical in vitro system; etc. In some embodiments, a Proximal tubule (PT)-Kidney-Chip microfluidic device is used for characterizing known transporter substrates and assess clinically recognized drug-transporter interactions in an in vitro system for predictive outcomes.

In some embodiments, a microfluidic PT-Kidney-chip expresses transporter molecules. In some embodiments, a microfluidic PT-Kidney-chip has cells expressing biomarkers responsive to nephrotoxins. In some embodiments, a PT-Kidney-chip is used for testing nephrotoxicity of a compound. Exemplary nephrotoxic compounds include but are not limited to Gentamicin, Cisplatin, etc. See, Table 1 for an exemplary evaluation of nephrotoxicity, e.g. endpoint analysis, in a microfluidic PT-Kidney-chip.

I. Human Proximal Tubule (PT)-Chip

In some embodiments, a microfluidic PT-Kidney-chip comprises primary proximal tubule kidney cells, including but not limited to proximal tubule kidney cells isolated from or derived from human and mammalian kidney tissues. In some embodiments, proximal tubule kidney cells are a mixture of cells isolated from or derived from more than one individual. In some embodiments, proximal tubule kidney cells are the majority of cells in a mixed population of kidney cells.

In some embodiments, a microfluidic PT-Kidney-chip comprises endothelial (vascular) cells in a channel on the opposite side of a membrane in contact with PT Kidney cells. In some embodiments, endothelial cells are HUVEC Human Umbilical Vein Endothelial Cells (HUVEC) cells. In some preferred embodiments, endothelial cells are Primary Human Glomerular Microvascular Endothelial Cells (HGMECs) or renal glomerular endothelial cells (GEC). Primary Human Glomerular Microvascular Endothelial Cell cultures may be initiated from decapsulated glomeruli isolated from normal human kidney cortical tissue. In some embodiments, HGMECs are obtained from commercial sources.

An early prototype of the PT Kidney-on-Chip with a luminar (upper) channel of human PT cells as a mixed population, without endothelial cells in a lower area under a polyester membrane, was made and used for toxicity testing, see, Jang, 2013. However, further optimization of cell sources and conditions are contemplated and described herein to improve the in vivo relevance of a microfluidic kidney PT model, for example, by using a mixed population of primary proximal tubule cells in addition to embodiments using endothelial cells in the vascular channel. In some embodiments, kidney cells were obtained from commercial sources. In some embodiments, kidney cells are contemplated for obtaining from segment specific kidney cells, see FIG. 3A, for examples of kidney segments.

Additional optimization of chip conditions (parameters) are contemplated with some examples provided herein, including but not limited to: Optimizing cell seeding numbers, choosing cell sources then selecting cell sources to use for seeding chips, identifying culture conditions to ensure robustness of the model and reproducibility; Optimized culture conditions to support a minimum of 2 week viability and function; Optimization of culture conditions to include physiologically relevant mechanical forces to imitate mechanical in vivo motion of the kidney tubule.

One embodiment of a human Proximal Tubule-Chip was engineered using the S-1 Chip from Emulate, Inc., See FIG. 3B.

A. Optimized PT Kidney-Chip Model And Exemplary Method For Providing a PT Kidney-On-Chip.

Exemplary Protocol for evaluating quality of PT cell sources in microfluidic devices including: Day 1: Seed Kidney glomerular endothelial cells; Day 3: Seed Proximal tubular cells. Day 4: Change media; Day 5: Begin flow and regulate flow cycle (speed); Days 3, 5 and 7: Take images of cells in devices. Test for barrier function, e.g. Inulin Leakage.

During the development of the present inventions, embodiments of a physiologically relevant Proximal tubule (PT)-Kidney-Chip microfluidic device was created and evaluated, See, Tables 2-3.

TABLE 2

Parameters Tested For Optimization including For Evaluating Robustness And Reproducibility of PT Kidney Chips.

| Parameters | Tested |
|---|---|
| PT Kidney Cell Sources | *Lonza, Biopredic, Cell Biologies, Sigma |
| Microvascular-Endothelial Cell Sources | Lonza, Biopredic, Cell Biologies, Sigma |
| Chip design | S1 (tall chip), HS (high shear chip) |
| Fluid flow rate (shear stress) | 30 µL/hr, 150 µL/hr |
| ECM | Kidney ECM (E1), Emulate ECM (E2) |
| Seeding | Proximal tubular cells, microvascular cells |

*Lonza Group Ltd, Basel Switzerland; Lonza Inc, Morristown, NJ; Biopredic International, Saint Grégoire - France, USA (Missouri); Cell Biologics, Chicago, IL; Sigma-Aldrich, Inc., St. Louis, MO, MilliporeSigma, Burlington, Massachusetts.

TABLE 3

Exemplary shear stress levels.

| | Apical Channel Shear Stress | Basal Channel Shear Stress |
|---|---|---|
| Low flow-S1 | 0.0003 dyn/cm$^2$ | 0.009 dyn/cm 2 |
| Low flow-HS | 0.05 dyn/cm$^2$ | 0.04 dyn/cm 2 |
| High flow-S1 | 0.0017 dyn/cm$^2$ | 0.05 dyn/cm 2 |
| High flow-HS | 0.23 dyn/cm$^2$ | 0.22 dyn/cm 2 |

After evaluating comparisons of parameters (variables) as described herein, one conclusion is that embodiments including a microfluidic S1 chip (device) provides a higher transport function and enhanced localization of transporter proteins than HS devices. Therefore, in preferred embodiments, the following parameters (Table 4) are provided, described and used in methods for assessing kidney functions in microfluidic devices.

The following Table 4 shows one embodiment of an optimized PT Kidney-Chip Model as supported by data shown and described herein. As described herein, a S1 chip provided PT kidney cells having a higher transport function and enhanced localization of transporter proteins than the same cells under the same conditions culture in HS chips. Thus, in preferred embodiments, a microfluidic S1 chip is used for providing a PT Kidney-Chip.

Exemplary Protocol for evaluating quality of PT cell sources in microfluidic devices including: Day 1: Seed Kidney glomerular endothelial cells; Day 3: Seed Proximal tubular cells. Day 4: Change media; Day 5: Begin flow and regulate flow cycle (speed); Days 3, 5 and 7: Take images of cells in devices. Test for barrier function, e.g. Inulin Leakage.

TABLE 4

Optimized PT Kidney-Chip Model.

| Parameters | Optimized Condition |
|---|---|
| Cell source | Human primary proximal tubule cells from Lonza |
| Chip design | S1-Tall channel chip (upper channel: 1000 µm wide × 1000 µm high) |
| Shear stress | Apical Channel Shear: 0.0017 dyn/cm$^2$ Channel Shear: 0.05 dyn/cm$^2$ |
| Flow rate | 150 µL/hr |
| ECM | Emulate ECM |
| Co-culture Seeding | Microvascular cells first and then proximal tubular cells. |

No significant inulin leakage was observed in embodiments of PT-Kidney-Chip tested indicating a tight barrier function for the different chip configurations, flow rates and ECM used.

Endothelial cells under high shear stress (≥0.04 dyn/cm$^2$) showed elongated morphology compared to the cells from chips under low shear stress.

Because in some embodiments, a S1 chip configuration provided higher transport function and enhanced localization of transporter proteins than a HS chip, we contemplate using S1 chips for functional transporter analysis.

TABLE 5

For Comparison, shear stress levels for other types of kidney cells.

| Cells | Shear Stress | Duration | Effects |
|---|---|---|---|
| Madin-Darby Canine Kidney (MDCK) cells (Cattaneo, et al., 2011) | 2 dyn/cm$^2$ | 6 hours | Disappearance of cell domes, rearrangement of cytoskeleton and tight junction protein. Tubular cells are sensitive to apical flow. |
| HK-2 immortalized cells (human kidney 2) is a proximal tubular cell (PTC) line derived from normal kidney then infected with human papilloma virus. (Maggiorani, et al., 2015) | 5 dyn/cm$^2$ | 48 hours | Changes in ZO-1 localization. Disappearance of cilia. Did not cause apoptosis or necrosis. FSS might contribute cell senescence. Possible tubular lesion. |
| Rat Kidney ductal cells. Human Proximal Tubular cells (Jang et al., 2011) | 0.2 dyn/cm$^2$ | 18 hours (short) | Enhanced cell polarization. Differentiated cytoskeletal morphology. Increased cilia formation. |
| Human Proximal Tubular cells as shown herein. | 0.2 dyn/cm$^2$ | 7-15 days (long) | Reduced number of cilia. Reduced creatinine and PAH transport. |

B. Exemplary Cell Sources; Culture Media; Cell Expansion; Preparing and Seeding Static Plates And Microfluidic Devices.

Exemplary cell sources and culture media are described in Example A, however it is not intended to limit sources of cells to commercial sources or to primary proximal human kidney cells. Indeed, in some embodiments cells are obtained from human biopsies. In some preferred embodiments, endothelial cells are seeded prior to proximal tubule cells with both cell types seeded on the same day. Therefore, the following exemplary method describes seeding both cell types into a fluidic device on the same day, see Example B. Although for some embodiments, e.g. cell evaluation on chip, endothelial cells are seeded at least one day prior to proximal tubule cells. See, Example C for seeding cells into microfluidic chips on separate days. See Example D for exemplary methods of preparing cells for seeding into static plates including culturing prior to use in fluidic devices, i.e. chips. See, Example E for co-culture conditions and read-outs after seeding microfluidic devices. See, also, exemplary Chip Activation and ECM-Chip sections for preparing chips prior to seeding.

When pipetting to fill each channel, 50 µL volume is generally used for the top channel, and 20 µL is used for the bottom channel. These volumes allow for simple pipetting and a slight overfill to avoid bubbles or dry channels. All wash steps, unless otherwise stated, are performed using 200 µL of the specific wash solution. While 50 µL (top channel) and 20 µL (bottom channel) are standard volumes used throughout the protocol, there can be some flexibility in the actual volumes used. Top Channel: 35-50 µL. Bottom Channel: 15-20 µL.

A P200 pipette with a sterile pipette tip is used to add solution directly to the channels of the chip, as when coating, washing, and seeding cells prior to attaching the chip to culture module. To introduce solution to the channels, place the pipette tip perpendicular to chip channel inlet, ensuring that the tip is securely in the port, and steadily dispense liquid through the channel. Introduce liquid to the bottom channel before pipetting into the top channel.

Example A—Exemplary Cell Sources And Culture Media

Exemplary Cells: Top channel-human Renal Proximal Tubule Epithelial Cells (hRPTECs), e.g. Lonza, RPTEC #CC-2553); and Bottom channel-Primary Human Glomerular microvascular Endothelial cells (Cell Systems. ACBRI 128), expand to P7 (e.g. passage 7). Additional examples of commercial cell sources include P3 Proximal Tubular (PT) cells from Biopredic International (biopredic.com); P1 PT cells from Lonza (lonza.com); etc. In one embodiment, Proximal tubule cells from the Lonza showed better morphology compared to Biopredic, i.e. more cubical shapes, so a method was developed for evaluating commercial cell sources, e.g. for choosing one lot of cells for a group of experiments, see FIG. 10A. Although human PT cells from Lonza were used for many of the experiments described herein, however other cell sources were used in experiments as labeled.

Exemplary PT Kidney Cell Media Formulations:
Media. Renal Epithelial Growth Medium (REGM™ Lonza, CC-3190), REGM Singlequots, Lonza) or Renal Epithelial Cell Growth Medium 2 (REGM2), from PromoCell, Cat #C-26130), low-serum cell culture medium for primary human renal epithelial cells.
Base hRPTEC Culture Medium (500 mL): REBM™ (Renal Epithelial Cell Growth Basal Medium) (e.g. Lonza, e.g. CC-3191) 492 mL; REGM™ SingleQuots™ Supplement Pack (e.g. Lonza, e.g. EpCC-4127)-0.5 mL each: Human Epidermal Growth Factor (hEGF); Insulin; Hydrocortisone; Transferrin; Triiodothyronine; Epinephrine; 1% Pen/Strep (e.g. Sigma P4333) (5 mL). FBS and gentamicin sulfate was not used from this Supplement Pack.
Complete hRPTEC Maintenance Medium (e.g. 50 mL): Base (h)RPTEC Culture Medium (e.g. 49.75 mL) and 0.5% FBS (e.g. Sigma, e.g. No. F4135) or Human Serum (e.g. 0.250 mL).
Complete hRPTEC Culture Medium: Base hRPTEC Culture Medium (49.75 mL) with 0.5% FBS.
Bottom channel-human Renal Microvascular Endothelial Cells (hRMVEC).
Kidney endothelial cell medium (Cell Systems, 4ZO-500); CSC Medium (Kit), Endothelial Medium & Supplements, Cell Systems 4Z3-500); Culture Boost™, 50× Supplement, Cell Systems 4CB-500.
Exemplary Microvascular Endothelial Cell Media Formulations:
Kidney endothelial cell medium (Cell Systems, 4ZO-500). Renal Kidney Endothelial Cell Culture Medium: Base hRMVEC Culture Medium (e.g. 500 mL): Complete Classic Medium (e.g. Cell Systems Cell Culture Medium (CSC)) (e.g. 485 mL); with 1% Pen/Strep (Sigma, e.g. 5 mL); and 2% Cell Systems Culture-boost (Cat. #4Z0-500) (e.g.10 mL).
Complete hRMVEC Culture Medium With Serum, e.g. 10%.
Complete hRMVEC Culture Medium (e.g. 50 mL): Base hRMVEC Culture Medium (above, e.g. 45 mL) plus 10% FBS (Sigma) e.g. 5 mL).

Example B—Exemplary PT Kidney-Chip Protocols (Methods) For Seeding Co-Cultures On The Same Day In one embodiment, both hRMVECs and hRPTECs are sequentially added to (seeded into) a microfluidic Device, i.e. Chip, on the same day, e.g. Day 0.

Expand cell numbers of kidney glomerular endothelial cells "HGMVEC: hHGMVEC" or Renal Microvascular Endothelial Cells "hRMVECs" for 2-3 days. Expand cell numbers of PT kidney Cells for 3-4 days. See Example C for additional information. See, Example D for preparing cells. Preparing for Seeding Chips:
1. Transfer ECM-coated chips, within closed and sterile 150 mm Petri dishes, from an incubator into the biosafety cabinet (BSC), for maintaining sterility upon removing the Petri dish cover.
2. Fully aspirate ECM from both channels.
3. Pipette 200 µL of warm complete hRMVEC maintenance medium to the bottom channel of each chip. Wash the channel by aspirating the outflow, while leaving media in the channel.
4. Pipette 200 µL of warm complete hRPTEC maintenance medium to the top channel of each chip. Was the channel by aspirating the outflow, while leaving media in the channel.
5. Cover the 150 mm dish and return chips to the incubator until the cells are ready for seeding.

Day 0: hRMVECs and hRPTECs to Chip
1. Prepare Seeding Medium for both cell types and warm at 37° C.
2. Prepare Chips, i.e. activate and coat with ECM, See Example G for surface preparation of microfluidic chips.
3. Harvest hRMVECs for seeding.
4. Seed hRMVECs in Complete seeding medium to the bottom channel. Seed any remaining hRMVECs into a plate as control for cell quality. If desired, transwells can be used as controls.
5. Seed hRPTECs in Complete hRPTEC seeding medium to the top channel. Seed any remaining hRPTECs into a plate as control for cell quality. If desired, transwells can be used as controls.
6. Allow cells to attach for 2.5-3 hrs post-seeding, or until cells have attached.
7. Gravity wash both channels and prepare chips for an overnight static incubation condition, with pipette tips inserted into channel openings, with PT Kidney cells in hRPTECs Maintenance Medium.
8. Gravity wash with tips (3 hours post-seeding).
9. Start flow on Day 1; flow rate to 60 μL/hour for both top and bottom channels.

Example C—Exemplary PT Kidney-Chip Protocols (Methods) For Seeding Co-Cultures On Separate Days In another embodiment, hRMVECs and hRPTECs are added to, i.e. seeded into, a microfluidic device on separate Days, e.g. Day −1 and Day 0; Day 0 and Day 1. See example B for additional information.

One embodiment of a brief exemplary timeline is described as: Day −2: Chip coating; Day −1: Seeding endothelial cells; Day 0: Seeding proximal tubule epithelial cells; Day 0-7: Maintain chips; Day 7: Start Experiment (Study), e.g. 72 hours; and Day 10: End 72 hour Experiment (Study). Exemplary readouts include but are not limited to: Morphology, phase contrast microscopic images; immunohistology, immunofluorescent images; barrier function (in particular for kidney-chips, etc.); gene expression; and Troponin I release (in particular for heart-chips, i.e. cardiac-chips).

A more detailed exemplary timeline, e.g. (proximal-tubule) Kidney-chip is described herein.

Day −4 or Day−3: Human Primary Proximal Tubular Cell Preparation.
1. Expand Human Primary Proximal Tubular cells in 6-well plate (Collagen IV coated) for 3-4 days, see Example D.

Day −3 or Day −2: Endothelial Cell Preparation.
Expand cell numbers of kidney glomerular endothelial cells "HGMVEC: hHGMVEC" or Renal Microvascular Endothelial Cells "hRMVECs" for 2-3 days. See, Example D.

Day −1 or Day 0: Embodiments of Chip activation; wash and coating
1. Wash the top and bottom channels with 200 μl of 70% ethanol, each channel.
2. Aspirate all of the fluid from both channels.
3. Wash both channels with 200 μl of sterile water, each channel.
4. Aspirate all the fluid from both channels.
5. Wash both channels with 200 μl of ER2 buffer each.
6. Add working solution of ER1 (0.5 mg/ml final concentration, 5 mg ER1/10 ml ER2) to top (50 ul) and bottom (20 μl) channels.
7. Activate the channel with UV light for 20 min.
8. Gently aspirate ER1 from both channels.
9. Wash both channels with 200 μl of ER2, each channel.
10. Wash both channels with 200 μl of PBS, each channel.
11. Aspirate PBS from both channels gently.
12. Add ECM in PBS (Collagen IV (50 μg/ml)+ Matrigel (100 μg/ml)) to top (50 μl) and bottom (20 μl) channels of a standard S-1 closed top tall channel chip. In one contemplated embodiment, a high shear chip may be used with 15 μl each for top and bottom channels.
13. Incubate the chip at 37° C. overnight.
14. Next day, gently wash the channel with endothelial media and begin seeding cells ino the bottom channel
15. Incubate the chip at 37° C. overnight.

Day 0 of Day 1: Endothelial cell seeding (e.g. hGEMVECs).
1. Expand kidney endothelial cells for 2-3 days, see Example D.
2. Prepare Complete hRMVEC seeding medium and warm at 37° C.
3. On day of cell seeding, trypsinize cells and spin at 900×g for 10 min at 4° C.
4. Count the cells then dilute the hRMVECs with warm Complete hRMVEC Seeding Medium to a final cell density of $2.0 \times 10^6$–$5 \times 10^6$ cells/ml density for a S1 tall channel chip then add 15 to 20 μL of cells into the bottom channel inlet port, while aspirating the outflow fluid from the chip surface. (Avoid direct contact). For a high shear chip, dilute cells at $10 \times 10^6$ cells/ml then add 10 μl of cells into bottom channel. Final cell concentration is approximately 100,000 cells/chip in Complete hRMVEC Maintenance Medium. When hRMVECs are not as proliferative as expected, the concentration may be increased up to $4 \times 10^6$ cells/mL in order to achieve a confluent monolayer within the channel. Seed any remaining hRMVECs into a plate as control for cell quality. If desired, Transwell cultures can be used as controls.
5. Flip the chip (e.g. using a Chip Cradle) and incubate for 90 minutes (min) at 37° C. in an incubator, then flip back to upright position.
6. Add media on top of the inlet and outlet port, gravity washing the bottom channel and feeding.
7. Incubate for 1 day.
8. Prior to proximal tubule cell seeding, stop flow using tips for (blocking) bottom channel.

PT Kidney Cell seeding.
Day 1 or Day 2: Proximal tubular cell seeding.
1. Expand Human Primary Proximal Tubular cells in 6 well plates, see Example D.
2. On day of cell seeding, trypsinize the cells and spin at 900× g for 10 min at 4° C.
3. Count the cells then dilute to $2 \times 10^6$ cells/ml in media for a tall channel chip and seed 40 μl into top channel. For high shear chip, make $8 \times 10^6$ cells/ml (or $10 \times 10^6$ cells/ml) density and seed 10 μl (or up to 50 μl) of cells into top channel. Final cell concentration is 80,000 cells per chip.
4. Incubate for 90 min at 37° C. incubator.
5. Add media REGM (or 1:1 REGM: Kidney endothelial medium) on top of the inlet and outlet port, gravity washing and feeding using tips.
6. Incubate for 1-2 days static (i.e. no flow).

Example D—Exemplary Preparation of Cells for Seeding into Static Plates Including Culturing Prior to Seeding into Fluidic Devices, i.e. Chips Exemplary Static Tissue Culture Plates: 48-well Tissue culture plates; 6 well plates; T-75 flasks, and Corning® BioCoat™ Collagen IV Multiwall Tissue Culture (TC) Plates (Corning #354428).

In some embodiments, PDMS coated 48 well plate systems are used.

Exemplary Conditions: ECM coating of well plates for evaluating proximal tubular cell development.

Exemplary ECM: Collagen IV; Corning® BioCoat™ Collagen IV Multiwall Tissue Culture (TC) Plates; and Attachment Factor™.

Coat 6 well plates with Collagen IV (50 μg/ml)/Matrigel (100 μg/ml) for at least 2 hours (h) at 37° C., or use a Col IV coated plate (e.g. Corning #354428). Wash with Dulbecco's phosphate-buffered saline (DPBS) and seed Renal Proximal tubular cells at 180,000 cells per well (20,000 cells/cm$^2$). Culture for overnight or up to 3-4 days at 37° C.

and 5% $CO_2$. Exchange with fresh warm complete hRPTEC Culture Medium every other day until used for seeding a Chip.

Attachment Factor™: Apply a thin coat of pre-warmed (37° C.) Attachment Factor™ to the bottom surface for covering the entire bottom of the tissue culture plate, flask, etc. Use at least 5 mL per T-75 culture flask. Let the reagent sit 5 to 10 seconds or until media is added to the culture dish, then aspirate the Attachment Factor replacing it with 20-30 ml of fresh growth media (Complete hRMVEC Culture Medium) and incubate at 37° C. until media is at 37° C. Maintain temperature until the culture dish is removed from the incubator for seeding. The culture dish surface is activated for use immediately: rinsing or drying are not required or recommended.

Attachment Factor™ refers to an extracellular matrix (ECM) product (e.g. Cell Systems, Kirkland, Wash., Catalog number 4Z0-210) that promotes cell attachment to tissue culture surfaces and encourages correct polarity and cytoskeletal organization.

C. Thawing and Maintaining PT Kidney Cells for seeding into microfluidic chip.
1. Thaw the vial(s) of cells by immersing in a 37° C. water bath. Closely observe while gently agitating and remove from the water bath just before the last of the ice disappears.
2. Spray vial(s) with 70% ethanol and dry prior to placing them in the BSC.
3. Immediately transfer the contents of the vial into 3 mL of warm Complete hRPTEC Culture Medium in a sterile 15 mL conical tube.
4. Rinse the vial with 1 mL of warm Complete hRPTEC Culture Medium and collect in the 15 mL tube.
5. Bring the volume to 15 mL with warm Complete hRPTEC Culture Medium.
6. Centrifuge 200× g for 5 minutes at room temperature.
7. Aspirate and discard supernatant, leaving approximately 100 µL of medium covering the pellet.
8. Loosen the cell pellet by gently flicking the tube.
9. Re-suspend cells in 15 mL of Complete RPTEC Culture Medium.
10. Aspirate and discard excess Attachment Factor from the T75 flask that was prepared earlier. Note: Rinsing and/or drying the flask prior to adding cells is not necessary.
11. Add the hRPTEC suspension to the pre-warmed T75 flask.
12. Incubate overnight at 37° C. and 5% $Co_2$.
13. Exchange with fresh warm Complete hRPTEC Culture Medium every other day until used for seeding in the Chip.
14. hRPTECs are seeded in the top channel in hRPTECs Maintenance Medium.

D. Thawing and Maintaining Renal Microvascular Endothelial Cells (hRMVECs) for seeding into microfluidic chip.
1. Thaw the vial(s) of cells by immersing in a 37° C. water bath. Closely observe while gently agitating and remove from the water bath just before the last of the ice disappears.
2. Spray vial(s) with 70% ethanol and wipe dry prior to placing them in the BSC.
3. Immediately transfer the contents of the vial into 3 mL of warm Complete hRMVEC Culture Medium in a sterile 15 mL conical tube.
4. Rinse the vial with 1 mL of Complete hRMVEC Culture Medium and collect in the 15 mL tube.
5. Bring the volume to 15 mL with Complete hRMVEC Culture Medium.
6. Centrifuge 200× g for 5 minutes at room temperature.
7. Aspirate and discard supernatant, leaving approximately 100 µL of medium covering the pellet.
8. Loosen the cell pellet by gently flicking the tube.
9. Re-suspend cells in 15 mL of Complete hRMVEC Culture Medium.
10. Aspirate and discard excess Attachment Factor from the T75 flask that was prepared earlier. Note: Rinsing and/or drying the flask prior to adding cells is not necessary.
11. Add the hRMVECs suspension to the freshly coated T75 flask.
12. Incubate overnight at 37° C. and 5% $CO_2$.
13. Exchange with fresh Complete hRMVEC Culture Medium every other day until use for seeding in the chip.

E. Harvesting hRMVECs. hRMVECs in culture are harvested and counted for seeding the bottom channels. HRMVECs are adjusted to a density of $2\times10^6$ cells/mL prior to seeding the bottom channel. If the hRMVECs are not as proliferative as expected, the concentration can be increased up to $4\times10^6$ cells/mL in order to achieve a confluent monolayer within the channel.
1. Bring the culture flask containing hRMVECs from the incubator into the BSC.
2. Aspirate culture media and add 15 mL of 1X DPBS to wash the culture surface. Aspirate the DPBS wash.
3. Add 3 mL of trypsin-EDTA to the flask. Incubate for 2 to 3 minutes at 37° C.
4. Tap the side of the flask gently, and inspect the culture under the microscope to assess complete detachment of cells from the culture surface.
5. Add 9 mL of warm complete hRMVEC maintenance medium to the flask and pipette gently to mix, while collecting all cells from the culture surface.
6. Transfer the contents of the flask (12 mL) into a sterile 15 mL conical tube.
7. Add 3 mL of warm complete HRMVEC culture medium to bring the total volume of the tube to 15 mL.
8. Centrifuge hRMVECs at 200× g for 5 minutes at room temperature.
9. While the cells are in the centrifuge, prepare a Trypan Blue counting solution in a 1.5 mL tube:
   40 µL Complete hRMVEC maintenance medium
   5 µL Trypan Blue
10. Carefully aspirate the supernatant, leaving approximately 100 µL of medium above the cell pellet. Note: The cell pellet will be very small. Aspirate carefully.
11. Loosen the cell pellet by flicking the tube gently.
12. Using a P1000 pipette, gently resuspend the cells by adding 400 µL of warm Complete hRMVEC Maintenance Medium.
13. Pipette gently to create a homogeneous mixture, and transfer 5 µL of the cell suspension to the Trypan Blue counting solution. (This will make a 1:10 dilution.)

Example E—Exemplary Co-Culture Conditions and Read Outs after Seeding Microfluidic Devices One embodiment, Day 4: Start flow at 30 µl/hr-150 µl/hr.
1. Warm media degassing using Steriflip for 15 min at 37° C. bead bath.
2. Incubate the media at 37° C. in an incubator after loosening the cap, i.e. unscrewing the cap a bit, but not enough to allow contamination of the media, to ensure gas equilibration.
3. Add 3 ml media in Inlet port and 0.3 ml in Outlet port Reservoir.
4. Prime the perfusion manifold in the culture module.
5. Connect the chip to the perfusion manifold and start flow.
6. Change media every other day.
7. Culture for 6-7 days.

Day 2+: Effluent sampling and media replenishment.
Days 7-10: Nephrotoxin Testing And Readouts.
Outflow from chips, (e.g. S1—closed top chip; and high shear (HS) chip) was collected for certain readouts. For reference, kidney endothelial media contains 5% FBS while the kidney epithelial media contains 0.5% FBS (fetal bovine serum).
Read outs include but are not limited to: a Kidney injury panel from MSD (K15189D, K15188D); Kidney gene expression: transporters (MRP2, 4, MDR1, MATE1/2-K, OAT1, OAT2, OAT3, OATP4C. OCT2, MRP1/3/5/6, etc.); Immunostaining: antibodies (MRP2, 4, MDR1, MATE1/2-K, OAT1, OAT2, OAT3, OATP4C, OCT2, MRP1/3/5/6, etc.).

Exemplary Day 8: Kidney Chip Fixation And Readouts, e.g. RNA isolation.
1. Observe and record: Cell Morphology.
2. Immunostaining and observe: e.g., antibodies against AQPT1, OAT1, Megalin, Sodium potassium ATPase.
3. Measure Gene expression: e.g., Aqpt1, OAT1, GGt1, Glut1, MRP2, MRP4, Megalin, SGLT1, SGLT2, Sodium potassium ATPase, ZO-1.

F. Design of Microfluidic Device For Providing A Proximal Tubule Kidney Chip.

Figure 1A:
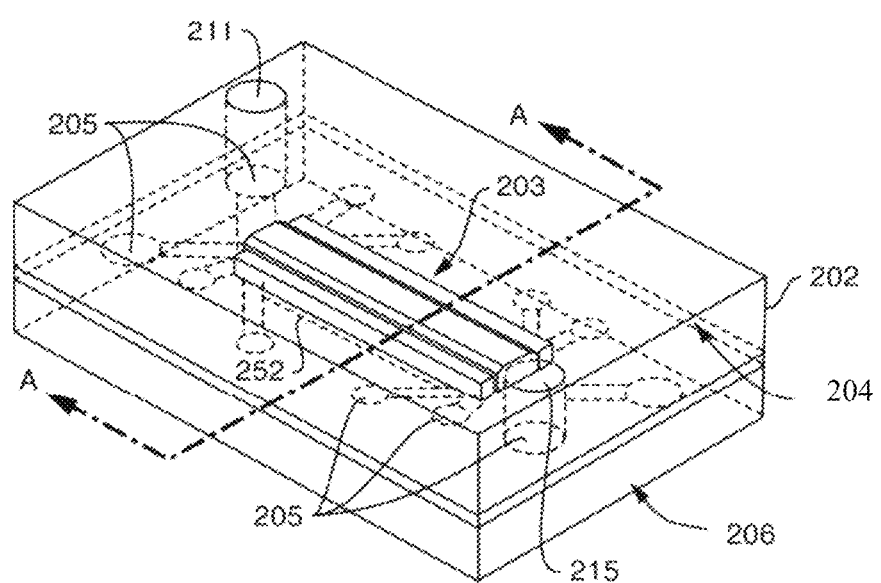
FIG. 1A illustrates one exemplary perspective view of a microfluidic device 200 with microfluidic channels 203 in accordance with one exemplary embodiment.
Figure 1B:
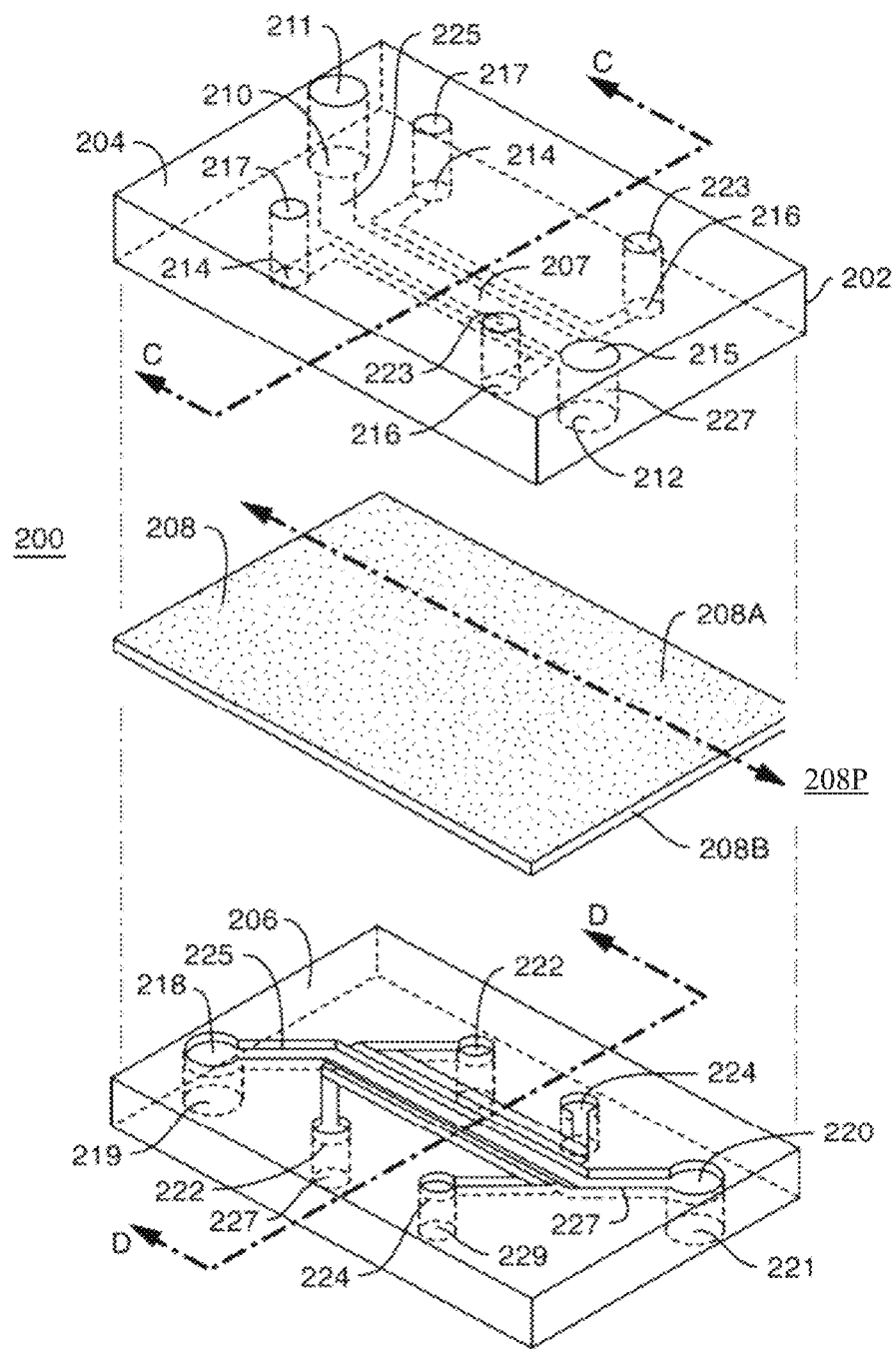
FIG. 1B illustrates one exemplary exploded view of the device 200 in accordance with an embodiment, showing a microfluidic channel 203 in a top piece 204 and a microfluidic channel in a bottom piece 206, separated by a membrane 208.
Figure 1C:
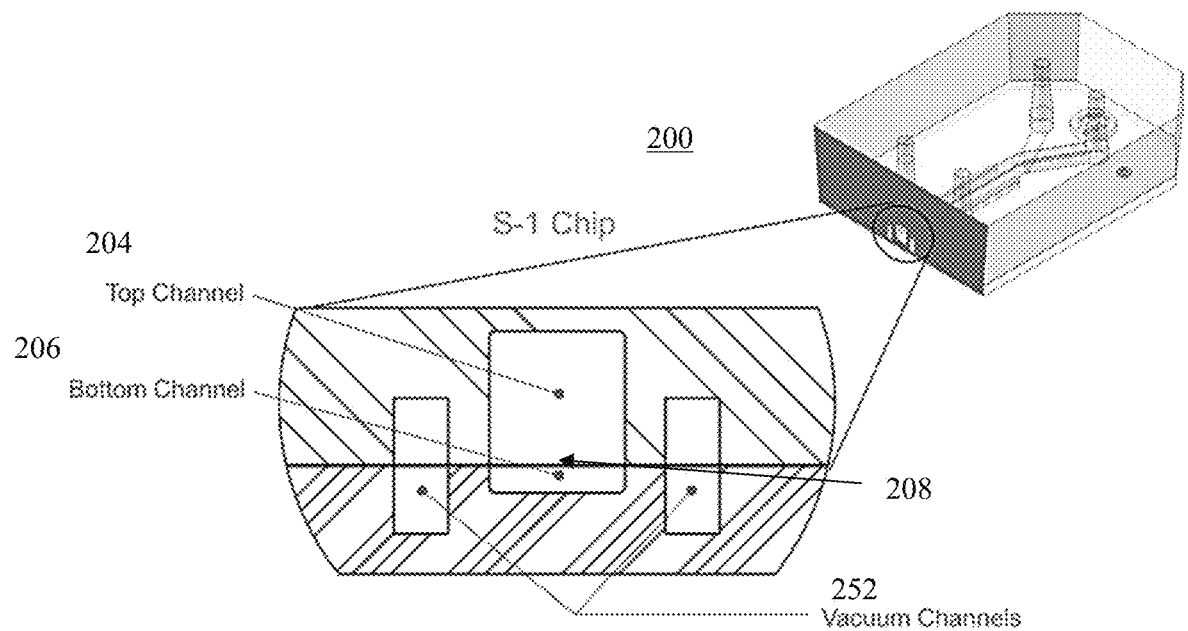
FIG. 1C illustrates exemplary S-1 polydimethylsiloxane (PDMS) Tall channel Chip and High Shear Chip, microfluidic device 200, as shown in FIG. 1A and FIG. 1B, showing one embodiment of a top (upper) channel 204 and bottom (lower) channel 206, having a stretchable porous PDMS membrane that is coated with extracellular matrix (ECM), and two vacuum channels 252. Dark line separating top and bottom channel is membrane 208. Also shown is one exemplary schematic of a HS human Proximal Tubule-Chip containing an upper channel (1 mm high×1 mm wide) and a lower channel (0.2 mm high×1 mm wide), separated by a porous PDMS membrane that is coated with extracellular matrix (ECM).
Figure 1D:
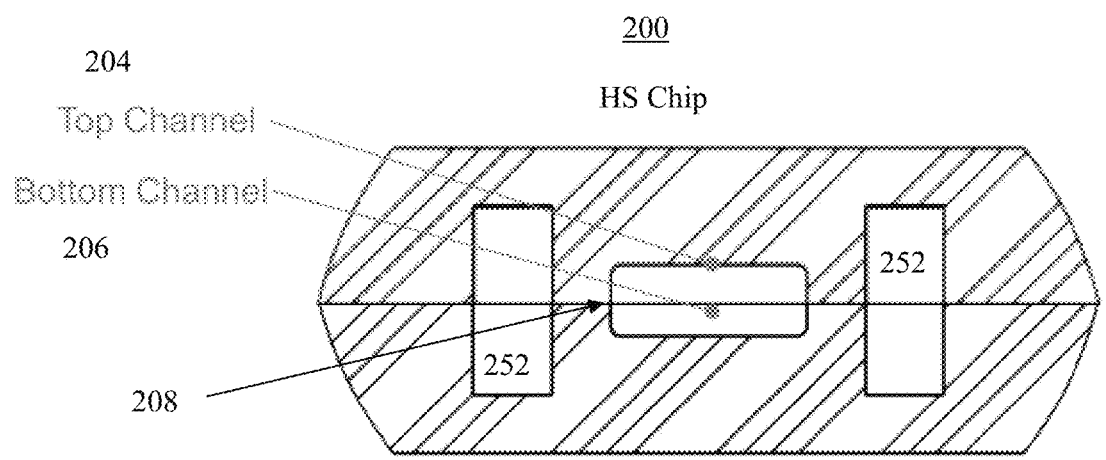
FIG. 1D illustrates one embodiment of a High shear (HS) chip (PDMS). One exemplary embodiment of the upper channel is 1000 μm wide×100 μm high).

One embodiment of a human Proximal Tubule-Chip was engineered using one embodiment of a S-1 Chip from Emulate, Inc., see FIGS. 1A-1B. Thus, in some embodiments, a microfluidic chip has an upper channel measuring e.g. 1 mm wide×200 m tall. In some embodiments, a S-1 microfluidic chip may be used for a microfluidic Glomerulus Kidney chip. In some embodiments, a S-1 microfluidic chip may be used for a microfluidic Collecting Duct Kidney chip. See additional exemplary embodiments of microfluidic Kidney chips illustrated in FIGS. 1C-D, showing a S-1 tall channel chip, e.g. 1 mm wide×1 mm high and a high shear (HS) chip, e.g. 1 mm wide×100 µm tall.

Exemplary Microfluidic Chips: S-1 (Tall channel) closed top stretchable chip and a High shear (HS) stretchable chip, under flow shear. Each tested with different shear stress (low and high flow rate); ECM etc.

Exemplary Top Channel Dimensions: 1000 µm×1000 m. Area: 28.0 mm². Volume: 28.041 µL. Imaging distance from bottom of chip to top of membrane: 850 µm.

Exemplary Bottom Channel Dimensions: 1000 µm (wide)×200 µm (high). Area: 24.5 mm².
Volume: 5.6 µL.
Exemplary Co-Culture Region: 17.1 mm².
Exemplary Membrane: Pore diameter 7.0 µm; Pore spacing 40 µm (hexagonally packed); Thickness 50 µm.

Exemplary S1 Microfluidic Chip Fluid Volume: For each channel, 50 µL volume is generally used for the top channel, and 20 µL is used for the bottom channel. However, there can be some flexibility in the actual volumes used: Top Channel: 35-50 µL and Bottom Channel: 15-20 µL. Wash steps, unless otherwise stated, are typically performed using 200 µL of the specific wash solution.

See, Section 2, below, on Exemplary surface activation of chips, prior to coating with ECM.

FIG. 1A illustrates one exemplary perspective view of a microfluidic device 200 with microfluidic channels 203 in accordance with one exemplary embodiment.

FIG. 1B illustrates one exemplary exploded view of the device 200 in accordance with an embodiment, showing a microfluidic channel 203 in a top piece 204 and a microfluidic channel in a bottom piece 206, separated by a membrane 208.

FIG. 1C illustrates exemplary S-1 polydimethylsiloxane (PDMS) Tall channel Chip and High Shear Chip, microfluidic device 200, as shown in FIG. 1A and FIG. 1B, showing one embodiment of a top (upper) channel 204 and bottom (lower) channel 206, having a stretchable porous PDMS membrane that is coated with extracellular matrix (ECM), and two vacuum channels 252. Dark line separating top and bottom channel is membrane 208. Also shown is one exemplary schematic of a HS human Proximal Tubule-Chip containing an upper channel (1 mm high×1 mm wide) and a lower channel (0.2 mm high×1 mm wide), separated by a porous PDMS membrane that is coated with extracellular matrix (ECM).

FIG. 1D illustrates one embodiment of a High shear (HS) chip (PDMS). One exemplary embodiment of the upper channel is 1000 µm wide×100 µm high).

Figure 2A:
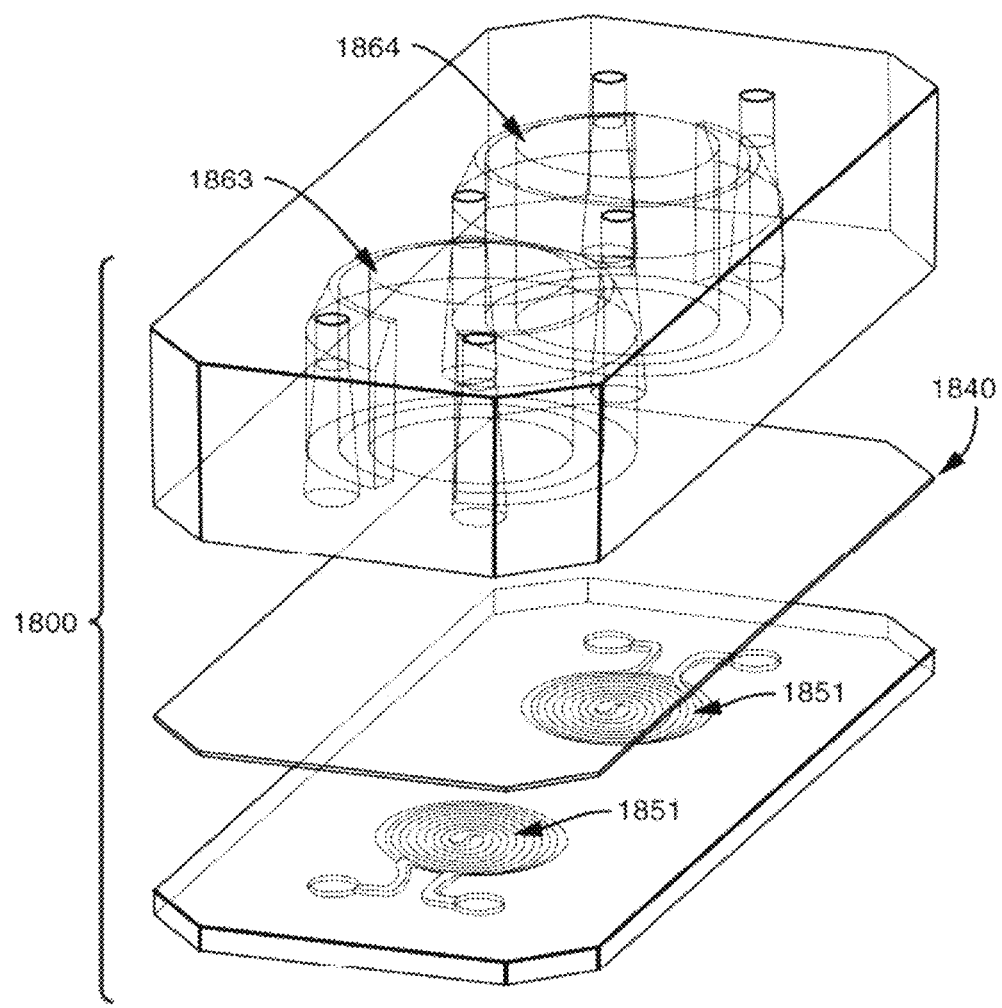
FIG. 2A shows one exemplary schematic of an open top microfluidic chip.
Figure 2B:
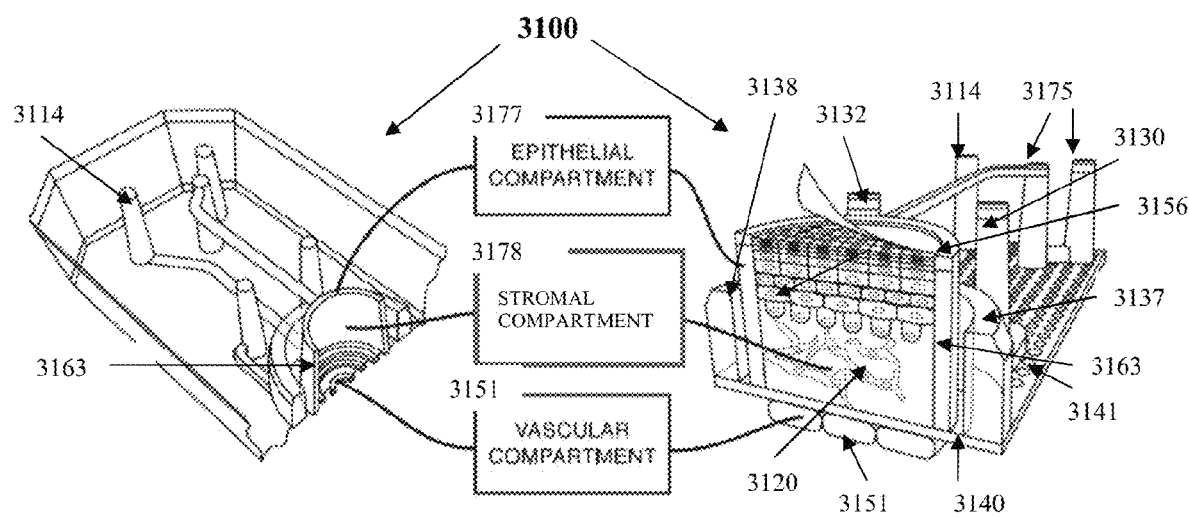
FIG. 2B shows two exemplary schematic embodiments of an open top microfluidic chip 3100 modeling a simulated kidney organ comprising epithelium, e.g. kidney epithelium. One embodiment is a schematic of a partial open top chip demonstrating channels 3151 and open stromal area 3178 in relation to cellular compartments in the chip (left). One embodiment is a schematic of a partial open top chip additionally demonstrating cells in the compartments of the chip (right).

In some embodiments, a microfluidic Kidney chip is an open-top chip, see, FIGS. 2A-2B.

FIG. 2A shows one exemplary schematic of an open top microfluidic chip.

FIG. 2B shows two exemplary schematic embodiments of an open top microfluidic chip 3100 modeling a simulated kidney organ comprising epithelium, e.g. kidney epithelium. One embodiment is a schematic of a partial open top chip demonstrating channels 3151 and open stromal area 3178 in relation to cellular compartments in the chip (left). One embodiment is a schematic of a partial open top chip additionally demonstrating cells in the compartments of the chip (right).

II. Proximal Tubule-Chips

A. Proximal Tubule-Chip Has A Polarized Monolayer.

The Proximal Tubule-Chip formed polarized monolayer showing defined and orderly expression of the epithelial tight junction protein ZO-1 and the endothelial adherent protein VE-Cadherin. Polarized proximal tubular epithelial cells expressed specific makers known to be abundant along the proximal tubule, including beta-catenin, occludin, aquaporin 1 (AQP1), and Na/K-ATPase, and presented cilia and brush border. See, FIGS. 4A-B.

Figure 4A:
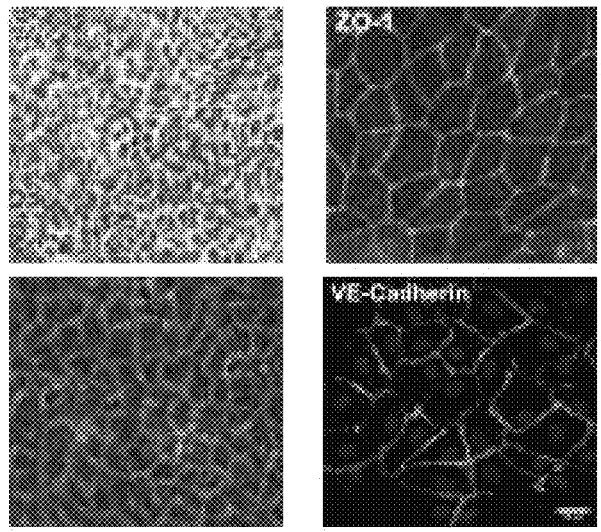
FIG. 4A-B shows exemplary microscopic images of cells within a human Proximal Tubule-Chip demonstrating a polarized epithelial monolayer: top channel (upper panels) and bottom channel (lower panels).
Figure 4B:
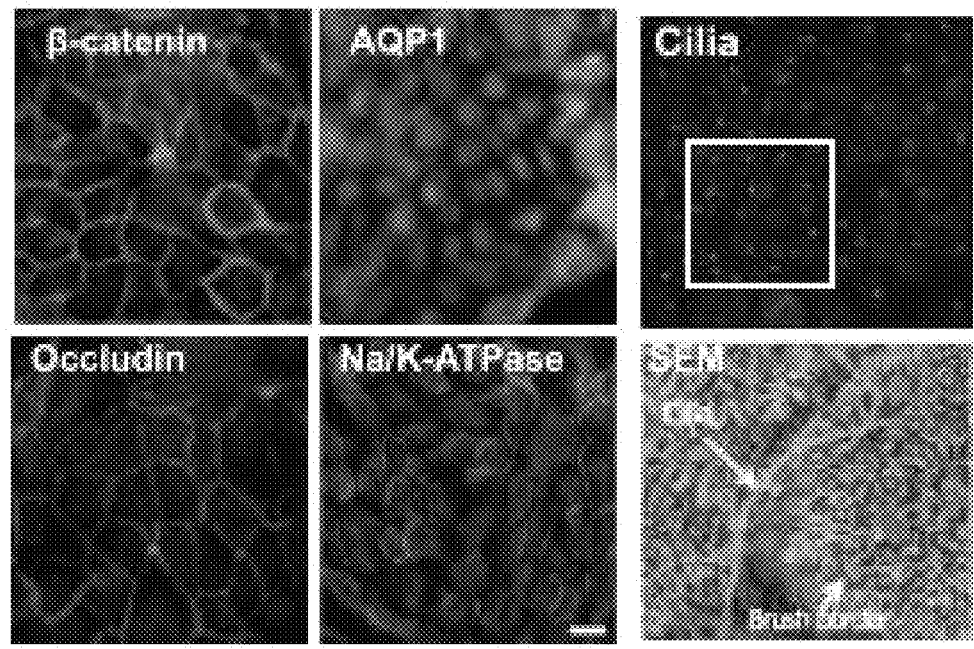

FIG. 4A-B shows exemplary microscopic images of cells within a human Proximal Tubule-Chip demonstrating a polarized epithelial monolayer: top channel (upper panels) and bottom channel (lower panels).

FIG. 4A shows exemplary microscopic images demonstrating a defined and orderly expression of the epithelial tight junction protein ZO-1 (upper right, green) and the endothelial adherent protein VE-Cadherin (lower right, green). Nuclei staining is colored blue.

FIG. 4B shows exemplary microscopic images of proximal tubule cells demonstrating polarized proximal tubular epithelial cells expressing specific biomarkers known to be abundant along the in vivo human proximal tubule, including in the upper channel: beta-catenin (red), aquaporin 1 (AQP1) (green), and representative cilia (green), (cilia staining as in Jang, 2013 in a different chip configuration without endothelial cells), and Na/K-ATPase (pink), with scanning electron microscope (SEM) images showing cilia and a brush border, see lower right panel, labeled arrows. In the lower channel, occludin (green). Cell source: Lonza; Chip type: S1 Tall Channel; Flow: 30 µL/hr culture module. Blue stained nuclei.

B. Functional Assessment of Transporter Molecules.

Relative gene expression of SGLT2, AQP1, and Na+/K+ ATPase was measured in control passage 1 (P1) proximal tubule cell populations compared to Proximal Tubule-Chip. Western blot analysis confirmed expression of uptake and efflux transporters such as P-glycoprotein (P-gp) and OCT2 (SLC22A2).

In some embodiments, biochemical characterization of chips is compared to transwell cultures. In some embodiments, qPCR markers include but are not limited to: Na/K-ATPase, AQP1, MATE1 and MATE2K, OAT1 and OAT3, P-gp. In some embodiments, immunofluorescent (IF) markers, i.e. proteins, include but are not limited to: Na/K-ATPase, AQP1, OAT1, OAT3, etc.

PT kidney cells on chip show exemplary Active Transporter Expression corresponding to function by qPCR; Immunostaining and Western Blotting, see, FIG. 5A-B. In some embodiments, gene expression is contemplated for measurement by RNA-seq Analysis.

Figure 5A:
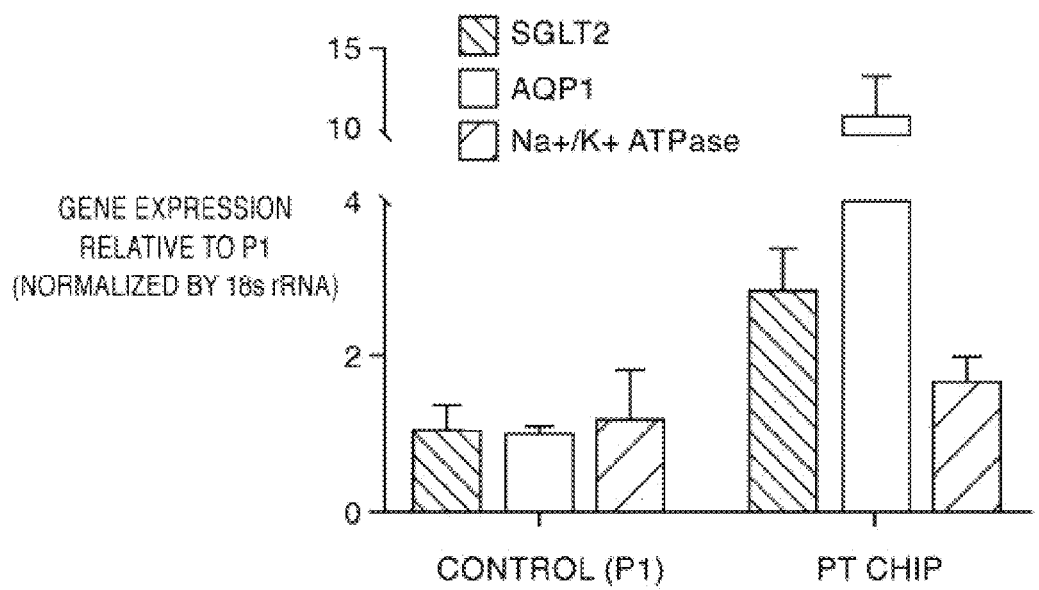
FIG. 5A-B shows exemplary relative gene expression (FIG. 5A) of SGLT2, AQP1, and Na+/K+ ATPase measured by qPCR in control passage 1 (P1) proximal tubule cell vs Proximal Tubule-Chip. Cell source: Lonza; Chip type: S1 Tall Channel; Flow: 30 µL/hr culture module. Western blot analysis (FIG. 5B) confirmed expression of uptake and efflux transporters such as P-glycoprotein (P-gp) and OCT2 (SLC22A2). Glyceraldehyde 3-phosphate dehydrogenase (GAPDH) shows a relative protein loading amount. Cell source: ScienCell; Chip type: Tall Channel; Flow: 60 µL/hr peristaltic pump.
Figure 5B:
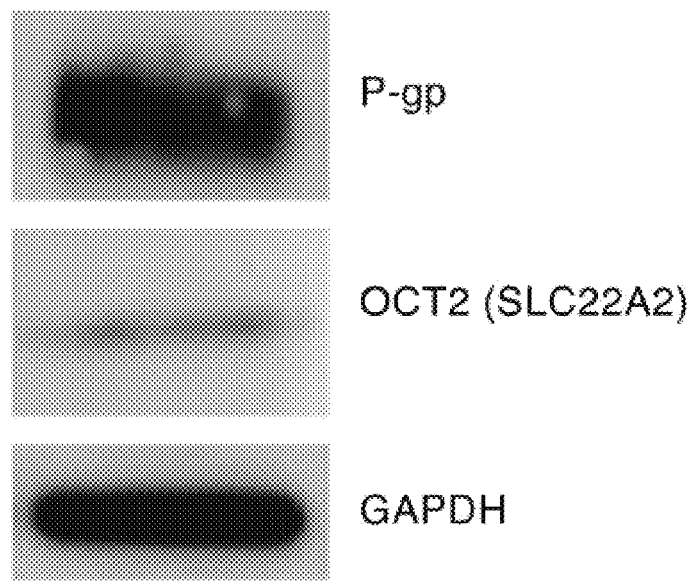

FIG. 5A-B shows exemplary relative gene expression (FIG. 5A) of SGLT2, AQP1, and Na+/K+ ATPase measured by qPCR in control passage 1 (P1) proximal tubule cell vs Proximal Tubule-Chip. Cell source: Lonza; Chip type: S1 Tall Channel; Flow: 30 µL/hr culture module. Western blot analysis (FIG. 5B) confirmed expression of uptake and efflux transporters such as P-glycoprotein (P-gp) and OCT2 (SLC22A2). Glyceraldehyde 3-phosphate dehydrogenase (GAPDH) shows a relative protein loading amount. Cell source: ScienCell; Chip type: Tall Channel; Flow: 60 µL/hr peristaltic pump.

Transporter-mediated secretion of p-aminohippuric acid (PAH) and creatinine from luminal (apical) to vascular (basal) channels then in reverse (basal to apical) was measured in effluent collected from a Proximal Tubule Kidney-Chip.

Figure 6A:
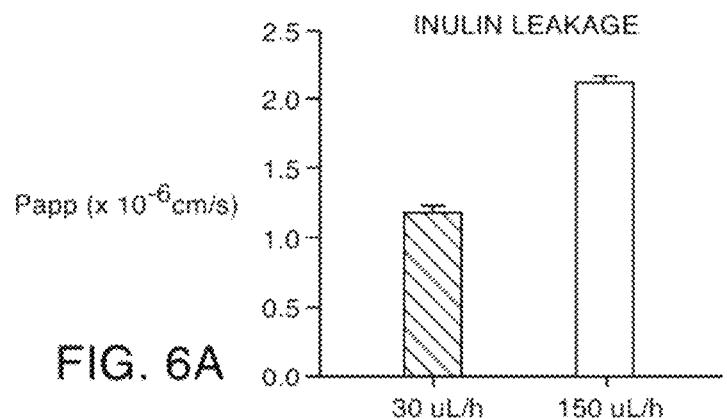
FIG. 6A shows that in one embodiment of a Proximal Tubule-Chip inulin permeability (leakage) was measured under two different flow rates, e.g. 30 ul/hr and 150 ul/hr.

FIG. 6A shows that in one embodiment of a Proximal Tubule-Chip inulin permeability (leakage) was measured under two different flow rates, e.g. 30 ul/hr and 150 ul/hr.

Figure 6B:
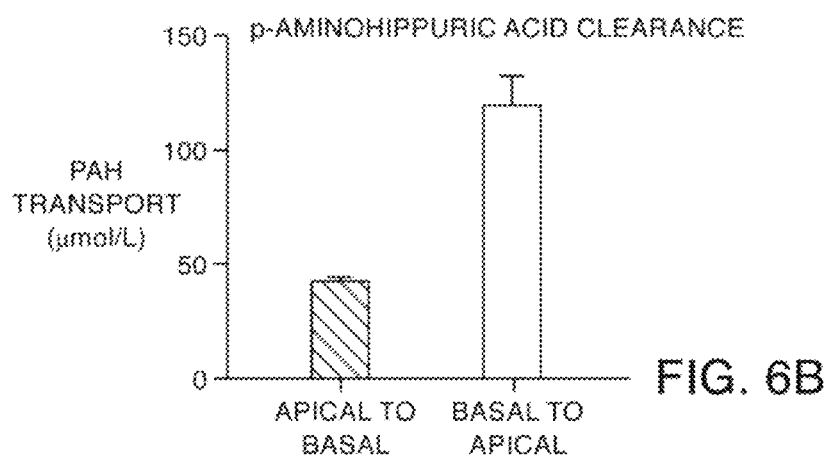
FIG. 6B and FIG. 6C shows that in one embodiment of a Proximal Tubule-Chip Transporter-mediated secretion of p-aminohippuric acid (PAH) and creatinine from the vascular channel to the luminal channel (basal to apical) was measured on Chip. As opposed to significantly less apical to basal transport. Cell source: Lonza; HRMEC; Chip type: S1; Flow: 60 µL/hr by culture module.
Figure 6C:
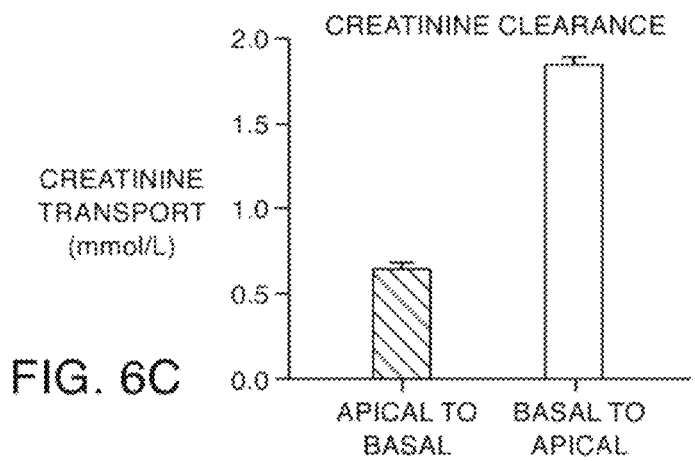

FIG. 6B and FIG. 6C shows that in one embodiment of a Proximal Tubule-Chip Transporter-mediated secretion of p-aminohippuric acid (PAH) and creatinine from the vascular channel to the luminal channel (basal to apical) was measured on Chip. As opposed to significantly less apical to basal transport. Cell source: Lonza; HRMEC; Chip type: S1; Flow: 60 µL/hr by culture module.

Proximal Tubule Kidney-Chip efflux movement of Metformin from the vascular channel to the luminal channel was measured in a time-dependent manner.

Figure 7:
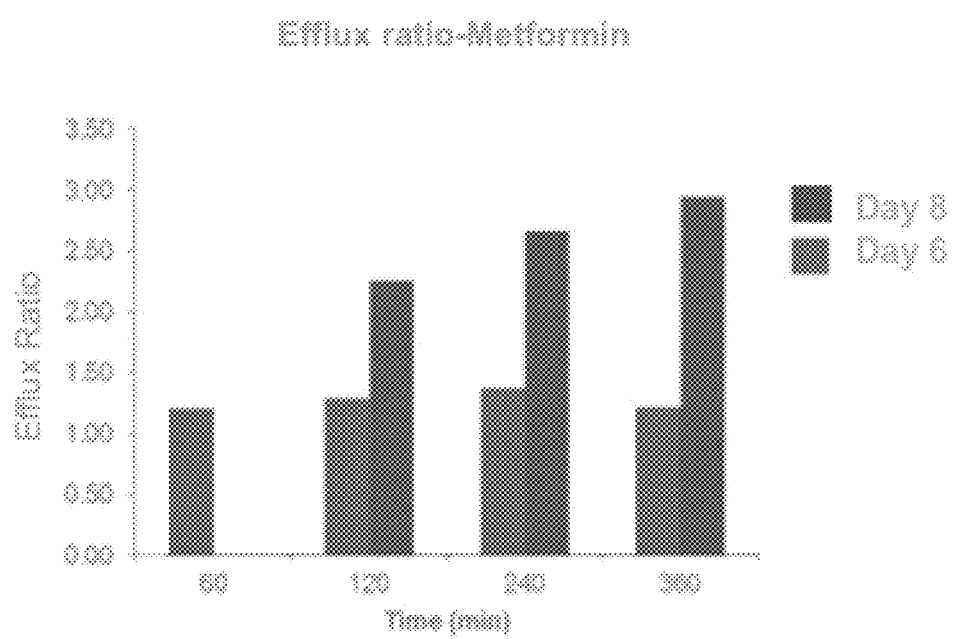
FIG. 7 shows that one embodiment of a Proximal Tubule-Chip, day 8, exhibited significant efflux of Metformin from the vascular channel to the luminal channel measured in a time-dependent manner as opposed to day 6 co-cultures. These results indicate that Metformin, creatinine, and PAH are actively transported by their respective proximal tubule transporters at 120, 240 and 260 minutes of incubation. Cell source: Lonza; HRMEC; Chip type: S1; Flow: 30 µL/hr by culture module.

FIG. 7 shows that one embodiment of a Proximal Tubule-Chip, day 8, exhibited significant efflux of Metformin from the vascular channel to the luminal channel measured in a time-dependent manner as opposed to day 6 co-cultures. These results indicate that Metformin, creatinine, and PAH are actively transported by their respective proximal tubule transporters at 120, 240 and 260 minutes of incubation. Cell source: Lonza; HRMEC; Chip type: S1; Flow: 30 µL/hr by culture module.

These results suggest that metformin, creatinine, and PAH are actively transported by their respective proximal tubule transporters.

C. Megalin Protein Expression And Resorptive Capability Of The Proximal Tubule Epithelium On-Chip.

One embodiment of a Proximal Tubule-Chip exhibited abundant megalin protein expression and resorptive capability of the proximal tubule epithelium by uptaking FITC-labeled human albumin. Megalin protein refers to Low density lipoprotein-related protein 2 also known as LRP2. Thus, PT kidney cells on chip show an exemplary transporter expression corresponding to function, see, FIG. 8.

Figure 8:
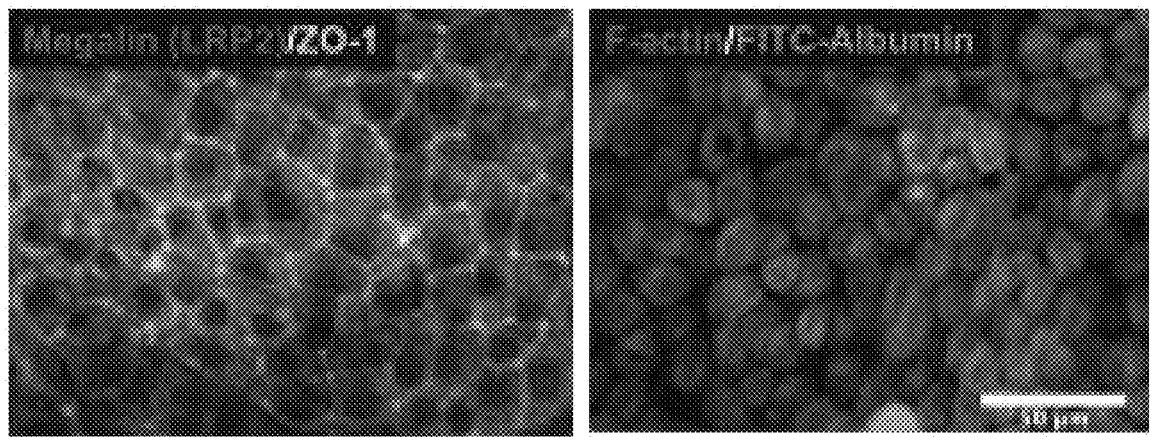
FIG. 8 shows that one embodiment of a Proximal Tubule-Chip exhibited abundant megalin protein expression (red) compared to ZO-1 (blue), left panel and resorptive capability of the proximal tubule epithelium by uptaking FITC-labeled human albumin (green), compared to F-actin staining (blue), right panel. Bar=50 µm. Cell source: ScienCell; Chip type: Tall Channel; 60 µL/hr peristaltic pump.

FIG. 8 shows that one embodiment of a Proximal Tubule-Chip exhibited abundant megalin protein expression (red) compared to ZO-1 (blue), left panel and resorptive capability of the proximal tubule epithelium by uptaking FITC-labeled human albumin (green), compared to F-actin staining (blue), right panel. Bar=50 m. Cell source: ScienCell; Chip type: Tall Channel; 60 µL/hr peristaltic pump.

D. Gentamicin Induced Toxicity in Proximal Tubule-Chip.

Figure 9A:
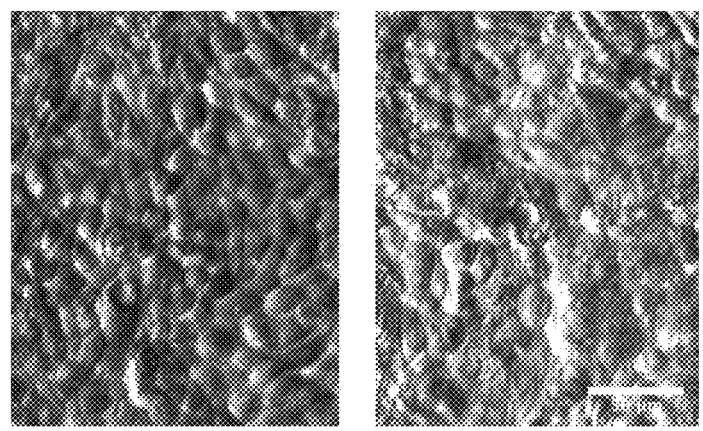
FIG. 9A-B shows that one embodiment of a Proximal Tubule-Chip exhibited Gentamicin Toxicity. Cell source: Lonza; Chip type: Tall Channel; 60 µL/hr culture module.
Figure 9B:
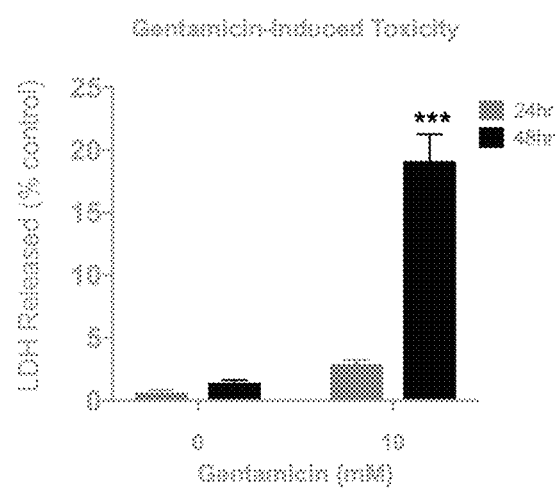

The Proximal Tubule Kidney-Chip replicates Gentamicin-induced toxicity after exposure to 10 mM of gentamicin for 48 hours. Microscopic analysis of the proximal tubular epithelium shows structural damage coupled with significant increase in LDH in medium effluent and increase active caspase-3 in cells lysates. TUNEL assay also reveals significant DNA damage FIG. 9A-B shows that one embodiment of a Proximal Tubule-Chip exhibited Gentamicin Toxicity. Cell source: Lonza; Chip type: Tall Channel; 60 µL/hr culture module.

FIG. 9A shows exemplary phase contract microscopic analysis of the proximal tubular epithelium (control-left panel: treated-right panel). Lower panels show lower power images of corresponding Gentamicin treatments (control-left panel: treated with Gentamicin-right panel). (Lonza cells; S1; Flow: 60µ/hr provided by a culture module).

FIG. 9B shows exemplary Gentamicin-Induced Toxicity by LDH release in medium effluent (% control) that revealed significant cell damage after 10 mM of Gentamicin treatment for 48 hours. (*** $p<0.001$). Cell source: Lonza. Flow: 30 µL/hr with a culture module.

In some embodiments, Proximal Tubule-Chips are evaluated for biomarkers of function and/or injury, e.g. Kidney Injury Marker 1 (KIM-1), etc.

In summary, we created a Proximal Tubule-Chip that recapitulates in vivo relevant tissue-tissue interface of the kidney proximal tubule. This kidney Proximal Tubule-Chip exhibited polarized epithelium and endothelium that reproduced baseline functions of the proximal tubule in vitro and demonstrated active transporters functions that are involved in normal kidney functions. These results suggest that the Proximal Tubule-Chip represents a physiologically relevant system for drug discovery and development applications.

The following sections demonstrate additional embodiments of Proximal Tubule Kidney-Chips and provides exemplary methods for testing potential drug treatments and testing compounds for improving kidney functions.

III. Kidney-Chip Model Optimization: Exemplary Materials and Methods for Evaluating and Comparing Embodiments of Microfluidic Device (Chip) Design Configurations, Culturing Conditions and Architecture: Comparative Evaluation of PT Kidney-Chip Parameters During the development of the present inventions, materials and methods were evaluated for Kidney-Chip Model Optimization. Optimization of a PT Kidney-Chip refers to determining parameters for supporting morphological and functional PT Kidney cells on chip for long term cultures including but not limited to evaluating: primary PT Kidney cell sources, chip configuration (design), flow rates (fluid shear stress), ECM compositions for coating plates for use in passaging PT Kidney cells and for coating a PDMS membrane (e.g. membrane 208) for PT Kidney cell attachment in microfluidic chips; Seeding density; etc.

Figure 10A:
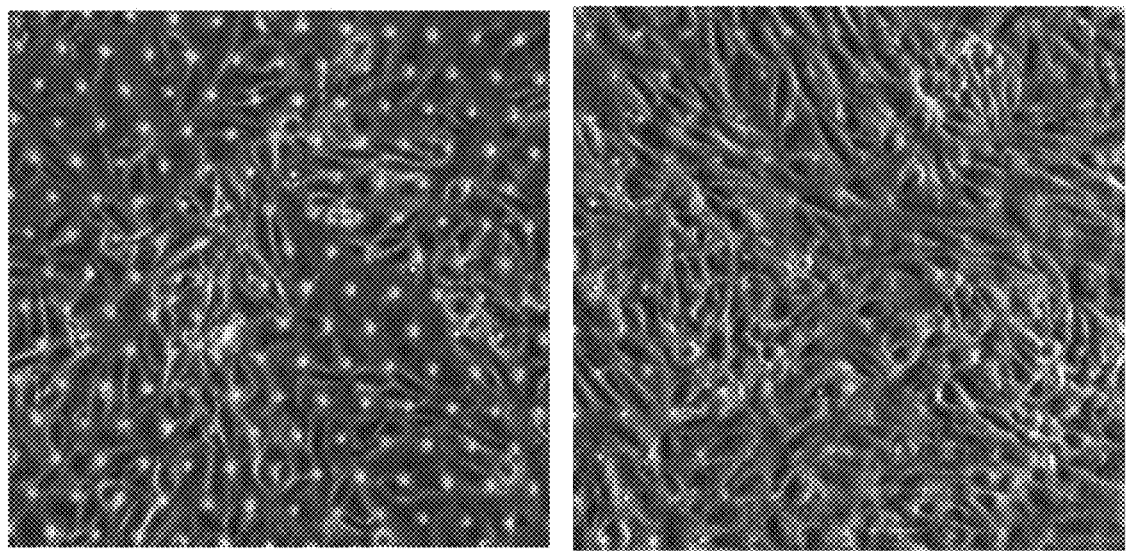
FIG. 10A shows exemplary results comparing morphology of Human PT cell samples obtained from Biopredic to Human PT cell samples obtained from Lonza, cultured in duplicate, but separate, microfluidic devices. For comparison.

Kidney-Chip Model Optimization: Cell Source. In some embodiments, examples of parameters include but are not limited to testing commercial sources of cells for choosing an optimal cell source. For examples shown herein, the following examples of commercial cell sources were evaluated: BioPredic, Lonza, ScienCells, Cell Biologics, and Sigma. In some embodiments, examples of parameters include but are not limited to evaluating seeding density (e.g. 80,000 cells/chip). In some embodiments, Human PT cells were obtained from Biopredic and from Lonza. FIG. 10A.

Additional parameters tested for optimizing growth, morphology and function of a PT-Kidney chip are briefly listed as follows.

Kidney-Chip Model Optimization: Microfluidic Chip (device) Designs. In some embodiments, examples of parameters include but are not limited to evaluating chip configuration (design), e.g. S1 tall channel chip versus a High Shear chip. See microfluidic chip examples for S1 and HS chips in FIGS. 1C and 1D. In exemplary embodiments, a S-1 Chip (tall channel chip) and an HS Chip were fabricated, seeded, and used for comparative growth, morphology and function of cultured kidney cells. Morphological observations of human primary PT cells seeded into a microfluidic chip were evaluated comparing two types of chip configurations, i.e. S1 tall and HS, two types of ECM, i.e. E1 and E2, as described herein, under either low or high flow.

Kidney-Chip Model Optimization: Flow Rates/Fluid Shear Stress. In some embodiments, examples of parameters include but are not limited to evaluating Fluid shear stress (e.g. low flow versus high flow, e.g. 30 µl/h versus 150 µl/h). In some embodiments, low and high flow rates were used for producing corresponding low and high shear stress in different embodiments of Kidney-Chip microfluidic devices, e.g. S-1 tall channel chip, HS chip, etc., for comparing growth, morphology and function of cultured kidney cells. Kidney-Chip Model Optimization: ECM. In some embodiments, examples of parameters include but are not limited to evaluating ECM coating of membrane on the epithelial cell side (e.g. ECM1 (KidneySpec) versus ECM2 (Collagen IV plus Matrigel). See Table 11 for comparative ECM1-ECM2. ECM was used for coating plates for culturing PT kidney cells and coating the PT Kidney cell side of the PDMS membrane of the Microfluidic Chips. Kidney-Chip Model Optimization: Barrier Function. Comparative embodiments of PT-Kidney-Chips were evaluated for barrier function.

Exemplary readouts for evaluating embodiments of PT-Kidney-Chips include but are not limited to morphology observations; gene expression; immunohistology of biomarkers, etc. As one example, collect N=3 devices as samples for RNA isolation for each treatment. As one example, immunostain N=3 devices for biomolecule expression for each treatment. As one example, immunostain top channel: Double stain of mouse anti-Sodium Potassium ATPase (anti-mouse visualization)+rabbit anti-aquaporin (anti-rabbit visualization). As one example, immunostain bottom channel: F-actin, far-red emission under florescence microscopy. As one example, immunostain Top channel: Double stain of rabbit anti-OAT1 (anti-rabbit visualization)+ mouse anti MRP2 (anti-mouse visualization). As one example, immunostain bottom channel: rabbit VE-Cadherin (anti-rabbit visualization).

A. Proximal Tubular Kidney Cell Comparisons.

In some embodiments, kidney proximal tubule cells are compared between different commercial sources and lots (i.e. samples). Thus, an exemplary method of evaluating a PT kidney cell source for use in fluidic devices is described herein. In some embodiments, kidney proximal tubule cell samples are compared growing in static cultures. In some embodiments, kidney proximal tubule cell samples are compared growing in microfluidic cultures under flow.

In some embodiments, kidney PT cells are seeded into microfluidic devices (chips) as described herein.

One method for accessing and passing PT Kidney cells (derived from a biopssy, commercially obtained, i.e. testing cell lots, in culture for use as healthy normal PT Kidney cells on chip (e.g. Quality Acceptance Criteria) includes AQP1 Na/K-ATPase expression, high albumin uptake, cuboidal morphology. Thus, in one embodiment, a method for evaluating the quality of human renal proximal tubule cells as normal healthy cells includes immunostaining for AQP1 (positive AQP1), high expression of Na/K-ATPase (primarily in the basal area of the cell layer) (positive Na/K-ATPase), high albumin uptake, cuboidal morphology, etc. Additional criteria may include expression of ZO-1, Megalin, OAT1, OCT2, acetylated tubulin, etc.

Therefore, under culture conditions described herein, and the cells provided at that time, proximal tubule cells obtained from the Lonza showed better morphology compared to cells obtained from Biopredic. Exemplary functional tests by the vendor: e.g. TEER (178 ohms/cm$^2$) and Rhodamin 123 uptake assay. Thus, in some preferred embodiments during the development of the present inventions, proximal tubule kidney cells obtained from the Lonza are preferred over proximal tubule kidney cells obtained from Biopredic. Exemplary cells include RPTEC from Lonza, i.e. Human Proximal Tubular Epithelial Cells (Cat. #CC-2553).

Figure 10B:
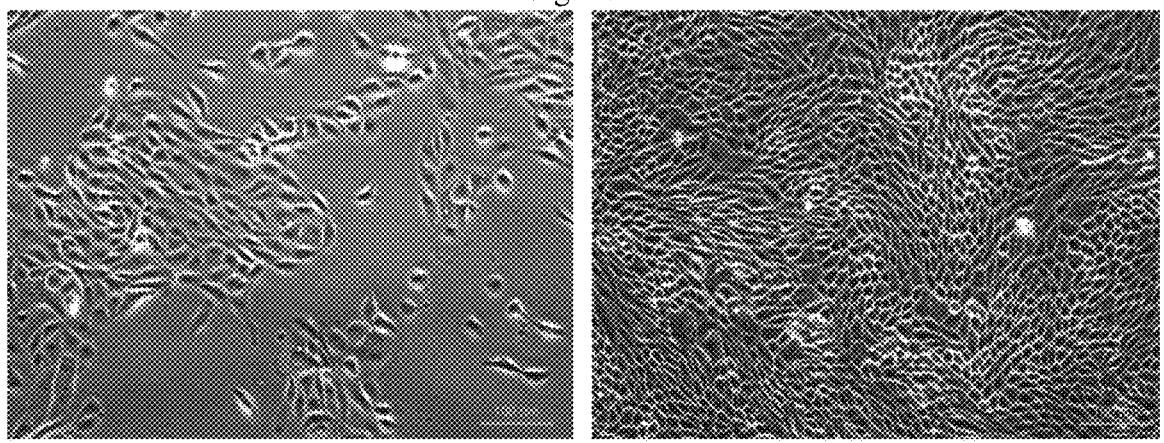
FIG. 10B shows exemplary results comparing morphology of Renal Proximal Tubular Epithelial Cells growing on plates, left Day 1 on Well plate, P2. Right, Day 5 on Well plate, P2. Normal morphology of Proximal tubular epithelial cells are observed for cells growing on both well plates and microfluidic devices.

FIG. 10A shows exemplary results comparing morphology of Human PT cell samples obtained from Biopredic to Human PT cell samples obtained from Lonza, cultured in duplicate, but separate, microfluidic devices. For comparison, FIG. 10B shows exemplary results comparing morphology of Renal Proximal Tubular Epithelial Cells growing on plates, left Day 1 on Well plate, P2. Right, Day 5 on Well plate, P2. Normal morphology of Proximal tubular epithelial cells are observed for cells growing on both well plates and microfluidic devices.

Thus, in some preferred embodiments, proximal tubule cells obtained from Lonza are preferred over cells obtained from Biopredic, or other commercial PT cell sources, for use during the development of the present inventions. However, in some embodiments as described and shown herein, PT Kidney cells were used obtained from Biopredic and CellScience in addition to Lonza.

In some embodiments, PT kidney cells are cultured under static conditions on-plate. In some embodiments, kidney PT cells are seeded into culture plate (static) cultures for expanding numbers of kidney PT cells. In some embodiments, kidney PT cells are seeded into culture plate (static) cultures for providing kidney PT cells for seeding microfluidic chips.

In one embodiment, a method for evaluating the quality of human Renal Microvascular Endothelial Cells as normal healthy cells includes immunostaining for one or more of VE-cadherin (preferred), Factor VIII antigen, acetyl-LDL uptake. Number of plateable days, Up to 2 passages. One example for accessing and passing endothelial cells as healthy normal cells includes staining for VE-cadherin expression providing a continually stained outline of the endothelial cells in the cell layer. Exemplary cells include HGMVEC (Primary Human Glomerular microvascular Endothelial cells) from Cell Systems, i.e. (Cat. #ACBRI 128. Exemplary Kidney endothelial cell medium includes Complete Classic Medium With Serum and CultureBoost from Cell Systems (Cat. #4Z0-500).

In addition to biomarker tests for cells, cell populations for use in PT-Kidney chips have a viability >80% when revived from cryostorage. Where cells were derived from cadavers, cause of death was unrelated to liver disease or virus.

Passage refers to harvesting cells in culture before or at confluency then plated onto a tissue culture plate or seeded into the microfluidic device. P1 refers to cells that were passaged 1 time. Thus P1 cells were passaged one time then directly observed before P2 or collected for evaluation before P2. P2 refers to cells passaged 2 times, and so on.

In general cells may be obtained from biopsies and prior to a first passage. Donors are 0-80 years of age, any gender, any ethnicity, any weight, documented level of smoking, did not report to be a heavy drinker, no substance abuse, specifically no cocaine or heroin use, and no positive serology for HIV, Hepatitis B and Hepatitis C. Number of plateable days, 5+ days. Cell population viability is >80%. Where cells were derived from cadavers, cause of death was unrelated to kidney disease or virus.

B. Biomarker Evaluation.

In some embodiments, Proximal Tubule-Chips are evaluated for biomarkers of function and/or injury, e.g. Kidney Injury Marker 1 (KIM-1), etc. In some embodiments, end point analysis includes but is not limited to morphological observations and measurements; immunohistochemistry of biomarker protein; gene expression analysis, e.g. OAT1, OAT3, CLU, KIM1, etc. One example of a housekeeping gene (i.e. a gene expressed in the majority of eukaryotic cells this is used for comparing levels of gene expression is 18S ribosomal RNA (rRNA), a component of eukaryotic cytoplasmic ribosomes.

The following are exemplary proteins and/or genes contemplated as biomarkers for assessing cells cultured in Kidney chips. In some embodiments, such biomarkers are evaluated as an endpoint for methods including but not limited to: evaluating the quality of cells cultured on-chip; determining toxicity levels of a compound; determining toxicity levels of a treatment for enhancing kidney function; determining toxicity levels of a known drug; determining toxicity levels of a test drug; etc.

The following genes and their expressed protein, or status of protein, e.g. acetylated tubulin, are listed including exemplary criteria for determining normal expression levels and/ or as a guide for determining an increase in levels or a decrease when the opposite type of level is determined, e.g. for acetylated tubulin shows a 30% decrease in expression per unit area in a transwell culture. For those biomarkers without a guide for evaluating expression, generally at least a one-fold change or a statistical significance compared to a control or another treatment is considered a change in expression. For biomarkers in the form of expressed genes, e.g. mRNA, a normal/healthy expression level or change in expression, such as an increased mRNA fold change refers to at least one of the following: an increased amount of mRNA and/or localization of protein expression compared to conventional culture system (~2× fold change); a similar mRNA level to day 0 proximal tubule cell as an option; etc.

Acetylated tubulin protein is associated with microtubule-stabilization and microtubule dynamics in living cells. An acetylated tubulin level that is at least a 30% increase in levels per unit area versus a per unit area in a transwell culture is considered one biomarker for establishing that PT kidney cells cultured on chip are healthy and normal. Lower acetylated tubulin levels (or relative deacetylated tubulin) are considered a biomarker for unhealthy PT kidney cells.

AQP1 (Aquaporin 1 (Channel-Forming Integral Protein, 28 kDa)) refers to an integral membrane protein and its coding gene. One embodiment comprising an increase in AQP1 includes one or more of an increase in mRNA fold change and localization compared to a conventional culture system (~2× fold change); a similar mRNA level to day 0 proximal tubule cell as a fold change for mRNA. Localization of cellular expression is qualitative, in part because expression is typically in the apical region of a cuboidal type of PT kidney cell.

ATP1A1 (ATPase Na+/K+ Transporting Subunit Alpha 1) refers to a P-type cation (positive charged ion) transport ATPase integral membrane protein and its coding gene.

GGT (Gamma-Glutamyltransferase 1) refers to an enzyme protein and its coding gene.

GLUT1 (Glucose transporter 1) refers to a glucose transporter protein; its coding gene may be referred to as SLC2A1 (Solute Carrier Family 2 Member 1).

KIM1 (Kidney Injury Molecule-1) refers to a transmembrane protein whose ectodomain may be shed from cells. In vivo, KIM1 levels may be measured in urine for determining levels of kidney function (i.e. a relative absence of KIM1 protein), including normal kidney function or as an indication of acute kidney injury, i.e. measurable levels of KIM1 protein. Acute kidney injury refers to a rapid decline in glomerular filtration rate.

LRP2 (Low-Density Lipoprotein Receptor-Related Protein 2) refers to a protein and its coding gene.

MATE1 Multidrug And Toxin Extrusion 1 (SLC47A1 (Solute Carrier Family 47 Member 1)) refers to a protein and its coding gene.

MATE2K/Multidrug And Toxin Extrusion 2 (SLC47A2 (Solute Carrier Family 47 Member 2)) refers to a protein and its coding gene.

MRP4 (ATP Binding Cassette Subfamily C Member 4); its coding gene may be referred to as an ABCC4 Gene.

Na/K-ATPase refers to protein belongs to the family P-type cation transport ATPases, and to the subfamily of Na+/K+-ATPases. Localization of cellular expression is qualitative, in part because expression is typically in the basal region of a cuboidal type of PT kidney cell.

OAT refers to a family of multispecific organic anion transporters (OATs), genes and their expressed proteins. OAT1 may also refer to human Solute carrier family 22 member 6/8 (SLC22A6/8) genes and NKT. OAT3 may also refer to human Solute Carrier Family 22 (Organic Anion Transporter), Member 8 genes.

OCT2 (Organic cation transporter 2) (also referred to as Solute carrier family 22 member 2 (SLC22A2)) refers to a gene encoding and its expressed protein expressed on the basolateral (blood) side of proximal tubule kidney cells. OCT2 protein transporters may function as a renal uptake transporter.

P-glycoprotein (P-gp) or ATP-binding cassette (ABC) transporter, refers to a plasma membrane protein which acts as a localized drug transport, e.g. drug efflux pump. Genes encoding P-gp may have alternative splicing and the use of endogenous alternative promoters may result in multiple transcript variants.

SGLT2 (Solute Carrier Family 5 Member 2) refers to a sodium-dependent glucose transport protein; its coding gene may be referred to as a SLC5A2Gene.

TJP1 (Tight Junction Protein 1) refers to a membrane-associated guanylate kinase (MAGUK) protein and its coding gene.

The following show exemplary results comparing biomarker expression relative to passage 1 PT epithelial cells. Passage 1 (P1) refers to Proximal tubule cells obtained from a vial directly from a commercial vendor. Passage 2 (P2) refers to Proximal tubule cells from passage 2 in plate. Passage 3 (P3) refers to Proximal tubule cells from passage 3 in a plate. Kidney-Chip for this example refers to P3 proximal tubule cells seeded onto then cultured in a microfluidic chip.

TABLE 6

Raw Ct Data Used For Comparative Baseline Biomarker Gene Expression Relative to 18S rRNA.

| | OAT1 | KIM1 | OCT2 | 18s rRNA |
|---|---|---|---|---|
| Passage 1 | 30.47355 | 24.70793 | 33.7008 | 13.42414 |
| Passage 2 | 29.78605 | 25.64494 | 35.98594 | 13.28774 |
| Passage 3 | 29.11833 | 25.62439 | 34.13898 | 13.45991 |
| Kidney-chip | 29.56075 | 24.72784 | 35.26197 | 12.98591 |

Figure 11:
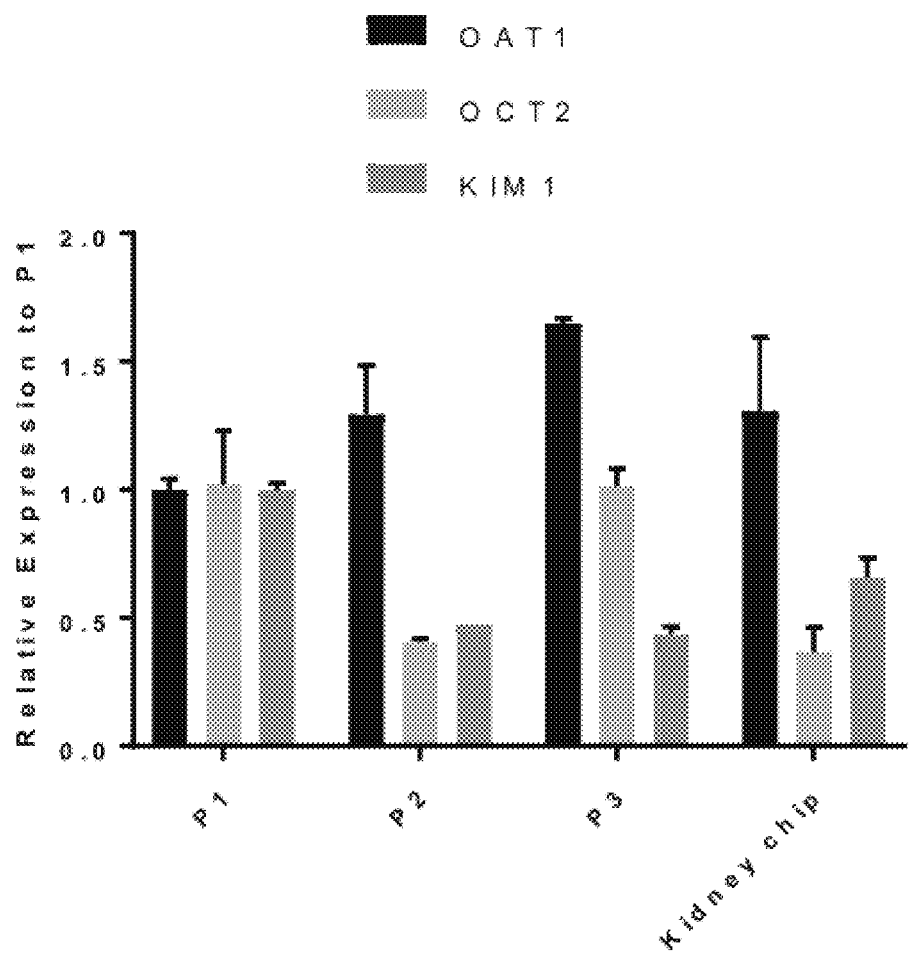
FIG. 11 shows exemplary results comparing mRNA expression in PT kidney cells at P1, P2, P3 cultured on-plates and after culturing on a Kidney-chip, showing results for biomarker expression, i.e. OAT2, OCT2 and KIM1, relative to P1.

FIG. 11 shows exemplary results comparing mRNA expression in PT kidney cells at P1, P2, P3 cultured on-plates and after culturing on a Kidney-chip, showing results for biomarker expression, i.e. OAT2, OCT2 and KIM1, relative to P1 cells.

These results demonstrated that passage 1, 2, and 3 cells and expressed OAT1 and OCT2. In contrast, OAT3 was not detected with the primers used in this experiment.

For comparison to baseline mRNA expression and because a portion of KIM-1 may be released from cells, levels of KIM1 protein, e.g. ng/day/million cells, were measured before and after treatment with an exemplary known nephrotoxic compound, Gentamicin, as described in Table 16. KIM1 protein was measured in PT Kidney cells co-cultured with HUVECs or Glomular endothelial cells. Expression levels were not at levels expected for in vitro samples undergoing cytotoxic activity using either type of endothelial cells. It was contemplated that an assay designed for use with in vitro samples would provide a more accurate result of KIM1 protein expression.

Figure 12:
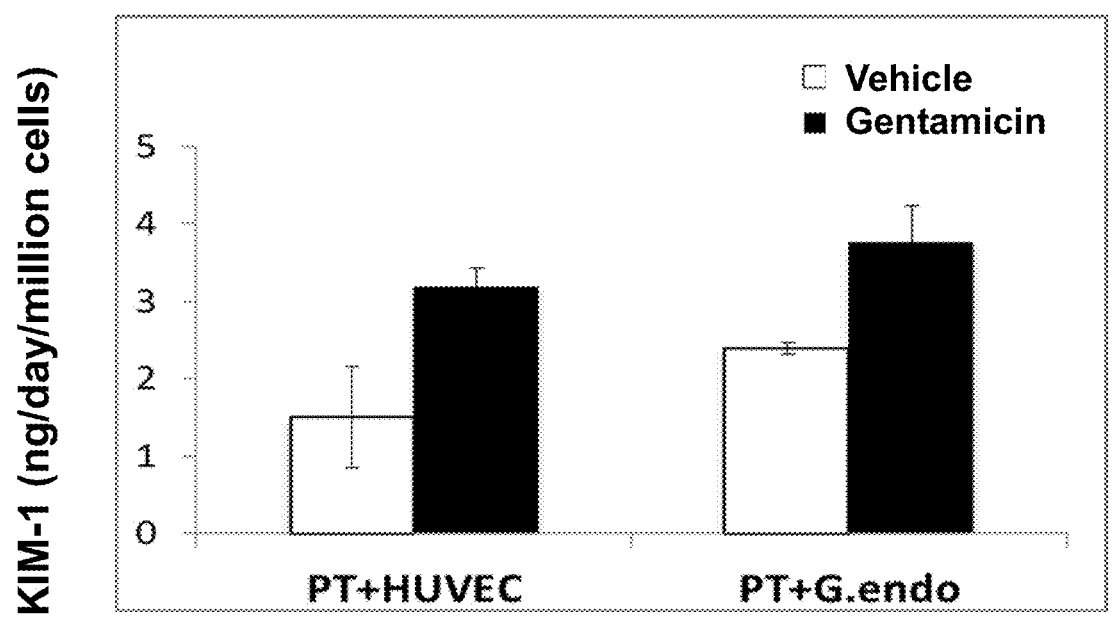
FIG. 12 shows exemplary results obtained from a commercial kit that was designed for measuring KIM1 protein in clinical (in vivo) samples. PT Kidney cells co-cultured with HUVECs or Glomular endothelial cells in microfluidic devices were treated with Gentamicin as described herein.

FIG. 12 shows exemplary results obtained from a commercial kit that was designed for measuring KIM1 protein in clinical (in vivo) samples. PT Kidney cells co-cultured with HUVECs or Glomerular endothelial cells in microfluidic devices were treated with Gentamicin as described herein. KIM1 refers to a functional biomarker and as an early injury marker, therefore it was contemplated that using cells at an earlier time point during nephrotoxicity evaluations, would allow for observing more substantial amounts of protein.

Additional contemplated biomarkers may be added as a cytotoxicity marker in a gene expression analysis panel.

Additional timepoints contemplated for sampling include 3, 6, and 24 hrs, for one example, after contact with a potential nephrotoxic compound. In some embodiments, effluent sample analysis is contemplated for analyzing released biomarkers into the effluent fluid.

Thus, in some embodiments, biomarkers that are released from cells may be evaluated (e.g. Multiplex Kidney Injury Panel Human Kits from MSD (Meso Scale Discovery): e.g. Kidney Injury Panel Human Kit: Calbindin, Clusterin, KIM-1, Osteoactivin, trefoil factor 3 (TFF3), vascular endothelial growth factor A (VEGF-A), glutathione S-transferase alpha (αGST), may be measured. In some embodiments, functional analysis is contemplated after contact with a potential nephrotoxic compound.

One exemplary protocol for evaluating quality of PT kidney cell sources in tissue culture plates, includes seeding tissue culture plates: Day 1: Seed Proximal tubular cells; Day 2: Change media; and Day 3: Harvest cells. In some embodiments, Day 3 cells are harvested as extracts for RNA analysis.

C. Proximal Tubular Kidney Cell Comparisons In Relation To Chip Configurations.

In some embodiments, examples of parameters include but are not limited to evaluating chip configuration (design), e.g. S1 tall channel chip versus a High Shear chip. See microfluidic chip examples for S1 and HS chips in FIGS. 1C and 1D.

Both S1 and HS chips support healthy PT Kidney cells on microfluidic platforms as shown by little LDH Release (%) up to 14 days in culture. Further, little cell death was observed in the S 1—Apical or Basal regions and HS—Apical or Basal regions.

Figure 14:
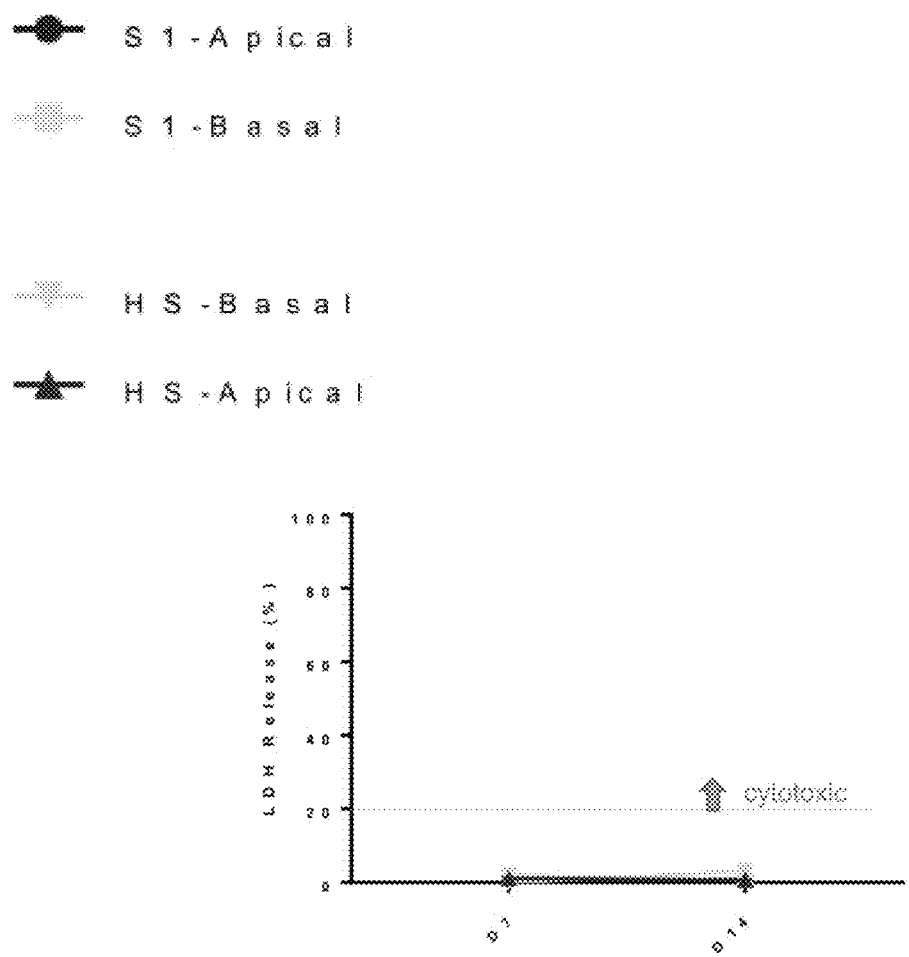
FIG. 14 shows exemplary Chip Viability. No significant cell death found in both S1 and HS chip systems. N=6.

FIG. 14 shows exemplary Chip Viability (i.e. viability of cells on the chip). No significant cell death found in either S1 and HS chip systems. N=6.

Biomarkers for Barrier function: Expression patterns of platelet endothelial cell adhesion molecule (PECAM-1) also known as cluster of differentiation 31 (CD31), may be associated with the level of barrier function. CD31 associates with maintaining and restoring the vascular permeability barrier following disruption of the endothelial cell junction. As an inhibitory receptor for circulating platelets and leukocytes, PECAM-1 is highly expressed at endothelial cell-cell junctions, where it functions as an adhesive stress-response protein to both maintain endothelial cell junctional integrity and speed restoration of the vascular permeability barrier following inflammatory or thrombotic challenge. Thus, PECAM-1/CD31 is associated with maintaining and restoring the vascular permeability barrier following disruption of the endothelial cell junction.

Cells cultured in one embodiment of a S1 chip showed clear junction between cells compared to the cells cultured in one embodiment of a HS chip. See, FIG. 15.

Figure 15:
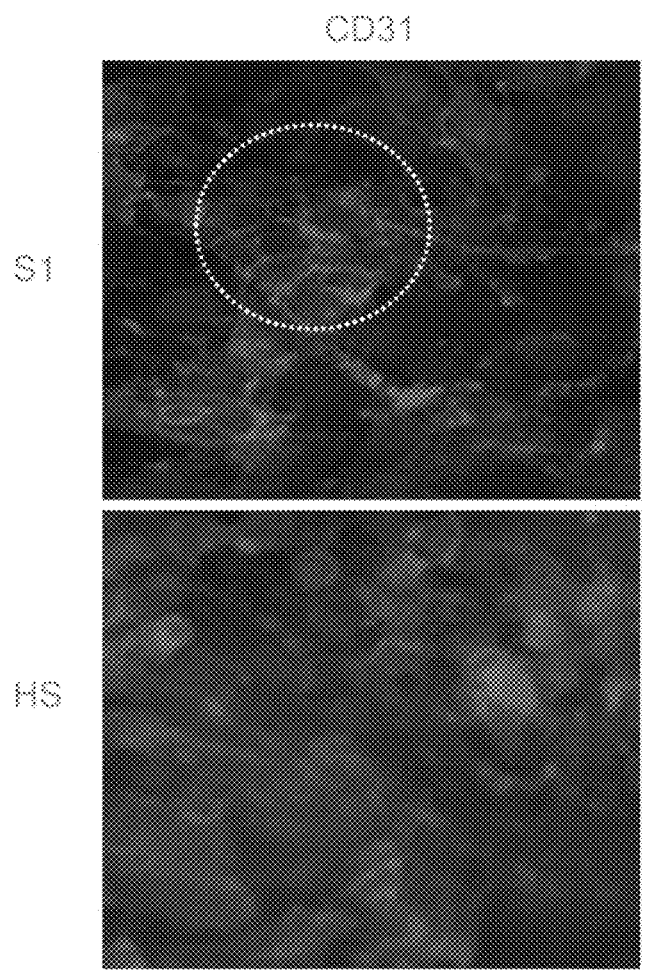
FIG. 15 shows exemplary Glomerular Microvascular Endothelial Cells expressing PECAM-1/CD31 protein. CD31—red; nuclei-blue.

FIG. 15 shows exemplary Glomerular Microvascular Endothelial Cells expressing PECAM-1/CD31 protein. CD31—red; nuclei-blue.

D. Proximal Tubular Kidney Cell Comparisons In Relation To configurations Of Microfluidic Chips and flow rates/shear stress.

In some embodiments, examples of parameters include but are not limited to evaluating Fluid shear stress (e.g. low flow versus high flow, e.g. 30 ul/h versus 150 ul/h) in both tall channel (S1) and high shear (HS) configurations of microfluidic devices. See, Table 7.

TABLE 7

Exemplary Microfluidic Chip Comparative Parameters Kidney for Evaluating primary human proximal tubular kidney cell development in Tall channel chip versus High shear chip. Flow Rates And Fluid Shear Stress.

| Chip Configuration | Channel | Low flow rate 30 µL/hr | High flow rate 150 µL/hr |
|---|---|---|---|
| Tall channel-S1 chip (1000 µm wide by × 1000 µm high/tall) | Top-apical | Shear stress: 0.0003 dyn/cm$^2$ | Shear stress: 0.0017 dyn/cm$^2$ |
| | Bottom-basal | Shear stress: 0.009 dyn/cm$^2$ | Shear stress: 0.05 dyn/cm$^2$ |
| High shear-HS chip (1000 µm wide × 100 µm high) | Top-apical | Shear stress: 0.05 dyn/cm$^2$ | Shear stress: 0.23 dyn/cm$^2$ (physiological shear stress) |
| | Bottom-basal | Shear stress: 0.04 dyn/cm$^2$ | Shear stress: 0.22 dyn/cm$^2$ |

Morphology—Proximal Tubular Cells

Morphological observations of human primary PT cells seeded into a microfluidic chip were evaluated comparing two types of chip configurations, i.e. S1 tall and HS. In some embodiments chip configurations were under either low fluid flow or high fluid flow.

Figure 13A:
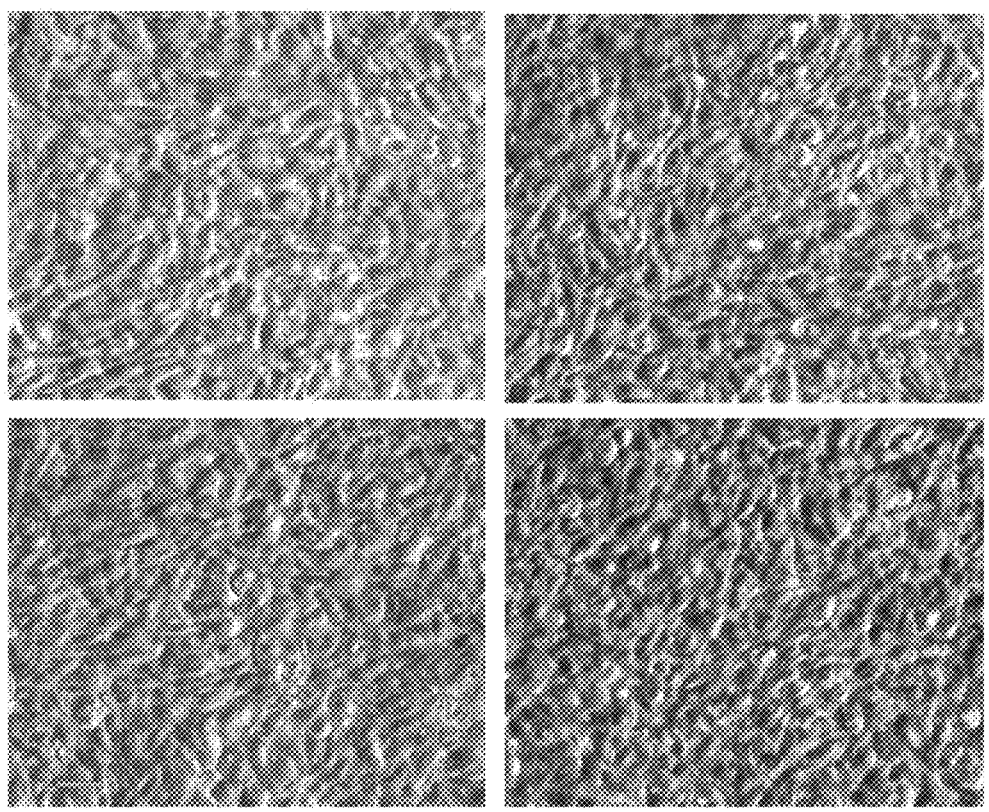
FIG. 13A shows exemplary results comparing Morphology (Day 7) results where PT cells in the High shear chip showed somewhat 3D (cuboidal) shape than the cells in the S-1 Tall channel chip. Left panels: Tall Channel. Right panels: High Shear. Upper panels: 30 µl/h. Lower panels: 150 µl/h. Scale bar-50 µm.

FIG. 13A shows exemplary results comparing Morphology (Day 7) results where PT cells in the High shear chip showed somewhat 3D (cuboidal) shape than the cells in the S-1 Tall channel chip. Left panels: Tall Channel. Right panels: High Shear. Upper panels: 30 µl/h. Lower panels: 150 µl/h. Scale bar=50 µm.

Figure 13B:
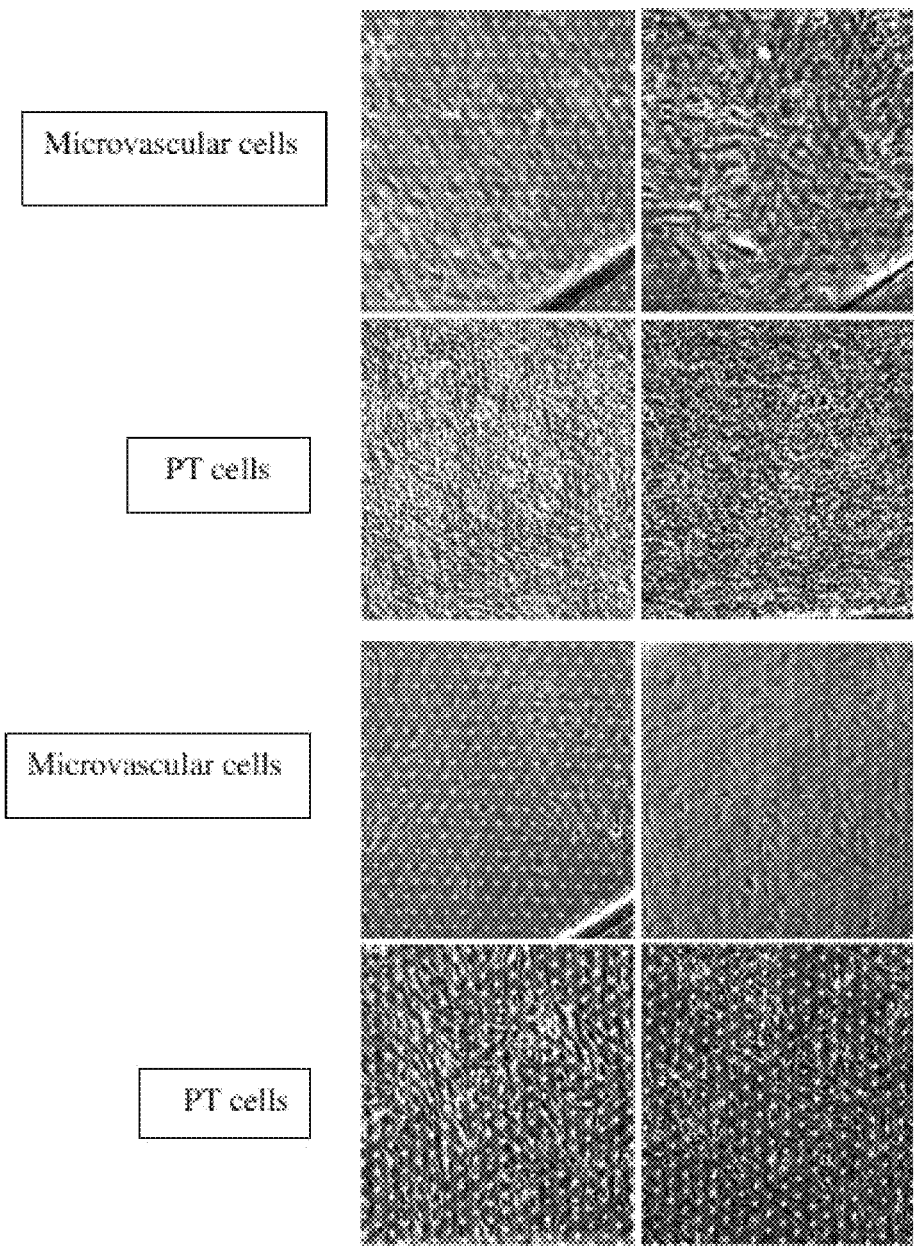
FIG. 13B shows exemplary results comparing Morphology (Days 1 (left set of panels) and Day 7 right set of panels) showing PT Kidney cells in one channel and microvascular cells in the opposing channel separated by a PDMS membrane. Upper panels, S-1 Tall channel chip. Lower panels, HS chip.

FIG. 13B shows exemplary results comparing Morphology (Days 1 (left set of panels) and Day 7 right set of panels) showing PT Kidney cells in one channel and microvascular cells in the opposing channel separated by a PDMS membrane. Upper panels, S-1 Tall channel chip. Lower panels, HS chip.

E. Effects on Biomarker Proteins under different Configurations Of Microfluidic Chips, And Flow rates.

Gene Expression Data: e.g. Raw Data. Total RNA collected was estimated about 3-5 µg per chip. For qPCR 2.5 ng of mRNA was used per each reaction. OAT3 primer—did not detect a transcript. Ct (cycle threshold) refers to a number of cycles after which a fluorescent signal is considered to cross the threshold for expression (i.e. exceeds background level). A lower Ct value than 9 (<9) is not ideal for calculation of automatic baseline of Ct. Measurement of KIM1 expression in vitro has challenges (Kokura et al., 2016).

Figure 16:
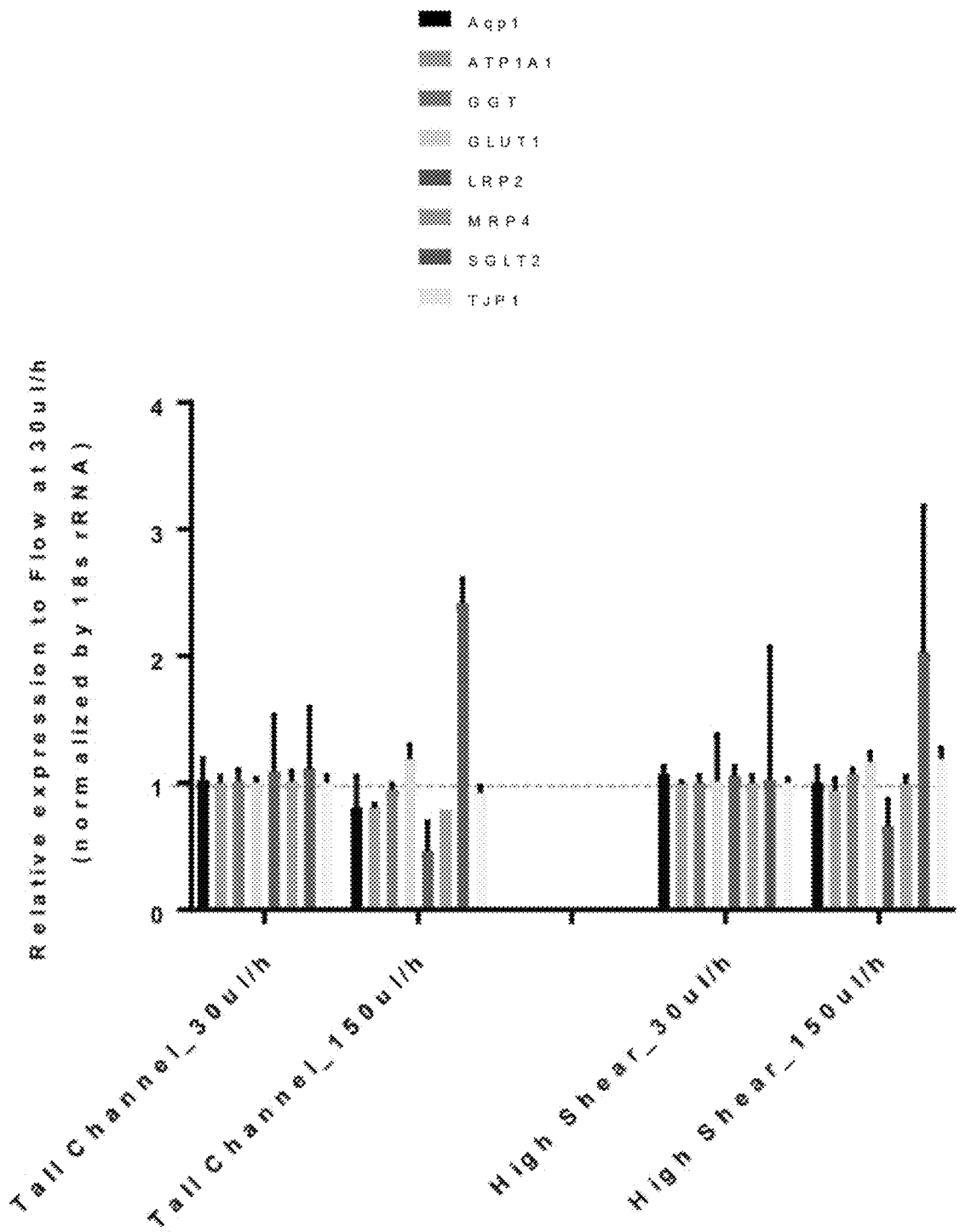
FIG. 16 shows exemplary PT-Kidney-Chip flow (rate) effect on gene expression results comparing embodiments of Tall Channel (S1) devices vs. high shear (HS) devices at low (30 µl/hr) vs. high (150 µl/hr) flow rates (in both channels) on Day 7. Human PT cells were from Lonza, using the E2 ECM condition. Gene expression baseline is calculated as relative expression to flow at 30 µl/hr (blue dotted line) (normalized by 18 s rRNA).

FIG. 16 shows exemplary PT-Kidney-Chip flow (rate) effect on gene expression results comparing embodiments of Tall Channel (S1) devices vs. high shear (HS) devices at low (30 µl/hr) vs. high (150 µl/hr) flow rates (in both channels) on Day 7. Human PT cells were from Lonza, using the E2 ECM condition. Gene expression baseline is calculated as relative expression to flow at 30 µl/hr (blue dotted line) (normalized by 18s rRNA).

Figure 17:
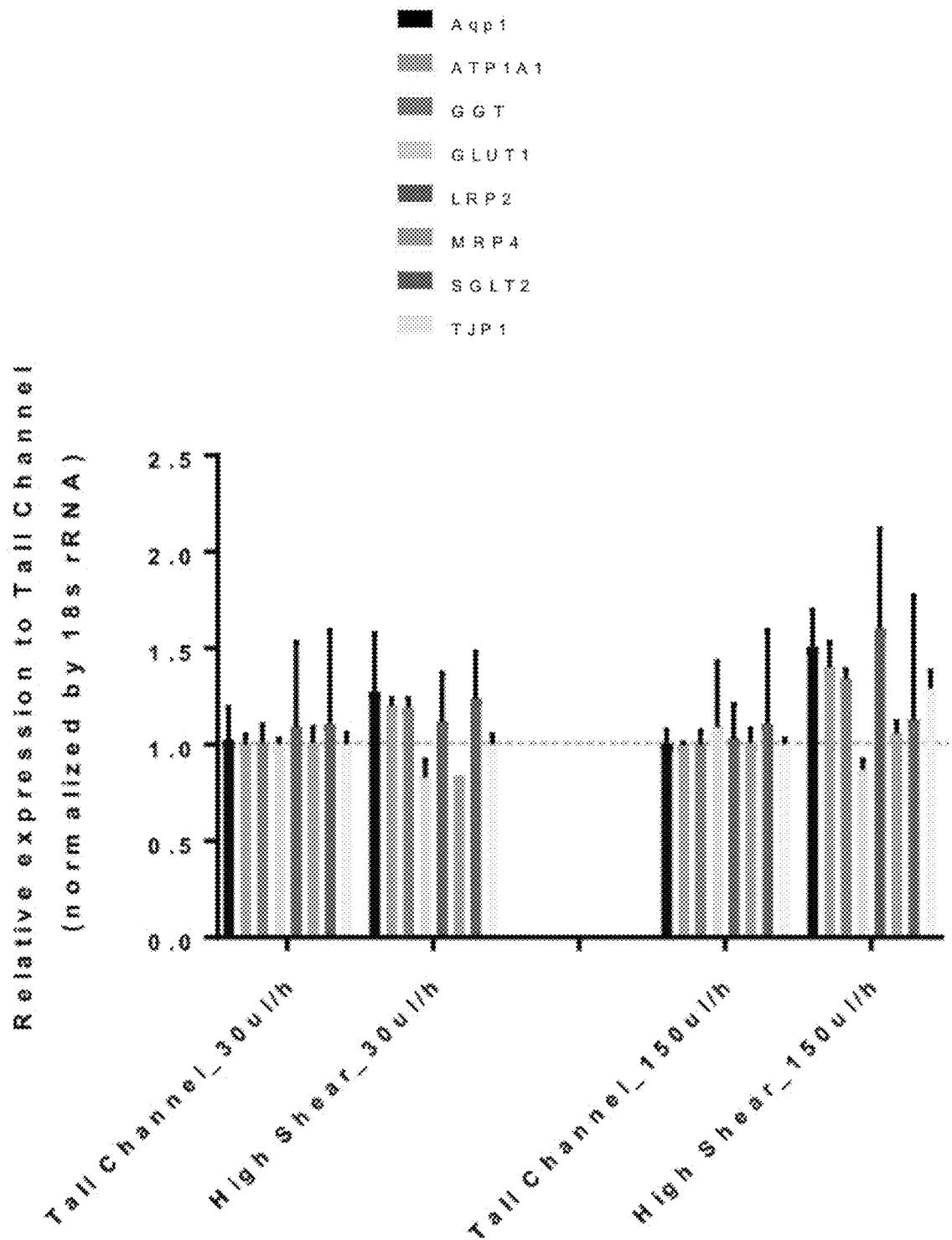
FIG. 17 shows exemplary PT-Kidney-Chip flow (rate) effect on gene expression results comparing embodiments of Tall Channel (S1) devices vs. high shear (HS) devices at low (30 µl/hr) vs. high (150 µl/hr) flow rates (in both channels) on Day 7. OAT1 and OAT3 expression in HS chip were higher than that of S1 chip. Similar expression of Na/K ATPase, LRP2 and AQP1 in both chips Gene expression baseline is calculated as relative expression to a Tall channel chip for low (30 µl/hr) and high (150 µl/hr) flow rates (normalize by 18S rRNA), respectively.

FIG. 17 shows exemplary PT-Kidney-Chip flow (rate) effect on gene expression results comparing embodiments of Tall Channel (S1) devices vs. high shear (HS) devices at low (30 µl/hr) vs. high (150 µl/hr) flow rates (in both channels) on Day 7.

OAT1 and OAT3 expression in HS chip were higher than that of S1 chip. Similar expression of Na/K ATPase, LRP2 and AQP1 in both chips Gene expression baseline is calculated as relative expression to a Tall channel chip for low (30 µl/hr) and high (150 µl/hr) flow rates (normalize by 18S rRNA), respectively.

Figure 18:
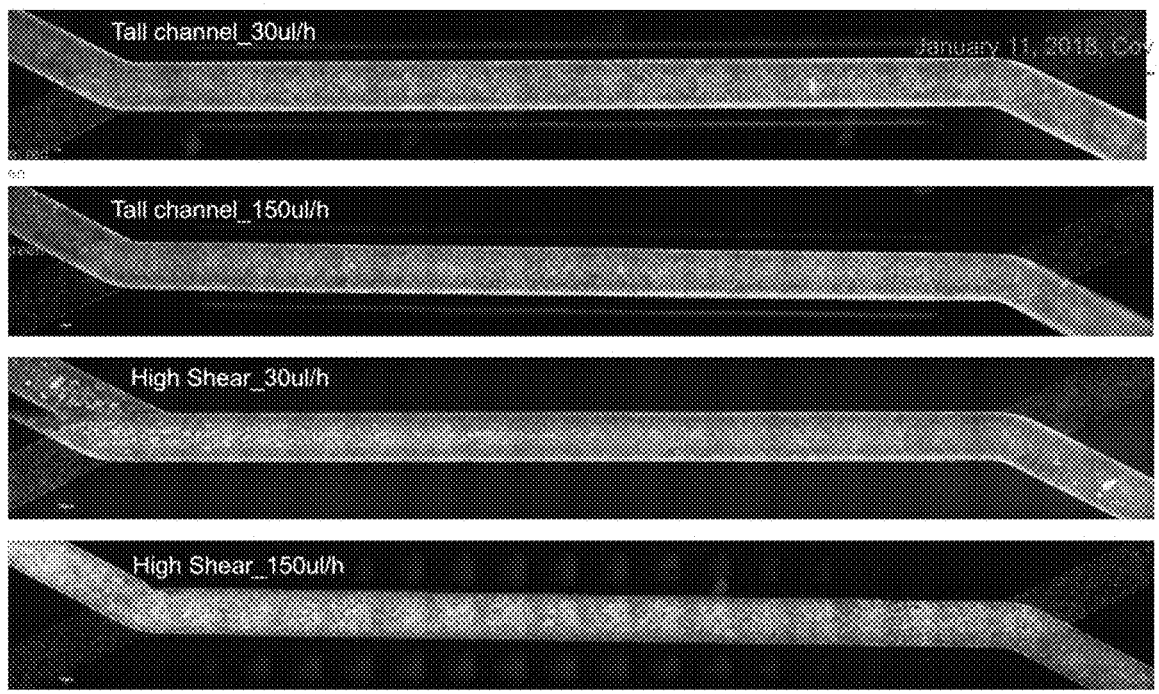
FIG. 18 shows exemplary results showing differences in transporter molecule expression between two exemplary microfluidic devices and two different flow rates. Upper panels show immunostaining results of the top channel stained for Na+/K+ ATPase (red) Aquaporin (green) and nuclear material stained with DAPI colored blue; bottom channel stained for VE-Cadherin (green) and nuclear material stained with DAPI colored blue.

FIG. 18 shows exemplary results showing differences in transporter molecule expression between two exemplary microfluidic devices and two different flow rates. Upper panels show immunostaining results of the top channel stained for Na+/K+ ATPase (red) Aquaporin (green) and nuclear material stained with DAPI colored blue; bottom channel stained for VE-Cadherin (green) and nuclear material stained with DAPI colored blue.

From top panel to the bottom panel: Tall channel device with a flow rate of 30 µl/hr; Tall channel device with a flow rate of 150 µl/hr; High Shear channel device with a flow rate of 30 µl/hr; and a High Shear channel device with a flow rate of 150 µl/hr.

Exemplary Immunohistochemistry Method for observation of immunostained and chemically stained cells using a florescent microscope.

Kidney glomerular endothelial cells from Lonza were seeded onto embodiments of chip configurations under different shear stress (low fluid flow or high fluid flow rates). The next day, Proximal tubular cells were seeded on ECM2 coated membranes in the opposite channel. Media was changed to fresh on the following day, the chip was connected to a culture module device, regulate cycle. Bright field images for morphological observations were taken on Day 3, Day 5 and Day 7. Endpoint analysis included immunostaining; RNA isolation for gene expression, etc. Immunostaining: Top channel: Double stain of anti-Sodium Potassium ATPase (anti-mouse)+anti-aquaporin (anti-rabbit). Bottom: F-actin stain, e.g. Alexa Fluor® phalloidin, provides far-red fluorescence. Top: Double stain of anti-OAT1 (anti-rabbit)+anti MRP2 (anti-mouse). Bottom: VE-Cadherin (anti-rabbit).

FIG. 77 shows exemplary results showing differences in transporter molecule expression between two exemplary microfluidic devices and two different flow rates. Upper panels show immunostaining results of the top channel stained for MRP2 (red); OAT1 (green) nuclear material stained with DAPI, colored blue; Phalloidin visualized using Cy5, colored light blue. Bottom channel stained for VE-Cadherin (green); nuclear material stained with DAPI, colored blue; and Phalloidin visualized using Cy5, colored light blue.

From top panel to the bottom panel: Tall channel device with a flow rate of 30 µl/hr; Tall channel device with a flow rate of 150 µl/hr; High Shear channel device with a flow rate of 30 µl/hr; and a High Shear channel device with a flow rate of 150 µl/hr.

TABLE 8

Exemplary Shear Rates in Apical and Basal Channels.

| S1 | apical | 0.0017 dyn/cm$^2$ |
|---|---|---|
| | basal | 0.05 dyn/cm$^2$ |
| HS | apical | 0.23 dyn/cm$^2$ |
| | basal | 0.22 dyn/cm$^2$ |

FIG. 20 shows exemplary results IHC (immunohistochemistry)-Data: High shear chip device with high flow, stain 1. Aquaporin 1 (green); Na+, K+-ATPase (red).

FIG. 21 shows exemplary results IHC-Data: High shear chip device with high flow, stain 2. OAT1 (green); MRP2 (red).

FIG. 22 shows exemplary results IHC-Data: High shear chip device with low flow, stain 1. Aquaporin 1 (green); Na+, K+-ATPase (red).

FIG. 23 shows exemplary results IHC-Data: High shear chip device with low flow, stain 2. OAT1 (green); MRP2 (red).

FIG. 24 shows exemplary results IHC-Data: Tall channel chip device with high flow, stain 1. Aquaporin 1 (green); Na+, K+-ATPase (red).

FIG. 25 shows exemplary results IHC-Data: Tall channel chip device with high flow, stain 2. OAT1 (green); MRP2 (red).

FIG. 26 shows exemplary results IHC-Data: Tall channel chip device with low flow, stain 1. Aquaporin 1 (green); Na+, K+-ATPase (red).

FIG. 27 shows exemplary results IHC-Data: Tall channel chip device with low flow, stain 2. OAT1 (green); MRP2 (red).

F. Passaging PT Kidney cells over time and Chip configuration under low and high fluid flow effects on Biomarker expression. Passaged RPTC didn't seems to affect AQP1 and OCT2 expression. Increased fluid shear might induce AQP1 and OCT2 expression FIG. 28 shows an exemplary quantification AQP1 (upper) and OCT2 (lower) Gene Expression relative to Primary Renal Proximal Tubule Epithelial Cells; Normal, Human (RPTC) P2 cells (used as a control) (normalize by 18S rRNA). RPTC cells in different chip configurations, under low or high flow.

FIG. 29A shows exemplary polarization and cuboidal morphology of Renal Proximal Epithelial Cells co-cultured in one embodiment of a PT-Kidney Cell Chip. Immunostaining of. Aquaporin 1 (green)/Na/K-ATPase (red). Left panels: Low flow; right panels: High flow. S1 upper row. HS lower row. AQP1 and Na/K-ATPase expression in S1 chip under high flow condition showed increased expression than the cells from HS chip.

FIG. 29B shows exemplary Immunostaining of Kidney Microvascular Endothelial Cells. Glomerular Endothelial Cells (F-actin (pink)/Nuclei (blue)). Cells under high shear stress showed elongated morphology compared to the cells from low shear stress.

G. Effects Of Microfluidic Chip Configurations Flow Rates And Extracellular Matrix (ECM).

In some embodiments, biomarker expression is compared between types of chip configurations and flow rates.

In some embodiments two types of ECM were compared, i.e. E1 and E2, in some embodiments under either low or high flow. In some embodiments, ECM representative of a region of the kidney is used for coating the membrane of a microfluidic device. For examples, see Kidney International (1999) 56, 2016-2024, and FIG. 3A.

ECM 1: 20 µg/ml of Kidney ECM from East River Biosolutions. Derived from healthy acellular porcine kidney, TissueSpec™ kidney matrix is rich in
- basement membrane proteins including collagen IV, laminins, and fibronectin and regulates pathways in kidney development—including ureteric bud branching morphogenesis, renal tubule differentiation, glomerular assembly, and nephron formation
- as well as in kidney repair and disease.

In some embodiments, kidney tissue ECM may be derived directly from biopsies.

ECM 2: 50 µg/ml of Collagen IV+100 µg/ml of Matrigel.

It is not meant to limit the type of ECM used for coating membranes on the epithelial side for enhancing epithelial cell attachment and growth. Additional types of ECM contemplated for testing include but are not limited to Lonza Kidney Matrix and Bpredic Kidney Matrix, etc.

In some embodiments, biomarker expression is compared between types of ECM, chip configurations and flow rates.

See Table 11. E1 refers to the use of Kidney ECM from Eastriver Biosolutions. E2 refers to the use of Emulate kidney ECM composition.

As one example, compare kidney proximal tubular cell development in Tall channel chip versus High shear chip with different shear stress (low and high flow rate).

TABLE 9

Kidney-Chip Model Optimization - Flow Rate and Fluid Shear Stress.

| | | 30 ul./hr | 150 uL/h |
|---|---|---|---|
| S1 Tall Channel chip (1000 µm wide by × 1000 µm tall) | Top | 0.0003 dyn/cm$^2$ | 0.0017 dyn/cm$^2$ |
| | Bottom | 0.009 dyn/cm$^2$ | 0.009 dyn/cm$^2$ |
| HS chip (1000 µm wide × 100 µm tall) | Top | 0.05 dyn/cm$^2$ | 0.23 dyn/cm$^2$ |
| | Bottom | 0.04 dyn/cm$^2$ | 0.22 dyn/cm$^2$ |

TABLE 10

Chip Configurations.

| | | Low flow rate (n = 6) | High flow rate (n = 6) |
|---|---|---|---|
| Tall channel chip (1000 µm × 1000 µm) | Top | 30 µl/hr, Shear stress: 0.0003 dyn/cm$^2$ | 150 uL/hr, Shear stress: 0.0017 dyn/cm$^2$ |
| | Bottom | 30 µl/hr, Shear stress: 0.009 dyn/cm$^2$ | 150 uL/hr, Shear stress: 0.009 dyn/cm$^2$ |
| High shear (HS) chip (1000 µm × 100 µm) | Top | 30 µl/hr, Shear stress: 0.05 dyn/cm$^2$ | 150 µl/hr, Shear stress: 0.23 dyn/cm$^2$ (physiological shear stress) |
| | Bottom | 30 µl/hr, Shear stress: 0.04 dyn/cm$^2$ | 150 µl/hr, Shear stress: 0.22 dyn/cm$^2$ |

TABLE 11

Experimental Groups.

| Microfluidic Chip (device) Type: | Flow rate | ECM |
|---|---|---|
| S1 chip (1000 µm × 1000 µm) | Low flow (30 µL/hr) | E1 |
| | | E2 |
| | High flow (150 µL/hr) | E1 |
| | | E2 |
| HS chip (1000 µm × 100 µm) | Low flow (30 µL/hr) | E1 |
| | | E2 |
| | High flow (150 µL/hr) | E1 |
| | | E2 |

One exemplary protocol for evaluating quality of PT cell sources in microfluidic devices, includes: Day 1: under static conditions, seeding Kidney glomerular endothelial cells; Day 3: under static conditions, seeding Proximal tubular cells; Day 4: Change media; Day 5: Connect to flow and begin flowing fluids through upper and lower channels, and regulate cyclic stretching. In some embodiments, record images of cellular morphology, e.g. Day 3, Day 5 and Day 7.

H. Evaluation Of Function In Relation To Chip Configuration, Flow Rates And Extracellular Matrix (ECM) Under Different Flow Rates.

Exemplary Readouts include: Biomarkers, e.g. Immunostaining then observing using an Immunofluorescence Microscope; Albumin Uptake; Morphology; Barrier Function; etc.

In some embodiments, a Well Plate is compared (versus) embodiments of a PT-Kidney Chip. Some examples are provided below.

Immunofluorescence Microscope: polarization of PT cells: Aquaporin 1 localized on apical and Na+/K+ ATPase localized on basolateral of proximal tubular cells.

FIG. 28 shows an exemplary quantification AQP1 (upper) and OCT2 (lower) Gene Expression relative to Primary Renal Proximal Tubule Epithelial Cells; Normal, Human (RPTC) P2 cells (used as a control) (normalize by 18S rRNA). RPTC cells in different chip configurations, under low or high flow.

FIG. 29A shows exemplary polarization and cuboidal morphology of Renal Proximal Epithelial Cells co-cultured in one embodiment of a PT-Kidney Cell Chip. Immunostaining of. Aquaporin 1 (green)/Na/K-ATPase (red). Left panels: Low flow; right panels: High flow. S1 upper row. HS lower row. AQP1 and Na/K-ATPase expression in S1 chip under high flow condition showed increased expression than the cells from HS chip.

FIG. 29B shows exemplary Immunostaining of Kidney Microvascular Endothelial Cells. Glomerular Endothelial Cells (F-actin (pink)/Nuclei (blue)). Cells under high shear stress showed elongated morphology compared to the cells from low shear stress.

Example F—In-Situ Visualization of Fluorescently Labeled Albumin

In some embodiments, a PT-Kidney-Chip creates in vitro regulation of protein absorption in the human kidney. In vivo, the proximal tubule reabsorbs nearly the entire amount of albumin that is filtered by the glomerulus through receptor-mediated endocytosis and consecutive lysosomal hydrolysis. Thus, in some embodiments, a Proximal Tubule Kidney-Chip can be used to monitor fluorescently labeled albumin uptake. The following is an exemplary method for observing FITC-labeled albumin uptake by renal proximal tubule epithelial cells (RPTEC) on a Proximal Tubule Kidney-Chip. From a 100 µg/mL Albumin-FITC (e.g. Human Albumin FITC (Rockland, 009-0233)) solution in RPTEC serum-free medium, add to channel then incubate in the dark at 37° C. for 15 min. Chips can be fixed immediately after Albumin-FITC uptake: e.g., 4% paraformaldehyde (PFA) for 15 minutes at room temperature in the dark. Additional staining and immunostaining may be done for further immunofluorescence imaging.

Albumin Uptake.

ECM2 showed slightly higher albumin uptake compared to ECM1 (ECM2>ECM1)

Slightly low albumin uptake in low flow HS chip compared to other conditions (High flow>low flow).

FIG. 30A shows an exemplary quantitative analysis for albumin uptake showing a trend towards higher albumin uptake under higher flow chip conditions with an ECM2 coating. FIG. 30A shows immunofluorescent micrographs. FIG. 30B is a chart showing relative fluorescence units of albumin uptake between different embodiments of PT Kidney chips (normalized by control).

Morphology at Day 8;

Uniform monolayer and cuboidal morphology of proximal tubular cells in HS chips. FIG. 31 shows micrographs demonstrating an exemplary uniform monolayer and cuboidal morphology at Day 8 of PT Kidney cells co-cultured in microfluidic chips. From left to right, S1 chip-ECM1; S1 chip-ECM2; HS chip-ECM1; HS chip-ECM2. Upper row shows results using low shear (30 µL/h). Lower row shows results using high shear (150 µL/h). Lonza cells.

FIG. 32 shows immunofluorescent micrographs demonstrating exemplary polarization of PT cells. HF-S1-ECM2. Upper left image shows Aquaporin 1 (green), Na/K-ATPase (red), F-actin (pink) and Nuclei in blue. Upper left image shows Na/K-ATPase (red) and Nuclei in blue. Lower image shows Z-section images along the top and right side, where the apical region is at the top or far right showing the majority of Aquaporin 1 (green) while the majority of Na/K-ATPase (red) is in the basolateral region below the apical region. Lonza cells.

Comparison of Static Well-plates, Chip configurations and ECM under different flow rates.

In some embodiments, examples of parameters evaluated in respect to quality of cell samples (or commercial lots) include but are not limited to evaluating growth in tissue culture plates (static) coated with ECM prior to seeding cells into the plates.

Thus, in some embodiments, ECM conditions are compared using static cultures on-plate, see Table 12. Exemplary Collagen IV was obtained from Millipore-Sigma, i.e. Collagen Type IV from human cell cultures (Cat. #C6745-1ML). Exemplary Matrigel was obtained from Corning, i.e. Corning Matrigel Basement Membrane Matrix, LDEV-free, 10 mL (Cat. #354234).

TABLE 12

Exemplary ECM Conditions On Static Tissue Culture Plates.

| | ECM Condition | Proximal tubule |
|---|---|---|
| ECM test using PDMS on 48 well plate system | Condition 1. Collagen IV at 50 µg/mL plus Matrigel 100 µg/ml (control) | P3 PT cells from Biopredic |
| | Condition 2. KidneySpec ECM (native tissue-specific extracellular matrix) shop.eastriverbio.com shop.xylyxbio.com | P1 PT cells from Lonza |

Exemplary gene expression: Well plate versus Kidney Chip.

As one example, PT cells cultured in well plates vs. microfluidic chips were compared. As one exemplary result, overall (see expression above the dotted blue line), embodiments of Kidney-Chips, Biopredic PT cells, generally showed higher gene expression than well plates. Kidney Matrix may induce slightly higher aquaporin 1 and SGLT2 gene expression. See, FIG. 31.

FIG. 33 shows exemplary Gene Expression: Well Plate versus Kidney Chip. These exemplary results further show a comparison of Lonza PT cells vs. Biopredic PT cells cultured in well plates vs. two different embodiments of microfluidic devices as described herein. PT cells were cultured in embodiments of tall channel (S1) microfluidic devices vs. high shear (HS) microfluidic devices, each under low vs. high flow rates. Additionally, ECM comparison results are shown between Matrigel and a commercial Kidney Matrix, as described herein. Expression was evaluated as a relative expression to Biopredic TC_ColIV+ Matrigel (normalized by 18s rRNA).

FIG. 34 shows exemplary Gene Expression: Well Plate versus Kidney Chip using ECM2 coated membranes and Human Renal PT cells (RPTC) from Lonza. P2 proximal tubule cells were typically used in Kidney-Chips. RPTC (P0)-Control; RPTC (P2); RPTC (P2) seeded into an S1 PT-Kidney Chip; RPTC (P2) seeded into an HS PT-Kidney Chip. Stable SGLT2 expression in RPTC P0, P2 and kidney chip. AQP1 and Sodium/potassium ATPase expression were increased in kidney chip.

I. Evaluation of Barrier Function; Biomarkers, Etc. In Relation to Chip Configuration, Flow and ECM Experimental parameters described in Table 12 were used for comparatively evaluating two types of ECM. Immunostaining Experimental conditions included: Chip configuration: S1 versus High shear configuration. Flow shear: 30 ul/h versus 150 ul/h. ECM coating: ECM1 (KidneySpec) versus ECM2 (Collagen IV). Top Channel: Kidney proximal tubular cells were stained with an Anti-Aquaporin 1; and Anti-Sodium/potassium ATPase for apical vs. basal expression, respectively; F-actin using Phalloidin; Nuclear stain. Bottom Channel: Glomerular endothelial cells were stained with an Anti-VE-Cadherin, F-actin using Phalloidin; and a Nuclear stain.
Barrier Function: Inulin Leakage: Percent % Inulin leakage into the basal channel, where inulin was added to the apical channel, was measured however for the embodiments tested there was no significant inulin leakage in PT Kidney-Chips indicating the presence of a tight barrier. Small Molecule Leakage: Percent 3 kDa Dextran leakage where dextran was added to one channel then measured in outflow samples from the opposing channel for determining barrier function. See biomarkers for barrier function described herein, that may also be used for evaluating chip configurations and parameters, in addition to drug testing.

FIG. 35A demonstrates that no significant inulin leakage was measured and apparent permeability was similar, FIG. 35B, compared between the embodiments/conditions tested using a PT Kidney-Chip indicating the presence of a tight barrier function. % Inulin leakage into the basal channel on the Y-axis, test conditions shown on the X-axis. S1 chip-LF-ECM1; S1 chip-LF-ECM2; S1 chip-HF-ECM1; S1 chip-HF-ECM2; HS chip-LF-ECM1; HS chip-LF-ECM2; HS chip-HF-ECM1; HS chip-HF-ECM2. Lonza cells.
Morphology; Biomarkers.

FIG. 36 shows exemplary polarization of human Renal Proximal Epithelial Cells co-cultured in different embodiments of a PT Kidney chip. From left to right: S1-E1; S1-E2; HS-E1; HS-E2. Low flow upper panels. High-flow lower panels. Aquaporin 1—green. Na/K-ATPase —red.

FIG. 37 shows exemplary Immunostaining of Kidney Microvascular Endothelial Cells. Glomerular Endothelial Cells (VE-Cadherin (green)/F-actin (pink)/Nuclei (blue)). From left to right: S1-E1; S1-E2; HS-E1; HS-E2. Low flow left, high flow right.
Albumin Uptake: Higher albumin uptake in HS chips with high shear. ECM2 showed slightly higher albumin uptake compared to ECM1 (ECM2>ECM1). Slightly lower albumin uptake in low flow HS chip compared to other conditions (High flow>low flow) FIG. 38 demonstrates exemplary higher albumin uptake in HS chips with high shear (high flow) by florescence microscopy. From left to right, S1 chip-ECM1; S1 chip-ECM2; HS chip-ECM1; HS chip-ECM2. Upper row shows results using low flow (30 μL/h). Lower row shows results using high flow (150 μL/h). Lonza cells.
Biomarker expression in relation to ECM.

FIG. 39 shows exemplary immunostaining for cells in a top channel: Renal Proximal Epithelial Cells (Aquaporin 1—green/Na/K-ATPase—red/Nuclei—blue). Low flow rate (30 μl/hour). High Shear Chip left panels; S1 chip right panels; upper row ECM1 (KidneySpec); lower row ECM2 (Col IV).

The following charts and figures describe and show exemplary results of immunostaining for the listed markers.

| Flow rate | Chip configuration | | ECM | |
|---|---|---|---|---|
| | High shear | S1 | ECM1 | ECM2 |
| 30 μl/hour | S1 chip showed higher AQP1 expression. | | ECM2 - supported homogenous cell growth | |

FIG. 39 shows exemplary immunostaining for cells in a top channel: Renal Proximal Epithelial Cells (Aquaporin 1—green/Na/K-ATPase—red/Nuclei—blue). Low flow rate (30 μl/hour). High Shear Chip left panels; S1 chip right panels; upper row ECM1 (KidneySpec); lower row ECM2 (Col IV).

| Flow rate | Chip configuration | | ECM | |
|---|---|---|---|---|
| | High shear | S1 | ECM1 | ECM2 |
| 150 μl/hour | AQP1 expression appears to be higher in S1 chip compared to the high shear chip. | | ECM1 - appears to support higher AQP expression. ECM2 - homogenous cell growth. | |

FIG. 40 shows exemplary immunostaining for cells in a top channel: Renal Proximal Epithelial Cells (Aquaporin 1—green/Na/K-ATPase—red/Nuclei—blue). High flow rate (150 μl/hour). High Shear Chip left panels; S1 chip right panels; upper row ECM1 (KidneySpec); lower row ECM2 (Col IV).

| Flow rate | Chip configuration | | ECM | |
|---|---|---|---|---|
| | High shear | S1 | ECM1 | ECM2 |
| 30 μl/hour | High shear chip supported homogenous expression of VE-Cadherin. | | ECM1-induced aggregation of cells. | |

FIG. 41 shows exemplary immunostaining for Bottom channel cells: Golmerular endothelial cells (VE-Cadherin—green/F-actin—pink/Nuclei—blue). Low flow rate (30 μl/hour). High Shear Chip left panels; S1 chip right panels; upper row ECM1 (KidneySpec); lower row ECM2 (Col IV).

| Flow rate | Chip configuration | | ECM | |
|---|---|---|---|---|
| | High shear | S1 | ECM1 | ECM2 |
| 150 μl/hour | Bottom channel of S1/ECM1 chip had bubbles High shear chip supported homogenous cell growth and high expression of VE-Cadherin. | | ECM2-homogenous cell growth. | |

FIG. 42 shows exemplary immunostaining for Bottom channel cells: Golmerular endothelial cells (VE-Cadherin/F-actin/Nuclei—blue). High flow rate (150 μl/hour). High Shear Chip left panels; S1 chip right panels; upper row ECM1 (KidneySpec); lower row ECM2 (Col IV).

FIG. 43 shows exemplary immunostaining under High flow in high shear chip with ECM1 (KidneySpec). Top channel (upper two rows of panels): Renal Proximal Epithelial Cells (Aquaporin 1—green/Na/K-ATPase—red/F-actin—pink/Nuclei—blue) and Bottom channel: Golmerular endothelial cells (VE-Cadherin—green/F-actin—pink/Nuclei—blue).

FIG. 44 shows exemplary immunostaining under High flow in Tall channel chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 45 shows exemplary immunostaining under High flow in high shear chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 46 shows exemplary immunostaining under High flow in Tall Channel chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 47 shows exemplary immunostaining under Low flow in high shear chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 48 shows exemplary immunostaining under Low flow in tall channel chip with ECM1 (KidneySpec). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 49 shows exemplary immunostaining under Low flow inhigh shear chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

FIG. 50 shows exemplary immunostaining under Low flow in tall channel chip with ECM2 (Col IV). Top channel (upper two rows of images): Renal Proximal Epithelial Cells (Aquaporin 1—green/Na/K-ATPase—red/Nuclei—blue) and Bottom channel (lower two rows of images): Golmerular endothelial cells (VE-Cadherin—green/F-actin—pink/Nuclei—blue).

J. Evaluation Of Function In Relation To Chip Configuration, Flow Rates And Extracellular Matrix (ECM): CLINICAL PHARMACOLOGY.

In some embodiments, function of a PT-Kidney Chip in relation to Chip Configuration, Flow Rates And Extracellular Matrix (ECM) was evaluated. In some embodiments, function is evaluated for use in clinical pharmacology. Functions included but were not limited to albumin uptake (e.g. Quantitative Analysis), Creatinine Secretion (transport) and PAH Secretion (transport).

The following are examples of PT Kidney chips evaluated for creatinine Secretion; PAH Secretion; PAH Transport, etc.

TABLE 13

PAH Transport

| | Conditions | Fluid Shear |
|---|---|---|
| 1 | Low flow-S1 | 0.0003 dyn/cm 2 |
| 2 | Low flow-HS | 0.05 dyn/cm 2 |
| 3 | High flow-S1 | 0.0017 dyn/cm 2 |
| 4 | High flow-HS | 0.23 dyn/cm 2 |

PAH mass balance PAH mass transport.
Both flow conditions showed balanced PAH mass.
Increased fluid shear appeared to reduce PAH transport Example G—Creatinine Quantification Assay The Proximal Tubule Kidney-Chip is designed to recapitulate the complex mechanisms that regulate protein absorption and clearance in the human kidney. In some embodiments, creatinine levels are quantified from effluent samples. Because of functions performed by the kidney in controlling the osmolarity of the human blood, safety assessment of new drug candidates frequently rely on the accurate measurement of organ specific biomarkers, including creatinine. Additionally, measurement of soluble creatine secreted by the distal portion of the kidney is an indicator for appropriate clinical diagnostics and treatment of kidney diseases. Creatinine (2-amino-1-methyl-5H-imadazol-4-one) is a metabolite of creatine. Creatinine is also a metabolite of phosphocreatine (p-creatine or creatine phosphate).

Creatinine levels will change depending on cell injury status, or based on donor-to-donor variability. Therefore, sample dilutions may need to be modified to accommodate different experimental conditions or cells from different donors. It is therefore recommended to run a preliminary study in order to define optimal dilution factors and timepoints for media sampling.

To measure creatinine secretion in the Proximal Tubule Kidney-Chip, the vascular compartment is perfused with medium containing 1 mg/dL of human creatinine, while the secretion of creatinine in the top channel is measured from chip effluent. Exemplary assay flow rate (Proximal Tubule Kidney-Chip) during this assays is 60 µL/hour. In some embodiments, samples of effluent are collected in outlet reservoirs of the module. In preferred embodiments, there is no dilution of effluent when using an exemplary commercial kit, e.g. Invitrogen™ Creatine Urinary Detection Kit (Thermo Fisher EIACUN as described at thermofisher.com, downloaded Jun. 20, 2019).

Creatinine Secretion; Creatinine loss (BI-BO) about 2.5-4 mM in bottom channel. About 50% creatinine filtration (TO/BO) in low flow. Higher apical creatinine secretion (TO) in low flow compared to high flow group.

FIG. 51A-C shows exemplary Creatinine Secretion under low and high flow rates. BI: bottom inlet; BO: bottom outlet; TO: top outlet and Lonza cells. FIG. 51B Creatinine loss (mM); FIG. 51C Creatinine Filtration (%) and FIG. 51A Apical Creatinine (mM).

Example H—Creatinine Transport Assay

In some embodiments, creatinine transport is determined in relation to chip configuration and low vs. high flow. Creatinine Secretion: Creatinine Loss (BI-BO); Creatinine filtration (TO/BO); Apical Creatinine (TO).

FIG. 53A-B shows an exemplary Creatinine Mass Balance and Creatinine Transport on PT-Kidney-chips under low and high flow on both S1 tall channel chips and HS chips.

Example I—Para-Aminohippuric Acid (PAH) Evaluation of Simulated Kidney Function Para-aminohippuric acid (PAH) is actively secreted by the proximal tubules then is filtered out by the glomeruli into urine. PAH is used in clinical pharmacology as an indicator of kidney function. PAH is administered to patients for determining clearance rates is used as a measurement of effective renal plasma flow (eRPF). Reasons for using PAH include that it has a high clearance when kidneys are normally functioning, it is essentially nontoxic at the plasma concentrations reached with recommended doses, and its analytical determination is relatively simple and apparently accurate. At low plasma concentrations (1.0 to 2.0 mg/100 mL), an average of 90 percent of PAH is cleared by the kidneys from the renal blood stream in a single circulation.

PAH is also used to measure the functional capacity of the renal tubular secretory mechanism or transport maximum (TmPAH). This is accomplished by elevating the plasma concentration to levels (40-60 mg/100 mL) sufficient to saturate the maximal capacity of the tubular cells to secrete PAH.

Inulin clearance is generally measured during TmPAH determinations since glomerular filtration rate (GFR) must be known before calculations of secretory transport maximum (Tm) measurements can be done (see DOSAGE AND ADMINISTRATION, Calculations).

FIG. 53 shows exemplary PAH Secretion under low and high flow rates. BI: bottom inlet; BO: bottom outlet; TO: top outlet and Lonza cells.

PAH loss (BI-BO) is about 20-40 ug/ml in bottom channel. PHA transport (TO/BO) about 20% in low flow. Higher PAH secretion (TO) in low flow compared to high flow group.

FIG. 78 shows exemplary PAH Mass Balance and shows exemplary PAH mass Transport on PT-Kidney-chips under low and high flow on both S1 tall channel chips and HS chips.

Example J—Material Absorption

In some embodiments, Material Absorption is one exemplary readout. When testing compounds added to a PT Kidney Chip, a determination of material absorption is made for that compound. The following is a exemplary method for determining material adsorption of a compound.

Study Conditions. Study approach: Each experiment includes a number of controls and test conditions. These allow us to tease out: Adsorption to the vial/well-plate. Absorption vs. adsorption to the tested material.
1. Dissolve the small molecule in an aqueous phase (medium) and incubate it with the tested material.
2. Measure the concentration of small molecule remaining in the aqueous phase (using mass spec, plate reader).
3. Curve-fit the measured data to quantify the absorption and diffusion parameters.

TABLE 14

Exemplary Experimental Goals.

| Condition | Question Being Addressed |
|---|---|
| 3 samples per condition | — |
| Media Type: REGM (serum-free) | — |
| Materials | What is the ad/absorption into system components? |
| Chip material | |
| Pod material | |
| Glass (negative control) | |
| Five Dosing Compounds Digoxin, Topotecan, Valsertan, Estron-3-sulfate, Quinidine (Digoxin backup) | What is the compound-specific absorption? |
| Five Timepoints 1, 8, 24, 48, 72 hr | Is compound loss time dependent - what are the dynamics? |

Material Absorption—Results.

5 compounds evaluated for absorption into Kidney-Chip and perfusion manifold materials. Minimal absorption of Estrone-3-sulfate, Topotecan, Digoxin and Valsartan into system materials. Recovered compound concentration similar for glass (non-absorbing control) and tested materials. Appreciable absorption of Quinidine (Digoxin backup) into chip material M1 (red)—Chip Material; M2 (blue)—perfusion manifold material; C1 (green)—Glass (control); and C2 (purple)—Dosing Media.

FIG. 55 shows Minimal absorption into chip material in all four compounds except Quinidine.

Summary I: Model Optimization & Characterization: Exemplary Results.
1. Exemplary identification of optimal proximal cell lot, e.g. from Lonza, showing better morphology than the other cell lots or cells from other commercially obtained PT cells that were tested (e.g. BioPredic).
2. No significant inulin leakage observed under test conditions of PT-kidney-chip indicating tight barrier function for test embodiments of a PT-kidney-chip.
3. Uniform monolayer and cuboidal morphology of proximal tubular cells in HS chips. 4. Enhanced staining of AQP1 and sodium/potassium ATPase in S1 chip with high flow where endothelial cells had elongated morphology in high shear stress (>0.04 dyn/cm$^2$).
5. Both ECM 1 and ECM 2 supported proximal tubular cell growth and tissue development.
6. Gene expression analysis showed higher expression of MATE1, MATE2-K and OAT3 in high shear chip with ECM2.
7. High flow induced higher Albumin uptake compared to the low flow.
8. High flow induced increased expression of AQP1 and OCT2 genes.
9. Slightly higher albumin uptake in ECM2 with high flow condition than ECM1 with low flow.
10. Creatinine and PAH transport data showed minimal loss of compound in the chip (near 100% recovery), and molecule transport shown to occur across the tissue in the Kidney-Chip.
11. Minimal drug absorption into system materials observed for four compounds of interest (Estron-3-Sulfate, Topotecan, Digoxin, Valsartan). In contrast, Quinidine, the backup compound for Digoxin, did absorb into the chip material.

Example K-Alkaline Phosphatase (ALP) Assay

Alkaline phosphatases (ALPs) refer to a family of cell surface glycoproteins that catalyze the hydrolysis of phosphomonoesters with release of inorganic phosphate. In some embodiments, Alkaline Phosphatase (ALP) activity of a PT-Kidney Chip is quantified as one exemplary readout from effluent or cell lysate samples. Exemplary assay flow rate (Proximal Tubule Kidney-Chip) during this assay is 60 µL/hour.

To measure ALP activity in the Proximal Tubule Kidney-Chip, chip effluent is collected as a sample and tested. In some embodiments, samples of effluent are collected in outlet reservoirs of the module. In preferred embodiments, there is no dilution of effluent when using an exemplary commercial kit, e.g. AttoPhos® AP Fluorescent Substrate System (Promega, S1000 or S1001, e.g. promega.com, instructions downloaded Jun. 20, 2019). The AttoPhos® AP Fluorescent Substrate System uses a highly sensitive fluorescent alkaline phosphate substrate that maintains a low fluorescence signal until enzymatically acted upon, yielding detection of ALP to as little as 0.1 attomole.

ALP levels will change depending on cell injury status or based on donor-to-donor variability. Therefore, sample dilutions may need to be modified to accommodate different experimental conditions or cells from different donors.

IV. Methods Of Using A Microfluidic Human Proximal Tubule Kidney Cell Chip

In some embodiments, an experimental design was used comprising: Human proximal tubule cells from Lonza and human glomerular endothelial cells from Cell Systems seeded into S1 tall channel microfluidic chips as described herein. Culture duration was at least 15 days. In some embodiments, an endpoint readout comprised: Morphology observations; Inulin Leakage; PAH Secretion; Albumin Uptake; immunostaining of biomarkers; etc. for up to a 15 day co-culture on-chip.

Additional exemplary endpoint assays (for use on chosen days during culture of PT Kidney cells on-chip) contemplated for use include but are not limited to: LDH (lactate dehydrogenase) leakage associated with kidney cell damage: cytotoxicity marker, LDH is released from membrane-damaged cells.; NAG (N-Acetyl-p-D-Glucosaminidase) secretion associated with level of kidney metabolism: an intracellular lysosomal enzyme present in proximal tubular epithelial cells. In vivo, presence of NAG in the urine shows an organelle (lyzozome) impairment in proximal tubule.; CC-3 (Human Cleaved Caspase-3): apoptosis marker, Caspase-3 is a cytoplasmic cysteine protease involved in the activation cascade of caspases responsible for execution of apoptosis; ROS (Reactive oxygen species): marker of toxicity, reactive oxygen species (ROS) are well-established molecules responsible for the toxic effects of oxidative stress.; KIM-1 (Kidney Injury Molecule-1): biomarker for human renal proximal tubule injury; TUNEL (terminal deoxynucleotidyl transferase (TdT)-mediated dUTP nick end labeling): apoptosis detection marker.; Morphology: captures morphological changes due to cell injury that can culminate to either necrosis or apoptosis.

A. Drug Transporter Gene Expression (mRNA).

Embodiments of an optimized PT-Kidney on-Chip, as described herein, will be characterized to determine physiological relevance for drug transporter expression. In some embodiments, expression of transporters will be determined in epithelial cells cultured in a PT-on-Kidney-Chip for demonstrating expression (mRNA) of apical (luminal) and basolateral (blood side) transporters compared to human kidney cortex: examples of genes associated with a function include but are not limited to: Apical secretion: MRP2, MRP4, MDR1, MATE1/2-K; Apical reabsorption: OAT4, OCTN1, OCTN2; Basolateral uptake: OAT1, OAT2, OAT3, OATP4C1, OATP4A1, OCT2; Basolateral efflux: MRP1, MRP3, MRP5, MRP6, etc. In some embodiments, expression of transporters will be determined in endothelial cells co-cultured in a PT-Kidney-Chip.

Additional transporters associated with functional PT kidney cells include MDR1, MATE1, MATE2-K, OAT1, OAT3, OCT2, and PEPT2. MDR1 (multidrug resistance mutation 1) refers to a gene encoding P-glycoprotein. PEP2 (Peptide Transporter 2) refers to a protein expressed by SLC15A2 genes associated with absorption of small peptides and peptide-like drugs, from the tubular filtrate.

B. Drug Transporter Protein Expression.

In one embodiment, an optimized PT-Kidney on-Chip comprises a top channel seeded with human kidney proximal tubular cells and a bottom channel seeded with human glomerular endothelial cells. In one embodiment, the optimized PT-Kidney on-Chip is cultured for up to 14 days. In one embodiment, the optimized PT-Kidney on-Chip has readouts including immunostaining and confocal imaging for identifying expression of biomarkers including: for human kidney proximal tubular cells in the upper channel, using anti-Aquaporin 1; anti-Sodium/potassium ATPase; F-actin Phalloidin stain; and a nuclear stain; and for glomerular endothelial cells in the lower channel, anti-VE-Cadherin; F-actin Phalloidin stain; and a nuclear stain.

Biomarkers evaluated by qPCR and immunofluorescence (F) staining for biochemical characterization of cells culture in chips and transwells include but are not limited to: Na/K-ATPase, AQP1, MATE1, MATE-2K, OAT1 and OAT-3, P-gp, etc. In some embodiments, biomarker expression is compared between sets of duplicate microfluidic chips where each set has a different treatment, e.g. cells obtained from different sources, different samples, different compounds, different drugs, etc. In some embodiments, biomarker expression is compared between microfluidic chips and transwells cultures of PT kidney cells. Biomarkers evaluated by immunofluorescence (F) staining include but are not limited to: a/K-ATPase, AQP1, OAT1, OAT3.

C. Functional Assessments.

In some embodiments, Proximal Tubule-Chips are evaluated for function (i.e. a functional assessment), such as during evaluation of a cell source cultured on-chip; before or after contact with a compound or drug; etc. In some embodiments, methods for endpoint evaluations comprise functional assays. Exemplary functional assays include but are not limited to: Albumin uptake; Barrier function; Clusterin (MSD or ELISA); Creatinine transport; KIM-1 (MSD or ELISA); Mass spec (for net drug transport); Osteopontin (MSD or ELISA), etc. In some embodiments, a functional assay comprises evaluation of an outflow sample, including but not limited to determining clusterin levels; KIM-1 levels; osteopointin levels; etc. The following are exemplary criteria for measuring a change in function: Albumin uptake levels are considered elevated when there is higher albumin uptake by PT cells in chips compared to transwells (~2× fold change); Barrier function—Lower apparent permeability in chips compared to transwells (~2× fold change); Clusterin (MSD or ELISA)—Elevated clusterin levels in outflow compared to vehicle control; Creatinine; KIM-1 (MSD or ELISA)—Elevated KIM-1 levels in outflow compared to vehicle control; Mass spec (for net drug transport)—Higher net transport in chips compared to transwells (~2× fold change); Osteopontin (MSD or ELISA)—Elevated osteopontin cytokine levels in outflow compared to vehicle control; etc. In some embodiments, cytokine levels in apical outflow will be measured. Nephrotoxicity biomarkers include KIM-1; Clusterin; and Osteopontin.

D. Functional Assessment of Transporter Molecules.

In some embodiments, functional assessment will be done for the following renal transporters including but are not limited to: MDR1, MATE1, MATE2-K, OAT1, OAT3, OCT2, and PEPT2.

The reference Table 15 below will be used to select appropriate substrates for the seven transporters listed above. In some embodiments, may be done for additional transporter molecules. In some embodiments, a probe substrate will be applied to lumen compartment and vascular compartment separately. Samples will be taken from both donor and receiver compartments after incubation at different time points. Samples may be analyzed by liquid scintillation counter or by LC-MS/MS. In some embodiments, apparent permeability, fold reabsorption (PermeabilityL-B/PermeabilityB-L), and fold secretion (PermeabilityL-B/PermeabilityB-L) will be determined. In some embodiments, selective inhibitors may be used.

In some embodiments, addition of radiolabels, such as $^{14}C$-mannitol and $^{14}C$-caffeine will be used to check paracellular and transcellular permeability. In some embodiments, addition of labels that are nonradiolabels will be added.

TABLE 15

Exemplary transporter-substrate pairs (i.e. probe substrates) for corresponding transporters, for use in transporter PT kidney cell functional evaluations.

| Transporter | PT Location | Function | Substrate |
|---|---|---|---|
| Tier 1 | | | |
| MDR1 | Apical | Efflux/Secretion | $^3H$-Digoxin |
| MATE1 | Apical | Efflux/Secretion | $^{14}C$-Metformin, $^{14}C$-TEA |
| MATE2-K | Apical | Efflux/Secretion | $^{14}C$-Metformin, $^{14}C$-TEA |
| OAT1 | Basolateral | Uptake/Secretion | $^{14}C$-PAH |
| OAT3 | Basolateral | Uptake/Secretion | $^3H$-Estrone-3-sulfate |
| OCT2 | Basolateral | Uptake/Secretion | 14C-Metformin, $^{14}C$-TEA |
| PEPT2 | Apical | Uptake/Reabsorption | $^3H$-Glycylsarcosine |
| Tier 2 | | | |
| MRP2 | Apical | Efflux/Secretion | $^3H$-Valsartan |
| MRP4 | Apical | Efflux/Secretion | $^3H$-Topotecan |
| OAT4 | Apical | Dual (Exchanger) | $^3H$-Estrone-3-sulfate |
| OCTN1 | Apical | Dual (Exchanger) | $^3H$-Ergothioneine, $^{14}C$-TEA |
| OCTN2 | Apical | Dual (Exchanger) | $^{14}C$-Carnitine |
| OAT2 | Basolateral | Uptake/Secretion | $^3H$-Deoxyguanosine |
| OATP4A1 | Basolateral | Uptake/Secretion | unknown |
| OATP4C1 | Basolateral | Uptake/Secretion | unknown |
| MRP1 | Basolateral | Efflux/Reabsorption | $^3H$-Leukotriene C4, $^3H$-Estrone-3-sulfate |
| MRP3 | Basolateral | Efflux/Reabsorption | $^3H$-Leukotriene C4 |
| MRP5 | Basolateral | Efflux/Reabsorption | $^3H$-cGMP |
| MRP6 | Basolateral | Efflux/Reabsorption | $^3H$-Leukotriene C4 |

In summary, a Proximal Tubule-Chip was created and produced that recapitulates in vivo relevant tissue-tissue interface of the kidney proximal tubule. This kidney Proximal Tubule-Chip exhibited polarized epithelium and endothelium that reproduced baseline functions of the proximal tubule in vitro and demonstrated active transporters functions that are involved in normal kidney functions. These results suggest that the Proximal Tubule-Chip represents a physiologically relevant system for drug discovery and development applications.

In one embodiment, a Proximal Tubule-Chip is used for evaluating active transport of pharmaceutical compounds. In one embodiment, a Proximal Tubule-Chip is used for determining clinical relevance of renal transporter-based drug interactions using a non-clinical in vitro system.

In one embodiment, a Proximal Tubule-Chip is used for evaluating known transporter substrates and assesses clinically recognized drug-transporter interactions in an in vitro system for predictive outcomes. In one embodiment, a Proximal Tubule-Chip is used for evaluating test or unknown transporter substrates and assess drug-transporter interactions in an in vitro system.

In one embodiment, a Proximal Tubule-Chip is used for determining clinical relevance of renal transporter-based drug interactions using a non-clinical in vitro system. In one embodiment, a Proximal Tubule-Chip is used for determining drug transporter expression. In one embodiment, a Proximal Tubule-Chip is used for determining renal Transporter-Based Drug Interactions. In one embodiment, a Proximal Tubule-Chip is used for determining drug-induced neophrotoxicity.

In one embodiment, a Proximal Tubule-Chip supports a minimum of 2-week cell viability and function.

In one embodiment, a Proximal Tubule-Chip has physiologically relevant mechanical forces to imitate mechanical motion of the tubule.

In one embodiment, a Proximal Tubule-Chip expresses transporter molecules, using methods for demonstrating expression (mRNA) of apical (luminal) and basolateral (blood side) transporters. In one embodiment, transporter molecule expression in a Proximal Tubule-Chip is compared to human kidney cortex: for example, comparing Apical secretion: MRP2,4,MDR1, MATE1/2-K; Apical reabsorption: OAT4, OCTN1,2; Basolateral uptake: OAT1,2,3, OATP4C1, OATP4A1, OCT2 and Basolateral efflux: MRP1, 3,5,6, etc.

In one embodiment, exemplary transporter molecules include but are not limited to: MDR1, MATE1, MATE2-K, OAT1, OAT3, OCT2, and PEPT2.

In one embodiment, an exemplary probe substrate will be applied to lumen compartment and vascular compartment separately. In one embodiment, samples will be taken from both donor and receiver compartments after incubation at different time points. Samples will be analyzed by liquid scintilation counter or by LC-MS/MS as needed. In one embodiment, Apparent permeability, fold reabsorption (PermeabilityL-B/PermeabilityB-L), and fold secretion (PermeabilityL-B/PermeabilityB-L) will be determined. In one embodiment, Selective inhibitors may be used. In one embodiment, 14C-mannitol and 14C-caffeine may be used to check paracellular and transcellular permeability.

Contemplated uses for embodiments of PT-Kidney-On-Chip include areas of Safety and Risk Assessments and Pharmacokinetics, including physiologically based pharmacokinetic (PBPK) modeling, as described in more detail herein.

V. Uses Related to Safety and Risk Assessments; Nephrotoxin Testing

Applications of a Proximal Tubule Kidney-Chip as described herein, include but at not limited to areas such as Safety and Risk Assessment, e.g. Drug-Induced Nephrotoxicity Testing. Such testing includes but is not limited to Acute Tubular Injury Assays for assessing acute toxic responses (e.g. apoptosis, necrosis, etc) as a PT Kidney chip response to added compounds; Biomarker Identification using multiplex assay kits and gene analysis and measuring Mechanisms of Action for Testing known/suspected mechanism of toxicity via specific transporter functions (uptake/efflux/inhibition/induction) and phenotypes of toxicity; etc.

Embodiments of Proximal Tubule Kidney-Chips comprise co-cultures of human primary PT Kidney cells as noted from Lonza, ScienCell or Biopredic, and endothelial cells. Endothelial cells used in co-cultures on-chip in the vascular channel for data shown herein in this section are Primary Human Renal Microvascular Endothelial Cells (HRMEC) unless otherwise noted. It is not intended to limit endothelial cells to HRMECs, as other types of endothelial cells described herein may also be used. Embodiments of Proximal Tubule Kidney-Chips used for data shown in figures for this section include S1, Tall Channel and HS chips, as noted. Fluid flow was provided by the investigator (interogator), a syringe pump, peristaltic pump or culture module.

In some embodiments, Proximal Tubule-Chips treated with a nephrotoxic compound are evaluated for biomarkers of function and/or injury, e.g. Kidney Injury Marker 1 (KIM-1), etc. In addition to Gentamicin treatment described herein, Cisplatin, etc.

In some preferred embodiments, Cisplatin and vehicle control dosing were by adding to the basal channel. In other embodiments, Cisplatin and vehicle control dosing were by adding to the apical channel. Biomarker levels in apical outflow that were measured included Kidney injury marker 1 (KIM-1) (by MSD assay or ELISA); Clusterin (MSD assay or ELISA) and Osteopintin (MSD assay or ELISA).

TABLE 16

Induction of Nephrotoxicity Using Gentamicin and Cisplatin as exemplary toxins.

|  | Vehicle for Gentamicin | Gentamicin (10 mM) | Vehicle for Cisplatin | Cisplatin (100 μM) |
| --- | --- | --- | --- | --- |
| Kidney-Chip (Co-culture of Proximal tubular cells and Kidney endothelial cells) | N = 3 | N = 3 | N = 3 | N = 3 |
| Dosing time at Day 7 for 24 h | PBS (0.5%) | + | DMSO (0.1%) | + |
| Morphology | Normal | Damaged | Normal | Damaged |
| RNA lysate at Day 8 | 300 μl | 300 μl | 300 μl | 300 μl |

Results of Gentamicin treatment of a PT Kidney chip included observations that vehicle controls showed well-developed Kidney Proximal tubular epithelial cells at day 8 while there were clear morphological changes after Gentamicin treatment. See, FIG. 79 and below.

FIG. 56 shows exemplary Gentamicin Toxicity Testing: Morphology Observations.

Gentamicin treatment, right image; exemplary control cells, left image (Lonza cells; S1; Flow: 30 μL/hr provided by a culture module).

Results of Cisplatin treatment of a PT Kidney chip included observations that vehicle controls showed well-developed Kidney Proximal tubular epithelial cells at day 8 while there were clear morphological changes after Cisplatin treatment.

A. Gentamicin Toxicity Testing: Acute Tubular Injury Assays And biomarker identification; Function: Cidofovir, Cyclosporine (CsA).

In some embodiments, a PT-Kidney-Chip is used for determining Acute Tubular Injury And Biomarker Identification of responses to nontoxic and toxic compounds.

Embodiments of PT-Kidney-Chips were contacted with test compounds resulting in acute tubular injury for determining biomarker identification of toxicity.

Readouts included morphology observations, Lactate Dehydrogenase (LDH) Assays and observing levels of expression of known human urinary renal dysfunction biomarkers, e.g. Kidney Injury Molecule-1 (KIM-1), whose expression is markedly up-regulated in the proximal tubule in the post-ischemic kidney. An ectodomain of KIM-1 is shed from cells.

Some exemplary results of Gentamicin Toxicity tests with readouts including morphology are shown in FIGS. 9A-B (Lonza cells; S1; Flow: 60 μL/hr provided by a culture module) and FIG. 56 (Lonza cells; S1; Flow: 30 μL/hr provided by a culture module). Readouts show structural damage of epithelial layer cause by exposure to Gentamicin.

Embodiments of PT-Kidney-Chips were exposed to one of the following test compounds for inducing PT-cell toxicity tests: 75 μM Cidofovir, 25 μM Cyclosporine A (CsA), and 10 mM Gentamicin for up to 48 hours. Cell toxicity was assessed at certain time points (e.g. 6 hr, 24 hr, & 48 hr).

FIG. 57 shows exemplary Gentamicin Toxicity Testing: Acute Tubular Injury and biomarker identification: LDH and relative KIM-1 release, respectively, in response to 75 μM Cidofovir, 25 μM Cyclosporine (CsA), and 10 mM Gentamicin. (Biopredict PT Kidney cells; HRMEC; High Shear Chip; fluid flow: 60 μL/hr provided by a Syringe pump).

Embodiments of a Proximal Tubule Kidney-Chip replicates Gentamicin-induced toxicity after exposure to 10 mM of gentamicin for 48 hours. Microscopic analysis of the proximal tubular epithelium shows structural damage coupled with significant increases in LDH in medium effluent, reactive oxygen species (ROS), and urinary N-acetyl-beta-(D)-glucosaminidase activity (NAG) in medium effluent and increase active caspase-3 in cells lysates.

FIG. 58 shows exemplary Gentamicin Toxicity Testing: LDH, NAG, reactive oxygen species (ROS), reactive nitrogen species (RNS); Active Caspase, & morphology. (PT Kidney cells-Lonza; HRMEC; S1; Flow: 60 μL/hr provided by a culture module).

Embodiments of a Proximal Tubule Kidney-Chip replicates Gentamicin-induced toxicity after exposure to 10 mM of gentamicin for 48 hours. Microscopic analysis of the proximal tubular epithelium shows structural damage coupled with significant increases in LDH in medium effluent and increase active caspase-3 in cells lysates. A TUNEL assay also reveals significant DNA damage.

FIG. 59 A-D shows exemplary Gentamicin Toxicity Testing: FIG. 59B LDH and FIG. 59A Morphology, FIG. 59C TUNEL, FIG. 59D Active Caspse-3. (Lonza PT Kidney cells; HRMEC; S1; Flow: 60 μL/hr provided by a culture module).

B. Cisplatin Toxicity Testing: Acute Tubular Injury Assays And biomarker identification.

Toxicity tests with readouts including morphology. End point analysis: Morphology; Gene expression analysis (OAT1, OAT3, CLU, KIM1, etc.). Exemplary Readouts of LDH, NAG, ROS, Active Caspase, & morphology.

1. Morphology Acute Tubular Injury: Cisplatin Toxicity Testing.

Exemplary results of Cisplatin Toxicity show morphological structural damage of epithelial layer cause by exposure to 10 μM Cisplatin.

FIG. 60 shows exemplary Cisplatin Toxicity Testing: Acute Tubular Injury during as structural damage of epithelial layer caused by exposure to 10 μM Cisplatin. Control left, treated right. (PT Kidney cells-Lonza; HRMEC; S1; Flow: 30 µL/hr provided by a culture module).

2. Toxicity Application: Cisplatin Toxicity Testing.

Severe morphological changes coupled with cell detachment was observed in chips treated with 30 µM cisplatin at day 6 of treatment. Morphological changes correlate with increase LDH and a decrease in intracellular NAG concentration.

However, in relation to Tattoo Safety Testing, no such changes were observed in co-cultured endothelial cells (GIMVEC). Decreases in intracellular NAG concentration were observed at 16 ppm of TiO2, representative of a toxin found in tattoo inks.

FIG. 61A-C shows exemplary Cisplatin Toxicity Testing: FIG. 61B-C LDH, FIG. 61D NAG & FIG. 61A morphology. Tattoo ink (TiO2) toxicity is compared to Cisplatin Toxicity. (PT Kidney cells-Lonza; HRMEC; S1; Flow: 60 µL/hr provided by a culture module).

Morphological observations were following immunohistochemistry, F-actin green, upper panel and yellow, lower panel.

3. Cisplatin Toxicity Testing: Acute Tubular Injury; Mechanism of Action; Biomarker Identification compared using two different types of endothelial cells.

FIG. 62 A-E shows exemplary Cisplatin Toxicity Testing: Acute Tubular Injury; Biomarker Identification (KIM-1); Mechanism of Action, e.g. Cytoskeletal rearrangement, in response to two different types of endothelium co-cultured with human PT cells, e.g. Human renal microvascular endothelial cells (HRMEC) and Human Umbilical Vein Endothelial Cells (HUVEC). FIG. 62A-C P-gp1, AQP1 and Kim-1 were evaluated, (PT Kidney cells-ScienCell; Tall Channel; Flow: 60 µL/hr provided by a peristaltic pump). Morphological observations were following immunohistochemistry, FIG. 62D F-actin white/green, upper panel and FIG. 62E white/yellow, lower panel. (PT Kidney cells-Lonza; S1; Flow: 60 µL/hr provided by a culture module).

Chips were treated with 150 µM of cisplatin for 24 hrs followed by 4 weeks of culture under fluidic conditions. Significantly high levels of LDH and NAG activity were measured in treated chip effluent compared to controls. Microscopic analysis of the proximal tubular epithelium shows structural damage in epithelium along with an increase in permeability.

FIG. 63 A-D shows exemplary Cisplatin (CDDP) Toxicity Testing: Acute Tubular Injury; Biomarker Identification; and Mechanism of Action: FIG. 63B NAG, FIG. 63C LDH, FIG. 63A Permeability, FIG. 63D Immunostaining, e.g. ZO-1 (yellow), nuclei (blue). (PT Kidney cells-ScienCell; HRMEC; Tall Channel; Flow: 60 µL/hr provided by a peristaltic pump).

Chips were treated with 100 µM of cisplatin for 24 hrs following for 4 weeks culture under fluidic condition. Significantly high level of LDH and NAG activity were measured in treated chip effluent compared to controls. Microscopic analysis of the proximal tubular epithelium shows structural damage in epithelium. Some treated chips were used for cisplatin test results after 29 days in culture.

FIG. 64 A-E shows exemplary Cisplatin Toxicity Testing: Acute Tubular Injury; Biomarker Identification; and Mechanism of Action: FIG. 64A LDH, FIG. 64B Total ROS, FIG. 64C Albumin uptake, and FIG. 64D Kim-1. RPTEC (Primary Human Renal Proximal Tubule Epithelial *Cells*) and RGMEC (Primary Human *Glomerular Microvascular Endothelial Cells*). (PT Kidney-Biopredict cells; HRMEC; High Shear Chip; Flow: 60 µL/hr provided by interrogator). FIG. 64E Morphology showing (PT Kidney cells-BioPre-dict; HRMEC; High Shear Chip; Flow: 60 µL/hr provided by interrogator). Primary Human Glomerular microvascular Endothelial cells, Cell Systems (Cat. #ACBRI 128).

4. Cisplatin Toxicity Testing: Acute Tubular Injury; Biomarker Identification; Mechanism of Action at a Clinically Relevant Dose.

Cisplatin is used as a gold standard nephrotoxicant for embodiments of PT-Kidney Chips (model) in multiple experiments, showing similar results. Low dose treatment effects were not captured by LDH or NAG, but showed changes at the molecular level.

Chips were expose to 6 µM of cisplatin (approximately 20 mg/m$^2$) for 72 hours. Western blot analysis of the cells following the cisplatin regimen revealed an increase in OCT2 protein and a decrease in P-gp1 (% change in expression relative to control). Significant increases were observed in several kidney injury markers, e.g. alpha GST, Calbindin, Clustrin, KIM-1, Osteoactivin A, TFF3 and VEGF (relative to control).

FIG. 65A-C shows exemplary Cisplatin Toxicity Testing: Acute Tubular Injury; Mechanism of Action: FIG. 65C Kidney Injury Marker Panel (MSD) and FIG. 65A western blot; FIG. 65B. (PT Kidney cells-ScienCell; HRMEC; Tall Channel; Flow: 60 µL/hr provided by a peristaltic pump). Gene Expression.

TABLE 17

Comparative Raw Ct value of Exemplary Nephrotoxic Compounds.

|  | OAT1 | OAT3 | CLU (Clusterin) | KIM1 | 18s RNA * |
|---|---|---|---|---|---|
| Vehicle for Cisplatin | 32.19343 | 34.63958 | 19.05483 | 23.07212 | 5.930649 |
| Cisplatin | 34.46181 | 27.23148 | 21.15388 | 26.69387 | 6.419013 |
| Vehicle for Gentamicin | 33.48098 | — | 19.58166 | 23.94926 | 6.039489 |
| Gentamicin | 33.91764 | 35.64763 | 18.6417 | 23.4566 | 5.52518 |

* A raw Ct of 18s rRNA is estimated at around 9-15 cycles as recommended by the primer vendor.

VI. Uses Related to Pharmacokinetics

Applications of a Proximal Tubule Kidney-Chip as described herein, include but at not limited to areas such as Pharmacokinetics, e.g. for determining rate of renal clearance. Such testing includes but is not limited to Renal Clearance for assessing efflux ratio of substrates/compounds and estimate proximal tubule contribution (secretion) to renal clearance; Transporter Function for measuring substrate uptake/efflux; Renal Transporter-Based Drug Interactions, i.e. Drug transport; Drug-Drug Interactions for determining competitive vs. inhibitory effects of compounds.

Embodiments of Proximal Tubule Kidney-Chips comprise co-cultures of human primary PT Kidney cells as noted from Lonza, ScienCell or Biopredic, and endothelial cells. Endothelial cells used in co-cultures on-chip in the vascular channel for data shown herein in this section are Primary Human Renal Microvascular Endothelial Cells (hRMEC) unless otherwise noted. It is not intended to limit endothelial cells to HRMECs, as other types of endothelial cells described herein may also be used. Embodiments of Proximal Tubule Kidney-Chips used for data shown in figures for this section include S1, Tall Channel and HS chips, as noted.

Renal Clearance Applications include exemplary Cisplatin assays; +/−Creatinine; +/−Probenecid.

A. Transporter Function for measuring substrate uptake/efflux.

Exemplary data related to Transporter Function related to Tubular functions, e.g. Reabsorption and secretion, are shown in FIGS. 5A-B, 6B-C, and 7-8, for Metformin efflux, and described below.

1. Transporter function: Active Transporter Expression Assessment and drug transport studies.

In some embodiments, readouts included Gene Expression-Data, i.e. relative mRNA expression to GAPDH expression.

Increased MATE1, MATE2K, OAT1 and OAT3 expression was observed under high flow (high flow>low flow). ECM2 coated membranes had higher gene expression than ECM1 coated membranes under high flow of HS chips, with the exception of P-gp. In general, ECM2>ECM1 in regards to transporter molecule expression. In general, High shear chips showed higher levels of relative transporter molecule expression.

FIG. 66 shows exemplary Transporter function: Active Transporter Expression Assessment comparing chip configurations under low and high fluid flow. Exemplary transporter molecules include MATE1, MATE2K, OAT1, OAT3 and P-gp gene expression under Low flow-S1 chip; High flow-S1 chip; Low flow-HS chip; High flow-HS chip in addition to ECM1 (blue) vs. ECM2 (grey). Relative Expression of Markers comparing Chip Configurations: AQP1A1; LRP2; AQP1; OCT2, OAT1; and OAT3. (PT Kidney cells-Lonza; HS & S1; Flow: 30 µL/hr & 150 µL/hr provided by a culture module).

2. Transporter function: Active Transporter Expression Assessment (Confocal imaging of immunohistochemistry staining).

In some embodiments, readouts including Confocal imaging were used for better spatial localization analysis of transporter and functionally associated biomarkers of transporter function. Cilia function as cellular sensor and has role for epithelial differentiation and regeneration, where cilia defects might implicate polycystic kidney diseases (Maggiorani et al., 2015). Therefore, acetylated tubulin was included as a biomarker of function along with AQP1, Megalin, Oat3, Na/K-ATPase and Oat1.

Cells in S1 chip configurations showed increased localization of membrane proteins compared to the cells from HS chip, both having ECM2 coated membranes.

FIG. 67 shows exemplary Active Transporter Expression Assessment: Confocal imaging Kidney Proximal Tubular Cells on chip. Left to right: AQP1 (green); Megalin (red); Acetylated tubulin (red); Oat3 (green); Na/K-ATPase (red); Oat1 (green) and nuclei (blue). S1 upper row, high shear lower row. (PT Kidney cells-Lonza; HS & S1; Flow: 60 µL/hr provided by a culture module).

Because it appeared that acetylated tubulin was increased at least in the S1 chip configuration over the HS chip configuration, acetylated tubulin was quantified for comparisons.

Thus, higher amounts of acetylated tubulin was measured in S1 chip configurations compared to HS chip configurations (quantified by ImageJ).

FIG. 68 shows exemplary Acetylated Tubulin: S1 Kidney Chip versus HS Kidney Chip, both membranes coated with ECM2. Immunoflorescence images showing acetylated tubulin (light color), left S1, right HS. acetylated tubulin per cm2 shows quantitavely there is more in S1 than in HS. (PT Kidney cells-Lonza; HS & S1; Flow: 60 µL/hr provided by a culture module).

B. Renal Transporter-Based Drug Interactions.

Active transporter function assessment: Renal Clearance; Transporter function; Drug interaction.

| Parameters Tested | |
|---|---|
| Cell source | Lonza, Biopredic, Cell Biologics, Sigma |
| Chip design | S1, HS (high shear chip) |
| Fluid shear stress | 30 µL/hr, 150 µL/hr |
| ECM | Kidney ECM (E1), Emulate ECM (E2) |
| Seeding | Proximal tubular cells, microvascular cells |

Example L—Functional Assessment: Renal Clearance

In one embodiment, Cisplatin is one example of a compound used for measuring a Function of a Kidney Proximal Tubule-Chip, i.e. Renal Clearance.

Renal Clearance refers to assessing efflux ratio of substrates/compounds and estimating proximal tubule contribution (secretion) to renal clearance. In some embodiments, renal clearance may be used in Drug Testing for determining effects on Kidney functions: such as Renal Clearance; Drug interaction; Efflux Testing; and Transporter function. Renal Clearance may be measured by the amount of fluorescent albumin uptake by renal epithelial cells as determined by imaging analysis; Creatinine net transport from basal to apical. In some embodiments, benchmark values will be compared against transwells and then compared to in vivo levels. Assess efflux ratio of substrates/compounds and estimate proximal tubule contribution (secretion) to renal clearance.

In one embodiment of a PT Kidney Chip, active transport of pharmaceutical compounds is measured. In one embodiment of a PT Kidney Chip, active transport of pharmaceutical compounds is measured in the presence of an inhibitor compound, e.g. Probenecid for reducing creatinine secretion. In one embodiment of a PT Kidney Chip, active transport of pharmaceutical compounds is measured in the presence of a compound for enhancing a function, e.g. Cimetidine. In one embodiment, a PT Kidney Chip is used in order to determine clinical relevance of renal transporter-based drug interactions using a non-clinical in vitro system. In one embodiment of a PT Kidney Chip, creatinine and certain drugs are actively secreted in the proximal tubule.

FIG. 80 shows exemplary Renal Cisplatin Clearance assays. Left, Cisplatin Inlet/Exit Concentration (µM). Right, Cisplatin Exit Concentration VM). (PT Kidney cells—ScienCell; Tall Channel; Flow: 60 µL/hr provided by a peristaltic pump).

Example M—Functional Assessment: Secretion of Creatinine and PAH: A to B and B to A The following are exemplary materials and methods for use in assays for measuring transport as secretion of Creatinine and PAH.

FIG. 70 illustrates active transport between the PT kidney epithelial cells and microvasculature endothelial cells in a PT-Kidney-Chip (upper) A to B and B to A. An illustration of an exemplary experimental plan (lower) is provided for assessing functionality of active transporters of proximal tubule epithelial cells using the proximal tubule Kidney Chip (lower). Functionality includes transporter function; drug interaction; and renal clearance for exemplary drugs Metformin and Digoxin. Metformin or Digoxin administered in the apical channel then after a washout the other drug is administered in the basal channel. (PT Kidney cells-Lonza; HS & S1; Flow: 30 μL/hr provided by a culture module).

After activation, S1 (tall channel) chips and high shear chips are coated with Emulate ECM (i.e. Col IV+ Matrigel) on the side of the membrane (typically the top channel) intended for seeding with PT Kidney Cells. For monocultures, proximal tubular cells are seeded into the channel with the ECM coated membrane. For co-culturing PT Kidney Cells (system), glomerular microvascular endothelial cells are seeded on bottom channel and incubated for overnight. The following day, proximal tubular cells are seeded into the top channel (where the membrane is coated with ECM) and cultured for 2 days under static conditions, i.e. no fluid flow. Chips will be connected to a culture module at day 3 along with starting flow at 150 ul/h for both channels. Media should be replenished daily. At day 7, PAH and Creatinine will be dosed Apically under a 150 ul/h flow rate then A to B transport will be measured. Initial collection (after 2 hours) will be discard and during the following 22 hours effluent fluid (media) will be collected at desired times for measurements. At day 8, PAH and Creatinine will then be dosed Basally at 150 ul/h flow rate and B to A transport will be measured. Initial collection during 2 hours will be discarded and over the following 22 hours, the media will be collected for measurement. At day 9, the chip will be return to culture mode and cultured for additional 14 days. At day 14 PAH and Creatinine will be dosed Apically at 150 ul/h flow rate and A to B transport will be measured. Initial collection (2 hours) will be discard and during the following 22 hours the media will be collected for measurement. At day 15, PAH and Creatinine will be dosed Basally at 150 ul/h flow rate and B to A transport will be measured. Initial collection during 2 hours will be discarded and the following 22 hours, the media will be collected for measurement.

2. Drug Interactions: Compound Efflux Testing Transporter function. Functional Assessments: Secretion of Creatinine and PAH: A to B and B to A.

Creatinine Mass Balance: No significant creatinine loss (inlet/outlet) was observed in embodiments of microfluidic PT-Kidney-Chip system.

Summary: There was significant active transport showing by higher B-A transport than A-B transport. High shear condition (HS) showed lower secretion of creatinine than the lower shear condition (S1). High flow (HS) chip in low flow condition showed some creatinine loss (or uptake by the cells). High flow condition did not appear to promote increased creatinine transport. Day 8 showed higher secretion than day 15. (PT Kidney cells-Lonza; Chip type: HS & S1; Flow: 30 μL/hr provided by a culture module).

In some embodiments, an inhibitor, such as Probenecid, is added to a PT Kidney Chip demonstrating a trend in a reduction in creatinine secretion (transport) of about 10%. No significant creatinine loss (inlet/outlet) was observed in the embodiments tested herein, i.e. S and HS chip configurations.

TABLE 18

Kidney-Chip Model Optimization Showing Selected Conditions Used for Some of the Functional Assessments.

| Parameters | Test Comparisons | Selected |
| --- | --- | --- |
| Cell source | Lonza vs. Biopredic vs. Cell Biologics vs. Sigma | Lonza |
| Chip design | S1 vs. HS (high shear chip) | S1 and HS show equivalent results |
| Fluid shear stress | 30 μL/hr vs. 150 μL/hr | 150 μL/hr |
| ECM | Kidney ECM, Emulate ECM | Emulate ECM |
| Seeding | Proximal tubular cells in relation to microvascular cells | Microvascular cells first and then proximal tubular cells |

TABLE 19

Exemplary Experimental Conditions For Testing Effects of Drugs on transport functions.

| | S1 chip (S1) | High shear chip (HS) | PAH | Creatinine | A to B | B to A |
| --- | --- | --- | --- | --- | --- | --- |
| Co-culture | N = 6 | N = 6 | 500 μg/ml (2.57 mM) | 3 mg/ml (26.52 mM) | Day 7, Day 14 | Day 8, Day 15 |
| Flow rate | 150 μL/hr | 150 μL/hr | — | — | — | — |
| Shear stress | Top: 0.0017 dyn/cm$^2$ Bottom: 0.05 dyn/cm$^2$ | Top: 0.23 dyn/cm$^2$ Bottom: 0.22 dyn/cm$^2$ | — | — | — | — |
| Inhibitors | — | — | N = 3 control N = 3 with Cimetidine (3 mM) | N = 3 control N = 3 with Probenecid (1 mM) | Day 7+ inhibitors for 3 hrs | — |

There does not appear to be significant differences between chip configurations in relation to Creatinine Transport as a fraction of Creatinine recovered.

FIG. 71 shows exemplary Compound Efflux Testing Transporter function: Renal Clearance and Drug interaction: as a fraction of Creatine recovered on Day 8 and Day 15. (PT Kidney cells-Lonza; Chip type: HS & S1; Flow: 30 μL/hr provided by a culture module).

Drug interaction; Renal Clearance; Creatine transport. There was significant active transport showing higher B-A transport than A-B transport. High shear condition (HS) showed lower secretion of creatinine than the lower shear condition (S1). Day 8 showed higher secretion than day 15.

FIG. 72 shows exemplary Compound Efflux Testing Transporter function: Renal Clearance; Drug interaction and Transporter function. Creatine transport (m mol/L) Day 8 and Day 15. (PT Kidney cells-Lonza; Chip type: HS & S1; Flow: 30 µL/hr provided by a culture module).

3. Creatinine Transport (Basal to Apical) with Inhibitor.

In S1 chip, some trend in reduction (10%) of creatinine secretion with the inhibitor Probenecid treated sample, but statistically not significant. Inhibitor was incubated for 3 hours.

FIG. 73 shows exemplary Creatinine Transport (m mol/L), Basal to Apical (B to A), in the presence of an inhibitor Probenecid Day 7 on S1 and HS chips. (PT Kidney cells-Lonza; Chip type: HS & S1; Flow: 30 µL/hr provided by a culture module).

PAH Mass Balance. No significant PAH loss (inlet/outlet) in the chip system. FIG. 74 shows exemplary Compound Efflux Testing as fraction of PAH recovered Day 8 and Day 15. (PT Kidney cells-Lonza; Chip type: HS & S1; Flow: 30 µL/hr provided by a culture module).

PAH Transport. There was significant active transport showing by higher B-A than A-B transport. High shear condition (HS) showed lower secretion of PAH than the lower shear condition (S1) at Day 8. Day 8 had higher secretion than on day 15.

FIG. 75 shows exemplary Compound Efflux Testing Transporter function as PAH transport (m mol/L). Readouts Day 8 and Day 15. (PT Kidney cells-Lonza; Chip type: HS & S1; Flow: 30 µL/hr provided by a culture module).

PAH Transport (Basal to Apical) with Inhibitor. In S1 chip, some trend in reduction (10%) of PAH secretion with the inhibitor Cimetidine treated chip, but statistically not significant.

FIG. 81 shows exemplary PAH Transport in the presence of an inhibitor Cimetidine treatment Day 7 on S1 chips. Readouts Day 8 (shown) and Day 15. (PT Kidney cells-Lonza; Chip type: HS & S1; Flow: 30 µL/hr provided by a culture module).

4. Drug-Drug Interactions.

In some embodiments, PT-Kidney Chips are contemplated for use in identifying Drug-Drug Interactions. In one embodiment, identifying Drug-Drug Interactions is used for determining competitive vs. inhibitory effects of test compounds.

For one example, drug dosing via apical (A) and basal (B) channels (separately) to determine A to B and B to A transport during apical dosing of inhibitor is contemplated for drug pairs as described herein. Creatinine and PHA transport measurements are provided herein as an example of this type of drug dosing assay.

In some embodiments, one drug is administered for transport measurements, such as Digoxin transport (apical to basal then basal to apical); Metformin (apical to basal and basal to apical); Tetraethylammonium (TEA), e.g. such as tetraethylammonium chloride and tetraethylammonium bromide, referring to an experimental drug (apical to basal and basal to apical), etc. In some embodiments, a drug is radiolabeled prior to administration.

In some embodiments, net transport in the presence of inhibitors is contemplated for measurement in effluent by mass spectrometry (MS). In some embodiments, identification of drug metabolites resulting from drug-drug interactions is contemplated in effluent from treated embodiments of PT-Kidney Chips. Concurrent perfusion of transporter inhibitor and drug is contemplated to lead to decreased A to B net transport of the drug.

Drug dosing is via apical (A) and basal (B) channels (separately) to determine A to B and then B to A transport. Examples of drug/inhibitor pairs contemplated for testing are as follows. In some embodiments, a test drug is a radiolabeled drug. Exemplary drug pairs: Metformin/Cimetidine; Benzylpenicillin/Probenecid; Methotrexate/Piperacillin or Tazobactam; Digoxin/Valspodar; Cefaclor/Losartan. In some embodiments, at least 3 duplicate chips are tested per drug, i.e. A to B, and the same three chips used per drug B to A. See, FIG. 58.

5. Reabsorption As An Indication Of Renal Function: Drug Testing.

In one embodiment of a PT Kidney Chip, the majority of filtered albumin is reabsorbed in the proximal tubule. In one embodiment of a PT Kidney Chip, the majority of filtered albumin is reabsorbed in the proximal tubule via endocytic receptors, such as megalin and cubilin.

In one embodiment of a PT Kidney Chip, the PT epithelial cells do not function to reabsorb as much albumin as a PT Kidney Chip seeded with PT epithelial cells having a normal function. In further embodiments, such lower functioning PT epithelial cells on chip are treated with a drug for increasing reabsorbtion of albumin. In one embodiment of a PT Kidney Chip, glucose, amino acids, and inorganic phosphate are resorbed. In one embodiment of a PT Kidney Chip, glucose, amino acids, and inorganic phosphate are resorbed via secondary active transport through co-transport channels. In some embodiments of a PT Kidney Chip, the disruption of a transport system is determined when reabsorption is lower than in a PT Kidney Chip having normal reabsorption levels. In some embodiments of a PT Kidney Chip, the disruption of a transport system is an early marker of kidney damage and toxicity.

Example N—Glucose Reabsorption Quantification

Exemplary quantification of reabsorption of glucose from PT-Kidney-Chip effluent.

The kidney contributes to glucose homeostasis through the processes of gluconeogenesis, glucose filtration, glucose reabsorption, and glucose consumption. In healthy patients, up to 180 g/day of glucose is filtered by the renal glomerulus, and nearly all of it is subsequently reabsorbed in the proximal tubule. The proximal tubule reabsorbs filtered glucose via the sodium glucose symporter (SGLT2), whereas intracellular glucose is transported to the intestinal space by glucose transporters (i.e., GLUT2). Mather and Carol Pollock, "Glucose handling by the kidney." Kidney International (2011) 79 (Suppl 120), S1-S6; doi:10.1038/ki.2010.509.

Exemplary materials, a commercial assay kit, e.g. Amplex Red Glucose/Glucose Oxidase Assay Kit (Life Technologies, A22189) and a Glucometer.

The following are exemplary steps for chip treatment and effluent collection.

Prepare reagents and standards; obtain a glucose using an assay kit (e.g. Amplex Red Glucose/Glucose Oxidase Assay Kit (Life Technologies, A22189)) or measure chip effluent directly with a glucometer. Effluent collected from the bottom channel is used to measure glucose. For measuring glucose reabsorption, use glucose-free medium to perfuse the bottom channel of the Kidney-Chip. Glucose present in media that is perfused through the top channel will not affect the results.

Recommended assay flow rate (Proximal Tubule Kidney-Chip) 60 µL/hr. Recommended effluent dilution (Proximal Tubule Kidney-Chip): No dilution needed when a glucometer is utilized, such that a 5-10 µL loading volume of effluent is recommended. Sample dilution may need to be adjusted further to accommodate for any experimental modifications by the user. Glucose levels will change depending on cell culture media used, cell injury status, or based on donor-to-donor variability. Therefore, sample dilutions may need to be modified to accommodate different experimental conditions or cells from different donors. Run assay as described on vendor site (e.g. thermofisher, cataloge product A22189, downloaded Jun. 10, 2019).

TABLE 20

Kidney-Chip Model Optimization Showing Selected Conditions For Functional Assessments.

| Parameters | Test Comparisons | Selected |
|---|---|---|
| Cell source | Lonza vs. Biopredic vs. Cell Biologics vs. Sigma | Lonza |
| Chip Configuration (design) | S1 vs. HS (high shear chip) | S1 and HS show equivalent results |
| Fluid shear stress | 30 µL/hr vs. 150 µL/hr | 150 µL/hr |
| ECM | Kidney ECM, Emulate ECM | Emulate ECM |
| Seeding | Proximal tubular cells in relation to microvascular cells | Microvascular cells first and then proximal tubular cells |

Summary II: Functional Assessment.
1. Optimized PT-kidney-chip supported normal morphology and good cell viability (robustness), i.e. uniform monolayer and cuboidal morphology of proximal tubular cells.
2. Optimized PT-kidney-chip provided sufficient recovery of both Creatinine and PAH tested without a significant loss of either compound.
3. Creatinine and PAH transport data showed minimal loss of compound in the chip (near 100% recovery), and molecule transport shown to occur across the tissue in the Kidney-Chip.
4. Transport studies showed higher B to A secretion than A to B, suggesting active transport of Creatinine and PAH in optimized PT-kidney-chip.
5. In S1 chip, addition of Inhibitors such as Cimetidine and Probenecid resulted in slight reduction of Creatinine and PAH secretion (statistically not significant).
6. Cells from S1 chip showed more defined junction between cells compared to the cells from HS chip.
7. Higher number of acetylated tubulin (function as mechanosensory) in S1 chip than HS chip.
8. Gene expression analysis showed similar expression of Na/K ATPase, AQP1 and OCT2 in both chips, but higher expression of OAT1 and OAT3 in high shear chip than S1.
9. Overall kidney chip supported consistent expression of SGLT2 (S1 marker) and enhanced expression of AQP1 and Na/K ATPase compared to cells a well plate.

Example O—Exemplary Embodiments of a PT-Kidney-Chip

For one embodiment, human proximal tubule cells were obtained from Lonza and human glomerular endothelial cells were obtained from Cell Systems, then used for seeding chips for providing co-cultures as described herein. However, it is not meant to limit a PT-Kidney-Chip to a particular cell source, indeed other sources of cells were used for some of the examples shown and described herein, while other sources of cells are contemplated for use. For one embodiment, human proximal tubule cells were obtained from Lonza. For one embodiment, human proximal tubule cells were obtained commercially. For one embodiment, human Primary Microvascular Endothelial Cells (HMECs) were commercially obtained, e.g. Cell Biologics. For one embodiment, Human Umbilical Vein Endothelial Cells (HUVEC) were obtained. For one embodiment, human Renal microvascular endothelial cells (HRMEC) were commercially obtained, e.g. Cell Biologics.

In one embodiment, a PT Kidney chip is referred to as a "S1" or "S-1" or "tall channel chip" comprising a membrane coated with E2, under high flow. For this embodiment of a PT Kidney chip, immunostaining for Aquaporin 1 is localized on the apical surface while immunostaining for Na+/K+ ATPase is localized on basolateral surface of proximal tubular cells.

Co-culture duration was up to 15 days from the time of seeding PT cells. Exemplary end points include but are not limited to: morphology; measuring functional levels, such as inulin leakage; creatinine secretion; PAH Secretion; PAH transport; albumin uptake; and Immunostaining for visualizing biomarkers.

C. A Model to Study Renal Transporters.

In part, as described herein, kidney organ and tissues play a role in elimination of xenobiotics and endogenous compounds through its complicated and efficient uptake and efflux transporting systems. Predicting potential drug-drug interactions in humans using in vitro systems are needed for testing drug disposition and toxicity. Currently available cell-based experimental models, however, often fail to predict renal transporter activity and are not scalable to a predictive clinical outcome due to in vitro-in vivo discrepancy. To overcome the challenges, we successfully developed a human Proximal Tubule Kidney-Chip model for assessment of renal transporter-based drug-drug interactions as described herein.

As a partial summary of information obtained using microfluidic PT kidney-chips described herein, gene expression of renal transporters is shown, including p-glycoprotein (P-gp), multidrug and toxin extrusion (MATE) 1, MATE2-K, organic anion transporter (OAT) 1 and 3, and organic cation transporter (OCT2), by real-time quantitative polymerase chain reaction. Data presented herein, in part see below, additionally shows efflux activities using probe substrates including digoxin mediated by P-gp, tetraethylammonium and metformin mediated collaboratively by OCT1/2, MATE1, and MATE2-K, and para-aminohippuric acid mediated by OAT1/3.

Additional transporter Tier 1 test substrates/substances include but are not limited to: 1. Digoxin; 2. Metformin; 3. TEA; 4. PAH; 5. Estrone-3-sulfate (E3S); 6. Glycylsarcosine. In some embodiments, microfluidic devices are treated with a substance followed by a 30 minute flushing cycle. In some embodiments, microfluidic devices under go 100 ul/hr of flow during transported function measurements. Additional embodiments are presented in Tables 21 and 22.

TABLE 21

Exemplary Experimental Embodiments. Experimental Embodiments.

| Flushing Flow Rate | 600 (µL/hr) |
|---|---|
| Flushing duration | 30 (min) |
| Dosing Flow Rate | 100 (µL/hr) |
| Exposure Duration | 60 (min) |
| Dosing concentration | 2 (µM) |

TABLE 22

Exemplary Experimental Chip Conditions.
Chip Conditions

| Compounds | 1st Dosing | Washout Volume (µL) | | | 2nd Dosing | N |
|---|---|---|---|---|---|---|
| Single | A->B | 100 | 200 | 300 | B->A | 3 |
| Compound | B->A | 100 | 200 | 300 | A->B | 3 |

Example:
At least 6 chips per compound/substance.

Media: Around 10 mL was used for mixing with each compound/substance to be analyzed, but it turned out to not be sufficient for providing enough to cover at least three different calibration curves, quality controls and for providing data. Therefore more than 10 mL was used for providing each mixture of the substance.

Additional transport studies were done using Metformin, Digoxin, and TEA comparing different flow rates. The following is a brief summary.

At least one embodiment of a Proximal Tubule Kidney-Chip model demonstrated efflux activities as functional assessments of kidney transporter molecules in embodiments of PT kidney chips from Day 8 to at least Day 14.

Permeability from the vascular (V) to luminal (L) direction ($P_{app}(V-L)$) and permeability from the luminal to vascular direction ($P_{app}(L-V)$) were determined along with calculating the efflux ratio ($P_{app}(V-L)/P_{app}(L-V)$). Some of the samples returned a BLQ (below limit of quantitation), especially for digoxin condition 1 and 2 samples. However, the values were included in the calculations to calculate the efflux ratio. Briefly, the results are presented in the following figures.

Digoxin—Good efflux ratios were observed for each condition tested (efflux ratio >5), indicating the P-gp function. Apparent permeability values calculated were in reasonable expected ranges. The efflux ratio for conditions 1 and 2 might be higher that expected as the basal receiver samples were BLQ that were included in the calculations for obtaining a value for the efflux ratio.

FIG. 77 shows exemplary efflux ratios and permeability of Digoxin treated embodiments of a PT Kidney chip on Days 8 and 9.

The efflux ratio of $^3$H-digoxin (1 uM) ranged from 4.6 to 6.5 in the presence of vehicle control and was completely abolished by a P-gp specific inhibitor, e.g., Zosuquidar (2 uM). FIG. 78 shows exemplary efflux ratios and permeability of Day 14 Digoxin treated compared to Digoxin coadministered with an inhibitor, e.g. Zosuquidar (Zos), to embodiments of a PT Kidney chip.

Etraethylammonium (TEA)—efflux ratios (>2) were observed in the conditions tested with reasonable expected ranges of apparent permeability values. In this embodiment, positive data was observed when using TEA.

FIG. 79 shows exemplary efflux ratios and permeability of etraethylammonium (TEA) treated embodiments of a PT Kidney chip on Days 8, 9 and 12. Day 9 data is show comparing 100 uL/hr flow rtes with 200 uL/hr flow rates. Also shown is a pH decrease in the epithelial media on Day 12.

The efflux ratio of $^{14}$C-tetraethylammonium (5 uM) ranged from 3.7 to 6.9 in the presence of vehicle control and was greatly reduced by another inhibitor, e.g., cimetidine (100 uM).

FIG. 80 shows exemplary efflux ratios and permeability of Day 14 TEA treated compared to TEA coadministered with an inhibitor, e.g. cimetidine, to embodiments of a PT Kidney chip.

Metformin—The efflux ratio for conditions tested here was less than 2. In other embodiments, positive data (efflux ratio >2) was observed. For condition 1, the efflux ratio is closer to 2, however, there was a difference between the replicates which skewed the data positive.

FIG. 81 shows exemplary efflux ratios and permeability of Metformin treated embodiments of a PT Kidney chip on Days 8 and 12 at different flow rates.

The efflux ratio of $^{14}$C-metformin (5 uM) ranged from 2 to 2.7 in the presence of vehicle control and was completely reduced by inhibitor cimetidine (100 uM).

FIG. 82 shows exemplary efflux ratios and permeability of Day 8 Metformin treated compared to Metformin coadministered with an inhibitor, e.g. cimetidine, to embodiments of a PT Kidney chip.

FIG. 83 shows exemplary efflux ratios and permeability of Day 10 Metformin treated compared to Metformin coadministered with an inhibitor, e.g. cimetidine, to embodiments of a PT Kidney chip.

The efflux ratio of $^3$H-para-aminohippuric acid (PAH) ranged from 2.4 to 2.7.

FIG. 84 shows exemplary efflux ratios, and efflux ratios as a percent change from control, and permeability of p-aminohippuric acid (PAH) treated embodiments of a PT Kidney chip on Days 8 and 12 at different flow rates.

FIG. 85 shows exemplary efflux ratios and permeability of Day 10 Estrone-3-sulfate (E3S) treated compared to E3S coadministered with an inhibitor, e.g. probenicid, to embodiments of a PT Kidney chip.

Additional experimental results are described in the following figures.

FIG. 86 shows exemplary transport activity data showing a loss of transporter activity of a substrate over time in Transwell kidney cell cultures (e.g. Digoxin for testing P-pg transporter molecule, TEA for testing Oct 2 transporter molecules, Meformin for testing MATE1/MATE2-K transporter molecules, and PHA for testing OAT1 transporter molecules). Bar graphs show transport and efflux ratio comparisons between Day 8 and Day 14 of Papp A to B then Papp B to A of exemplary substrates for each transporter molecules.

FIG. 87 shows exemplary chip based activity of apical membrane transporters showing maintenance of transport activity of a substrate over time in embodiments of Kidney-chips, as opposed to kidney cells in transwells, e.g. as in FIG. 86 (e.g. Digoxin for P-pg transporter molecules and Meformin for MATE1/MATE2-K transporter molecules). Bar graphs show transport and efflux ratio comparisons between Day 8 and Day 14 of Papp A to B then Papp B to A of exemplary substrates. Efflux ratio >2 is considered active transport. An efflux ratio less than 2 is not considered to show active transport.

FIG. 88 shows exemplary chip-based activity of basolateral membrane transporters showing maintenance of transport activity a substrate over time in embodiments of Kidney-chips (e.g. P1HA for OAT1 transporter molecules and TEA for OCT 2 transporter molecules). Bar graphs show transport and efflux ratio comparisons between Day 8 and Day 14 of Papp A to B then Papp B to A of exemplary substrates. Efflux ratio >2 is considered active transport. An efflux ratio less than 2 is not considered to show active transport.

Therefore, embodiments of in vitro PT kidney-chips are used for assessing the in vivo role of human renal transporters in drug disposition and drug interactions. Thus, embodiments of microfluidic devices such as PT kidney-chips described herein, are contemplated for use as a model for obtaining more accurate (better) predictions for in vivo drug actions.

DETAILED DESCRIPTION OF INVENTION

The present invention relates to microfluidic fluidic devices, methods and systems as microfluidic kidney on-chips, e.g. human Proximal Tubule-Kidney-Chip, Glomerulus (Kidney)-Chip, Collecting Duct (Kidney)-Chip. Such devices, methods and systems may be used for drug testing by (for example) measuring changes in transporter biomarkers, e.g. gene and protein expression of transporter molecules and injury molecules, e.g. changes in acetylated tubulin, along with changes in functions such as for albumin uptake, glucose transport, creatinine transport, PAH Transport, drug transport, and renal clearance. Further, such devices, methods and systems may be used for determining drug-drug interactions and their effect upon renal transporter functions. They may be used for pre-clinical and clinical drug development for treating kidney diseases and for personalized medicine.

Embodiments include methods for seeding microfluidic chips with a sample, such as seeding kidney cells obtained from one source, in numerous duplicate closed or open top chips, then challenging the chosen chip with a test compound, e.g. by contacting with an agent; drug, infection with a pathogen, i.e. bacterial, viral, fungal; etc., Such contacting may be by using either a single concentration or one specific dilution or a dilution series tested on a group of duplicate chips under flow during incubation, either during or after contacting. In some embodiments, a blood sample would be flowed over contacted cells in said chip. In some embodiments, a white blood cell sample would be flowed over contacted cells in said chip.

After which, effluent fluid would be sampled at certain time points for collecting samples, in some embodiments. In some embodiments, blood cells from a blood sample flowed through the chip would be collected for analysis. In other embodiments, cells would be lysed within the microchannel then flushed into the effluent tubing for collection for further processing, such as for RNA isolation by cesium chloride centrifugation, etc.

Isolated sample material would then be used to assess a profile of one or more cell type involved in the chip, including but not limited to cells located within the chip, cells attached to the chip, cells flowing through the chip, e.g. blood cells, compounds released by cells that were flowed over or in contact with treated cells.

As non-limiting examples, test agents may include chemicals, such as pesticides, herbicides, fungicides, pathogens, toxins, in the environment, etc.

I. Microfluidic Chips, Devices and Systems

Microfluidic chips, devices, and systems contemplated for use include but are not limited to chips described in Bhatia and Ingber, "Microfluidic organs-on-chips." Nature Biotechnology, 32(8):760-722, 2014; and related patent applications; and further include a wide range of chips of which some are briefly described in Zhang and Radisic, "Organ-on-a-chip devices advance to market." Lab On A Chip, (2017), for some examples, herein incorporated by reference in its entirety. The following section is merely for providing nonlimiting examples of embodiments that may find use as microfluidic devices. Moreover, exemplary embodiments of ECM, gels, etc., may find use with any microfluidic device used for microfluidic kidney-chips. It is not meant to limit the type of cells added to organ-chips, including but not limited to white blood cells, immune cells, etc.

It is not meant to limit the type of treatment of a fluidic kidney-chip, including but not limited to inflammatory induction, such as TNF-alpha treatment, inflammatory mediator treatment, etc. Thus, in some embodiments, fluidic kidney-chips as described herein are contemplated for use for decoupling cell populations, e.g. analyzing separate cell samples from the same chip.

In some embodiments, readouts measure the effect of inflammatory cytokines on organ-chips as described herein, for one example, to measure the effect upon fluidic kidney-chip barrier function and cytokine release. In some embodiments, readouts are from assays, such as barrier function, including particle diffusion, transepithelial electric resistance (TEER), apparent permeability, immunohistochemistry, etc.

More specifically, one embodiment of a kidney Proximal Tubule-Chip, e.g. one embodiment of a kidney-on-a-chip is contemplated for use in which human kidney proximal tubular epithelial cells are cultured on top of a porous membrane separating two channels, enabling analysis of transcellular transport, uptake and secretion. In some embodiments, a kidney-chip comprises human kidney cultured on top of a porous membrane separating two channels. Parenchyma refers to epithelial tissue (including renal tubules and corpuscles) whereas blood vessels, nerves, and supporting connective tissue of the kidney comprise kidney stroma.

II. Closed Top Chips

The present disclosure relates to fluidic kidney-chip, such as fluidic devices comprising one or more cells types for the simulation one or more of the function of kidney glomerular components, nephrons, etc. Accordingly, the present disclosure additionally describes closed-top kidney-chips, see, e.g. schematic in FIGS. 1A-B. In some embodiments, a fluidic kidney chip is a closed top device.

FIGS. 1A-1B illustrates a perspective view of the devices in accordance with some embodiments described herein. For example, as shown in FIGS. 1A-1B, the device 200 can include a body 202 comprising a first structure 204 and a second structure 206 in accordance with an embodiment. The body 202 can be made of an elastomeric material, although the body can be alternatively made of a non-elastomeric material, or a combination of elastomeric and non-elastomeric materials. It should be noted that the microchannel design 203 is only exemplary and not limited to the configuration shown in FIG. 1A-1B. While operating chambers 252 (e.g., as a pneumatics (pressurized air) means to actuate the membrane 208, see the International Appl. No. PCT/US2009/050830 for further details of the operating chambers, the content of which is incorporated herein by reference in its entirety) are shown in FIGS. 1A-1B, they are not required in all of the embodiments described herein. In some embodiments, the devices do not comprise operating chambers on either side of the first chamber and the second chamber. For example, FIG. 1B shows a device that does not have an operating channel on either side of the first chamber and the second chamber. As another example, FIG. 1C and FIG. 1D, shows a device that does have an operating channel 8 on both sides of the first chamber and the second chamber. In other embodiments, the devices described herein can be configured to provide other means to actuate the membrane, e.g., as described in the International Pat. Appl. No. PCT/US2014/071570, the content of which is incorporated herein by reference in its entirety.

In some embodiments, various organ chip devices described in the International Patent Application Nos. PCT/US2009/050830; PCT/US2012/026934; PCT/US2012/068725; PCT/US2012/068766; PCT/US2014/071611; and PCT/US2014/071570, the contents of each of which are incorporated herein by reference in their entireties, can be modified to form the devices described herein. For example, the organ chip devices described in those patent applications can be modified in accordance with the devices described herein.

The first structure 204 and/or second structure 206 can be fabricated from a rigid material, an elastomeric material, or a combination thereof. As used herein, the term "rigid" refers to a material that is stiff and does not bend easily, or maintains very close to its original form after pressure has been applied to it. The term "elastomeric" as used herein refers to a material or a composite material that is not rigid as defined herein. An elastomeric material is generally moldable and curable, and has an elastic property that enables the material to at least partially deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible/stretchable but does not resume its original form or position after pressure has been applied to it and removed thereafter. The terms "elastomeric" and "flexible" are interchangeably used herein.

In some embodiments, the material used to make the first structure and/or second structure or at least the portion of the first structure 204 and/or second structure 206 that is in contact with a gaseous and/or liquid fluid can comprise a biocompatible polymer or polymer blend, including but not limited to, polydimethylsiloxane (PDMS), polyurethane, polyimide, styrene-ethylene-butylene-styrene (SEBS), polypropylene, polycarbonate, cyclic polyolefin polymer/copolymer (COP/COC), or any combinations thereof. As used herein, the term "biocompatible" refers to any material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood.

Additionally or alternatively, at least a portion of the first structure 204 and/or second structure 206 can be made of non-flexible or rigid materials like glass, silicon, hard plastic, metal, or any combinations thereof.

The membrane 208 can be made of the same material as the first structure 204 and/or second structure 206 or a material that is different from the first structure 204 and/or second structure 206 of the devices described herein. In some embodiments, the membrane 208 can be made of a rigid material. In some embodiments, the membrane is a thermoplastic rigid material. Examples of rigid materials that can be used for fabrication of the membrane include, but are not limited to, polyester, polycarbonate or a combination thereof. In some embodiments, the membrane 208 can comprise a flexible material, e.g., but not limited to PDMS. Additional information about the membrane is further described below.

In some embodiments, the first structure and/or second structure of the device and/or the membrane can comprise or is composed of an extracellular matrix polymer, gel, and/or scaffold. Any extracellular matrix can be used herein, including, but not limited to, silk, chitosan, elastin, collagen, proteoglycans, hyaluronic acid, collagen, fibrin, and any combinations thereof.

The device in FIG. 1A can comprise a plurality of access ports 205. In addition, the branched configuration 203 can comprise a tissue-tissue interface simulation region (membrane 208 in FIG. 1B) where cell behavior and/or passage of gases, chemicals, molecules, particulates and cells are monitored. FIG. 1B illustrates an exploded view of the device in accordance with an embodiment. In one embodiment, the body 202 of the device 200 comprises a first outer body portion (first structure) 204, a second outer body portion (second structure) 206 and an intermediary membrane 208 configured to be mounted between the first and second outer body portions 204, 206 when the portions 204, 206 are mounted to one another to form the overall body.

The first outer body portion or first structure 204 can have a thickness of any dimension, depending, in part, on the height of the first chamber 204. In some embodiments, the thickness of the first outer body portion or first structure 204 can be about 1 mm to about 100 mm, or about 2 mm to about 75 mm, or about 3 mm to about 50 mm, or about 3 mm to about 25 mm. In some embodiments, the first outer body portion or first structure 204 can have a thickness that is more than the height of the first chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the first outer body portion or first structure 204 as thin as possible such that cells on the membrane can be visualized or detected by microscopic, spectroscopic, and/or electrical sensing methods.

The second outer body portion or second structure 206 can have a thickness of any dimension, depending, in part, on the height of the second chamber 206. In some embodiments, the thickness of the second outer body portion or second structure 206 can be about 50 m to about 10 mm, or about 75 µm to about 8 mm, or about 100 µm to about 5 mm, or about 200 m to about 2.5 mm. In one embodiment, the thickness of the second outer body portion or second structure 206 can be about 1 mm to about 1.5 mm. In one embodiment, the thickness of the second outer body portion or second structure 206 can be about 0.2 mm to about 0.5 mm. In some embodiments, the second outer first structure and/or second structure portion 206 can have a thickness that is more than the height of the second chamber by no more than 5 mm, no more than 4 mm, no more than 3 mm, no more than 2 mm, no more than 1 mm, no more than 500 microns, no more than 400 microns, no more than 300 microns, no more than 200 microns, no more than 100 microns, no more than 70 microns or less. In some embodiments, it is desirable to keep the second outer body portion or second structure 206 as thin as possible such that cells on the membrane can be visualized or detected by microscopic, spectroscopic, and/or electrical sensing methods.

In some embodiments, the first chamber and the second chamber can each independently comprise a channel. The channel(s) can be substantially linear or they can be non-linear. In some embodiments, the channels are not limited to straight or linear channels and can comprise curved, angled, or otherwise non-linear channels. It is to be further understood that a first portion of a channel can be straight, and a second portion of the same channel can be curved, angled, or otherwise non-linear. Without wishing to be bound by a theory, a non-linear channel can increase the ratio of culture area to device area, thereby providing a larger surface area for cells to grow. This can also allow for a higher amount or density of cells in the channel.

FIG. 1B illustrates an exploded view of the device in accordance with an embodiment. As shown in FIG. 1B, the first outer body portion or first structure 204 includes one or more inlet fluid ports 210 in communication with one or more corresponding inlet apertures 211 located on an outer surface of the first structure 204. The device 200 can be connected to a fluid source via the inlet aperture 211 in which fluid travels from the fluid source into the device 200 through the inlet fluid port 210.

Additionally, the first outer body portion or first structure 204 can include one or more outlet fluid ports 212 in communication with one or more corresponding outlet apertures 215 on the outer surface of the first structure 204. In some embodiments, a fluid passing through the device 200 can exit the device to a fluid collector or other appropriate component via the corresponding outlet aperture 215. It should be noted that the device 200 can be set up such that the fluid port 210 is an outlet and fluid port 212 is an inlet.

In some embodiments, as shown in FIG. 1B, the device 200 can comprise an inlet channel 225 connecting an inlet fluid port 210 to the first chamber 204. The inlet channels and inlet ports can be used to introduce cells, agents (e.g., but not limited to, stimulants, drug candidate, particulates), airflow, and/or cell culture media into the first chamber 204.

The device 200 can also comprise an outlet channel 227 connecting an outlet fluid port 212 to the first chamber 204. The outlet channels and outlet ports can also be used to introduce cells, agents (e.g., but not limited to, stimulants, drug candidate, particulates), airflow, and/or cell culture media into the first chamber 204.

Although the inlet and outlet apertures 211, 215 are shown on the top surface of the first structure 204 and are located perpendicular to the inlet and outlet channels 225, 227, one or more of the apertures 211, 215 can be located on one or more lateral surfaces of the first structure and/or second structure such that at least one of the inlet and outlet apertures 211, 215 can be in-plane with the inlet and/or outlet channels 225, 227, respectively, and/or be oriented at an angle from the plane of the inlet and/or outlet channels 225, 227.

In another embodiment, the fluid passing between the inlet and outlet fluid ports can be shared between the first chamber 204 and second chamber 206. In either embodiment, characteristics of the fluid flow, such as flow rate, fluid type and/or composition, and the like, passing through the first chamber 204 can be controllable independently of fluid flow characteristics through the second chamber 206 and vice versa.

In some embodiments, while not necessary, the first structure 204 can include one or more pressure inlet ports 214 and one or more pressure outlet ports 216 in which the inlet ports 214 are in communication with corresponding apertures 217 located on the outer surface of the device 200. Although the inlet and outlet apertures are shown on the top surface of the first structure 204, one or more of the apertures can alternatively be located on one or more lateral sides of the first structure and/or second structure. In operation, one or more pressure tubes (not shown) connected to an external force source (e.g., pressure source) can provide positive or negative pressure to the device via the apertures 217. Additionally, pressure tubes (not shown) can be connected to the device 200 to remove the pressurized fluid from the outlet port 216 via the apertures 223. It should be noted that the device 200 can be set up such that the pressure port 214 is an outlet and pressure port 216 is an inlet. It should be noted that although the pressure apertures 217, 223 are shown on the top surface of the first structure 204, one or more of the pressure apertures 217, 223 can be located on one or more side surfaces of the first structure 204.

Referring to FIG. 1B, in some embodiments, the second structure 206 can include one or more inlet fluid ports 218 and one or more outlet fluid ports 220. As shown in FIG. 1B, the inlet fluid port 218 is in communication with aperture 219 and outlet fluid port 220 is in communication with aperture 221, whereby the apertures 219 and 221 are located on the outer surface of the second structure 206. Although the inlet and outlet apertures are shown on the surface of the second structure, one or more of the apertures can be alternatively located on one or more lateral sides of the second structure.

As with the first outer body portion or first structure 204 described above, one or more fluid tubes connected to a fluid source can be coupled to the aperture 219 to provide fluid to the device 200 via port 218. Additionally, fluid can exit the device 200 via the outlet port 220 and outlet aperture 221 to a fluid reservoir/collector or other component. It should be noted that the device 200 can be set up such that the fluid port 218 is an outlet and fluid port 220 is an inlet.

In some embodiments, the second outer body portion and/or second structure 206 can include one or more pressure inlet ports 222 and one or more pressure outlet ports 224. In some embodiments, the pressure inlet ports 222 can be in communication with apertures 227 and pressure outlet ports 224 are in communication with apertures 229, whereby apertures 227 and 229 are located on the outer surface of the second structure 206. Although the inlet and outlet apertures are shown on the bottom surface of the second structure 206, one or more of the apertures can be alternatively located on one or more lateral sides of the second structure. Pressure tubes connected to an external force source (e.g., pressure source) can be engaged with ports 222 and 224 via corresponding apertures 227 and 229. It should be noted that the device 200 can be set up such that the pressure port 222 is an outlet and fluid port 224 is an inlet. In some embodiments where the operating channels (e.g., 252 shown in FIG. 1A) are not mandatory, the first structure 204 does not require any pressure inlet port 214, pressure outlet port 216. Similarly, the second structure 206 does not require any pressure inlet port 222 or pressure outlet port 224.

In an embodiment, the membrane 208 is mounted between the first structure 204 and the second structure 206, whereby the membrane 208 is located within the first structure 204 and/or second structure 206 of the device 200 (see, e.g., FIG. 1B). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, the membrane 208 in one embodiment can be made of a material which allows the membrane 208 to undergo stress and/or strain in response to an external force (e.g., cyclic stretching or pressure). In one embodiment, the membrane 208 can be made of a material which allows the membrane 208 to undergo stress and/or strain in response to pressure differentials present between the first chamber 204, the second chamber 206 and the operating channels 252. Alternatively, the membrane 208 is relatively inelastic or rigid in which the membrane 208 undergoes minimal or no movement.

In some embodiments where the device simulates a function of a proximal-tubule tissue, the membrane can be rigid.

The first chamber 204 and/or the second chamber 206 can have a length suited to the need of an application (e.g., a physiological system to be modeled), desirable size of the device, and/or desirable size of the view of field. In some embodiments, the first chamber 204 and/or the second chamber 206 can have a length of about 0.5 cm to about 10 cm. In one embodiment, the first chamber 204 and/or the second chamber 206 can have a length of about 1 cm to about 3 cm. In one embodiment, the first chamber 204 and/or the second chamber 206 can have a length of about 2 cm.

The width of the first chamber and/or the second chamber can vary with desired cell growth surface area. The first chamber 204 and the second chamber 206 can each have a range of width dimension (shown as W in FIG. 1B) between 100 microns and 50 mm, or between 200 microns and 10 mm, or between 200 microns and 1500 microns, or between 400 microns and 1 mm, or between 50 microns and 2 mm, or between 100 microns and 5 mm. In some embodiments, the first chamber 204 and the second chamber 206 can each have a width of about 500 microns to about 2 mm. In some embodiments, the first chamber 204 and the second chamber 206 can each have a width of about 1 mm.

In some embodiments, the widths of the first chamber and the second chamber can be configured to be different, with the centers of the chambers aligned or not aligned. In some embodiments, the channel heights, widths, and/or cross sections can vary along the length of the devices described herein.

The heights of the first chamber and the second chamber can vary to suit the needs of desired applications (e.g., to provide a low shear stress, and/or to accommodate cell size). The first chamber and the second chamber of the devices described herein can have the same heights or different heights. In some embodiments, the height of the second chamber 206 can be substantially the same as the height of the first chamber 204.

In some embodiments, the height of at least a length portion of the first chamber 204 (e.g., the length portion where the cells are designated to grow) can be substantially greater than the height of the second chamber 206 within the same length portion. For example, the height ratio of the first chamber to the second chamber can be greater than 1:1, including, for example, greater than 1.1:1, 1.5:1, 2:1, 2.5:1, 3:1, 3.5:1, 4:1, 4.5:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 45:1, 50:1. In some embodiments, the height ratio of the first chamber to the second chamber can range from 1.1:1 to about 50:1, or from about 2.5:1 to about 50:1, or from 2.5 to about 25:1, or from about 2.5:1 to about 15:1. In one embodiment, the height ratio of the first chamber to the second chamber ranges from about 1:1 to about 20:1. In one embodiment, the height ratio of the first chamber to the second chamber ranges from about 1:1 to about 15:1. In one embodiment, the height ratio of the first chamber to the second chamber can be about 10:1.

The height of the first chamber 204 can be of any dimension, e.g., sufficient to accommodate cell height and/or to permit a low shear flow. For example, in some embodiments, the height of the first chamber can range from about 100 m to about 50 mm, about 200 µm to about 10 mm, about 500 µm to about 5 mm, or about 750 um to about 2 mm. In one embodiment, the height of the first chamber can be about 150 um. In one embodiment, the height of the first chamber can be about 1 mm.

The height of the second chamber 206 can be of any dimension provided that the flow rate and/or shear stress of a medium flowing in the second chamber can be maintained within a physiological range, or does not cause any adverse effect to the cells. In some embodiments, the height of the second chamber can range from 20 µm to about 1 mm, or about 50 µm to about 500 µm, or about 75 µm to about 400 µm, or about 100 µm to about 300 µm. In one embodiment, the height of the second chamber can be about 150 µm. In one embodiment, the height of the second chamber can be about 100 µm.

The first chamber and/or the second chamber can have a uniform height along the length of the first chamber and/or the second chamber, respectively. Alternatively, the first chamber and/or the second chamber can each independently have a varying height along the length of the first chamber and/or the second chamber, respectively. For example, a length portion of the first chamber can be substantially taller than the same length portion of the second chamber, while the rest of the first chamber can have a height comparable to or even smaller than the height of the second chamber.

In some embodiments, the first structure and/or second structure of the devices described herein can be further adapted to provide mechanical modulation of the membrane. Mechanical modulation of the membrane can include any movement of the membrane that is parallel to and/or perpendicular to the force/pressure applied to the membrane, including, but are not limited to, stretching, bending, compressing, vibrating, contracting, waving, or any combinations thereof. Different designs and/or approaches to provide mechanical modulation of the membrane between two chambers have been described, e.g., in the International Patent App. Nos. PCT/US2009/050830, and PCT/US2014/071570, the contents of which are incorporated herein by reference in their entireties, and can be adapted herein to modulate the membrane in the devices described herein.

In some embodiments, the devices described herein can be placed in or secured to a cartridge. In accordance with some embodiments of some aspects described herein, the device can be integrated into a cartridge and form a monolithic part. Some examples of a cartridge are described in the International Patent App. No. PCT/US2014/047694, the content of which is incorporated herein by reference in its entirety. The cartridge can be placed into and removed from a cartridge holder that can establish fluidic connections upon or after placement and optionally seal the fluidic connections upon removal. In some embodiments, the cartridge can be incorporated or integrated with at least one sensor, which can be placed in direct or indirect contact with a fluid flowing through a specific portion of the cartridge during operation. In some embodiments, the cartridge can be incorporated or integrated with at least one electric or electronic circuit, for example, in the form of a printed circuit board or flexible circuit. In accordance with some embodiments of some aspects described herein, the cartridge can comprise a gasketing embossment to provide fluidic routing.

In some embodiments, the cartridge and/or the device described herein can comprise a barcode. The barcode can be unique to types and/or status of the cells present on the membrane. Thus, the barcode can be used as an identifier of each device adapted to mimic function of at least a portion of a specific tissue and/or a specific tissue-specific condition. Prior to operation, the barcode of the cartridge can be read by an instrument so that the cartridge can be placed and/or aligned in a cartridge holder for proper fluidic connections and/or proper association of the data obtained during operation of each device. In some embodiments, data obtained from each device include, but are not limited to, cell response, immune cell recruitment, intracellular protein expression, gene expression, cytokine/chemokine expression, cell morphology, functional data such as effectiveness of an endothelium as a barrier, concentration change of an agent that is introduced into the device, or any combinations thereof.

In some embodiments, the device can be connected to the cartridge by an interconnect adapter that connects some or all of the inlet and outlet ports of the device to microfluidic channels or ports on the cartridge. Some examples interconnect adapters are disclosed in U.S. Provisional Application No. 61/839,702, filed on Jun. 26, 2013, and the International Patent Application No. PCT/US2014/044417 filed Jun. 26, 2014, the contents of each of which are hereby incorporated by reference in their entirety. The interconnect adapter can include one or more nozzles having fluidic channels that can be received by ports of the device described herein. The interconnect adapter can also include nozzles having fluidic channels that can be received by ports of the cartridge.

In some embodiments, the interconnect adaptor can comprise a septum interconnector that can permit the ports of the device to establish transient fluidic connection during operation, and provide a sealing of the fluidic connections when not in use, thus minimizing contamination of the cells and the device. Some examples of a septum interconnector are described in U.S. Provisional Application No. 61/810,944 filed Apr. 11, 2013, the content of which is incorporated herein by reference in its entirety.

Membrane: The membrane 208 is oriented along a plane 208P parallel to the x-y plane between the first chamber 204 and the second chamber 206 as shown in FIG. 1B. It should be noted that although one membrane 208 is shown in FIG. 1B, more than one membrane 208 can be configured in devices which comprise more than two chambers. The membrane separating the first chamber and the second chamber in the devices described herein can be porous (e.g., permeable or selectively permeable), non-porous (e.g., non-permeable), rigid, flexible, elastic or any combinations thereof. Accordingly, the membrane 208 can have a porosity of about 0% to about 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable.

As used interchangeably herein, the terms "non-porous" and "non-permeable" refer to a material that does not allow any molecule or substance to pass through. In some embodiments, the membrane can be porous and thus allow molecules, cells, particulates, chemicals and/or media to migrate or transfer between the first chamber 204 and the second chamber 206 via the membrane 208 from the first chamber 204 to the second chamber 206 or vice versa.

As used herein, the term "porous" generally refers to a material that is permeable or selectively permeable. The term "permeable" as used herein means a material that permits passage of a fluid (e.g., liquid or gas), a molecule, a whole living cell and/or at least a portion of a whole living cell, e.g., for formation of cell-cell contacts. The term "selectively permeable" as used herein refers to a material that permits passage of one or more target group or species, but act as a barrier to non-target groups or species. For example, a selectively-permeable membrane can allow passage of a fluid (e.g., liquid and/or gas), nutrients, wastes, cytokines, and/or chemokines from one side of the membrane to another side of the membrane, but does not allow whole living cells to pass therethrough. In some embodiments, a selectively-permeable membrane can allow certain cell types to pass therethrough but not other cell types.

The permeability of the membrane to individual matter/species can be determined based on a number of factors, including, e.g., material property of the membrane (e.g., pore size, and/or porosity), interaction and/or affinity between the membrane material and individual species/matter, individual species size, concentration gradient of individual species between both sides of the membrane, elasticity of individual species, and/or any combinations thereof. A porous membrane can have through-holes or pore apertures extending vertically and/or laterally between two surfaces 208A and 208B of the membrane (FIG. 1B), and/or a connected network of pores or void spaces (which can, for example, be openings, interstitial spaces or hollow conduits) throughout its volume. The porous nature of the membrane can be contributed by an inherent physical property of the selected membrane material, and/or introduction of conduits, apertures and/or holes into the membrane material.

In some embodiments, a membrane can be a porous scaffold or a mesh. In some embodiments, the porous scaffold or mesh can be made from at least one extracellular matrix polymer (e.g., but not limited to collagen, alginate, gelatin, fibrin, laminin, hydroxyapatite, hyaluronic acid, fibroin, and/or chitosan), and/or a biopolymer or biocompatible material (e.g., but not limited to, polydimethylsiloxane (PDMS), polyurethane, styrene-ethylene-butylene-styrene (SEBS), poly(hydroxyethylmethacrylate) (pHEMA), polyethylene glycol, polyvinyl alcohol and/or any biocompatible material described herein for fabrication of the device first structure and/or second structure) by any methods known in the art, including, e.g., but not limited to, electrospinning, cryogelation, evaporative casting, and/or 3D printing. See, e.g., Sun et al. (2012) "Direct-Write Assembly of 3D Silk/Hydroxyapatite Scaffolds for Bone Co-Cultures." Advanced Healthcare Materials, no. 1: 729-735; Shepherd et al. (2011) "3D Microperiodic Hydrogel Scaffolds for Robust Neuronal Cultures." Advanced Functional Materials 21: 47-54; and Barry III et al. (2009) "Direct-Write Assembly of 3D Hydrogel Scaffolds for Guided Cell Growth." Advanced Materials 21: 1-4, for examples of a 3D biopolymer scaffold or mesh that can be used as a membrane in the device described herein.

In some embodiments, a membrane can comprise an elastomeric portion fabricated from a styrenic block copolymer-comprising composition, e.g., as described in the International Pat. App. No. PCT/US2014/071611, can be adopted in the devices described herein, the contents of each of which are incorporated herein by reference in its entirety. In some embodiments, the styrenic block copolymer-comprising composition can comprise SEBS and polypropylene.

In some embodiments, a membrane can be a hydrogel or a gel comprising an extracellular matrix polymer, and/or a biopolymer or biocompatible material. In some embodiments, the hydrogel or gel can be embedded with a conduit network, e.g., to promote fluid and/or molecule transport. See, e.g., Wu et al. (2011) "Omnidirectional Printing of 3D Microvascular Networks." Advanced Materials 23: H178-H183; and Wu et al. (2010) "Direct-write assembly of biomimetic microvascular networks for efficient fluid transport." Soft Matter 6: 739-742, for example methods of introducing a conduit network into a gel material.

In some embodiments, a porous membrane can be a solid biocompatible material or polymer that is inherently permeable to at least one matter/species (e.g., gas molecules)

and/or permits formation of cell-cell contacts. In some embodiments, through-holes or apertures can be introduced into the solid biocompatible material or polymer, e.g., to enhance fluid/molecule transport and/or cell migration. In one embodiment, through-holes or apertures can be cut or etched through the solid biocompatible material such that the through-holes or apertures extend vertically and/or laterally between the two surfaces of the membrane 208A and 208B. It should also be noted that the pores can additionally or alternatively incorporate slits or other shaped apertures along at least a portion of the membrane 208 which allow cells, particulates, chemicals and/or fluids to pass through the membrane 208 from one section of the central channel to the other.

The pores of the membrane (including pore apertures extending through the membrane 208 from the top 208A to bottom 208B surfaces thereof and/or a connected network of void space within the membrane 208) can have a cross-section of any size and/or shape. For example, the pores can have a pentagonal, circular, hexagonal, square, elliptical, oval, diamond, and/or triangular shape.

The cross-section of the pores can have any width dimension provided that they permit desired molecules and/or cells to pass through the membrane. In some embodiments, the pore size of the membrane should be big enough to provide the cells sufficient access to nutrients present in a fluid medium flowing through the first chamber and/or the second chamber. In some embodiments, the pore size can be selected to permit passage of cells (e.g., immune cells and/or cancer cells) from one side of the membrane to the other. In some embodiments, the pore size can be selected to permit passage of nutrient molecules. In some embodiments, the width dimension of the pores can be selected to permit molecules, particulates and/or fluids to pass through the membrane 208 but prevent cells from passing through the membrane 208. In some embodiments, the width dimension of the pores can be selected to permit cells, molecules, particulates and/or fluids to pass through the membrane 208. Thus, the width dimension of the pores can be selected, in part, based on the sizes of the cells, molecules, and/or particulates of interest. In some embodiments, the width dimension of the pores (e.g., diameter of circular pores) can be in the range of 0.01 microns and 20 microns, or in one embodiment, approximately 0.1-15 microns, or approximately 1-10 microns. In one embodiment, the pores have a width of about 7 microns.

In an embodiment, the porous membrane 208 can be designed or surface patterned to include micro and/or nanoscopic patterns therein such as grooves and ridges, whereby any parameter or characteristic of the patterns can be designed to desired sizes, shapes, thicknesses, filling materials, and the like.

The membrane 208 can have any thickness to suit the needs of a target application. In some embodiments, the membrane can be configured to deform in a manner (e.g., stretching, retracting, compressing, twisting and/or waving) that simulates a physiological strain experienced by the cells in its native microenvironment. In these embodiments, a thinner membrane can provide more flexibility. In some embodiments, the membrane can be configured to provide a supporting structure to permit growth of a defined layer of cells thereon. Thus, in some embodiments, a thicker membrane can provide a greater mechanical support. In some embodiments, the thickness of the membrane 208 can range between 70 nanometers and 100 µm, or between 1 µm and 100 µm, or between 10 and 100 µm. In one embodiment, the thickness of the membrane 208 can range between 10 µm and 80 µm. In one embodiment, the thickness of the membrane 208 can range between 30 µm and 80 µm. In one embodiment, the thickness of the membrane 208 can be about 50 µm.

While the membrane 208 generally have a uniform thickness across the entire length or width, in some embodiments, the membrane 208 can be designed to include regions which have lesser or greater thicknesses than other regions in the membrane 208. The decreased thickness area(s) can run along the entire length or width of the membrane 208 or can alternatively be located at only certain locations of the membrane 208. The decreased thickness area can be present along the bottom surface of the membrane 208 (i.e. facing second chamber 206), or additionally/alternatively be on the opposing surface of the membrane 208 (i.e. facing second chamber 204). It should also be noted that at least portions of the membrane 208 can have one or more larger thickness areas relative to the rest of the membrane, and capable of having the same alternatives as the decreased thickness areas described above.

In some embodiments, the membrane can be coated with substances such as various cell adhesion promoting substances or ECM proteins, such as fibronectin, laminin, various collagen types, glycoproteins, vitronectin, elastins, fibrin, proteoglycans, heparin sulfate, chondroitin sulfate, keratin sulfate, hyaluronic acid, fibroin, chitosan, or any combinations thereof. In some embodiments, one or more cell adhesion molecules can be coated on one surface of the membrane 208 whereas another cell adhesion molecule can be applied to the opposing surface of the membrane 208, or both surfaces can be coated with the same cell adhesion molecules. In some embodiments, the ECMs, which can be ECMs produced by cells, such as primary cells or embryonic stem cells, and other compositions of matter are produced in a serum-free environment.

In an embodiment, one can coat the membrane with a cell adhesion factor and/or a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is fibronectin, laminin, various collagen types, glycoproteins, vitronectin, elastins, fibrin, proteoglycans, heparin sulfate, chondroitin sulfate, keratin sulfate, hyaluronic acid, tenascin, antibodies, aptamers, or fragments or analogs having a cell binding domain thereof. The positively-charged molecule and/or the cell adhesion factor can be covalently bound to the membrane. In another embodiment, the positively-charged molecule and/or the cell adhesion factor are covalently bound to one another and either the positively-charged molecule or the cell adhesion factor is covalently bound to the membrane. Also, the positively-charged molecule or the cell adhesion factor or both can be provided in the form of a stable coating non-covalently bound to the membrane.

In an embodiment, the cell attachment-promoting substances, matrix-forming formulations, and other compositions of matter are sterilized to prevent unwanted contamination. Sterilization can be accomplished, for example, by ultraviolet light, filtration, gas plasma, ozone, ethylene oxide, and/or heat. Antibiotics can also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In some embodiments, the membrane and/or other components of the devices described herein can be treated using gas plasma, charged particles, ultraviolet light, ozone, or any combinations thereof.

Using the devices described herein, one can study biotransformation, absorption, as well as drug clearance, metabolism, delivery, and toxicity. The activation of xenobiotics can also be studied. The bioavailability and transport of chemical and biological agents across epithelial layers as in a tissue or organ, e.g., parenchyma, and endothelial layers as in blood vessels, and across the proximal tubule cells and/or endothelial cells for drug metabolism can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be detected and studied using the devices described herein. The impact of genetic content on response to the agents can be studied. The amount of protein and gene expression in response to chemical or biological agents can be determined. Changes in metabolism in response to chemical or biological agents can be studied as well using devices described herein.

In some embodiments, the devices described herein (e.g., a Proximal Tubule-Chip) can be used to assess the clearance of a test compound (substrate). For clearance studies, the disappearance of a test compound can be measured (e.g. using mass spec) in the media of the top chamber, bottom chamber, or both chambers (divided by a membrane comprising Proximal Tubule cells).

For example, in accordance to one aspect of the invention, a Proximal Tubule-Chip drug-metabolizing performance can be measured by i) disposing a substrate compound with known blood or kidney metabolites in the media of the top chamber, bottom chamber, or both chambers; and ii) measuring the amount of generated metabolite in the media of the top chamber, bottom chamber or both chambers (e.g. using mass spec). As is known in the art, the choice of the substrate and measured metabolite can help provide information on specific kidney drug-metabolism enzymes (e.g. CYP450 isoforms, CYP 2B6 and 3A5, Non-CYP Enzymes, etc.). Additional substrates (including drugs) for membrane transporter molecules may be a substrate such as Adefovir for OAT1 membrane transporters; substrate Cephradine for OAT1 membrane transporters; and substrate Balsartan for OAT1/OAT3 membrane transporters. Substrates for specific membrane transporter molecules are also shown in Table 23, below. Victim (aka substrate) drug was administered to either apical or basolateral side of one embodiment of a Kidney-Chip. An inhibitor compound was infused through both apical and basolateral channels. Papp was determined at multiple concentrations of inhibitor.

FIG. 89 shows exemplary concentration-dependent inhibition of high starting efflux ratio for Digoxin-Quinidine mediated DDI (P-gp). Victim is Digoxin. Perpetrator is Quinidine. Substrates for transporters are termed "victim". Inhibitors are termed "perpetrator". See, Table 23.

TABLE 23

Exemplary Assessment Of Drug-Transporter Interactions.

| Transport System | Victim | Perpetrator |
|---|---|---|
| P-pg | Digoxin | Quinidine |
| OCT1/MATE1/MATE2-K | TEA | Cimetidine |
| OCT2/MATE1/MATE2-K | Meformin | Cimetidine |
| OAT1 | PHA | Probenecid |
| OAT1 | Adefovir | Probenecid |

FIG. 90 shows exemplary assessment of drug-transporter interactions. Substrates for transporters are termed "victim". Inhibitors are termed "perpetrator". Transporter molecules are part of the transport system in Table 24.

TABLE 24

Assessment of Drug-Transporter Interactions.

| Transport System | Victim | Perpetrator | $IC_{50}$ (microM) |
|---|---|---|---|
| P-pg | Digoxin | Quinidine | 0.723 |
| OCT1/MATE1/MATE2-K | TEA | Cimetidine | 3.16 |
| OCT2/MATE1/MATE2-K | Meformin | Cimetidine | 4.41 |
| OAT1 | PHA | Probenecid | 6.71 |
| OAT1 | Adefovir | Probenecid | 12.5 |

One example of transporter activities of substrates is shown in comparative efflux ratios between in vitro Transwell cultures and Kidney-Chips in addition to comparative in vivo clinical data. See corresponding FIG. 91. Embodiments of a proximal tubule Kidney chip predicted a clearance value that is 85% of clinical value for Adefovir, 63% for Metformin, and 72% for PAH. Conversely, Transwell data predicts clearance of 25%, with similar clearance estimates as would be estimated considering glomerular filtration alone.

FIG. 91 shows exemplary prediction of clearance comparing in vitro prediction clearance (clinical values) vs. Transwell and Kidney-Chip data when no inhibitor is used. Bar graphs show exemplary comparisons between clinical values, Transwell cultures and Kidney-chips as total clearance (mL/min). For each substrate group: the left bar=clinical values, the middle bar=Transwell data, the right bar=Kidney-Chip data. See, also Table 25.

TABLE 25

Exemplary Prediction of clearance when no inhibitor compound is used. Exemplary comparisons between clinical values, Transwells and Kidney-chips as Efflux Ratios.

| Substrate | Transwell Efflux Ratio | Kidney-Chip Efflux Ratio | Distal Tubule Reabsorption |
|---|---|---|---|
| Adefovir | — | 2.01+/−0.11 | Minimal |
| Digoxin | 2.28+/−0.38 | 8.34+/−0.83 | Significant |
| Metformin | 1.12+/−0.12 | 3.26+/−0.41 | Minimal |
| PHA | 1.37+/−0.20 | 4.84+/−0.57 | Minimal |
| TEA | 1.11+/−0.06 | 6.95+/−0.60 | — |

In some embodiments, the devices described herein (e.g., a Proximal Tubule-Chip) can be used to assess the induction or inhibition potential of a test compound. For induction or inhibition studies a variety of tests are contemplated. For example, induction of a transporter or drug metabolism enzyme in the kidney may cause a drug-drug interaction leading to unwanted side-effects (toxicity); a change the efficacy of a drug or renal failure. A reliable and practical CYP3A induction assay with human hepatocytes in a 96-well format has been reported, where various 96-well plates with different basement membranes were evaluated using prototypical inducers, rifampicin, phenytoin, and carbamazepine. See Drug Metab. Dispo. (2010) Nov.; 38(11): 1912-6.

According to one aspect of the invention, the induction or inhibition potential of a test compound at a test concentration can be evaluated by i) disposing the test compound in the media of the top chamber, bottom chamber or both chambers at the test concentration; ii) exposing the device for a selected period of time; and iii) assessing the induction or inhibition of kidney enzymes by comparing proximal kidney cell performance to a measurement performed before the test compound was applied, to a measurement performed on a Proximal Tubule-on-Chip that was subjected to a lower concentration of test compound (or no test compound at all), or both. In some embodiments, the proximal kidney cell performance measurement can comprise an RNA expression level. In some embodiments, the proximal kidney cell performance measurement comprises assessing albumin release. In some embodiments, the proximal kidney cell performance measurement comprises assessing albumin resportion. In some embodiments, the proximal kidney cell performance measurement comprises assessing drug transporter function. In some embodiments, the proximal kidney cell performance measurement comprises assessing drug-metabolizing capacity.

In some embodiments, the devices described herein (e.g., a Proximal Tubule-Chip) can be used to identify in vivo metabolites of a test compound or agent, and optionally the in vivo ratio of these metabolites. According to one aspect of the invention, in vivo metabolites can be identified by i) disposing a test compound or agent in the media of the top chamber, bottom chamber, or both chambers; and ii) measuring the concentration of metabolites in the media of the top chamber, bottom chamber, or both chambers. In some embodiments, the measuring of the concentration of metabolites comprises mass spectroscopy.

In some embodiments, the devices described herein (e.g., a Proximal Tubule-Chip) can be used to identify the toxicity of a test compound or agent at a test concentration. According to one aspect of the invention, toxicity can be evaluated by i) disposing a test compound in the media of the top chamber, bottom chamber, or both chambers; and ii) measuring one or more toxicity endpoints selected from the list of leakage of cellular enzymes (e.g., lactose dehydrogenase, alanine aminotransferase, aspartate aminotransferase) or material (e.g., adenosine triphosphate), variation in RNA expression, inhibition of drug-metabolism capacity, reduction of intracellular ATP (adenosine triphosphate), cell death, apoptosis, and cell membrane degradation.

Exemplary Methods of Making the Devices Described Herein.

Embodiments of various devices comprising a first chamber, a second chamber, and a membrane can enable us to leverage the control of microfluidic technology for device fabrication. In some embodiments, the devices described herein can be manufactured using any conventional fabrication methods, including, e.g., injection molding, embossing, etching, casting, machining, stamping, lamination, photolithography, or any combinations thereof. Soft lithography techniques are described in "Soft Lithography in Biology and Biochemistry," by Whitesides, et al., published Annual Review, Biomed Engineering, 3.335-3.373 (2001), as well as "An Ultra-Thin PDMS Membrane As A Bio/Micro-Nano Interface: Fabrication And Characterization", by Thangawng et al., Biomed Microdevices, vol. 9, num. 4, 2007, p. 587-95, both of which are hereby incorporated by reference.

Without wishing to be limiting, in some embodiments, the devices described herein can be produced as a monolithic device or as individual components (e.g., a first structure comprising a first chamber, a second structure comprising a second chamber, and a membrane), which can then be assembled together to form a device described herein. Each individual component can be produced by a conventional manufacturing method such as injection molding, extrusion, casting, lamination, embossing, compression molding, solvent casting, an additive manufacturing method (e.g., 3D printing), or any combinations thereof.

Once the first and second structures 204, 206 are formed and removed from their respective molds, the access ports can be made to access the chambers.

The membrane 208 can be engineered for a variety of purposes, some discussed above.

In some embodiments, the membrane 208 can be sandwiched between the first structure and the second structure, e.g., using an appropriate adhesive or epoxy, physical clamping and/or plasma bond between the two PDMS surfaces, in order to form a fluidic seal between the membrane with the first structure and the second structure.

After forming the body of the devices described herein, the first side of the membrane can be coated with an ECM composition according to one or more embodiments described herein. After formation of the ECM composition, tissue specific cells, e.g., hepatocytes, can be grown thereon.

In some embodiments, at least one layer of cells comprising blood vessel-associated cells (e.g., fibroblasts, smooth muscle cells, and/or endothelial cells) can be cultured on the second side of the membrane.

A. Closed Top Microfluidic Chips Without Gels.

In one embodiment, closed top gut-on-chips, or other type of organ-chip, do not contain gels, either as a bulk gel or a gel layer. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer.

Additional embodiments are described herein that may be incorporated into closed top chips without gels.

B. Closed Top Microfluidic Chips With Gels.

In one embodiment, closed top gut-on-chips do contain gels, such as a gel layer, or bulk gel, including but not limited to a gel matrix, hydrogel, etc. Thus, in one embodiment, the device generally comprises (i) a first structure defining a first chamber; (ii) a second structure defining a second chamber; and (iii) a membrane located at an interface region between the first chamber and the second chamber to separate the first chamber from the second chamber, the membrane including a first side facing toward the first chamber and a second side facing toward the second chamber, wherein the first and second chambers are enclosed. In some embodiments, the device further comprises a gel. In some embodiments, the gel is a continuous layer. In some embodiments, the gel is a layer of approximately the same thickness across the layer. In some embodiments, the gel is a discontinuous layer. In some embodiments, the gel has different thicknesses across the layer. In some embodiments, the first side of the membrane may have a gel layer. In some embodiments, a gel is added to the first side of the membrane without an ECM layer. The first side of the membrane may have an extracellular matrix composition disposed thereon, wherein the extracellular matrix (ECM) composition comprises an ECM coating layer. In some embodiments, an ECM gel layer e.g. ECM overlay, is located over the ECM coating layer. In some embodiments, the gel layer is above the ECM coating layer. In some embodiments, the ECM coating layer may have a gel layer on the bottom, i.e. the side facing the membrane. In some embodiments, the gel overlays the ECM gel layer.

Additional embodiments are described herein that may be incorporated into closed top chips with gels.

C. Closed Top Microfluidic Chips With Simulated Lumens.

A closed top gut-on-chip comprising a gel-lined simulated lumen may be used for generating a more physiological relevant model of gastrointestinal tissue. In some embodiments, closed top gut-on-chips further comprise a gel simulated three-dimensional (3-D) lumen. In other words, a 3-D lumen may be formed using gels by providing simulated intestinal villi (e.g. viscous fingers) and/or mimicking intestinal folds. In a preferred embodiment, the gel forms a lumen, i.e. by viscous fingering patterning.

Using viscous fingering techniques, e.g. viscous fingering patterning, a simulated intestinal lumen may be formed by numerous simulated intestinal villi structures. Intestinal villi (singular: villus) refer to small, finger-like projections that extend into the lumen of the small intestine. For example, healthy small intestine mucosa contains these small finger-like projections of tissue that are present along the lumen as folds of circular plica finger-like structures. A villus is lined on the luminal side by an epithelia cell layer, where the microvillus of the epithelial cells (enterocytes) faces the lumen (i.e. apical side). Viscous fingers may be long and broad, for mimicking villi in the duodenum of the small intestine, while thinner or shorter viscous fingers may be used for mimicking villi in other parts of the gastrointestinal tract. As one example, viscous fingers may be formed and used to mimic epithelial projections in the colon.

Methods to create three-dimensional (3-D) lumen structures in permeable matrices are known in the art. One example of a 3-D structure forming at least one lumen is referred to as "viscous fingering". One example of viscous fingering methods that may be used to for form lumens, e.g. patterning lumens, is described by Bischel, et al. "A Practical Method for Patterning Lumens through ECM Hydrogels via Viscous Finger Patterning." J Lab Autom. 2012 April; 17(2): 96-103, Author manuscript; available in PMC 2012 Jul. 16, herein incorporated by reference in its entirety. In one example of a viscous finger patterning method for use with microfluidic gut-on-chips, lumen structures are patterned with an ECM hydrogel.

"Viscous" generally refers to a substance in between a liquid and a solid, i.e. having a thick consistency. A "viscosity" of a fluid refers to a measure of its resistance to gradual deformation by shear stress or tensile stress. For liquids, it corresponds to an informal concept of "thickness"; for example, honey has a much higher viscosity than water.

"Viscous fingering" refers in general to the formation of patterns in "a morphologically unstable interface between two fluids in a porous medium."

A "viscous finger" generally refers to the extension of one fluid into another fluid. Merely as an example, a flowable gel or partially solidified gel may be forced, by viscous fingering techniques, into another fluid, into another viscous fluid in order to form a viscous finger, i.e. simulated intestinal villus.

In some embodiments, the lumen can be formed by a process comprising (i) providing the first chamber filled with a viscous solution of the first matrix molecules; (ii) flowing at least one or more pressure-driven fluid(s) with low viscosity through the viscous solution to create one or more lumens each extending through the viscous solution; and (iii) gelling, polymerizing, and/or cross linking the viscous solution. Thus, one or a plurality of lumens each extending through the first permeable matrix can be created.

In another embodiment, gel is added to a channel for making a lumen.

In some embodiments as described herein, the first and second permeable matrices can each independently comprise a hydrogel, an extracellular matrix gel, a polymer matrix, a monomer gel that can polymerize, a peptide gel, or a combination of two or more thereof. In one embodiment, the first permeable matrix can comprise an extracellular matrix gel, (e.g. collagen). In one embodiment, the second permeable matrix can comprise an extracellular matrix gel and/or protein mixture gel representing an extracellular microenvironment, (e.g. MATRIGEL®. In some embodiments, the first and second permeable matrixes can each independently comprise a polymer matrix. Methods to create a permeable polymer matrix are known in the art, including, e.g. but not limited to, particle leaching from suspensions in a polymer solution, solvent evaporation from a polymer solution, sold-liquid phase separation, liquid-liquid phase separation, etching of specific "block domains" in block co-polymers, phase separation to block-co-polymers, chemically cross-linked polymer networks with defined permabilities, and a combination of two or more thereof.

Another example for making branched structures using fluids with differing viscosities is described in "Method And System For Integrating Branched Structures In Materials" to Katrycz, Publication number US20160243738, herein incorporated by reference in its entirety.

Regardless of the type of lumen formed by a gel and/or structure, cells can be attached to these structures either to lumen side of the gel and/or within the gel and/or on the side of the gel opposite the lumen. Thus, three-dimensional (3-D) lumen gel structures may be used in several types of embodiments for closed top microfluidic chips, e.g. epithelial cells can be attached to outside of the gel, or within the gel. In some embodiments, stoma cells are added within the gel. In some embodiments, stomal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into closed top chips with simulated 3D lumens containing a gel.

III. Open Top Microfluidic Chips

The present disclosure relates to gut-on-chips, such as fluidic devices comprising one or more cells types for the simulation one or more of the function of gastrointestinal tract components. Accordingly, the present disclosure additionally describes open-top gut-on-chips, see, e.g. schematic in FIG. 2A-2B. FIG. 2A shows an exemplary exploded view of one embodiment of an open-top chip device 1800, wherein a membrane 1840 resides between the bottom surface of the first chamber 1863 and the second chamber 1864 and the at least two spiral microchannels 1851. Open top microfluidic chips include but are not limited to chips having removable covers, such as removable plastic covers, paraffin covers, tape covers, etc.

FIG. 2B illustrates a cut-away view of one embodiment of a stretchable open top chip device showing the regional placement of cells (e.g., epithelial cells 3110 in an epithelial compartment, stromal cells 3120 in a stromal compartment and/or vascular cells 3151 in a vasclular compartment, i.e. lower channel). Partial views of an open top microfluidic chip 3100 modeling a simulated kidney organ comprising kidney epithelium. One embodiment shown is a schematic of a partial view of an open top chip demonstrating channels for a vascular area 3151 and fluid flow; an open stromal area (compartment) 3178 in relation to cellular compartments in the chip (left). One embodiment is a schematic of a partial open top chip additionally demonstrating cells in the compartments of the chip (right).

In one embodiment, the present invention contemplates a stretchable open top chip device 3100 comprising a chamber 3163 comprising an epithelial region 3177 and a stromal region 3178, e.g. dermal region. In one embodiment, the epithelial region comprises an epithelial cell layer. In one embodiment, the dermal region comprises a dermal cell layer, wherein said epithelial cell layer adheres to the surface of the dermal cell layer. In one embodiment, the device further comprises a spiral microchannel 3151 in fluid communication with a fluid inlet port 3114, wherein the microchannel comprises a plurality of vascular cells. In one embodiment, a membrane 3140 is placed between the chamber dermal cell layer and the microchannel plurality of vascular cells. In one embodiment, the device further comprises an upper microchannel with a circular chamber 3156 connected to a fluid or gas port pair 3175. In one embodiment, the device further comprises a first vacuum port 3130 connected to a first vacuum chamber 3137 and a second vacuum port 3132 connected to a second vacuum chamber 3138. In one embodiment, the membrane 3140 comprises a PDMS membrane comprising a plurality of pores 3141, wherein said pores 3141 are approximately 50 µm thick, approximately 7 µm in diameter, packed as 40 µm hexagons, wherein each pore has a surface area of approximately 0.32 cm$^2$. Although it is not necessary to understand the mechanism of an invention, it is believed that the pore surface area contacts a gel layer (if present).

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

Therefore, the present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.).

While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated gastrointestinal tissues.

The present invention contemplates a variety of uses for these open top microfluidic devices and methods described herein. In one embodiment, the present invention contemplates a method of topically testing an agent (whether a drug, food, gas, or other substance) comprising 1) providing a) an agent and b) microfluidic device comprising i) a chamber, said chamber comprising a lumen and projections into the lumen, said lumen comprising ii) a gel matrix anchored by said projections and comprising cell in, on or under said gel matrix, said gel matrix positioned above iii) a porous membrane and under iv) a removable cover, said membrane in contact with v) fluidic channels; 2) removing said removable cover; and 3) topically contacting said cells in, on or under said gel matrix with said agent. In one embodiment, said agent is in an aerosol. In one embodiment, agent is in a liquid, gas, gel, semi-solid, solid, or particulate form. These uses may apply to the open top microfluidic chips described below and herein.

A. Open Top Microfluidic Chips Without Gels.

In one embodiment, open top gut-on-chips do not contain gels, either as a bulk gel or a gel layer. Thus, the present invention also contemplates, in one embodiment, a layered structure comprising i) fluidic channels covered by ii) a porous membrane, said membrane comprising iii) a layer of cells and said membrane positioned below said cells. In one embodiment, there is a removable cover over the cells.

Additional embodiments are described herein that may be incorporated into open top chips without gels.

B. Open Top Microfluidic Chips With Gels.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer). Thus, in a preferred embodiment, the open-top microfluidic device comprises a gel matrix. In one embodiment, the open-top microfluidic device does not contain a bulk gel.

The present invention also contemplates, in one embodiment, a layered structure comprising i) fluidic channels covered by ii) a porous membrane, said membrane comprising iii) a layer of cells and said membrane positioned below iv) a gel matrix. In one embodiment, there is a removable cover over the gel matrix (and/or cells). It is not intended that the present invention be limited to embodiments with only one gel or gel layer. In one embodiment, the layered structure further comprises a second gel matrix (e.g. positioned under said membrane). The gel(s) or coatings can be patterned or not patterned. Moreover, when patterned, the pattern need not extend to the entire surface. For example, in one embodiment, at least a portion of said gel matrix is patterned. It is not intended that the present invention be limited by the nature or components of the gel matrix or gel coating. In one embodiment, gel matrix comprises collagen. A variety of thickness is contemplated. In one embodiment of the layered structure, said gel matrix is between 0.2 and 6 mm in thickness.

Also described is a simulated lumen further comprising gel projections into the simulated lumen. Thus, in yet another embodiment, the present invention contemplates a microfluidic device comprising i) a chamber, said chamber comprising a lumen and projections in the lumen, said lumen comprising ii) a gel matrix anchored by said projections, said gel matrix positioned above iii) a porous membrane, said membrane in contact with iv) fluidic channels. In one embodiment, said membrane comprises cells. The projections serve as anchors for the gel. The projections, in one embodiment, project outward from the sidewalls. The projections, in another embodiment, project upward. The projects, in another embodiment, project downward. The projections can take a number of forms (e.g. a T structure, a Y structure, a structure with straight or curving edges, etc.). In some embodiments, there are two or more projections; in other embodiments, there are four or more projections to anchor the gel matrix. In one embodiment, the membrane is above said fluidic channels.

In other embodiments, open top microfluidic chips comprise partial lumens as described herein for closed top chips. Thus, in some embodiments, open top microfluidic chips comprise lumens formed by viscous fingering described herein for closed top chips.

Lumen gel structures may be used in several types of embodiments for open top microfluidic chips, e.g. epithelial cells or parenchymal cells can be attached to outside of the gel, or within the gel. In some embodiments, stromal cells are added within the gel. In some embodiments, stromal cells are attached to the side of the gel opposite from the lumen. In some embodiments, endothelial cells are located below the gel on the side opposite the lumen. In some embodiments, endothelial cells may be present within the gel.

Additional embodiments are described herein that may be incorporated into open top chips with gels, with or without gels.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

IV. Chip Activation

In preferred embodiments, Closed-Top microfluidic devices were activated prior to ECM coating as described herein. In preferred embodiments, Closed-Top microfluidic devices as S1 and HS configurations were activated prior to ECM coating as described herein. In preferred embodiments, both upper and lower channels including a separating membrane were activated.

In some embodiments, an Open-Top Organ-Chip platform was chemically activated by Sulfo-SANPAH/buffer, such as HEPES buffer, treatment (Emulate, Inc). Briefly, Sulfo-SANPAH and buffer were mixed together as specified by the instructions and added to the bottom spiraled shaped microfluidic channel and circular stromal chamber. The platform was then UV treated for 20 minutes using UV oven (e.g. 365 nm light and the bulb that generate the UV light are 9 Watt).

A. Chip Activation Compounds.

In one embodiment, bifunctional crosslinkers are used to attach one or more extracellular matrix (ECM) proteins. A variety of such crosslinkers are available commercially, including (but not limited to) the following compounds:

ANB-NOS
(N-5-azido-2-nitrobenzoyloxysuccinimide)

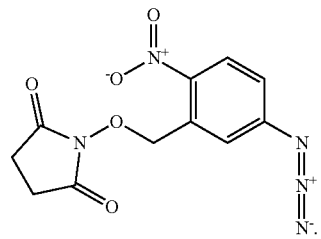

Sulfo-SAND (sulfosuccinimidyl 2-[m-azido-o-nitrobenzamido]ethyl-1,3'-dithiopropionate)

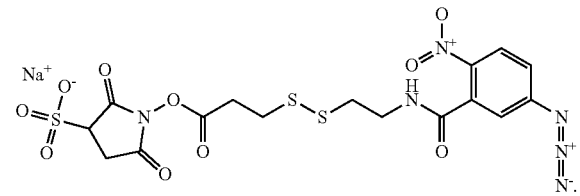

SANPAH (N-succinimidyl-6-[4'-azido-2'-nitrophenylamino]hexanoate)

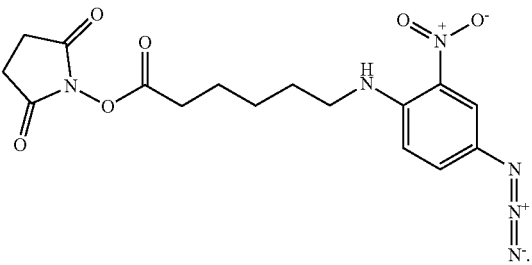

Sulfo-SANPAH (sulfosuccinimidyl-6-[4'-azido-2'-nitrophenylamino]hexanoate)

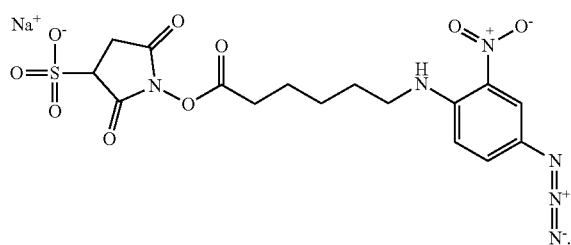

By way of example, sulfosuccinimidyl 6-(4'-azido-2'-nitrophenyl-amino) hexanoate or "Sulfo-SANPAH" (commercially available from Pierce) is a long-arm (18.2 angstrom) crosslinker that contains an amine-reactive N-hydroxysuccinimide (NHS) ester and a photoactivatable nitrophenyl azide. NHS esters react efficiently with primary amino groups (—$NH_2$) in pH 7-9 buffers to form stable amide bonds. The reaction results in the release of N-hydroxy-succinimide. When exposed to UV light, nitrophenyl azides form a nitrene group that can initiate addition reactions with double bonds, insertion into C—H and N—H sites, or subsequent ring expansion to react with a nucleophile (e.g., primary amines). The latter reaction path dominates when primary amines are present.

Sulfo-SANPAH should be used with non-amine-containing buffers at pH 7-9 such as 20 mM sodium phosphate, 0.15M NaCl; 20 mM HEPES; 100 mM carbonate/bicarbonate; or 50 mM borate. Tris, glycine or sulfhydryl-containing buffers should not be used. Tris and glycine will compete with the intended reaction and thiols can reduce the azido group.

For photolysis, one should use a UV lamp that irradiates at 300-460 nm. High wattage lamps are more effective and require shorter exposure times than low wattage lamps. UV lamps that emit light at 254 nm should be avoided; this wavelength causes proteins to photodestruct. Filters that remove light at wavelengths below 300 nm are ideal. Using a second filter that removes wavelengths above 370 nm could be beneficial but is not essential.

B. Exemplary Methods of Chip Activation.

Exemplary surface activation of chips: Sulfo-sanpah (Covachem, #13414), ER1 (ER-1) (0.5 mg/ml) in ER2 (ER-2) (50 mM HEPES buffer). Sulfo-sanpah is light-sensitive. Failure to protect ER-1 from light or use of Sulfo-sanpah solution that has not been freshly prepared will lead to failure of chips. Sulfo-sanpah is an eye irritant and must be handled in the BSC with proper gloves and eye protection. One embodiment of chip activation:
1. Prepare and sanitize hood working space.
2. S-1 Chip Handling—Use aseptic technique, hold Chip using Carrier
   a. Use 70% ethanol spray and wipe the exterior of Chip package prior to bringing into hood.
   b. Open package inside hood.
   c. Remove Chip and place in sterile Petri dish (6 Chips/Dish).
   d. Label Chips and Dish with respective condition and Lot #.
3. Surface Activation with Chip Activation Compound (light and time sensitive)
   a. Turn off light in biosafety hood (BSC).
   b. Allow vial of Chip Activation Compound powder to fully equilibrate to ambient temperature (to prevent condensation inside the storage container, as reagent is moisture sensitive). Approximately 10 to 15 minutes).
4. Reconstitute the Chip Activation Compound powder with ER-2 solution.
   a. Add 10 ml Buffer, such as HEPES, into a 15 ml conical covered with foil to protect it from light.
   b. Take 1 ml Buffer from above conical tube and add to chip Activation Compound (5 mg) bottle, pipette up and down to mix thoroughly and transfer to same conical tube.
   c. Repeat 3-5 times until chip Activation Compound is fully mixed in the conical tube.
NOTE: Chip Activation Compound is single use only, discard immediately after finishing Chip activation, solution cannot be reused.
Alternative to steps in No. 4, above:
   a. In the BSC, remove the small vial of ER-1 powder from the packet, and briefly tap the vial to concentrate the powder at the bottom.
   b. Add 1 mL of ER-2 to the vial, and transfer contents directly to the bottom of the 15 mL conical tube. Do not pipette to mix. Note: The color of the solution transferred to the conical tube will be deep red.
   c. Add an additional 1 mL of ER-2 to the ER-1 vial to collect any remaining material, and transfer the solution directly to the 15 mL conical tube. Note: The color of the transferred ER-1 solution will become lighter with each additional wash of the ER-1 bottle.
   d. Repeat Step 5 twice more, with an additional 1 mL of ER-2 each time.
   e. On the last addition of 1 mL ER-2 to the ER-1 bottle, cap the bottle and invert to collect any remaining ER-1 powder from the lid. Transfer the collected solution to the conical tube, bringing the total volume in the tube to 4 mL ER-1 solution.
   f. Add 6 mL of ER-2 solution to the 4 mL of ER-1 solution in the 15 mL conical tube (for a final working concentration of 0.5 mg/mL). Pipette gently to mix without creating bubbles. ER-1 should be fully dissolved within the ER-2 solution prior to use.
5. Wash channels.
   a. Inject 200 µl of 70% ethanol into each channel and aspirate to remove all fluid from both channels.
   b. Inject 200 µl of Cell Culture Grade Water into each channel and aspirate to remove all fluid from both c.
   c. Inject 200 µl of Buffer into each channel and aspirate to remove fluid from both channels.

6. Introduce ER-1 Solution to Channels: Inject Chip Activation Compound Solution (in buffer) in both channels.
    a. Use a P200 and pipette 200 µl to inject Chip Activation Compound/Buffer into each channel of each chip (200 µl should fill about 3 Chips (Both Channels)).
    b. Inspect channels by eye to be sure no bubbles are present. If bubbles are present, flush channel with Chip Activation Compound/Buffer until bubbles have been removed.
7. Activate and Wash Chips: UV light activation of Chip Activation Compound
    a. Place Chips into a 150 mm dish, then cover.
    b. Bring the 150 mm dish containing the ER-1-coated chips to a UV light box.
    c. Remove the cover from the 150 mm dish and place the open dish in the UV light box.
    d. UV light treat Chips for 20 minutes.
    e. While the Chips are being treated, prepare ECM Solution.
    f. After UV treatment, bring chips back to the BSC. Note: The light may be on in the BSC from this point forward.
    g. Fully aspirate the ER-1 solution from both channels, i.e., gently aspirate Chip Activation Compound/Buffer from channels via same ports until channels are free of solution.
    h. Carefully wash with 200 µl of Buffer (ER-2) solution through both channels and aspirate to remove all fluid from both channels.
    i. Carefully wash with 200 µl of sterile DPBS through both channels.
    j. Carefully aspirate DPBS from channels or leave cold DPBS inside the channels until ready to coat with ECM, then and move on to: ECM-to-Chip section.

VI. ECM-to-Chip

Exemplary ECM-coatings: Collagen IV (BD Corning, 50 µg/mL in Dulbecco's phosphate-buffered saline (DPBS) (without $Ca^{2+}$, $Mg^{2+}$); Matrigel (BD Corning, reduced growth factor, 100 µg/ml DPBS); KidneySpec ECM (Eastriverbio.com). In some embodiments, ECM comprises Collagen IV plus Matrigel. In some embodiments, ECM is a mixture of collagen I and fibronectin ECM proteins.

A. Prepare ECM Solution.

The ECM solution is prepared fresh each time by combining the individual ECM components with cold DPBS to the final working concentrations. The ECM solution will be used to coat both the top and bottom channels.

For human Proximal Tubule Kidney-Chips, the ECM working concentration is: Collagen IV: 50 µg/mL; Matrigel: 100 µg/mL.

1. Bring an ice bucket and ice to the BSC.
2. Thaw one aliquot of Collagen IV (1 mg/mL) on ice. Maintain all ECM components and mixture on ice at all times.
3. Calculate total volume of ECM solution needed to coat all chips.
    a. Volume required per chip=approximately 100 µL.
    b. For every 12 chips to coat, prepare 1.5 mL of ECM solution (12 chips×100 µL/chip+extra 300 µL=1.5 mL of ECM solution). (See calculation example below).
4. Combine components to prepare ECM working solution.
5. Keep the ECM solution on ice until ready to use.

Calculate total volume of ECM solution needed to coat Chips or hydrogel surfaces, these are exemplary ECM materials, as laminin may also be used with one or more ECM materials.

1. Volume required per Chip=50 ul/Channel.
2. ECM diluent: PBS, prepared on ice.
3. Stock Concentrations for ECM coating:
    a. Collagen IV: 1 mg/ml (200 µl aliquots in −20° C.).
    b. Fibronectin: 1 mg/ml (50 µl aliquots in 4° C.).
    c. Matrigel: 10 mg/ml (200 µl aliquots in −20° C.).
4. Working Concentrations for ECM coating:
    a. Collagen IV: 200 µg/ml.
    b. Fibronectin: 30 µg/ml.
5. Top Channel Coating: 50 µl Collagen IV (200 µg/ml) and Matrigel (100 g/ml).
6. Bottom Channel Coating: 50 µl Collagen IV (200 µg/ml) and Fibronectin (30 ug/ml).

B. Coat Chips with ECM: Load Channels with ECM solution.

1. Place Chips in BSC (hood).
2. Fully aspirate the cold DPBS from both channels.
3. Set and Use a P200 pipette to take up 100 µL of ECM solution. (100 µL volume total will be used per chip.)
4. Carefully introduce ECM solution through the bottom channel inlet until a small ECM droplet forms on the outlet.
5. Without releasing the pipetting plunger, take the pipette out from the bottom channel inlet, and move the pipette containing remaining ECM solution to the top channel inlet.
6. Introduce ECM solution through the top channel inlet, leaving small droplets of excess ECM solution on both ports in both channels.
7. Inspect channels to ensure that no bubbles are present. If bubbles are present, dislodge by washing the channel with ECM solution until all bubbles have been removed.
8. Repeat steps 1 through 7 for each chip.
9. Add 1.5 mL of DPBS to the cap of a 15 mL conical tube. Place the PBS cap in the 150 mm culture dish with the chips to provide extra humidity and seal the dish.
10. Incubate at 37° C. for a minimum of 2 hours up to overnight.

Alternatively, Steps 4-6:

4. Pipette 50 µl of Top Channel Coating into Top Channel—keep the pipette plunger depressed until you see fluid come out opposite end of the channel, then take another pipette tip (200 µl tip) to close the outlet port. Once closed off, carefully remove the pipette tip, leaving the tip in the inlet port.
5. Aspirate excess fluid from the surface of Chip (avoid direct contact with the port).
6. Repeat Steps 4-5, but with Bottom Channel Coating into Bottom Channel.

For best results, incubate the chips at 4° C. overnight, then at 37° C. for 1 hour the following day. Note: If desired, cells can be seeded the same day as chip activation and ECM coating, though incubation overnight is preferred. Chips can be ready for hepatocyte seeding 4 hours after adding the ECM and incubating chips at 37° C. If chips will be stored longer than overnight, store the chips at 4° C. for up to 2 days.

C. Exemplary Matrigel Coating.
1. Thaw Matrigel on ice and keep chilled to prevent solidification.
2. Prepare Matrigel.
    a. Matrigel Stock Concentration: 10 mg/ml.
    b. Matrigel Final Concentration: 250 µg/ml.
    c. Determine the volume of Matrigel needed to coat 50 µl of each Top Channel and resuspend accordingly in the appropriate cell culture media.
    d. Transfer the seeded Chips into the hood.
    e. Wash both channels of each chip twice with 200 µl media.
    f. Before inserting the tips, add a drop of media to prevent formation of bubbles.
    g. Leave 50 µl media in bottom channel (Tips inserted).
    h. Add 50 µl 250 ug/ml Matrigel to top channel (Tips inserted).
    i. Incubate at 37° C. overnight.

V. Cells-to-Chip-Chip Preparation Just Before Seeding

1. Transfer the ECM coated Chips into the hood.
    a. Gently wash Chips after ECM coating.
2. Pipette 200 µl of DPBS into bottom channel inlet port—keep the pipette plunger depressed until you see fluid come out opposite end of channel and aspirate outflow
3. Repeat the same procedure to wash top channel.
4. Pipette 200 µl of DPBS into top channel inlet port—keep the pipette plunger depressed until you see fluid come out opposite end of the channel, then take another pipette tip (200 µl) to close the outlet port. Once closed off, carefully remove the pipette tip, leaving the tip in the inlet port.
5. Repeat the same with the bottom channel. Place back in incubator until cells are ready.

EXPERIMENTAL

Example: RNA (Gene) Expression Profiling

Gene expression profiling refers to measurement of the activity (expression) of thousands of genes at once, to create a global picture of cellular function. As one example, RNA-Seq (Illumina, Inc. 5200 Illumina Way, San Diego, Calif. 92122), provides information on the sequences of genes in addition to their expression level.

As one example, total RNA can be extracted and used to generate biotin-labeled cRNA, e.g. using an Illumina Total-Prep RNA Amplification Kit (Ambion, Austin, Tex.). Biotin-labeled cRNA was then hybridized to Illumina HumanHT-12 whole genome expression beadchips (Illumina, San Diego, Calif.). The quality of the Illumina bead summary data can be assessed using the Bioconductor package Lumi. Data preprocessing may include variance stabilization and quantile normalization. To eliminate potentially confounding effects of RNA quality on gene expression, residuals may be calculated from the regression analysis of RIN values on gene expression and used for statistical analysis and WGCNA network construction. Outlier values may then be removed for each gene within a group using Grubbs' test ($p<0.05$). Statistical analysis comparing alcoholic and control groups may be performed using the Bioconductor package Limma to carry out a Bayesian two-tailed t-test. A false discovery rate (FDR) for each list of significantly regulated genes with nominal P values<0.05 may be estimated using the method of Benjamini and Hochberg (1995). Our systems approach to prioritizing individual genes may be based on integration of nominal statistical significance, gene network information and functional relevance. Therefore, to avoid omitting true positives, all genes with nominal P values <0.05 may be considered.

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

The invention claimed is:
1. A method of measuring clearance, comprising:
    a) providing a microfluidic device comprising a membrane, said membrane comprising a first surface and a second surface, said first surface comprising proximal tubule cells and said second surface comprising glomerular microvascular endothelial cells;
    b) culturing said proximal tubule cells and said glomerular microvascular endothelial cells under continuous flow of media;
    c) introducing an agent; and
    d) detecting clearance of said agent in said microfluidic device that predicts a clearance value that is at least 60% of the actual clinical clearance value for said agent.
2. The method of claim 1, wherein said proximal tubule cells are human primary proximal tubular epithelial cells.
3. The method of claim 1, wherein said membrane contains pores.
4. The method of claim 1, wherein the agent is a drug.
5. The method of claim 1, wherein the agent is metformin.
6. The method of claim 1, wherein said microfluidic device that predicts a clearance value that is at least 70% of the actual clinical clearance value for said agent.
7. The method of claim 1, wherein said microfluidic device that predicts a clearance value that is at least 80% of the actual clinical clearance value for said agent.

* * * * *